United States Patent
Gao et al.

(10) Patent No.: US 12,054,715 B2
(45) Date of Patent: *Aug. 6, 2024

(54) MODIFIED AAV CONSTRUCTS AND USES THEREOF

(71) Applicant: University of Massachusetts, Boston, MA (US)

(72) Inventors: Guangping Gao, Worcester, MA (US); Jun Xie, Worcester, MA (US); Phillip D. Zamore, Worcester, MA (US)

(73) Assignee: University of Massachusetts, Boston, MA (US)

( * ) Notice: Subject to any disclaimer, the term of this patent is extended or adjusted under 35 U.S.C. 154(b) by 427 days.

This patent is subject to a terminal disclaimer.

(21) Appl. No.: 17/316,769

(22) Filed: May 11, 2021

(65) Prior Publication Data

US 2021/0340539 A1     Nov. 4, 2021

Related U.S. Application Data

(63) Continuation of application No. 15/568,650, filed as application No. PCT/US2016/027848 on Apr. 15, 2016, now Pat. No. 11,046,955.

(60) Provisional application No. 62/152,602, filed on Apr. 24, 2015.

(51) Int. Cl.
| | |
|---|---|
| *C12N 15/113* | (2010.01) |
| *A61K 31/713* | (2006.01) |
| *C12N 15/11* | (2006.01) |
| *C12N 15/86* | (2006.01) |
| *C12Q 1/68* | (2018.01) |

(52) U.S. Cl.
CPC .......... *C12N 15/113* (2013.01); *A61K 31/713* (2013.01); *C12N 15/111* (2013.01); *C12N 15/86* (2013.01); *C12N 2310/11* (2013.01); *C12N 2310/141* (2013.01); *C12N 2310/531* (2013.01); *C12N 2330/51* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 5,478,745 A | 12/1995 | Samulski et al. | |
| 5,871,982 A | 2/1999 | Wilson et al. | |
| 6,001,650 A | 12/1999 | Colosi | |
| 6,156,303 A | 12/2000 | Russell et al. | |
| 6,177,403 B1 | 1/2001 | Stedman | |
| 6,251,677 B1 | 6/2001 | Wilson et al. | |
| 6,485,966 B2 | 11/2002 | Gao et al. | |
| 6,544,786 B1 | 4/2003 | Xiao et al. | |
| 6,953,690 B1 | 10/2005 | Gao et al. | |
| 6,962,815 B2 | 11/2005 | Bartlett | |
| 7,022,519 B2 | 4/2006 | Gao et al. | |
| 7,198,951 B2 | 4/2007 | Gao et al. | |
| 7,235,393 B2 | 6/2007 | Gao et al. | |
| 7,238,526 B2 | 7/2007 | Wilson et al. | |
| 7,427,396 B2 | 9/2008 | Arbetman et al. | |
| 7,456,015 B2 | 11/2008 | Bohn et al. | |
| 7,906,111 B2 | 3/2011 | Wilson et al. | |
| 8,222,221 B2 | 7/2012 | Corey et al. | |
| 8,524,446 B2 | 9/2013 | Gao et al. | |
| 8,734,809 B2 | 5/2014 | Gao et al. | |
| 9,217,155 B2 | 12/2015 | Gao et al. | |
| 9,249,424 B2 | 2/2016 | Wolf et al. | |
| 9,701,984 B2 | 7/2017 | Gao et al. | |
| 11,046,955 B2 | 6/2021 | Gao et al. | |
| 2001/0016355 A1 | 8/2001 | Samulski et al. | |
| 2002/0019050 A1 | 2/2002 | Gao et al. | |
| 2002/0164783 A1 | 11/2002 | Feldhaus | |
| 2002/0192823 A1 | 12/2002 | Bartlett | |
| 2003/0040101 A1 | 2/2003 | Wilson et al. | |
| 2003/0103939 A1 | 6/2003 | Engelhardt et al. | |
| 2003/0110526 A1 | 6/2003 | Brown et al. | |
| 2003/0119191 A1 | 6/2003 | Gao et al. | |
| 2003/0138772 A1 | 7/2003 | Gao et al. | |
| 2003/0207259 A1 | 11/2003 | Gao et al. | |
| 2003/0228282 A1 | 12/2003 | Gao et al. | |
| 2004/0101514 A1 | 5/2004 | Liu et al. | |
| 2004/0219528 A1 | 11/2004 | Morris et al. | |
| 2005/0014262 A1 | 1/2005 | Gao et al. | |
| 2005/0032219 A1 | 2/2005 | Aubourg et al. | |
| 2005/0037988 A1 | 2/2005 | Zamore et al. | |
| 2005/0137153 A1 | 6/2005 | McSwiggen et al. | |
| 2005/0197313 A1 | 9/2005 | Roelvink et al. | |
| 2005/0255086 A1 | 11/2005 | Davidson et al. | |

(Continued)

FOREIGN PATENT DOCUMENTS

| | | | |
|---|---|---|---|
| EP | 2261242 A1 | 12/2010 | |
| EP | 2468891 A2 | 6/2012 | |

(Continued)

OTHER PUBLICATIONS

International Search Report and Written Opinion PCT/US2016/027848, dated Jul. 26, 2016,.

(Continued)

*Primary Examiner* — Sean McGarry

(74) *Attorney, Agent, or Firm* — Wolf, Greenfield & Sacks, P.C.

(57) ABSTRACT

The present disclosure relates to the field of rAAV delivery of transgenes. In some aspects, the disclosure relates to RNAi. Provided herein are recombinant adeno-associated virus (rAAV) vectors comprising modified ITRs. In some embodiments, the modified ITRs comprise a sequence encoding a shRNA, miRNA, or AmiRNA.

18 Claims, 71 Drawing Sheets

Specification includes a Sequence Listing.

(56) References Cited

U.S. PATENT DOCUMENTS

| | | |
|---|---|---|
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0243526 A1 | 10/2007 | Kay et al. |
| 2007/0292410 A1 | 12/2007 | Cashman et al. |
| 2008/0075737 A1 | 3/2008 | Gao et al. |
| 2008/0075740 A1 | 3/2008 | Gao et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0215879 A1 | 8/2009 | DiPrimio et al. |
| 2009/0239240 A1 | 9/2009 | Chu |
| 2010/0104561 A1 | 4/2010 | Zhong et al. |
| 2010/0186103 A1 | 7/2010 | Gao et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| WO | WO 2003/042397 A2 | 5/2003 |
| WO | WO 2003/093460 A1 | 11/2003 |
| WO | WO 2004/108922 A2 | 12/2004 |
| WO | WO 2005/033321 A2 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2007/127264 A2 | 11/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/043936 A1 | 4/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 12/2014 |
| WO | WO 2015/121501 A1 | 8/2015 |
| WO | WO 2015/164786 A1 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

International Preliminary Report on Patentability PCT/US2016/027848, dated Nov. 2, 2017.

Extended European Search Report for Appl No. EP 16783632.9 dated Nov. 21, 2018.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Adachi et al., Drawing a high-resolution functional map of adeno-associated virus capsid by massively parallel sequencing. Nat Commun 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Boillee et al., Onset and progression in inherited ALS determined by motor neurons and microglia. Science. Jun. 2, 2006;312(5778):1389-92.

Borel et al., Recombinant AAV as a platform for translating the therapeutic potential of RNA interference. Mol Ther. Apr. 2014;22(4):692-701. doi: 10.1038/mt.2013.285. Epub Dec. 19, 2013.

Boudreau, et al. (2009) Artificial MicroRNAs as siRNA Shuttles: Improved Safety as Compared to shRNAs in vitro and in vivo. Molecular Therapy, vol. 17, No. 1, pp. 169-175. (Year: 2009).

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alphal-antitrypsin (AAT) vector in AAT-deficient adults. Hum Gene Ther. Dec. 2006;17(12):1177-86.

(56) References Cited

OTHER PUBLICATIONS

Brown et al., A microRNA-regulated lentiviral vector mediates stable correction of hemophilia B mice. Blood. Dec. 15, 2007;110(13):4144-52. Epub Aug. 28, 2007.
Brown et al., Endogenous microRNA can be broadly exploited to regulate transgene expression according to tissue, lineage and differentiation state. Nat Biotechnol. Dec. 2007;25(12):1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Buning et al., Receptor targeting of adeno-associated virus vectors. Gene Ther. Jul. 2003;10(14):1142-51.
Bussing et al., let-7 microRNAs in development, stem cells and cancer. Trends Mol Med. Sep. 2008; 14(9):400-9. doi: 10.1016/j.molmed.2008.07.001. Epub Jul. 31, 2008.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004; 1(2):106-13. Epub Jul. 1, 2004.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Cheng et al., Development of optimized AAV3 serotype vectors: mechanism of high-efficiency transduction of human liver cancer cells. Gene Ther. Apr. 2012;19(4):375-84. doi: 10.1038/gt.2011. 105. Epub Jul. 21, 2011.
Chiorini et al., Cloning and characterization of adeno-associated virus type 5. J Virol. Feb. 1999;73(2):1309-19.
Choi et al., Effects of adeno-associated virus DNA hairpin structure on recombination. J Virol. Jun. 2005;79(11):6801-7.
Choudhury et al., Identification of Novel vectors capable of CNS transduction in adult mice after single round selection using DNA shuffled AAV capsid library. Mol Ther. May 1, 2013;21(1):S1/.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)—CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Cruz et al., The promise of gene therapy for the treatment of alpha-1 antitrypsin deficiency. Pharmacogenomics. Sep. 2007;8(9):1191-8.

Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Elmen et al., LNA-mediated microRNA silencing in non-human primates. Nature. Apr. 2008;452(17):896-900.
Elmen et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Gadalla et al., Improved survival and reduced phenotypic severity following AAV9/MECP2 gene transfer to neonatal and juvenile

(56) References Cited

OTHER PUBLICATIONS male Mecp2 knockout mice. Mol Ther. Jan. 2013;21(1):18-30. doi:10.1038/mt.2012.200. Epub Sep. 25, 2012.

Gao et al., Erythropoietin gene therapy leads to autoimmune anemia in macaques. Blood. May 1, 2004; 103(9):3300-2. Epub Dec. 24, 2003.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Purification of recombinant adeno-associated virus vectors by column chromatography and its performance in vivo. Hum Gene Ther. Oct. 10, 2000;11(15):2079-91.

Gao et al., RAAV-mediated targeting in adult mice and its potential in generating animal models of tissue-specific somatic transgenics or knock down. Molecular Therapy. May 2008;16(1):S118-S119. Abstract 316.

Gentner et al., Stable knockdown of microRNA in vivo by lentiviral vectors. Nat Methods. Jan. 2009;6(1):63-6. doi: 10.1038/nmeth. 1277. Epub Nov. 30, 2008.

Girard et al., miR-122, a paradigm for the role of microRNAs in the liver. J Hepatol. Apr. 2008;48(4):648-56. doi: 10.1016/j.jhep.2008. 01.019. Epub Feb. 12, 2008.

Gramantieri et al., Cyclin G1 is a target of miR-122a, a microRNA frequently down-regulated in human hepatocellular carcinoma. Cancer Res. Jul. 1, 2007;67(13):6092-9.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

Haussecker et al., miR-122 continues to blaze the trail for microRNA therapeutics. Mol Ther. Feb. 2010;18(2):240-2. doi: 10.1038/mt. 2009.313.

Hernandez et al., Latent adeno-associated virus infection elicits humoral but not cell-mediated immune responses in a nonhuman primate model. J Virol. Oct. 1999;73(10):8549-58.

Horwich et al., Design and delivery of antisense oligonucleotides to block microRNA function in cultured Drosophila and human cells. Nat Protoc. 2008;3(10):1537-49. doi: 10.1038/nprot.2008.145.

Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.

Hutvagner et al., Sequence-specific inhibition of small RNA function. PLoS Biol. Apr. 2004;2(4):E98. Epub Feb. 24, 2004.

Iida et al., Systemic Delivery of Tyrosine-Mutant AAV Vectors Results in Robust Transduction of Neurons in Adult Mice. BioMed Res Int. 2013;2013.

Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.

Jakobsson et al., Lentiviral vectors for use in the central nervous system. Mol Ther. Mar. 2006;13(3):484-93. Epub Jan. 3, 2006.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Johnson et al., RAS is regulated by the let-7 microRNA family. Cell. Mar. 11, 2005;120(5):635-47.

Kaspar et al., Retrograde viral delivery of IGF-1 prolongs survival in a mouse ALS model. Science. Aug. 8, 2003;301(5634):839-42.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Krutzfeldt et al., Silencing of microRNAs in vivo with 'antagomirs'. Nature. Dec. 1, 2005;438(7068):685-9. Epub Oct. 30, 2005.

Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.

Kutay et al., Downregulation of miR-122 in the rodent and human hepatocellular carcinomas. J Cell Biochem. Oct. 15, 2006;99(3):671-8.

Lanford et al., Therapeutic silencing of microRNA-122 in primates with chronic hepatitis C virus infection. Science. Jan. 8, 2010;327(5962):198-201. Epub Dec. 3, 2009.

Lawlor et al., Efficient gene delivery and selective transduction of glial cells in the mammalian brain by AAV serotypes isolated from nonhuman primates. Mol Ther. Oct. 2009;17(10):1692-702. doi: 10.1038/mt.2009.170.

Lebherz et al., Gene therapy with novel adeno-associated virus vectors substantially diminishes atherosclerosis in a murine model of familial hypercholesterolemia. J Gene Med. Jun. 2004;6(6):663-72.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to BilaniukL].

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Intronic microRNA: discovery and biological implications. DNA Cell Biol. Apr. 2007;26(4):195-207.

Li et al., Protein trans-splicing as a means for viral vector-mediated in vivo gene therapy. Hum Gene Ther. Sep. 2008;19(9):958-64. doi: 10.1089/hum.2008.009.

Loiler et al., Targeting recombinant adeno-associated virus vectors to enhance gene transfer to pancreatic islets and liver. Gene Ther. Sep. 2003;10(18):1551-8.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Lux et al., Green fluorescent protein-tagged adeno-associated virus particles allow the study of cytosolic and nuclear trafficking. J Virol. Sep. 2005;79(18):11776-87.

Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Maguire et al., Gene therapy for the nervous system: challenges and new strategies. Neurotherapeutics. Oct. 2014;11(4):817-39. doi: 10.1007/s13311-014-0299-5.

(56) References Cited

OTHER PUBLICATIONS

Malinkevich et al., 1002. rAAV Mediated Delivery of Target Specific Micro RNA Sponges for Study of Micro RNA Function in Mouse Models. Gene regulation. May 1, 2009;17(1):S382.
Mandel et al., Recombinant adeno-associated viral vectors as therapeutic agents to treat neurological disorders. Mol Ther. Mar. 2006;13(3):463-83. Epub Jan. 18, 2006.
Matalon et al., Adeno-associated virus-mediated aspartoacylase gene transfer to the brain of knockout mouse for canavan disease. Mol Ther. May 2003;7(5 Pt 1):580-7.
Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004; 125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009; 17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Sen et al., Micromanaging vascular biology: tiny microRNAs play big band. J Vasc Res. 2009;46(6):527-40. doi: 10.1159/000226221. Epub Jun. 30, 2009.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Suckau et al., 851. The Effect of Genome Size and Design of scAAV Vectors on Efficiency of shRNA Expression and Gene Knockdown. May 1, 2007;15(1):S325.
Tanimizu et al., Downregulation of miR122 by grainyhead-like 2 restricts the hepatocytic differentiation potential of adult liver progenitor cells. Development. Dec. 2014;141(23):4448-56. doi: 10.1242/dev.113654. Epub Nov. 18, 2014.
Tenenbaum et al., Recombinant AAV-mediated gene delivery to the central nervous system. J Gene Med. Feb. 2004;6 Suppl 1:S212-22.
Tiwari et al., Artificial microRNA mediated gene silencing in plants: progress and perspectives. Plant Mol Biol. Sep. 2014;86(1-2):1-18. doi: 10.1007/s11103-014-0224-7. Epub Jul. 15, 2014. PMID: 25022825.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008; 16(6):1018-25. doi: 10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006; 12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.

(56) References Cited

OTHER PUBLICATIONS

Vermeulen et al., Double-stranded regions are essential design components of potent inhibitors of RISC function. RNA. May 2007;13(5):723-30. Epub Mar. 30, 2007.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Waldman et al., Applications of microRNA in cancer: Exploring the advantages of miRNA. Clin Transl Sci. Jun. 2009;2(3):248-9. doi: 10.1111/j.1752-8062.2009.00110.x.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions.J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. 2008;14(13):1327-40.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

EP 16783632.9, Nov. 21, 2018, Extended European Search Report.

P: Proximal to ITR
D: Distal to ITR

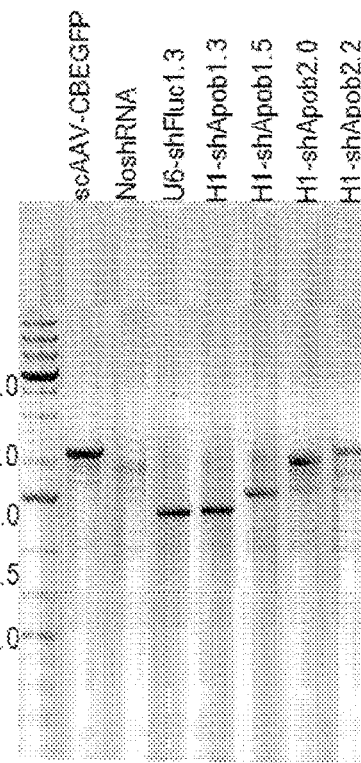

FIG. 7C

```
                    Passenger/mismatch    Loop           Guide
Four bulges    #19 TCCTTTCAGATGTCATAACTTCAAGAGATGTAGTACAGATGAAAGTC

#18 TCCTTTCAGATGTCATACATTCAAGAGATGTAGTACAGATGAAAGTC
Three bulges   #17 TCCTTTCATCTGTCATAACTTCAAGAGATGTAGTACAGATGAAAGTC
               #16 GACTTTCAGATGTCATAACTTCAAGAGATGTAGTACAGATGAAAGTC

#15 TCCTTTCAGATGTACTACATTCAAGAGATGTAGTACAGATGAAAGTC
               #14 GACTGGCAGATGTACTACATTCAAGAGATGTAGTACAGATGAAAGTC
               #13 TCCTTTCATCTGTCATACATTCAAGAGATGTAGTACAGATGAAAGTC
Two bulges     #12 GACTTTCAGATGTCATACATTCAAGAGATGTAGTACAGATGAAAGTC
               #11 TCCTTTCATCTGTACTAACTTCAAGAGATGTAGTACAGATGAAAGTC
               #10 GACTGGCATCTGTACTAACTTCAAGAGATGTAGTACAGATGAAAGTC
               #9  GACTTTCAGATGTACTAACTTCAAGAGATGTAGTACAGATGAAAGTC
               #8  GACTTTCATCTGTCATAACTTCAAGAGATGTAGTACAGATGAAAGTC

#7  GACTTTCATCTGTACTACATTCAAGAGATGTAGTACAGATGAAAGAG
               #6  CTCTTTCATCTGTACTACATTCAAGAGATGTAGTACAGATGAAAGTC
               #5  TCCTTTCATCTGTACTACATTCAAGAGATGTAGTACAGATGAAAGTC
One bulge      #4  GACTGGCATCTGTACTACATTCAAGAGATGTAGTACAGATGAAAGTC
               #3  GACTTTCAGATGTACTACATTCAAGAGATGTAGTACAGATGAAAGTC
               #2  GACTTTCATCTGTCATACATTCAAGAGATGTAGTACAGATGAAAGTC
               #1  GACTTTCATCTGTACTAACTTCAAGAGATGTAGTACAGATGAAAGTC Perfect match      GACTTTCATCTGTACTACATTCAAGAGATGTAGTACAGATGAAAGTC
```

FIG. 8A

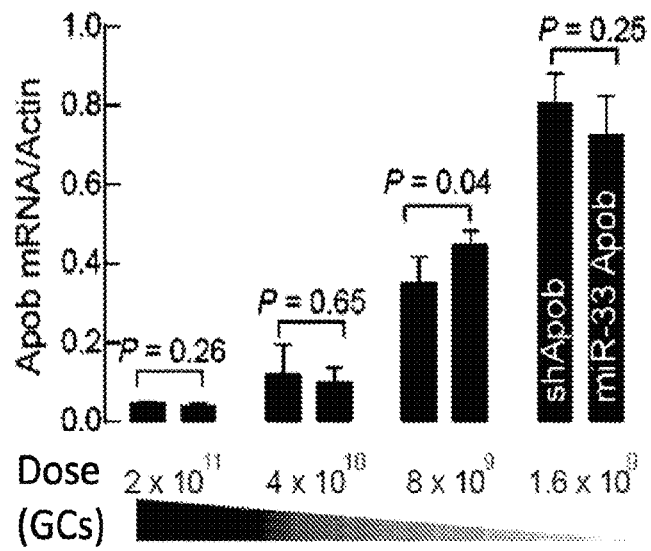
FIG. 10B
FIG. 11A
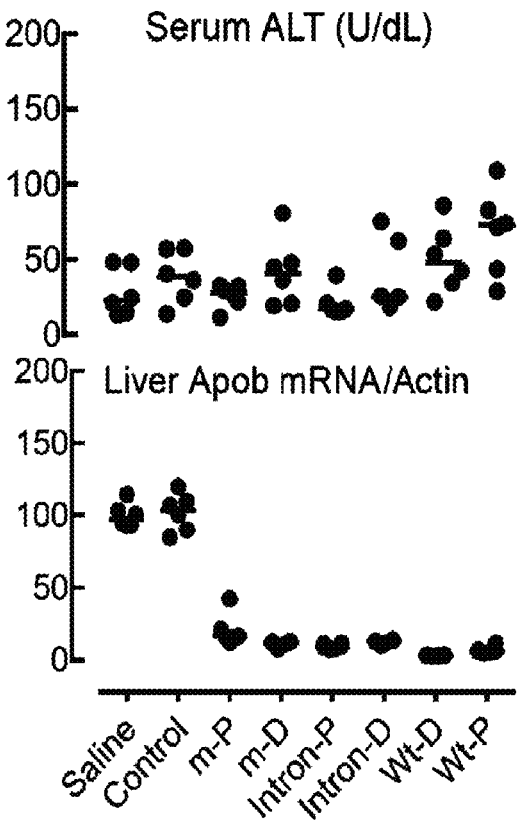
FIG. 11B

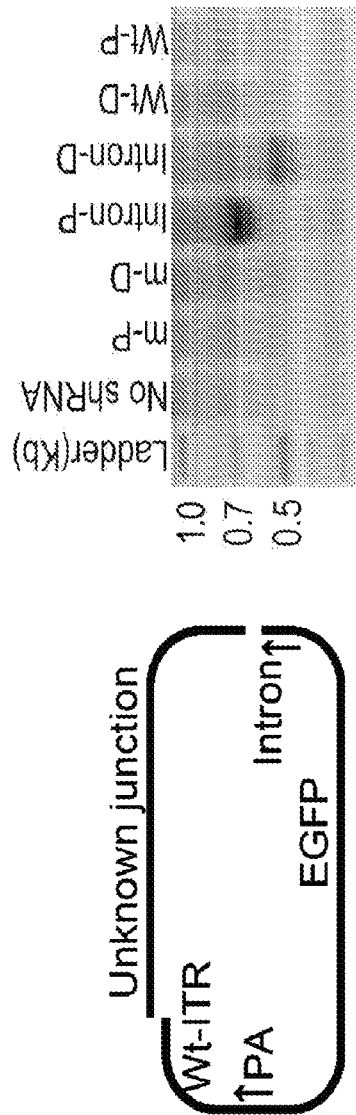

FIG. 11E

H1 promoter shApob passenger Loop *Unknown*         Intron-P                                                      Wt ITR
1. CAGATCTGACTTTCATCTGACTCTGTACTACACTCGCTCATTCGCTCGAGCTGACCAAAGGTCGCCCGACGCCCGGGCGGGCTTTGCCCGGGCGGGCCTCAGTGAGCGAGC
2. CAGATCTGACTTTCATCTGACTCTGTACTACA-------------------------------------GGTCGCCCGACGCCCGGGCGGGCTTTGCCCGGGCGGGCCTCAGTGAGCGAGC
3. CAGATCTGACTTTCATCTGACTCTGTACTACTCAC---------------CGGGCAAAGCCCGGGCGTCGGGCGACCTTTGGTCGCCCGGCCTTTGGTCGCCCCGCCTCAGTGAGCGAGC
4. CAGATCTGACTTTCATC-----------------------------------------------------------------------------CGGGCGGGCCTCAGTGAGCGAGC
5. CAGATCTGACTTTCATCTGACTA-------------------------------------------------------------------GCGGCGGGCCTCAGTGAGCGAGC
6. CAGATCTGACTTTCATCTGACTACATTC-----------------------------------------------------------GCGGCGGGCGGCCTCAGTGAGCGAGC
7. CAGATCTGACTTTCATCTGACTCTGTACTACAT-CT-------------CCAAAGGTCGCCCGACGCCCGGGCTTTGCCCGGGCGGGCCTTTGCCCGGGCGGGCCTCAGTGAGCGAGC Intron-D                Loop          shApob guide         Intron
1. CTCGCTCACTGAGGCCGCCCGGGCAAAGCCCGGGCGTCGGGCGACCTTTGGTCGCCCCGGCGTCAGTGTAGTACAGATGAAAGTCTTTTTCTAGTCTGCAGG
2. CTCGCTCACTGAGGCCGCCC----------------------------------------------------GATGAAAGTCTTTTTCTAGTCTGCAGG
3. CTCGCTCACTGAGGCCGACT-----------------C-------------------------------TGTAGTACAGATGAAAGTCTTTTTCTAGTCTGCAGG
4. CTCGCTCACTGAGGCCGCC---------------------------GA-------------------GATGTAGTACAGATGAAAGTCTTTTTCTAGTCTGCAGG
5. CTCGCTCACTGAGGCCGCCCGGGCAAAGCCCGGGCGTCGGGCGACC--------------------AATGTAGTACAGATGAAAGTCTTTTTCTAGTCTGCAGG
6. CTCGCTC----------------------------------------------------------TTTTTCTAGTCTGCAGG
    Wt ITR  *Unknown*

FIG. 11F

SEQUENCE LISTING

<160> NUMBER OF SEQ ID NOS: 80

<210> SEQ ID NO 1
<211> LENGTH: 5230
<212> TYPE: DNA
<213> ORGANISM: Artificial Sequence
<220> FEATURE:
<223> OTHER INFORMATION: Synthetic Polynucleotide

<400> SEQUENCE: 1

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
```

```
aagatcaatt cggtacaatt cacgcgtcga cattgattat tgactctggt cgttacataa    180
cttacggtaa atggcccgcc tggctgaccg cccaacgacc ccgcccattg acgtcaataa    240
tgacgtatgt tcccatagta acgccaatag ggactttcca ttgacgtcaa tgggtggagt    300
atttacggta aactgcccac ttggcagtac atcaagtgta tcatatgcca agtacgcccc    360
ctattgacgt caatgacggt aaatggcccg cctggcatta tgcccagtac atgaccttat    420
gggactttcc tacttggcag tacatctact cgaggccacg ttctgcttca ctctccccat    480 ctccccccccc tccccacccc caattttgta tttatttatt ttttaattat tttgtgcagc    540
gatgggggcg ggggggggggg ggggggggggc gcgcgccagg cggggcgggg cggggcgagg    600
ggcggggcgg ggcgaggcgg agaggtgcgg cggcagccaa tcagagcggc gcgctccgaa    660
agtttccttt tatggcgagg cggcggcggc ggcggcccta taaaaagcga agcgcgcggc    720
gggcgggagc gggatcagcc accgcggtgg cggccctaga gtcgatcgag gaactgaaaa    780
accagaaagt taactggtaa gtttagtctt tttgtctttt atttcaggtc tagcaattcg    840
aacgctgacg tcatcaaccc gctccaagga atcgcgggcc cagtgtcact aggcgggaac    900
acccagcgcg cgtgcgccct ggcaggaaga tggctgtgag ggacagggga gtggcgccct    960
gcaatatttg catgtcgcta tgtgttctgg gaaatcacca taaacgtgaa atgtctttgg   1020
atttgggaat cttataagtt ctgtatgaga ccacagatct gactttcatc tgtactacat   1080
tcaagagatg tagtacagat gaaagtcttt ttctagtctg caggaagaca atagcgtccc   1140
ggatccggtg gtggtgcaaa tcaaagaact gctcctcagt ggatgttgcc tttacttcta   1200
ggcctgtacg gaagtgttac ttctgctcta aaagctgcgg aattgtaccc gcggccgatc   1260
caccggtcgc caccatggtg agcaagggcg aggagctgtt caccggggtg gtgcccatcc   1320
tggtcgagct ggacggcgac gtaaacggcc acaagttcag cgtgtccggc gagggcgagg   1380
gcgatgccac ctacggcaag ctgaccctga agttcatctg caccaccggc aagctgcccg   1440
tgccctggcc caccctcgtg accaccctga cctacggcgt gcagtgcttc agccgctacc   1500
ccgaccacat gaagcagcac gacttcttca gtccgccat gcccgaaggc tacgtccagg   1560
agcgcaccat cttcttcaag gacgacggca actacaagac ccgcgccgag gtgaagttcg   1620
agggcgacac cctggtgaac cgcatcgagc tgaagggcat cgacttcaag gaggacggca   1680
acatcctggg gcacaagctg gagtacaact acaacagcca caacgtctat atcatggccg   1740
acaagcagaa gaacggcatc aaggtgaact tcaagatccg ccacaacatc gaggacggca   1800
gcgtgcagct cgccgaccac taccagcaga cacccccat cggcgacggc cccgtgctgc   1860
tgcccgacaa ccactacctg agcacccagt ccgccctgag caaagacccc aacgagaagc   1920
gcgatcacat ggtcctgctg gagttcgtga ccgccgccgg gatcactctc ggcatggacg   1980
agctgtacaa gtaaagcggc catcaagctt atcgataccg tcgactagag ctcgctgatc   2040
agcctcgact gtgccttcta gttgccagcc atctgttgtt tgcccctccc ccgtgccttc   2100
cttgaccctg gaaggtgcca ctcccactgt cctttcctaa taaaatgagg aaattgcatc   2160
gcattgtctg agtaggtgtc attctattct ggggggtggg gtgggggcagg acagcaaggg   2220 ggaggattgg gaagacaatt aggtagataa gtagcatggc gggttaatca ttaactacaa   2280 ggaacccta gtgatggagt tggccactcc ctctctgcgc gctcgctcgc tcactgaggc   2340
cgggcgacca aaggtcgccc gacgcccggg ctttgcccgg gcggcctcag tgagcgagcg   2400
agcgcgcagc cttaattaac ctaattcact ggccgtcgtt ttacaacgtc gtgactggga   2460
```

-continued

```
aaaccctggc gttacccaac ttaatcgcct tgcagcacat cccccttcg ccagctggcg      2520 taatagcgaa gaggcccgca ccgatcgccc ttcccaacag ttgcgcagcc tgaatggcga      2580
atgggacgcg ccctgtagcg gcgcattaag cgcggcgggt gtggtggtta cgcgcagcgt      2640
gaccgctaca cttgccagcg ccctagcgcc cgctcctttc gctttcttcc cttcctttct      2700
cgccacgttc gccggctttc cccgtcaagc tctaaatcgg gggctccctt tagggttccg      2760
atttagtgct ttacggcacc tcgacccaa aaaacttgat tagggtgatg gttcacgtag       2820
tgggccatcg ccctgataga cggttttcg cccttgacg ttggagtcca cgttctttaa       2880
tagtggactc ttgttccaaa ctggaacaac actcaaccct atctcggtct attcttttga     2940
tttataaggg attttgccga tttcggccta ttggttaaaa aatgagctga tttaacaaaa     3000
atttaacgcg aattttaaca aaatattaac gcttacaatt taggtggcac ttttcgggga     3060
aatgtgcgcg gaaccctat tgtttatt ttctaaatac attcaaatat gtatccgctc       3120
atgagacaat aaccctgata aatgcttcaa taatattgaa aaaggaagag tatgagtatt    3180
caacatttcc gtgtcgccct tattcccttt tttgcggcat tttgccttcc tgttttgct     3240 cacccagaaa cgctggtgaa agtaaaagat gctgaagatc agttgggtgc acgagtgggt   3300
tacatcgaac tggatctcaa cagcggtaag atccttgaga gttttcgccc cgaagaacgt    3360
tttccaatga tgagcacttt taaagttctg ctatgtggcg cggtattatc ccgtattgac    3420
gccgggcaag agcaactcgg tcgccgcata cactattctc agaatgactt ggttgagtac    3480
tcaccagtca cagaaaagca tcttacggat ggcatgacag taagagaatt atgcagtgct   3540
gccataacca tgagtgataa cactgcggcc aacttacttc tgacaacgat cggaggaccg   3600
aaggagctaa ccgcttttt gcacaacatg ggggatcatg taactcgcct tgatcgttgg    3660
gaaccggagc tgaatgaagc cataccaaac gacgagcgtg acaccacgat gcctgtagca    3720
atggcaacaa cgttgcgcaa actattaact ggcgaactac ttactctagc ttcccggcaa   3780
caattaatag actggatgga ggcggataaa gttgcaggac cacttctgcg ctcggccctt    3840
ccggctggct ggtttattgc tgataaatct ggagccggtg agcgtgggtc tcgcggtatc   3900
attgcagcac tggggccaga tggtaagccc tcccgtatcg tagttatcta cacgacgggg    3960
agtcaggcaa ctatggatga acgaaataga cagatcgctg agataggtgc ctcactgatt   4020
aagcattggt aactgtcaga ccaagtttac tcatatatac tttagattga tttaaaactt    4080 cattttaat ttaaaaggat ctaggtgaag atcctttttg ataatctcat gaccaaaatc     4140
ccttaacgtg agttttcgtt ccactgagcg tcagaccccg tagaaaagat caaaggatct    4200
tcttgagatc ctttttttct gcgcgtaatc tgctgcttgc aaacaaaaaa accaccgcta    4260
ccagcggtgg tttgtttgcc ggatcaagag ctaccaactc tttttccgaa ggtaactggc    4320
ttcagcagag cgcagatacc aaatactgtt cttctagtgt agccgtagtt aggccaccac    4380
ttcaagaact ctgtagcacc gcctacatac ctcgctctgc taatcctgtt accagtggct    4440
gctgccagtg gcgataagtc gtgtcttacc gggttggact caagacgata gttaccggat    4500
aaggcgcagc ggtcgggctg aacggggggt tcgtgcacac agcccagctt ggagcgaacg    4560
acctacaccg aactgagata cctacagcgt gagctatgag aaagcgccac gcttcccgaa    4620
gggagaaagg cggacaggta tccggtaagc ggcagggtcg gaacaggaga gcgcacgagg    4680
gagcttccag ggggaaacgc ctggtatctt tatagtcctg tcgggtttcg ccacctctga    4740
cttgagcgtc gatttttgtg atgctcgtca ggggggcgga gcctatgaaa aacgccagc     4800 aacgcggcct ttttacggtt cctggccttt tgctggcctt ttgctcacat gttctttcct    4860
```

| | |
|---|---|
| gcgttatccc ctgattctgt ggataaccgt attaccgcct ttgagtgagc tgataccgct | 4920 |
| cgccgcagcc gaacgaccga gcgcagcgag tcagtgagcg aggaagcgga agagcgccca | 4980 |
| atacgcaaac cgcctctccc cgcgcgttgg ccgattcatt aatgcagctg gcacgacagg | 5040 |
| tttcccgact ggaaagcggg cagtgagcgc aacgcaatta atgtgagtta gctcactcat | 5100 |
| taggcacccc aggctttaca ctttatgctt ccggctcgta tgttgtgtgg aattgtgagc | 5160 |
| ggataacaat ttcacacagg aaacagctat gaccatgatt acgccagatt taattaaggc | 5220 |
| cttaattagg | 5230 |

<210> SEQ ID NO 2
<211> LENGTH: 4922
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt cggtacaatt cacgcgtcga cattgattat tgactctggt cgttacataa | 180 |
| cttacggtaa atggcccgcc tggctgaccg cccaacgacc ccgccattg acgtcaataa | 240 |
| tgacgtatgt tcccatagta acgccaatag ggactttcca ttgacgtcaa tgggtggagt | 300 |
| atttacggta aactgcccac ttggcagtac atcaagtgta tcatatgcca agtacgcccc | 360 |
| ctattgacgt caatgacggt aaatggcccg cctggcatta tgcccagtac atgaccttat | 420 |
| gggactttcc tacttggcag tacatctact cgaggccacg ttctgcttca ctctccccat | 480 |
| ctccccccc tccccacccc caattttgta tttatttatt ttttaattat tttgtgcagc | 540 |
| gatggggcg gggggggggg gggggggggc gcgcgccagg cggggcgggg cggggcgagg | 600 |
| ggcggggcgg ggcgaggcgg agaggtgcgg cggcagccaa tcagagcggc gcgctccgaa | 660 |
| agtttccttt tatggcgagg cggcggcggc ggcggcccta taaaaagcga agcgcgcggc | 720 |
| gggcgggagc gggatcagcc accgcggtgg cggcccctaga gtcgatcgag gaactgaaaa | 780 |
| accagaaagt taactggtaa gtttagtctt tttgtctttt atttcaggtc ccggatccgg | 840 |
| tggtggtgca aatcaaagaa ctgctcctca gtggatgttg cctttacttc taggcctgta | 900 |
| cggaagtgtt acttctgctc taaaagctgc ggaattgtac ccgcggccga tccaccggtc | 960 |
| gccaccatgg tgagcaaggg cgaggagctg ttcaccgggg tggtgcccat cctggtcgag | 1020 |
| ctggacggcg acgtaaacgg ccacaagttc agcgtgtccg gcgagggcga gggcgatgcc | 1080 |
| acctacggca agctgaccct gaagttcatc tgcaccaccg gcaagctgcc cgtgccctgg | 1140 |
| cccaccctcg tgaccaccct gacctacggc gtgcagtgct tcagccgcta ccccgaccac | 1200 |
| atgaagcagc acgacttctt caagtccgcc atgcccgaag gctacgtcca ggagcgcacc | 1260 |
| atcttcttca aggacgacgg caactacaag acccgcgccg aggtgaagtt cgagggcgac | 1320 |
| accctggtga accgcatcga gctgaagggc atcgacttca aggaggacgg caacatcctg | 1380 |
| gggcacaagc tggagtacaa ctacaacagc cacaacgtct atatcatggc cgacaagcag | 1440 |
| aagaacggca tcaaggtgaa cttcaagatc cgccacaaca tcgaggacgg cagcgtgcag | 1500 |
| ctcgccgacc actaccagca gaacaccccc atcggcgacg gccccgtgct gctgcccgac | 1560 |
| aaccactacc tgagcaccca gtccgccctg agcaaagacc ccaacgagaa gcgcgatcac | 1620 |

```
atggtcctgc tggagttcgt gaccgccgcc gggatcactc tcggcatgga cgagctgtac    1680
aagtaaagcg gccatcaagc ttatcgatac cgtcgactag agctcgctga tcagcctcga    1740
ctgtgccttc tagttgccag ccatctgttg tttgcccctc ccccgtgcct tccttgaccc    1800
tggaaggtgc cactcccact gtcctttcct aataaaatga ggaaattgca tcgcattgtc    1860
tgagtaggtg tcattctatt ctggggggtg ggtggggca ggacagcaag ggggaggatt     1920
gggaagacaa ttaggtagat aagtagcatg gcgggttaat cattaactac aaggaacccc    1980
tagtgatgga gttggccact ccctctctgc gcgctcgctc gctcactgag gccgggcgac    2040
caaaggtcgc ccgacgcccg ggctttgccc gggcggcctc agtgagcgag cgagcgcgca    2100
gccttaatta acctaattca ctggccgtcg ttttacaacg tcgtgactgg gaaaaccctg    2160
gcgttaccca acttaatcgc cttgcagcac atccccctt cgccagctgg cgtaatagcg     2220
aagaggcccg caccgatcgc ccttcccaac agttgcgcag cctgaatggc gaatgggacg    2280
cgccctgtag cggcgcatta agcgcggcgg gtgtggtggt tacgcgcagc gtgaccgcta    2340
cacttgccag cgccctagcg cccgctcctt tcgctttctt cccttccttt ctcgccacgt    2400
tcgccggctt tccccgtcaa gctctaaatc gggggctccc tttagggttc cgatttagtg    2460
ctttacggca cctcgacccc aaaaaacttg attagggtga tggttcacgt agtgggccat    2520
cgccctgata cggttttt cgcccttga cgttggagtc cacgttcttt aatagtggac       2580
tcttgttcca aactggaaca cactcaacc ctatctcggt ctattctttt gatttataag     2640
ggattttgcc gatttcggcc tattggttaa aaaatgagct gatttaacaa aaatttaacg    2700
cgaattttaa caaaatatta acgcttacaa tttaggtggc acttttcggg gaaatgtgcg    2760
cggaacccct atttgtttat ttttctaaat acattcaaat atgtatccgc tcatgagaca    2820
ataaccctga taaatgcttc aataatattg aaaaaggaag agtatgagta ttcaacattt    2880
ccgtgtcgcc cttattccct tttttgcggc attttgcctt cctgtttttg ctcacccaga    2940
aacgctggtg aaagtaaaag atgctgaaga tcagttgggt gcacgagtgg gttacatcga    3000
actggatctc aacagcggta agatccttga gagttttcgc cccgaagaac gttttccaat    3060
gatgagcact tttaaagttc tgctatgtgg cgcggtatta cccgtattg acgccgggca    3120 agagcaactc ggtcgccgca tacactattc tcagaatgac ttggttgagt actcaccagt    3180
cacagaaaag catcttacgg atggcatgac agtaagagaa ttatgcagtg ctgccataac    3240
catgagtgat aacactgcgg ccaacttact tctgacaacg atcggaggac cgaaggagct    3300
aaccgctttt ttgcacaaca tgggggatca tgtaactcgc cttgatcgtt gggaaccgga    3360
gctgaatgaa gccataccaa acgacgagcg tgacaccacg atgcctgtag caatggcaac    3420
aacgttgcgc aaactattaa ctggcgaact acttactcta gcttcccggc aacaattaat    3480
agactggatg gaggcggata aagttgcagg accacttctg cgctcggccc ttccggctgg    3540
ctggtttatt gctgataaat ctggagccgg tgagcgtggg tctcgcggta tcattgcagc    3600
actggggcca gatggtaagc cctcccgtat cgtagttatc tacacgacgg ggagtcaggc    3660
aactatggat gaacgaaata gacagatcgc tgagataggt gcctcactga ttaagcattg    3720
gtaactgtca gaccaagttt actcatatat actttagatt gatttaaaac ttcattttta    3780
atttaaaagg atctaggtga agatcctttt tgataatctc atgaccaaaa tcccttaacg    3840
tgagttttcg ttccactgag cgtcagaccc cgtagaaaag atcaaggat cttcttgaga    3900 tcctttttt ctgcgcgtaa tctgctgctt gcaaacaaaa aaaccaccgc taccagcggt    3960
ggtttgtttg ccggatcaag agctaccaac tcttttccg aaggtaactg gcttcagcag    4020
```

```
agcgcagata ccaaatactg ttcttctagt gtagccgtag ttaggccacc acttcaagaa   4080
ctctgtagca ccgcctacat acctcgctct gctaatcctg ttaccagtgg ctgctgccag   4140
tggcgataag tcgtgtctta ccgggttgga ctcaagacga tagttaccgg ataaggcgca   4200
gcggtcgggc tgaacggggg gttcgtgcac acagcccagc ttggagcgaa cgacctacac   4260
cgaactgaga tacctacagc gtgagctatg agaaagcgcc acgcttcccg aagggagaaa   4320
ggcggacagg tatccggtaa gcggcagggt cggaacagga gagcgcacga gggagcttcc   4380
agggggaaac gcctggtatc tttatagtcc tgtcgggttt cgccacctct gacttgagcg   4440
tcgatttttg tgatgctcgt caggggggcg gagcctatgg aaaaacgcca gcaacgcggc   4500 cttttttacgg ttcctggcct tttgctggcc ttttgctcac atgttctttc ctgcgttatc   4560
ccctgattct gtggataacc gtattaccgc ctttgagtga gctgataccg ctcgccgcag   4620
ccgaacgacc gagcgcagcg agtcagtgag cgaggaagcg gaagagcgcc aatacgcaa    4680 accgcctctc cccgcgcgtt ggccgattca ttaatgcagc tggcacgaca ggtttcccga   4740
ctggaaagcg ggcagtgagc gcaacgcaat taatgtgagt tagctcactc attaggcacc   4800
ccaggcttta cactttatgc ttccggctcg tatgttgtgt ggaattgtga gcggataaca   4860
atttcacaca ggaaacagct atgaccatga ttacgccaga tttaattaag gccttaatta   4920
gg                                                                 4922
```

```
<210> SEQ ID NO 3
<211> LENGTH: 5075
<212> TYPE: DNA
<213> ORGANISM: Artificial Sequence
<220> FEATURE:
<223> OTHER INFORMATION: Synthetic Polynucleotide

<400> SEQUENCE: 3
```

```
cgcgtcgaca ttgattattg actctggtcg ttacataact tacggtaaat ggcccgcctg     60
gctgaccgcc caacgacccc gcccattgac gtcaataatg acgtatgttc ccatagtaac    120
gccaataggg actttccatt gacgtcaatg ggtggagtat ttacggtaaa ctgcccactt    180
ggcagtacat caagtgtatc atatgccaag tacgccccct attgacgtca atgacggtaa    240
atggcccgcc tggcattatg cccagtacat gaccttatgg gactttccta cttggcagta    300
catctactcg aggccacgtt ctgcttcact ctccccatct ccccccctc cccacccca     360 attttgtatt tatttatttt taattattt tgtgcagcga tggggcgggg ggggggggg     420 gggggggcgc gcgccaggcg gggcggggcg gggcgagggg cggggcgggg cgaggcggag    480
aggtgcggcg gcagccaatc agagcggcgc gctccgaaag tttccttta tggcgaggcg    540 gcggcggcg cggccctata aaagcgaag cgcgcggcgg gcgggagcgg gatcagccac     600
cgcggtggcg gccctagagt cgatcgagga actgaaaaac cagaaagtta actggtaagt    660
ttagtctttt tgtcttttat ttcagattgt cttcctgcag actagttatg cggcatcaga    720
gcagattgta ctgagagtgc accatagggg atcgggagat ctgtggtctc atacagaact    780
tataagattc ccaaatccaa agacatttca cgtttatggt gatttcccag aacacatagc    840
gacatgcaaa tattgcaggg cgccactccc ctgtccctca cagccatctt cctgccaggg    900
cgcacgcgcg ctgggtgttc ccgcctagtg acactgggcc gcgattcct tggagcgggt    960 tgatgacgtc agcgttcgaa ttgctagtcc cggatccggt ggtggtgcaa atcaaagaac   1020
tgctcctcag tggatgttgc ctttacttct aggcctgtac ggaagtgtta cttctgctct   1080
```

-continued

```
aaaagctgcg gaattgtacc cgcggccgat ccaccggtcg ccaccatggt gagcaagggc    1140
gaggagctgt tcaccggggt ggtgcccatc ctggtcgagc tggacggcga cgtaaacggc    1200
cacaagttca gcgtgtccgg cgagggcgag ggcgatgcca cctacggcaa gctgaccctg    1260
aagttcatct gcaccaccgg caagctgccc gtgccctggc ccaccctcgt gaccaccctg    1320
acctacggcg tgcagtgctt cagccgctac cccgaccaca tgaagcagca cgacttcttc    1380
aagtccgcca tgcccgaagg ctacgtccag gagcgcacca tcttcttcaa ggacgacggc    1440
aactacaaga cccgcgccga ggtgaagttc gagggcgaca ccctggtgaa ccgcatcgag    1500
ctgaagggca tcgacttcaa ggaggacggc aacatcctgg ggcacaagct ggagtacaac    1560
tacaacagcc acaacgtcta tatcatggcc gacaagcaga agaacggcat caaggtgaac    1620
ttcaagatcc gccacaacat cgaggacggc agcgtgcagc tcgccgacca ctaccagcag    1680 aacacccca tcggcgacgg ccccgtgctg ctgcccgaca accactacct gagcacccag    1740
tccgccctga gcaaagaccc caacgagaag cgcgatcaca tggtcctgct ggagttcgtg    1800
accgccgccg ggatcactct cggcatggac gagctgtaca agtaaagcgg ccatcaagct    1860
tatcgatacc gtcgactaga gctcgctgat cagcctcgac tgtgccttct agttgccagc    1920
catctgttgt ttgcccctcc cccgtgcctt ccttgaccct ggaaggtgcc actcccactg    1980
tcctttccta taaaatgag gaaattgcat cgcattgtct gagtaggtgt cattctattc    2040
tggggggtgg ggtggggcag gacagcaagg gggaggattg ggaagacaat taggtagata    2100
agtagcatgg cgggttaatc attaactaca aggaacccct agtgatggag ttggccactc    2160
cctctctgcg cgctcgctcg ctcactgagg ccgggcgacc aaaggtcgcc cgacgcccgg    2220
gctttgcccg gcggcctca gtgagcgagc gagcgcgcag ccttaattaa cctaattcac    2280
tggccgtcgt tttacaacgt cgtgactggg aaaaccctgg cgttacccaa cttaatcgcc    2340
ttgcagcaca tcccccttc gccagctggc gtaatagcga agaggcccgc accgatcgcc    2400
cttcccaaca gttgcgcagc ctgaatgcg aatgggacgc gccctgtagc ggcgcattaa    2460
gcgcggcggg tgtggtggtt acgcgcagcg tgaccgctac acttgccagc gccctagcgc    2520
ccgctccttt cgctttcttc ccttcctttc tcgccacgtt cgccggcttt ccccgtcaag    2580
ctctaaatcg ggggctccct ttagggttcc gatttagtgc tttacggcac ctcgacccca    2640
aaaaacttga ttagggtgat ggttcacgta gtgggccatc gccctgatag acggtttttc    2700
gccctttgac gttggagtcc acgttcttta atagtggact cttgttccaa actggaacaa    2760
cactcaaccc tatctcggtc tattcttttg atttataagg gattttgccg atttcggcct    2820
attggttaaa aaatgagctg atttaacaaa aatttaacgc gaattttaac aaaatattaa    2880
cgcttacaat ttaggtggca cttttcgggg aaatgtgcgc ggaacccta tttgtttatt    2940 tttctaaata cattcaaata tgtatccgct catgagacaa taaccctgat aaatgcttca    3000
ataatattga aaaggaaga gtatgagtat tcaacatttc cgtgtcgccc ttattccctt    3060
ttttgcggca ttttgccttc ctgtttttgc tcacccagaa acgctggtga agtaaaaga    3120 tgctgaagat cagttgggtg cacgagtggg ttacatcgaa ctggatctca acagcggtaa    3180
gatccttgag agttttcgcc ccgaagaacg ttttccaatg atgagcactt taaagttct    3240 gctatgtggc gcggtattat cccgtattga cgccgggcaa gagcaactcg gtcgccgcat    3300
acactattct cagaatgact tggttgagta ctcaccagtc acagaaaagc atcttacgga    3360
tggcatgaca gtaagagaat tatgcagtgc tgccataacc atgagtgata acactgcggc    3420
caacttactt ctgacaacga tcggaggacc gaaggagcta accgcttttt tgcacaacat    3480
```

```
ggggatcat gtaactcgcc ttgatcgttg ggaaccggag ctgaatgaag ccataccaaa    3540
cgacgagcgt gacaccacga tgcctgtagc aatggcaaca acgttgcgca aactattaac    3600
tggcgaacta cttactctag cttcccggca acaattaata gactggatgg aggcggataa    3660
agttgcagga ccacttctgc gctcggccct tccggctggc tggtttattg ctgataaatc    3720
tggagccggt gagcgtgggt ctcgcggtat cattgcagca ctggggccag atggtaagcc    3780
ctcccgtatc gtagttatct acacgacggg gagtcaggca actatggatg aacgaaatag    3840
acagatcgct gagataggtg cctcactgat taagcattgg taactgtcag accaagttta    3900
ctcatatata ctttagattg atttaaaact tcatttttaa tttaaaagga tctaggtgaa    3960
gatccttttt gataatctca tgaccaaaat cccttaacgt gagttttcgt tccactgagc    4020
gtcagacccc gtagaaaaga tcaaaggatc ttcttgagat cctttttttc tgcgcgtaat    4080
ctgctgcttg caaacaaaaa aaccaccgct accagcggtg gtttgtttgc cggatcaaga    4140
gctaccaact cttttttccga aggtaactgg cttcagcaga gcgcagatac caaatactgt    4200
tcttctagtg tagccgtagt taggccacca cttcaagaac tctgtagcac cgcctacata    4260
cctcgctctg ctaatcctgt taccagtggc tgctgccagt ggcgataagt cgtgtcttac    4320
cgggttggac tcaagacgat agttaccgga taaggcgcag cggtcgggct gaacggggg    4380 ttcgtgcaca cagcccagct tggagcgaac gacctacacc gaactgagat acctacagcg    4440
tgagctatga gaaagcgcca cgcttcccga agggagaaag gcggacaggt atccggtaag    4500
cggcagggtc ggaacaggag agcgcacgag ggagcttcca gggggaaacg cctggtatct    4560
ttatagtcct gtcgggtttc gccacctctg acttgagcgt cgatttttgt gatgctcgtc    4620 agggggggcgg agcctatgga aaaacgccag caacgcggcc ttttacggt tcctggcctt    4680 ttgctggcct tttgctcaca tgttctttcc tgcgttatcc cctgattctg tggataaccg    4740
tattaccgcc tttgagtgag ctgataccgc tcgccgcagc cgaacgaccg agcgcagcga    4800
gtcagtgagc gaggaagcgg aagagcgccc aatacgcaaa ccgcctctcc ccgcgcgttg    4860
gccgattcat taatgcagct ggcacgacag gtttcccgac tggaaagcgg gcagtgagcg    4920
caacgcaatt aatgtgagtt agctcactca ttaggcaccc caggctttac actttatgct    4980
tccggctcgt atgttgtgtg gaattgtgag cggataacaa tttcacacag gaaacagcta    5040
tgaccatgat tacgccagat ttaattaagg cctta    5075
```

<210> SEQ ID NO 4
<211> LENGTH: 5075
<212> TYPE: DNA
<213> ORGANISM: Artificial Sequence
<220> FEATURE:
<223> OTHER INFORMATION: Synthetic Polynucleotide

<400> SEQUENCE: 4

```
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctactcg aggccacgtt ctgcttcact ctccccatct cccccccctc ccacccccca     360
attttgtatt tatttatttt ttaattattt tgtgcagcga tgggggcggg ggggggggg      420
```

```
ggggggggcgc gcgccaggcg gggcggggcg gggcgagggg cggggcgggg cgaggcggag      480
aggtgcggcg gcagccaatc agagcggcgc gctccgaaag tttcctttta tggcgaggcg      540
gcggcggcgg cggccctata aaagcgaag cgcgcggcgg gcgggagcgg gatcagccac       600
cgcggtggcg gccctagagt cgatcgagga actgaaaaac cagaaagtta actggtaagt     660
ttagtctttt tgtcttttat ttcagtagca attcgaacgc tgacgtcatc aacccgctcc    720
aaggaatcgc gggcccagtg tcactaggcg ggaacaccca gcgcgcgtgc gccctggcag    780
gaagatggct gtgagggaca ggggagtggc gccctgcaat atttgcatgt cgctatgtgt    840
tctgggaaat caccataaac gtgaaatgtc tttggatttg ggaatcttat aagttctgta    900
tgagaccaca gatctcccga tccctatgg tgcactctca gtacaatctg ctctgatgcc     960
gcataactag tctgcaggaa gacaatgtcc cggatccggt ggtggtgcaa atcaaagaac   1020
tgctcctcag tggatgttgc ctttacttct aggcctgtac ggaagtgtta cttctgctct   1080
aaaagctgcg gaattgtacc cgcggccgat ccaccggtcg ccaccatggt gagcaagggc   1140
gaggagctgt tcaccggggt ggtgcccatc ctggtcgagc tggacggcga cgtaaacggc   1200
cacaagttca gcgtgtccgg cgagggcgag ggcgatgcca cctacggcaa gctgaccctg   1260
aagttcatct gcaccaccgg caagctgccc gtgcccctggc ccaccctcgt gaccaccctg   1320
acctacggcg tgcagtgctt cagccgctac cccgaccaca tgaagcagca cgacttcttc   1380
aagtccgcca tgcccgaagg ctacgtccag gagcgcacca tcttcttcaa ggacgacggc   1440
aactacaaga cccgcgccga ggtgaagttc gagggcgaca ccctggtgaa ccgcatcgag   1500
ctgaagggca tcgacttcaa ggaggacggc aacatcctgg ggcacaagct ggagtacaac   1560
tacaacagcc acaacgtcta tatcatggcc gacaagcaga agaacggcat caaggtgaac   1620
ttcaagatcc gccacaacat cgaggacggc agcgtgcagc tcgccgacca ctaccagcag   1680
aacaccccca tcggcgacgg ccccgtgctg ctgcccgaca ccactacct gagcacccag   1740 tccgccctga gcaaagaccc caacgagaag cgcgatcaca tggtcctgct ggagttcgtg   1800
accgccgccg ggatcactct cggcatggac gagctgtaca agtaaagcgg ccatcaagct   1860
tatcgatacc gtcgactaga gctcgctgat cagcctcgac tgtgccttct agttgccagc   1920
catctgttgt ttgccctc ccgtgcctt ccttgaccct ggaaggtgcc actcccactg    1980
tcctttccta ataaaatgag gaaattgcat cgcattgtct gagtaggtgt cattctattc   2040
tggggggtgg ggtggggcag gacagcaagg gggaggattg ggaagacaat taggtagata   2100
agtagcatgg cgggttaatc attaactaca aggaacccct agtgatggag ttggccactc   2160
cctctctgcg cgctcgctcg ctcactgagg ccgggcgacc aaaggtcgcc cgacgcccgg   2220
gctttgcccg gcggcctca gtgagcgagc gagcgcgcag ccttaattaa cctaattcac   2280
tggccgtcgt tttacaacgt cgtgactggg aaaaccctgg cgttacccaa cttaatcgcc   2340
ttgcagcaca tccccctttc gccagctggc gtaatagcga agaggcccgc accgatcgcc   2400
cttcccaaca gttgcgcagc ctgaatggcg aatgggacgc gccctgtagc ggcgcattaa   2460
gcgcggcggg tgtggtggtt acgcgcagcg tgaccgctac acttgccagc gccctagcgc   2520
ccgctccttt cgctttcttc ccttcctttc tcgccacgtt cgccggcttt cccgtcaag   2580 ctctaaatcg ggggctccct ttagggttcc gatttagtgc tttacggcac ctcgaccca   2640 aaaaacttga ttagggtgat ggttcacgta gtgggccatc gccctgatag acggttttc   2700 gccctttgac gttggagtcc acgttcttta atagtggact cttgttccaa actggaacaa   2760
cactcaaccc tatctcggtc tattcttttg atttataagg gattttgccg atttcggcct   2820
```

```
attggttaaa aaatgagctg atttaacaaa aatttaacgc gaattttaac aaaatattaa    2880
cgcttacaat ttaggtggca cttttcgggg aaatgtgcgc ggaaccccta tttgtttatt    2940
tttctaaata cattcaaata tgtatccgct catgagacaa taaccctgat aaatgcttca    3000
ataatattga aaaggaaga gtatgagtat tcaacatttc cgtgtcgccc ttattccctt    3060
ttttgcggca ttttgccttc ctgttttttgc tcacccagaa acgctggtga agtaaaaga    3120
tgctgaagat cagttgggtg cacgagtggg ttacatcgaa ctggatctca acagcggtaa    3180
gatccttgag agttttcgcc ccgaagaacg ttttccaatg atgagcactt ttaaagttct    3240
gctatgtggc gcggtattat cccgtattga cgccgggcaa gagcaactcg gtcgccgcat    3300
acactattct cagaatgact tggttgagta ctcaccagtc acagaaaagc atcttacgga    3360
tggcatgaca gtaagagaat tatgcagtgc tgccataacc atgagtgata acactgcggc    3420
caacttactt ctgacaacga tcggaggacc gaaggagcta accgcttttt tgcacaacat    3480
gggggatcat gtaactcgcc ttgatcgttg ggaaccggag ctgaatgaag ccataccaaa    3540
cgacgagcgt gacaccacga tgcctgtagc aatggcaaca acgttgcgca aactattaac    3600
tggcgaacta cttactctag cttcccggca acaattaata gactggatgg aggcggataa    3660
agttgcagga ccacttctgc gctcggccct tccggctggc tggtttattg ctgataaatc    3720
tggagccggt gagcgtgggt ctcgcggtat cattgcagca ctggggccag atggtaagcc    3780
ctcccgtatc gtagttatct acacgacggg gagtcaggca actatggatg aacgaaatag    3840
acagatcgct gagataggtg cctcactgat taagcattgg taactgtcag accaagttta    3900
ctcatatata ctttagattg atttaaaact tcattttaa tttaaaagga tctaggtgaa    3960
gatcctttt gataatctca tgaccaaaat cccttaacgt gagttttcgt tccactgagc    4020
gtcagacccc gtagaaaaga tcaaaggatc ttcttgagat ccttttttttc tgcgcgtaat    4080
ctgctgcttg caaacaaaaa aaccaccgct accagcggtg gtttgtttgc cggatcaaga    4140
gctaccaact ctttttccga aggtaactgg cttcagcaga gcgcagatac caaatactgt    4200
tcttctagtg tagccgtagt taggccacca cttcaagaac tctgtagcac cgcctacata    4260
cctcgctctg ctaatcctgt taccagtggc tgctgccagt ggcgataagt cgtgtcttac    4320
cgggttggac tcaagacgat agttaccgga taaggcgcag cggtcgggct gaacggggg    4380
ttcgtgcaca cagcccagct tggagcgaac gacctacacc gaactgagat acctacagcg    4440
tgagctatga gaaagcgcca cgcttcccga agggagaaag gcggacaggt atccggtaag    4500
cggcagggtc ggaacaggag agcgcacgag ggagcttcca gggggaaacg cctggtatct    4560
ttatagtcct gtcgggtttc gccacctctg acttgagcgt cgatttttgt gatgctcgtc    4620
aggggggcg agcctatgga aaacgccag caacgcggcc ttttacggt tcctggcctt    4680
ttgctggcct tttgctcaca tgttctttcc tgcgttatcc cctgattctg tggataaccg    4740
tattaccgcc tttgagtgag ctgataccgc tcgccgcagc cgaacgaccg agcgcagcga    4800
gtcagtgagc gaggaagcgg aagagcgccc aatacgcaaa ccgcctctcc ccgcgcgttg    4860
gccgattcat taatgcagct ggcacgacag gtttcccgac tggaaagcgg gcagtgagcg    4920
caacgcaatt aatgtgagtt agctcactca ttaggcaccc caggctttac actttatgct    4980
tccggctcgt atgttgtgtg gaattgtgag cggataacaa tttcacacag gaaacagcta    5040
tgaccatgat tacgccagat ttaattaagg cctta                              5075
```

<210> SEQ ID NO 5

<211> LENGTH: 5079
<212> TYPE: DNA
<213> ORGANISM: Artificial Sequence
<220> FEATURE:
<223> OTHER INFORMATION: Synthetic Polynucleotide

<400> SEQUENCE: 5

```
tagcaattcg aacgctgacg tcatcaaccc gctccaagga atcgcgggcc cagtgtcact      60
aggcgggaac acccagcgcg cgtgcgccct ggcaggaaga tggctgtgag ggacagggga     120
gtggcgccct gcaatatttg catgtcgcta tgtgttctgg gaaatcacca taaacgtgaa     180
atgtctttgg atttgggaat cttataagtt ctgtatgaga ccacagatct gactttcatc     240
tgtactacat tcaagagatg tagtacagat gaaagtcttt ttctagtctg caggaagaca     300
atagccgcgt cgacattgat tattgactct ggtcgttaca taacttacgg taaatggccc     360
gcctggctga ccgcccaacg accccgccca ttgacgtcaa taatgacgta tgttcccata     420
gtaacgccaa tagggacttt ccattgacgt caatgggtgg agtatttacg gtaaactgcc     480
cacttggcag tacatcaagt gtatcatatg ccaagtacgc ccctattga cgtcaatgac      540
ggtaaatggc ccgcctggca ttatgcccag tacatgacct tatgggactt tcctacttgg     600
cagtacatct actcgaggcc acgttctgct tcactctccc catctccccc cctccccac     660
ccccaatttt gtatttattt attttttaat tatttgtgc agcgatgggg gcggggggg      720
gggggggggg ggcgcgcgcc aggcggggcg gggcggggcg aggggcgggg cggggcgagg     780
cggagaggtg cggcggcagc caatcagagc ggcgcgctcc gaaagtttcc ttttatggcg     840
aggcggcggc ggcggcggcc ctataaaaag cgaagcgcgc ggcgggcggg agcgggatca     900
gccaccgcgg tggcggccct agagtcgatc gaggaactga aaaccagaa agttaactgg      960
taagtttagt cttttttgtct tttatttcag gtcccggatc cggtggtggt gcaaatcaaa    1020
gaactgctcc tcagtggatg ttgcctttac ttctaggcct gtacggaagt gttacttctg    1080
ctctaaaagc tgcggaattg tacccgcggc cgatccaccg gtcgccacca tggtgagcaa    1140
gggcgaggag ctgttcaccg gggtggtgcc catcctggtc gagctggacg gcgacgtaaa    1200
cggccacaag ttcagcgtgt ccggcgaggg cgagggcgat gccacctacg gcaagctgac    1260
cctgaagttc atctgcacca ccggcaagct gcccgtgccc tggcccaccc tcgtgaccac    1320
cctgacctac ggcgtgcagt gcttcagccg ctaccccgac cacatgaagc agcacgactt    1380
cttcaagtcc gccatgcccg aaggctacgt ccaggagcgc accatcttct tcaaggacga    1440
cggcaactac aagacccgcg ccgaggtgaa gttcgagggc gacaccctgg tgaaccgcat    1500
cgagctgaag ggcatcgact tcaaggagga cggcaacatc ctggggcaca agctggagta    1560
caactacaac agccacaacg tctatatcat ggccgacaag cagaagaacg gcatcaaggt    1620
gaacttcaag atccgccaca acatcgagga cggcagcgtg cagctcgccg accactacca    1680
gcagaacacc cccatcggcg acggccccgt gctgctgccc gacaaccact acctgagcac    1740
ccagtccgcc ctgagcaaag accccaacga gaagcgcgat cacatggtcc tgctggagtt    1800
cgtgaccgcc gccgggatca ctctcggcat ggacgagctg tacaagtaaa gcggccatca    1860
agcttatcga taccgtcgac tagagctcgc tgatcagcct cgactgtgcc ttctagttgc    1920
cagccatctg ttgtttgccc ctcccccgtg ccttccttga ccctggaagg tgccactccc    1980
actgtccttt cctaataaaa tgaggaaatt gcatcgcatt gtctgagtag gtgtcattct    2040
attctggggg gtggggtggg gcaggacagc aaggggagg attgggaaga caattaggta     2100
gataagtagc atggcgggtt aatcattaac tacaaggaac ccctagtgat ggagttggcc    2160
```

```
actccctctc tgcgcgctcg ctcgctcact gaggccgggc gaccaaaggt cgcccgacgc    2220
ccgggctttg cccgggcggc ctcagtgagc gagcgagcgc gcagccttaa ttaacctaat    2280
tcactggccg tcgttttaca acgtcgtgac tgggaaaacc ctggcgttac ccaacttaat    2340
cgccttgcag cacatccccc tttcgccagc tggcgtaata gcgaagaggc ccgcaccgat    2400
cgcccttccc aacagttgcg cagcctgaat ggcgaatggg acgcgccctg tagcggcgca    2460
ttaagcgcgg cgggtgtggt ggttacgcgc agcgtgaccg ctacacttgc cagcgcccta    2520
gcgcccgctc ctttcgcttt cttcccttcc tttctcgcca cgttcgccgg ctttccccgt    2580
caagctctaa atcgggggct ccctttaggg ttccgattta gtgctttacg gcacctcgac    2640
cccaaaaaac ttgattaggg tgatggttca cgtagtgggc catcgccctg atagacggtt    2700
tttcgccctt tgacgttgga gtccacgttc tttaatagtg gactcttgtt ccaaactgga    2760
acaacactca accctatctc ggtctattct tttgatttat aagggatttt gccgatttcg    2820
gcctattggt taaaaaatga gctgatttaa caaaaattta acgcgaattt taacaaaata    2880
ttaacgctta caatttaggt ggcacttttc ggggaaatgt gcgcggaacc cctatttgtt    2940
tatttttcta aatacattca aatatgtatc cgctcatgag acaataaccc tgataaatgc    3000
ttcaataata ttgaaaaagg aagagtatga gtattcaaca tttccgtgtc gcccttattc    3060
ccttttttgc ggcattttgc cttcctgttt ttgctcaccc agaaacgctg gtgaaagtaa    3120
aagatgctga agatcagttg ggtgcacgag tgggttacat cgaactggat ctcaacagcg    3180
gtaagatcct tgagagtttt cgccccgaag aacgttttcc aatgatgagc acttttaaag    3240
ttctgctatg tggcgcggta ttatcccgta ttgacgccgg gcaagagcaa ctcggtcgcc    3300
gcatacacta ttctcagaat gacttggttg agtactcacc agtcacagaa aagcatctta    3360
cggatggcat gacagtaaga gaattatgca gtgctgccat aaccatgagt gataacactg    3420
cggccaactt acttctgaca acgatcggag gaccgaagga gctaaccgct tttttgcaca    3480
acatggggga tcatgtaact cgccttgatc gttgggaacc ggagctgaat gaagccatac    3540
caaacgacga gcgtgacacc acgatgcctg tagcaatggc aacaacgttg cgcaaactat    3600
taactggcga actacttact ctagcttccc ggcaacaatt aatagactgg atggaggcgg    3660
ataaagttgc aggaccactt ctgcgctcgg cccttccggc tggctggttt attgctgata    3720
aatctggagc cggtgagcgt gggtctcgcg gtatcattgc agcactgggg ccagatggta    3780
agccctcccg tatcgtagtt atctacacga cggggagtca ggcaactatg gatgaacgaa    3840
atagacagat cgctgagata ggtgcctcac tgattaagca ttggtaactg tcagaccaag    3900
tttactcata tatactttag attgatttaa aacttcattt ttaatttaaa aggatctagg    3960
tgaagatcct ttttgataat ctcatgacca aaatccctta acgtgagttt cgttccact    4020 gagcgtcaga ccccgtagaa aagatcaaag gatcttcttg agatcctttt tttctgcgcg    4080
taatctgctg cttgcaaaca aaaaaaccac cgctaccagc ggtggtttgt ttgccggatc    4140
aagagctacc aactcttttt ccgaaggtaa ctggcttcag cagagcgcag ataccaaata    4200
ctgttcttct agtgtagccg tagttaggcc accacttcaa gaactctgta gcaccgccta    4260
catacctcgc tctgctaatc ctgttaccag tggctgctgc cagtggcgat aagtcgtgtc    4320
ttaccgggtt ggactcaaga cgatagttac cggataaggc gcagcggtcg ggctgaacgg    4380
ggggttcgtg cacacagccc agcttggagc gaacgaccta caccgaactg agatacctac    4440
agcgtgagct atgagaaagc gccacgcttc ccgaagggag aaaggcggac aggtatccgg    4500
```

| | |
|---|---|
| taagcggcag ggtcggaaca ggagagcgca cgagggagct tccaggggga aacgcctggt | 4560 |
| atctttatag tcctgtcggg tttcgccacc tctgacttga gcgtcgattt ttgtgatgct | 4620 |
| cgtcagggg gcggagccta tggaaaaacg ccagcaacgc ggccttttta cggttcctgg | 4680 |
| ccttttgctg gccttttgct cacatgttct ttcctgcgtt atcccctgat tctgtggata | 4740 |
| accgtattac cgcctttgag tgagctgata ccgctcgccg cagccgaacg accgagcgca | 4800 |
| gcgagtcagt gagcgaggaa gcggaagagc gcccaatacg caaaccgcct ctccccgcgc | 4860 |
| gttggccgat tcattaatgc agctggcacg acaggtttcc cgactggaaa gcgggcagtg | 4920 |
| agcgcaacgc aattaatgtg agttagctca ctcattaggc accccaggct ttacacttta | 4980 |
| tgcttccggc tcgtatgttg tgtggaattg tgagcggata caatttcac acaggaaaca | 5040 |
| gctatgacca tgattacgcc agatttaatt aaggcctta | 5079 |

<210> SEQ ID NO 6
<211> LENGTH: 5082
<212> TYPE: DNA
<213> ORGANISM: Artificial Sequence
<220> FEATURE:
<223> OTHER INFORMATION: Synthetic Polynucleotide

<400> SEQUENCE: 6

| | |
|---|---|
| gtcgctattg tcttcctgca gactagaaaa agactttcat ctgtactaca tctcttgaat | 60 |
| gtagtacaga tgaaagtcag atctgtggtc tcatacagaa cttataagat tcccaaatcc | 120 |
| aaagacattt cacgtttatg gtgatttccc agaacacata gcgacatgca aatattgcag | 180 |
| ggcgccactc ccctgtccct cacagccatc ttcctgccag ggcgcacgcg cgctgggtgt | 240 |
| tcccgcctag tgacactggg cccgcgattc cttggagcgg gttgatgacg tcagcgttcg | 300 |
| aattgctacg cgtcgacatt gattattgac tctggtcgtt acataactta cggtaaatgg | 360 |
| cccgcctggc tgaccgccca acgaccccgc ccattgacgt caataatgac gtatgttccc | 420 |
| atagtaacgc caatagggac tttccattga cgtcaatggg tggagtattt acggtaaact | 480 |
| gcccacttgg cagtacatca agtgtatcat atgccaagta cgccccctat tgacgtcaat | 540 |
| gacggtaaat ggcccgcctg gcattatgcc cagtacatga ccttatggga ctttcctact | 600 |
| tggcagtaca tctactcgag gccacgttct gcttcactct ccccatctcc cccccctccc | 660 |
| cacccccaat tttgtattta tttattttt aattattttg tgcagcgatg gggcgggg | 720 |
| gggggggggg ggggcgcgc gccaggcggg gcggggcggg gcgaggggcg gggcggggcg | 780 |
| aggcggagag gtgcggcggc agccaatcag agcggcgcgc tccgaaagtt tccttttatg | 840 |
| gcgaggcggc ggcggcggcg gccctataaa aagcgaagcg cgcggcgggc gggagcggga | 900 |
| tcagccaccg cggtggcggc cctagagtcg atcgaggaac tgaaaaacca gaaagttaac | 960 |
| tggtaagttt agtcttttg tcttttattt caggtcccgg atccggtggt ggtgcaaatc | 1020 |
| aaagaactgc tcctcagtgg atgttgcctt tacttctagg cctgtacgga agtgttactt | 1080 |
| ctgctctaaa agctgcggaa ttgtacccgc ggccgatcca ccggtcgcca ccatggtgag | 1140 |
| caagggcgag gagctgttca ccggggtggt gcccatcctg gtcgagctgg acggcgacgt | 1200 |
| aaacggccac aagttcagcg tgtccggcga gggcgagggc gatgccacct acggcaagct | 1260 |
| gaccctgaag ttcatctgca ccaccggcaa gctgcccgtg ccctggccca cctcgtgac | 1320 |
| cacccctgacc tacggcgtgc agtgcttcag ccgctacccc gaccacatga agcagcacga | 1380 |
| cttcttcaag tccgccatgc ccgaaggcta cgtccaggag cgcaccatct tcttcaagga | 1440 |
| cgacggcaac tacaagaccc gcgccgaggt gaagttcgag ggcgacaccc tggtgaaccg | 1500 |

```
catcgagctg aagggcatcg acttcaagga ggacggcaac atcctggggc acaagctgga    1560
gtacaactac aacagccaca acgtctatat catggccgac aagcagaaga acggcatcaa    1620
ggtgaacttc aagatccgcc acaacatcga ggacggcagc gtgcagctcg ccgaccacta    1680
ccagcagaac acccccatcg gcgacggccc cgtgctgctg cccgacaacc actacctgag    1740
cacccagtcc gccctgagca agacccccaa cgagaagcgc gatcacatgg tcctgctgga    1800
gttcgtgacc gccgccggga tcactctcgg catggacgag ctgtacaagt aaagcggcca    1860
tcaagcttat cgataccgtc gactagagct cgctgatcag cctcgactgt gccttctagt    1920
tgccagccat ctgttgtttg cccctccccc gtgccttcct tgaccctgga aggtgccact    1980
cccactgtcc tttcctaata aaatgaggaa attgcatcgc attgtctgag taggtgtcat    2040
tctattctgg ggggtggggt ggggcaggac agcaaggggg aggattggga agacaattag    2100
gtagataagt agcatggcgg gttaatcatt aactacaagg aacccctagt gatggagttg    2160
gccactccct ctctgcgcgc tcgctcgctc actgaggccg ggcgaccaaa ggtcgcccga    2220
cgcccgggct ttgcccgggc ggcctcagtg agcgagcgag cgcgcagcct taattaacct    2280
aattcactgg ccgtcgtttt acaacgtcgt gactgggaaa accctggcgt tacccaactt    2340
aatcgccttg cagcacatcc ccctttcgcc agctggcgta atagcgaaga ggcccgcacc    2400
gatcgccctt cccaacagtt gcgcagcctg aatggcgaat gggacgcgcc ctgtagcggc    2460
gcattaagcg cggcgggtgt ggtggttacg cgcagcgtga ccgctacact tgccagcgcc    2520
ctagcgcccg ctcctttcgc tttcttccct tcctttctcg ccacgttcgc cggctttccc    2580
cgtcaagctc taaatcgggg gctcccttta gggttccgat ttagtgcttt acggcacctc    2640
gacccccaaa aacttgatta gggtgatggt tcacgtagtg gccatcgccc tgatagacg    2700 gttttcgcc ctttgacgtt ggagtccacg ttctttaata gtggactctt gttccaaact    2760
ggaacaacac tcaaccctat ctcggtctat tcttttgatt tataagggat tttgccgatt    2820
tcggcctatt ggttaaaaaa tgagctgatt taacaaaaat ttaacgcgaa ttttaacaaa    2880
atattaacgc ttacaattta ggtggcactt ttcggggaaa tgtgcgcgga acccctattt    2940
gtttattttt ctaaatacat tcaaatatgt atccgctcat gagacaataa ccctgataaa    3000
tgcttcaata atattgaaaa aggaagagta tgagtattca acatttccgt gtcgccctta    3060 ttccctttt tgcggcattt tgccttcctg tttttgctca cccagaaacg ctggtgaaag    3120
taaaagatgc tgaagatcag ttgggtgcac gagtgggtta catcgaactg gatctcaaca    3180
gcggtaagat ccttgagagt tttcgccccg aagaacgttt tccaatgatg agcacttta    3240 aagttctgct atgtggcgcg gtattatccc gtattgacgc cgggcaagag caactcggtc    3300
gccgcataca ctattctcag aatgacttgg ttgagtactc accagtcaca gaaaagcatc    3360
ttacggatgg catgacagta agagaattat gcagtgctgc cataaccatg agtgataaca    3420
ctgcggccaa cttacttctg acaacgatcg gaggaccgaa ggagctaacc gcttttttgc    3480
acaacatggg ggatcatgta actcgccttg atcgttggga accggagctg aatgaagcca    3540
taccaaacga cgagcgtgac accacgatgc ctgtagcaat ggcaacaacg ttgcgcaaac    3600
tattaactgg cgaactactt actctagctt cccggcaaca attaatagac tggatggagg    3660
cggataaagt tgcaggacca cttctgcgct cggcccttcc ggctggctgg tttattgctg    3720
ataaatctgg agccggtgag cgtgggtctc gcggtatcat tgcagcactg gggccagatg    3780
gtaagccctc ccgtatcgta gttatctaca cgacggggag tcaggcaact atggatgaac    3840
```

```
gaaatagaca gatcgctgag ataggtgcct cactgattaa gcattggtaa ctgtcagacc    3900
aagtttactc atatatactt tagattgatt taaaacttca ttttaattt aaaaggatct    3960 aggtgaagat cctttttgat aatctcatga ccaaaatccc ttaacgtgag ttttcgttcc    4020
actgagcgtc agaccccgta gaaaagatca aaggatcttc ttgagatcct tttttttctgc    4080 gcgtaatctg ctgcttgcaa acaaaaaaac caccgctacc agcggtggtt tgtttgccgg    4140
atcaagagct accaactctt tttccgaagg taactggctt cagcagagcg cagataccaa    4200
atactgttct tctagtgtag ccgtagttag gccaccactt caagaactct gtagcaccgc    4260
ctacatacct cgctctgcta atcctgttac cagtggctgc tgccagtggc gataagtcgt    4320
gtcttaccgg gttggactca agacgatagt taccggataa ggcgcagcgg tcgggctgaa    4380
cggggggttc gtgcacacag cccagcttgg agcgaacgac ctacaccgaa ctgagatacc    4440
tacagcgtga gctatgagaa agcgccacgc ttcccgaagg gagaaaggcg gacaggtatc    4500
cggtaagcgg cagggtcgga acaggagagc gcacgaggga gcttccaggg ggaaacgcct    4560
ggtatcttta tagtcctgtc gggtttcgcc acctctgact tgagcgtcga ttttgtgat    4620 gctcgtcagg gggcggagc ctatggaaaa acgccagcaa cgcggccttt ttacggttcc    4680
tggccttttg ctggccttt gctcacatgt tctttcctgc gttatcccct gattctgtgg    4740
ataaccgtat taccgccttt gagtgagctg ataccgctcg ccgcagccga acgaccgagc    4800
gcagcgagtc agtgagcgag gaagcggaag agcgcccaat acgcaaaccg cctctccccg    4860
cgcgttggcc gattcattaa tgcagctggc acgacaggtt tcccgactgg aaagcgggca    4920
gtgagcgcaa cgcaattaat gtgagttagc tcactcatta ggcaccccag gctttacact    4980
ttatgcttcc ggctcgtatg ttgtgtggaa ttgtgagcgg ataacaattt cacacaggaa    5040
acagctatga ccatgattac gccagattta attaaggcct ta                     5082

<210> SEQ ID NO 7
<211> LENGTH: 4774
<212> TYPE: DNA
<213> ORGANISM: Artificial Sequence
<220> FEATURE:
<223> OTHER INFORMATION: Synthetic Polynucleotide

<400> SEQUENCE: 7
cgcgtcgaca ttgattattg actctggtcg ttacataact tacggtaaat ggcccgcctg     60
gctgaccgcc caacgacccc gcccattgac gtcaataatg acgtatgttc ccatagtaac    120
gccaataggg actttccatt gacgtcaatg ggtggagtat ttacggtaaa ctgcccactt    180
ggcagtacat caagtgtatc atatgccaag tacgccccct attgacgtca atgacggtaa    240
atggcccgcc tggcattatg cccagtacat gaccttatgg gactttccta cttggcagta    300
catctactcg aggccacgtt ctgcttcact ctccccatct cccccctc cccaccccca     360 attttgtatt tatttatttt ttaattattt tgtgcagcga tggggcgggg gggggggggg    420 ggggggcgc gcgccaggcg gggcggggcg gggcgagggg cggggcgggg cgaggcggag    480
aggtgcggcg gcagccaatc agagcggcgc gctccgaaag tttcctttta tggcgaggcg    540 gcggcggcg cggcccctata aaaagcgaag cgcgcggcg gcgggagcgg gatcagccac    600
cgcggtggcg gccctagagt cgatcgagga actgaaaaac cagaaagtta actggtaagt    660
ttagtctttt tgtctttttat ttcaggtccc ggatccggtg gtggtgcaaa tcaaagaact    720
gctcctcagt ggatgttgcc tttacttcta ggcctgtacg gaagtgttac ttctgctcta    780
aaagctgcgg aattgtaccc gcggccgatc caccggtcgc caccatggtg agcaagggcg    840
```

```
aggagctgtt caccggggtg gtgcccatcc tggtcgagct ggacggcgac gtaaacggcc    900
acaagttcag cgtgtccggc gagggcgagg gcgatgccac ctacggcaag ctgaccctga    960
agttcatctg caccaccggc aagctgcccg tgccctggcc caccctcgtg accaccctga   1020
cctacggcgt gcagtgcttc agccgctacc ccgaccacat gaagcagcac gacttcttca   1080
agtccgccat gcccgaaggc tacgtccagg agcgcaccat cttcttcaag gacgacggca   1140
actacaagac ccgcgccgag gtgaagttcg agggcgacac cctggtgaac cgcatcgagc   1200
tgaagggcat cgacttcaag gaggacggca acatcctggg gcacaagctg gagtacaact   1260
acaacagcca caacgtctat atcatggccg acaagcagaa gaacggcatc aaggtgaact   1320
tcaagatccg ccacaacatc gaggacggca gcgtgcagct cgccgaccac taccagcaga   1380
acacccccat cggcgacggc cccgtgctgc tgcccgacaa ccactacctg agcacccagt   1440
ccgccctgag caaagacccc aacgagaagc gcgatcacat ggtcctgctg gagttcgtga   1500
ccgccgccgg gatcactctc ggcatggacg agctgtacaa gtaaagcggc catcaagctt   1560
atcgataccg tcgactagag ctcgctgatc agcctcgact gtgccttcta gttgccagcc   1620
atctgttgtt tgcccctccc ccgtgccttc cttgaccctg gaaggtgcca ctcccactgt   1680
cctttcctaa taaaatgagg aaattgcatc gcattgtctg agtaggtgtc attctattct   1740
ggggggtggg gtggggcagg acagcaaggg ggaggattgg gaagacaatt aggtagataa   1800
gtagcatggc gggttaatca ttaactacaa ggaaccccta gtgatggagt tggccactcc   1860
ctctctgcgc gctcgctcgc tcactgaggc cgggcgacca aggtcgcccg acgcccggg    1920
cttttgcccgg gcggcctcag tgagcgagcg agcgcgcagc cttaattaac ctaattcact   1980
ggccgtcgtt ttacaacgtc gtgactggga aaaccctggc gttacccaac ttaatcgcct   2040
tgcagcacat ccccctttcg ccagctggcg taatagcgaa gaggcccgca ccgatcgccc   2100
ttcccaacag ttgcgcagcc tgaatggcga atgggacgcg ccctgtagcg gcgcattaag   2160
cgcggcgggt gtggtggtta cgcgcagcgt gaccgctaca cttgccagcg ccctagcgcc   2220
cgctcctttc gctttcttcc cttcctttct cgccacgttc gccggctttc cccgtcaagc   2280
tctaaatcgg gggctccctt tagggttccg atttagtgct ttacggcacc tcgaccccaa   2340
aaaacttgat tagggtgatg gttcacgtag tgggccatcg ccctgataga cggttttttcg   2400
cccctttgacg ttggagtcca cgttctttaa tagtggactc ttgttccaaa ctggaacaac   2460
actcaaccct atctcggtct attctttga tttataaggg attttgccga tttcggccta   2520
ttggttaaaa aatgagctga tttaacaaaa atttaacgcg aattttaaca aaatattaac   2580
gcttacaatt taggtggcac ttttcgggga aatgtgcgcg gaacccctat tgtttatttt   2640
ttctaaatac attcaaatat gtatccgctc atgagacaat aaccctgata aatgcttcaa   2700
taatattgaa aaaggaagag tatgagtatt caacatttcc gtgtcgccct tattcccttt   2760
tttgcggcat tttgccttcc tgttttttgct cacccagaaa cgctggtgaa agtaaaagat   2820
gctgaagatc agttgggtgc acgagtgggt tacatcgaac tggatctcaa cagcggtaag   2880
atccttgaga gttttcgccc cgaagaacgt tttccaatga tgagcacttt taaagttctg   2940
ctatgtggcg cggtattatc ccgtattgac gccgggcaag agcaactcgg tcgccgcata   3000
cactattctc agaatgactt ggttgagtac tcaccagtca gagaaaagca tcttacggat   3060
ggcatgacag taagagaatt atgcagtgct gccataacca tgagtgataa cactgcggcc   3120
aacttacttc tgacaacgat cggaggaccg aaggagctaa ccgcttttttt gcacaacatg   3180
```

| | |
|---|---|
| ggggatcatg taactcgcct tgatcgttgg gaaccggagc tgaatgaagc cataccaaac | 3240 |
| gacgagcgtg acaccacgat gcctgtagca atggcaacaa cgttgcgcaa actattaact | 3300 |
| ggcgaactac ttactctagc ttcccggcaa caattaatag actggatgga ggcggataaa | 3360 |
| gttgcaggac cacttctgcg ctcggccctt ccggctggct ggtttattgc tgataaatct | 3420 |
| ggagccggtg agcgtgggtc tcgcggtatc attgcagcac tggggccaga tggtaagccc | 3480 |
| tcccgtatcg tagttatcta cacgacgggg agtcaggcaa ctatggatga acgaaataga | 3540 |
| cagatcgctg agataggtgc ctcactgatt aagcattggt aactgtcaga ccaagtttac | 3600 |
| tcatatatac tttagattga tttaaaactt cattttaat ttaaaaggat ctaggtgaag | 3660 |
| atcctttttg ataatctcat gaccaaaatc ccttaacgtg agttttcgtt ccactgagcg | 3720 |
| tcagaccccg tagaaaagat caaaggatct cttgagatc cttttttct gcgcgtaatc | 3780 |
| tgctgcttgc aaacaaaaaa accaccgcta ccagcggtgg tttgtttgcc ggatcaagag | 3840 |
| ctaccaactc tttttccgaa ggtaactggc ttcagcagag cgcagatacc aaatactgtt | 3900 |
| cttctagtgt agccgtagtt aggccaccac ttcaagaact ctgtagcacc gcctacatac | 3960 |
| ctcgctctgc taatcctgtt accagtggct gctgccagtg gcgataagtc gtgtcttacc | 4020 |
| gggttggact caagacgata gttaccggat aaggcgcagc ggtcgggctg aacggggggt | 4080 |
| tcgtgcacac agcccagctt ggagcgaacg acctacaccg aactgagata cctacagcgt | 4140 |
| gagctatgag aaagcgccac gcttcccgaa gggagaaagg cggacaggta tccggtaagc | 4200 |
| ggcagggtcg gaacaggaga gcgcacgagg gagcttccag ggggaaacgc ctggtatctt | 4260 |
| tatagtcctg tcgggtttcg ccacctctga cttgagcgtc gatttttgtg atgctcgtca | 4320 |
| gggggggcgga gcctatggaa aaacgccagc aacgcggcct ttttacggtt cctggccttt | 4380 |
| tgctggcctt ttgctcacat gttctttcct gcgttatccc ctgattctgt ggataaccgt | 4440 |
| attaccgcct ttgagtgagc tgataccgct cgccgcagcc gaacgaccga gcgcagcgag | 4500 |
| tcagtgagcg aggaagcgga agagcgccca atacgcaaac cgcctctccc cgcgcgttgg | 4560 |
| ccgattcatt aatgcagctg gcacgacagg tttcccgact ggaaagcggg cagtgagcgc | 4620 |
| aacgcaatta atgtgagtta gctcactcat taggcacccc aggctttaca ctttatgctt | 4680 |
| ccggctcgta tgttgtgtgg aattgtgagc ggataacaat ttcacacagg aaacagctat | 4740 |
| gaccatgatt acgccagatt taattaaggc ctta | 4774 |

<210> SEQ ID NO 8
<211> LENGTH: 5109
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| ctgcgcgctc gctcgctcac tgaggccgcc cgggcaaagc ccgggcgtcg gcgaccttg | 60 |
| gtcgcccggc ctcagtgagc gagcgagcgc gcagagaggg agtgtagcca tgctctagga | 120 |
| agatcaattc ggtacaattc acgcgtcgac attgattatt gactctggtc gttacataac | 180 |
| ttacggtaaa tggcccgcct ggctgaccgc ccaacgaccc cgcccattga cgtcaataat | 240 |
| gacgtatgtt cccatagtaa cgccaatagg gactttccat tgacgtcaat gggtggagta | 300 |
| tttacggtaa actgcccact tggcagtaca tcaagtgtat catatgccaa gtacgccccc | 360 |
| tattgacgtc aatgacggta aatggcccgc ctggcattat gcccagtaca tgaccttatg | 420 |
| ggactttcct acttggcagt acatctactc gaggccacgt tctgcttcac tctccccatc | 480 |

```
tcccccccct cccaccccc aattttgtat ttatttattt tttaattatt ttgtgcagcg    540 atggggcgg ggggggggg ggggggggcg cgcgccaggc ggggcggggc ggggcgaggg    600
gcggggcggg gcgaggcgga gaggtgcggc ggcagccaat cagagcggcg cgctccgaaa    660
gtttcctttt atggcgaggc ggcggcggcg gcggccctat aaaaagcgaa gcgcgcggcg    720
ggcgggagcg ggatcagcca ccgcggtggc ggccctagag tcgatcgagg aactgaaaaa    780
ccagaaagtt aactggtaag tttagtcttt ttgtctttta tttcaggtcc cggatccggt    840
ggtggtgcaa atcaaagaac tgctcctcag tggatgttgc ctttacttct aggcctgtac    900
ggaagtgtta cttctgctct aaaagctgcg gaattgtacc cgcggccgat ccaccggtcg    960
ccaccatggt gagcaagggc gaggagctgt tcaccggggt ggtgcccatc ctggtcgagc   1020
tggacggcga cgtaaacggc cacaagttca gcgtgtccgg cgagggcgag ggcgatgcca   1080
cctacggcaa gctgaccctg aagttcatct gcaccaccgg caagctgccc gtgccctggc   1140
ccaccctcgt gaccaccctg acctacggcg tgcagtgctt cagccgctac cccgaccaca   1200
tgaagcagca cgacttcttc aagtccgcca tgcccgaagg ctacgtccag gagcgcacca   1260
tcttcttcaa ggacgacggc aactacaaga cccgcgccga ggtgaagttc gagggcgaca   1320
ccctggtgaa ccgcatcgag ctgaagggca tcgacttcaa ggaggacggc aacatcctgg   1380
ggcacaagct ggagtacaac tacaacagcc acaacgtcta tatcatggcc gacaagcaga   1440
agaacggcat caaggtgaac ttcaagatcc gccacaacat cgaggacggc agcgtgcagc   1500
tcgccgacca ctaccagcag aacaccccca tcggcgacgg ccccgtgctg ctgcccgaca   1560
accactacct gagcacccag tccgccctga gcaaagaccc caacgagaag cgcgatcaca   1620
tggtcctgct ggagttcgtg accgccgccg ggatcactct cggcatggac gagctgtaca   1680
agtaaagcgg ccatcaagct tatcgatacc gtcgactaga gctcgctgat cagcctcgac   1740
tgtgccttct agttgccagc catctgttgt ttgcccctcc ccgtgccttc cttgaccct    1800 ggaaggtgcc actcccactg tccttttccta ataaaatgag gaaattgcat cgcattgtct   1860
gagtaggtgt cattctattc tggggggtgg ggtggggcag gacagcaagg gggaggattg   1920
ggaagacaat agcaattcga acgctgacgt catcaacccg ctccaaggaa tcgcgggccc   1980
agtgtcacta gcggaaaca cccagcgcgc gtgcgccctg gcaggaagat ggctgtgagg    2040
gacaggggag tggcgccctg caatatttgc atgtcgctat gtgttctggg aaatcaccat   2100
aaacgtgaaa tgtctttgga tttgggaatc ttataagttc tgtatgagac cacagatctc   2160
ccgatcccct atggtgcact ctcagtacaa tctgctctga tgccgcataa ctagtctgca   2220
ggaagacaat ttaggtagat aagtagcatg gcgggttaat cattaactac aaggaacccc   2280
tagtgatgga gttggtaacc taattcactg gccgtcgttt tacaacgtcg tgactgggaa   2340
aaccctggcg ttacccaact taatcgcctt gcagcacatc cccctttcgc cagctggcgt   2400
aatagcgaag aggcccgcac cgatcgccct tcccaacagt tgcgcagcct gaatggcgaa   2460
tgggacgcgc cctgtagcgg cgcattaagc gcggcgggtg tggtggttac gcgcagcgtg   2520
accgctacac ttgccagcgc cctagcgccc gctcctttcg ctttcttccc ttcctttctc   2580
gccacgttcg ccggctttcc ccgtcaagct ctaaatcggg gctcccttt agggttccga   2640 tttagtgctt tacggcacct cgaccccaaa aaacttgatt agggtgatgg ttcacgtagt   2700
gggccatcgc cctgatagac ggttttcgc cctttgacgt tggagtccac gttctttaat   2760
agtggactct tgttccaaac tggaacaaca ctcaacccta tctcggtcta ttcttttgat   2820
```

-continued

```
ttataaggga ttttgccgat tcggcctat tggttaaaaa atgagctgat ttaacaaaaa    2880
tttaacgcga attttaacaa aatattaacg cttacaattt aggtggcact tttcggggaa    2940
atgtgcgcgg aacccctatt tgtttatttt tctaaataca ttcaaatatg tatccgctca    3000
tgagacaata accctgataa atgcttcaat aatattgaaa aaggaagagt atgagtattc    3060
aacatttccg tgtcgccctt attccctttt ttgcggcatt ttgccttcct gttttgctc    3120
acccagaaac gctggtgaaa gtaaaagatg ctgaagatca gttgggtgca cgagtgggtt    3180
acatcgaact ggatctcaac agcggtaaga tccttgagag ttttcgcccc gaagaacgtt    3240
ttccaatgat gagcactttt aaagttctgc tatgtggcgc ggtattatcc cgtattgacg    3300
ccgggcaaga gcaactcggt cgccgcatac actattctca gaatgacttg gttgagtact    3360
caccagtcac agaaaagcat cttacggatg gcatgacagt aagagaatta tgcagtgctg    3420
ccataaccat gagtgataac actgcggcca acttacttct gacaacgatc ggaggaccga    3480
aggagctaac cgcttttttg cacaacatgg gggatcatgt aactcgcctt gatcgttggg    3540
aaccggagct gaatgaagcc ataccaaacg acgagcgtga caccacgatg cctgtagcaa    3600
tggcaacaac gttgcgcaaa ctattaactg gcgaactact tactctagct tcccggcaac    3660
aattaataga ctggatggag gcggataaag ttgcaggacc acttctgcgc tcggcccttc    3720
cggctggctg gtttattgct gataaatctg gagccggtga gcgtgggtct cgcggtatca    3780
ttgcagcact ggggccagat ggtaagccct cccgtatcgt agttatctac acgacgggga    3840
gtcaggcaac tatggatgaa cgaaatagac agatcgctga gataggtgcc tcactgatta    3900
agcattggta actgtcagac caagtttact catatatact ttagattgat ttaaaacttc    3960
atttttaatt taaaaggatc taggtgaaga tccttttga taatctcatg accaaaatcc    4020
cttaacgtga gttttcgttc cactgagcgt cagaccccgt agaaaagatc aaaggatctt    4080
cttgagatcc ttttttttctg cgcgtaatct gctgcttgca acaaaaaaa ccaccgctac    4140
cagcggtggt ttgtttgccg gatcaagagc taccaactct ttttccgaag gtaactggct    4200
tcagcagagc gcagatacca atactgttc ttctagtgta gccgtagtta ggccaccact    4260
tcaagaactc tgtagcaccg cctacatacc tcgctctgct aatcctgtta ccagtggctg    4320
ctgccagtgg cgataagtcg tgtcttaccg ggttggactc aagacgatag ttaccggata    4380
aggcgcagcg gtcgggctga acggggggtt cgtgcacaca gcccagcttg gagcgaacga    4440
cctacaccga actgagatac ctacagcgtg agctatgaga aagcgccacg cttcccgaag    4500
ggagaaaggc ggacaggtat ccggtaagcg gcagggtcgg aacaggagag cgcacgaggg    4560
agcttccagg gggaaacgcc tggtatcttt atagtcctgt cgggtttcgc cacctctgac    4620
ttgagcgtcg atttttgtga tgctcgtcag ggggcggag cctatggaaa aacgccagca    4680
acgcggcctt tttacggttc ctggcctttt gctggccttt tgctcacatg ttctttcctg    4740
cgttatcccc tgattctgtg gataaccgta ttaccgcctt tgagtgagct gataccgctc    4800
gccgcagccg aacgaccgag cgcagcgagt cagtgagcga ggaagcggaa gagcgcccaa    4860
tacgcaaacc gcctctcccc gcgcgttggc cgattcatta atgcagctgg cacgacaggt    4920
ttcccgactg gaaagcgggc agtgagcgca acgcaattaa tgtgagttag ctcactcatt    4980
aggcacccca ggctttacac tttatgcttc cggctcgtat gttgtgtgga attgtgagcg    5040
gataacaatt tcacacagga aacagctatg accatgatta cgccagattt aattaaggcc    5100
ttaattagg                                                            5109
```

<210> SEQ ID NO 9
<211> LENGTH: 5172
<212> TYPE: DNA
<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| cgcgtcgaca | ttgattattg | actctggtcg | ttacataact | tacggtaaat | ggcccgcctg | 60 |
| gctgaccgcc | caacgacccc | gcccattgac | gtcaataatg | acgtatgttc | ccatagtaac | 120 |
| gccaataggg | actttccatt | gacgtcaatg | ggtggagtat | ttacggtaaa | ctgcccactt | 180 |
| ggcagtacat | caagtgtatc | atatgccaag | tacgccccct | attgacgtca | atgacggtaa | 240 |
| atggcccgcc | tggcattatg | cccagtacat | gaccttatgg | gactttccta | cttggcagta | 300 |
| catctactcg | aggccacgtt | ctgcttcact | ctccccatct | cccccccctc | cccaccccca | 360 |
| attttgtatt | tatttatttt | ttaattattt | tgtgcagcga | tgggggcggg | ggggggggg | 420 |
| ggggggcgc | gcgccaggcg | gggcggggcg | gggcgagggg | cggggcgggg | cgaggcggag | 480 |
| aggtgcggcg | gcagccaatc | agagcggcgc | gctccgaaag | tttccttta | tggcgaggcg | 540 |
| gcggcggcg | cggccctata | aaaagcgaag | cgcgcggcgg | gcgggagcgg | gatcagccac | 600 |
| cgcggtggcg | gccctagagt | cgatcgagga | actgaaaaac | cagaaagtta | actggtaagt | 660 |
| ttagtctttt | tgtcttttat | ttcagaattc | cccagtggaa | agacgcgcag | gcaaaacgca | 720 |
| ccacgtgacg | gagcgtgacc | gcgcgccgag | cgcgcgccaa | ggtcgggcag | gaagagggcc | 780 |
| tatttcccat | gattccttca | tatttgcata | tacgatacaa | ggctgttaga | gagataatta | 840 |
| gaattaattt | gactgtaaac | acaaagatat | tagtacaaaa | tacgtgacgt | agaaagtaat | 900 |
| aatttcttgg | gtagtttgca | gttttaaaat | tatgttttaa | aatggactat | catatgctta | 960 |
| ccgtaacttg | aaagtatttc | gatttcttgg | ctttatatat | cttgtggaaa | ggacgcggga | 1020 |
| tcccgcttac | gctgagtact | tcgattcaag | agatcgaagt | actcagcgta | agttttttcc | 1080 |
| aaagtcccgg | atccggtggt | ggtgcaaatc | aaagaactgc | tcctcagtgg | atgttgcctt | 1140 |
| tacttctagg | cctgtacgga | agtgttactt | ctgctctaaa | agctgcggaa | ttgtacccgc | 1200 |
| ggccgatcca | ccggtcgcca | ccatggtgag | caagggcgag | gagctgttca | ccggggtggt | 1260 |
| gcccatcctg | gtcgagctgg | acggcgacgt | aaacggccac | aagttcagcg | tgtccggcga | 1320 |
| gggcgagggc | gatgccacct | acggcaagct | gaccctgaag | ttcatctgca | ccaccggcaa | 1380 |
| gctgcccgtg | ccctggccca | ccctcgtgac | caccctgacc | tacggcgtgc | agtgcttcag | 1440 |
| ccgctacccc | gaccacatga | agcagcacga | cttcttcaag | tccgccatgc | ccgaaggcta | 1500 |
| cgtccaggag | cgcaccatct | tcttcaagga | cgacggcaac | tacaagaccc | gcgccgaggt | 1560 |
| gaagttcgag | ggcgacaccc | tggtgaaccg | catcgagctg | aagggcatcg | acttcaagga | 1620 |
| ggacggcaac | atcctggggc | acaagctgga | gtacaactac | aacagccaca | acgtctatat | 1680 |
| catggccgac | aagcagaaga | acggcatcaa | ggtgaacttc | aagatccgcc | acaacatcga | 1740 |
| ggacggcagc | gtgcagctcg | ccgaccacta | ccagcagaac | acccccatcg | gcgacggccc | 1800 |
| cgtgctgctg | cccgacaacc | actacctgag | cacccagtcc | gccctgagca | agacccccaa | 1860 |
| cgagaagcgc | gatcacatgg | tcctgctgga | gttcgtgacc | gccgccggga | tcactctcgg | 1920 |
| catggacgag | ctgtacaagt | aaagcggcca | tcaagcttat | cgataccgtc | gactagagct | 1980 |
| cgctgatcag | cctcgactgt | gccttctagt | tgccagccat | ctgttgtttg | cccctccccc | 2040 |
| gtgccttcct | tgaccctgga | aggtgccact | cccactgtcc | tttcctaata | aaatgaggaa | 2100 |

```
attgcatcgc attgtctgag taggtgtcat tctattctgg ggggtggggt ggggcaggac    2160 agcaagggggg aggattggga agacaattag gtagataagt agcatggcgg gttaatcatt   2220
aactacaagg aaccccctagt gatggagttg gccactccct ctctgcgcgc tcgctcgctc   2280
actgaggccg ggcgaccaaa ggtcgcccga cgcccgggct ttgcccgggc ggcctcagtg    2340
agcgagcgag cgcgcagcct taattaacct aattcactgg ccgtcgtttt acaacgtcgt    2400
gactgggaaa accctggcgt tacccaactt aatcgccttg cagcacatcc ccctttcgcc    2460
agctggcgta atagcgaaga ggcccgcacc gatcgccctt cccaacagtt gcgcagcctg    2520
aatggcgaat gggacgcgcc ctgtagcggc gcattaagcg cggcgggtgt ggtggttacg    2580
cgcagcgtga ccgctacact tgccagcgcc ctagcgcccg ctcctttcgc tttcttccct    2640
tcctttctcg ccacgttcgc cggctttccc cgtcaagctc taaatcgggg gctcccttta    2700
gggttccgat ttagtgcttt acggcacctc gaccccaaaa aacttgatta gggtgatggt    2760
tcacgtagtg ggccatcgcc ctgatagacg gttttttcgcc ctttgacgtt ggagtccacg   2820
ttctttaata gtggactctt gttccaaact ggaacaacac tcaaccctat ctcggtctat    2880
tcttttgatt tataagggat tttgccgatt tcggcctatt ggttaaaaaa tgagctgatt    2940
taacaaaaat ttaacgcgaa ttttaacaaa atattaacgc ttacaattta ggtggcactt    3000
ttcggggaaa tgtgcgcgga acccctattt gtttattttt ctaaatacat tcaaatatgt    3060
atccgctcat gagacaataa ccctgataaa tgcttcaata atattgaaaa aggaagagta    3120
tgagtattca acatttccgt gtcgccctta ttccctttttt tgcggcattt tgccttcctg    3180 ttttttgctca cccagaaacg ctggtgaaag taaaagatgc tgaagatcag ttgggtgcac    3240
gagtgggtta catcgaactg gatctcaaca gcggtaagat ccttgagagt tttcgccccg    3300
aagaacgttt tccaatgatg agcactttta aagttctgct atgtggcgcg gtattatccc    3360
gtattgacgc cgggcaagag caactcggtc gccgcataca ctattctcag aatgacttgg    3420
ttgagtactc accagtcaca gaaaagcatc ttacggatgg catgacagta agagaattat    3480
gcagtgctgc cataaccatg agtgataaca ctgcggccaa cttacttctg acaacgatcg    3540
gaggaccgaa ggagctaacc gcttttttgc acaacatggg ggatcatgta actcgccttg    3600
atcgttggga accggagctg aatgaagcca taccaaacga cgagcgtgac accacgatgc    3660
ctgtagcaat ggcaacaacg ttgcgcaaac tattaactgg cgaactactt actctagctt    3720
cccggcaaca attaatagac tggatggagg cggataaagt tgcaggacca cttctgcgct    3780
cggcccttcc ggctggctgg tttattgctg ataaatctgg agccggtgag cgtgggtctc    3840
gcggtatcat tgcagcactg gggccagatg gtaagccctc ccgtatcgta gttatctaca    3900
cgacggggag tcaggcaact atggatgaac gaaatagaca gatcgctgag ataggtgcct    3960
cactgattaa gcattggtaa ctgtcagacc aagtttactc atatatactt tagattgatt    4020
taaaacttca tttttaattt aaaaggatct aggtgaagat cctttttgat aatctcatga    4080
ccaaaatccc ttaacgtgag ttttcgttcc actgagcgtc agaccccgta gaaaagatca    4140
aaggatcttc ttgagatcct ttttttctgc gcgtaatctg ctgcttgcaa acaaaaaaac    4200
caccgctacc agcggtggtt tgtttgccgg atcaagagct accaactctt tttccgaagg    4260
taactggctt cagcagagcg cagataccaa atactgttct tctagtgtag ccgtagttag    4320
gccaccactt caagaactct gtagcaccgc ctacatacct cgctctgcta atcctgttac    4380
cagtggctgc tgccagtggc gataagtcgt gtcttaccgg gttggactca agacgatagt    4440
taccggataa ggcgcagcgg tcgggctgaa cggggggttc gtgcacacag cccagcttgg    4500
```

```
agcgaacgac ctacaccgaa ctgagatacc tacagcgtga gctatgagaa agcgccacgc    4560
ttcccgaagg gagaaaggcg gacaggtatc cggtaagcgg cagggtcgga acaggagagc    4620
gcacgaggga gcttccaggg ggaaacgcct ggtatcttta gtcctgtc gggtttcgcc     4680 acctctgact tgagcgtcga ttttttgtgat gctcgtcagg ggggcggagc ctatggaaaa    4740
acgccagcaa cgcggccttt ttacggttcc tggccttttg ctggccttt gctcacatgt     4800 tctttcctgc gttatcccct gattctgtgg ataaccgtat taccgccttt gagtgagctg    4860
ataccgctcg ccgcagccga acgaccgagc gcagcgagtc agtgagcgag gaagcggaag    4920
agcgcccaat acgcaaaccg cctctccccg cgcgttggcc gattcattaa tgcagctggc    4980
acgacaggtt tcccgactgg aaagcgggca gtgagcgcaa cgcaattaat gtgagttagc    5040
tcactcatta ggcaccccag gctttacact ttatgcttcc ggctcgtatg ttgtgtggaa    5100
ttgtgagcgg ataacaattt cacacaggaa acagctatga ccatgattac gccagattta    5160
attaaggcct ta                                                        5172

<210> SEQ ID NO 10
<211> LENGTH: 5172
<212> TYPE: DNA
<213> ORGANISM: Artificial Sequence
<220> FEATURE:
<223> OTHER INFORMATION: Synthetic Polynucleotide

<400> SEQUENCE: 10
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctactcg aggccacgtt ctgcttcact ctccccatct ccccccctc cccaccccca     360 attttgtatt tatttatttt ttaattatt tgtgcagcga tggggcggg gggggggggg     420 ggggggcgc gcgccaggcg gggcggggcg gggcgagggg cggggcgggg cgaggcggag     480
aggtgcggcg gcagccaatc agagcggcgc gctccgaaag tttcctttta tggcgaggcg     540 gcggcggcg cggccctata aaaagcgaag cgcgcggcgg gcgggagcgg gatcagccac     600
cgcggtggcg gccctagagt cgatcgagga actgaaaaac cagaaagtta actggtaagt     660
ttagtctttt tgtctttat ttcagaattc cccagtggaa agacgcgcag gcaaaacgca     720
ccacgtgacg gagcgtgacc gcgcgccgag cgcgcgccaa ggtcgggcag gaagagggcc     780
tatttcccat gattccttca tatttgcata tacgatacaa ggctgttaga gagataatta     840
gaattaattt gactgtaaac acaaagatat tagtacaaaa tacgtgacgt agaaagtaat     900
aatttcttgg gtagtttgca gttttaaaat tatgttttaa aatggactat catatgctta     960
ccgtaacttg aaagtatttc gatttcttgg gtttatatat cttgtggaaa ggacgcggga    1020
tcccgcttac gctgagtact tcgattcaag agatcgaagt actcagcgta agttttttcc    1080
aaagtcccgg atccggtggt ggtgcaaatc aaagaactgc tcctcagtgg atgttgcctt    1140
tacttctagg cctgtacgga agtgttactt ctgctctaaa agctgcggaa ttgtacccgc    1200
ggccgatcca ccggtcgcca ccatggtgag caagggcgag gagctgttca ccggggtggt    1260
gcccatcctg gtcgagctgg acggcgacgt aaacggccac aagttcagcg tgtccggcga    1320
```

```
gggcgagggc gatgccacct acggcaagct gaccctgaag ttcatctgca ccaccggcaa    1380
gctgcccgtg ccctggccca ccctcgtgac caccctgacc tacggcgtgc agtgcttcag    1440
ccgctacccc gaccacatga agcagcacga cttcttcaag tccgccatgc ccgaaggcta    1500
cgtccaggag cgcaccatct tcttcaagga cgacggcaac tacaagaccc gcgccgaggt    1560
gaagttcgag ggcgacaccc tggtgaaccg catcgagctg aagggcatcg acttcaagga    1620
ggacggcaac atcctggggc acaagctgga gtacaactac aacagccaca acgtctatat    1680
catggccgac aagcagaaga acggcatcaa ggtgaacttc aagatccgcc acaacatcga    1740
ggacggcagc gtgcagctcg ccgaccacta ccagcagaac ccccatcg gcgacggccc     1800 cgtgctgctg cccgacaacc actacctgag cacccagtcc gccctgagca agacccca    1860 cgagaagcgc gatcacatgg tcctgctgga gttcgtgacc gccgccggga tcactctcgg    1920
catggacgag ctgtacaagt aaagcggcca tcaagcttat cgataccgtc gactagagct    1980
cgctgatcag cctcgactgt gccttctagt tgccagccat ctgttgtttg ccctcccc      2040 gtgccttcct tgaccctgga aggtgccact cccactgtcc tttcctaata aaatgaggaa    2100
attgcatcgc attgtctgag taggtgtcat tctattctgg ggggtggggt ggggcaggac    2160 agcaagggg aggattggga agacaattag gtagataagt agcatggcgg gttaatcatt     2220
aactacaagg aacccctagt gatggagttg gccactccct ctctgcgcgc tcgctcgctc    2280
actgaggccg ggcgaccaaa ggtcgcccga cgcccgggct tgcccggc ggcctcagtg      2340 agcgagcgag cgcgcagcct taattaacct aattcactgg ccgtcgtttt acaacgtcgt    2400
gactgggaaa accctggcgt tacccaactt aatcgccttg cagcacatcc ccctttcgcc    2460
agctggcgta atagcgaaga ggcccgcacc gatcgccctt ccaacagtt gcgcagcctg     2520 aatggcgaat gggacgcgcc ctgtagcggc gcattaagcg cggcgggtgt ggtggttacg    2580
cgcagcgtga ccgctacact tgccagcgcc ctagcgcccg ctcctttcgc tttcttccct    2640
tcctttctcg ccacgttcgc cggctttccc cgtcaagctc taaatcgggg ctccctttta    2700
gggttccgat ttagtgcttt acggcacctc gaccccaaaa aacttgatta gggtgatggt    2760
tcacgtagtg gccatcgcc ctgatagacg ttttttcgcc ctttgacgtt ggagtccacg     2820
ttctttaata gtggactctt gttccaaact ggaacaacac tcaaccctat ctcggtctat    2880
tcttttgatt tataagggat tttgccgatt tcggcctatt ggttaaaaaa tgagctgatt    2940
taacaaaaat ttaacgcgaa ttttaacaaa atattaacgc ttacaattta ggtggcactt    3000
ttcggggaaa tgtgcgcgga accctatttt gtttattttt ctaaatacat tcaaatatgt    3060
atccgctcat gagacaataa ccctgataaa tgcttcaata atattgaaaa aggaagagta    3120
tgagtattca acatttccgt gtcgccctta ttcccttttt tgcggcattt tgccttcctg    3180 ttttgctca cccagaaacg ctggtgaaag taaaagatgc tgaagatcag ttgggtgcac     3240
gagtgggtta catcgaactg gatctcaaca gcggtaagat ccttgagagt tttcgccccg    3300
aagaacgttt tccaatgatg agcactttta aagttctgct atgtggcgcg gtattatccc    3360
gtattgacgc cgggcaagag caactcggtc gccgcataca ctattctcag aatgacttgg    3420
ttgagtactc accagtcaca gaaaagcatc ttacggatgg catgacagta agagaattat    3480
gcagtgctgc cataaccatg agtgataaca ctgcggccaa cttacttctg acaacgatcg    3540
gaggaccgaa ggagctaacc gcttttttgc acaacatggg ggatcatgta actcgccttg    3600
atcgttggga accggagctg aatgaagcca taccaaacga cgagcgtgac accacgatgc    3660
ctgtagcaat ggcaacaacg ttgcgcaaac tattaactgg cgaactactt actctagctt    3720
```

```
cccggcaaca attaatagac tggatggagg cggataaagt tgcaggacca cttctgcgct    3780
cggcccttcc ggctggctgg tttattgctg ataaatctgg agccggtgag cgtgggtctc    3840
gcggtatcat tgcagcactg gggccagatg gtaagccctc ccgtatcgta gttatctaca    3900
cgacggggag tcaggcaact atggatgaac gaaatagaca gatcgctgag ataggtgcct    3960
cactgattaa gcattggtaa ctgtcagacc aagtttactc atatatactt tagattgatt    4020
taaaacttca ttttttaattt aaaaggatct aggtgaagat cctttttgat aatctcatga    4080
ccaaaatccc ttaacgtgag ttttcgttcc actgagcgtc agaccccgta gaaaagatca    4140
aaggatcttc ttgagatcct ttttttctgc gcgtaatctg ctgcttgcaa acaaaaaaac    4200
caccgctacc agcggtggtt tgtttgccgg atcaagagct accaactctt tttccgaagg    4260
taactggctt cagcagagcg cagataccaa atactgttct tctagtgtag ccgtagttag    4320
gccaccactt caagaactct gtagcaccgc ctacatacct cgctctgcta atcctgttac    4380
cagtggctgc tgccagtggc gataagtcgt gtcttaccgg gttggactca agacgatagt    4440
taccggataa ggcgcagcgg tcgggctgaa cggggggttc gtgcacacag cccagcttgg    4500
agcgaacgac ctacaccgaa ctgagatacc tacagcgtga gctatgagaa agcgccacgc    4560
ttcccgaagg gagaaaggcg gacaggtatc cggtaagcgg cagggtcgga acaggagagc    4620
gcacgaggga gcttccaggg ggaaacgcct ggtatcttta tagtcctgtc gggtttcgcc    4680
acctctgact tgagcgtcga ttttgtgat gctcgtcagg gggcggagc ctatggaaaa    4740 acgccagcaa cgcggccttt ttacggttcc tggccttttg ctggccttttt gctcacatgt    4800 tctttcctgc gttatcccct gattctgtgg ataaccgtat taccgccttt gagtgagctg    4860
ataccgctcg ccgcagccga acgaccgagc gcagcgagtc agtgagcgag gaagcggaag    4920
agcgcccaat acgcaaaccg cctctccccg cgcgttggcc gattcattaa tgcagctggc    4980
acgacaggtt tcccgactgg aaagcgggca gtgagcgcaa cgcaattaat gtgagttagc    5040
tcactcatta ggcaccccag gctttacact ttatgcttcc ggctcgtatg ttgtgtggaa    5100
ttgtgagcgg ataacaattt cacacaggaa acagctatga ccatgattac gccagattta    5160
attaaggcct ta                                                        5172

<210> SEQ ID NO 11
<211> LENGTH: 5081
<212> TYPE: DNA
<213> ORGANISM: Artificial Sequence
<220> FEATURE:
<223> OTHER INFORMATION: Synthetic Polynucleotide

<400> SEQUENCE: 11
tagcaattcg aacgctgacg tcatcaaccc gctccaagga atcgcgggcc cagtgtcact      60
aggcgggaac acccagcgcg cgtgcgccct ggcaggaaga tggctgtgag ggacagggga     120
gtggcgccct gcaatatttg catgtcgcta tgtgttctgg gaaatcacca taaacgtgaa     180
atgtctttgg atttgggaat cttataagtt ctgtatgaga ccacagatct gactttcatc     240
tgtactacat tcaagagatg tagtacagat gaaagtctttt ttctagtctg caggaagaca     300
atagccgcgt cgacattgat tattgactct ggtcgttaca taacttacgg taaatggccc     360
gcctggctga ccgcccaacg acccgcccca ttgacgtcaa taatgacgta tgttcccata     420
gtaacgccaa tagggacttt ccattgacgt caatgggtgg agtatttacg gtaaactgcc     480
cacttggcag tacatcaagt gtatcatatg ccaagtacgc cccctattga cgtcaatgac     540
```

```
ggtaaatggc ccgcctggca ttatgcccag tacatgacct tatgggactt tcctacttgg    600
cagtacatct actcgaggcc acgttctgct tcactctccc catctccccc ccctccccac    660
ccccaatttt gtatttattt attttttaat tattttgtgc agcgatgggg gcggggggggg   720 gggggggggg ggcgcgcgcc aggcggggcg gggcggggcg aggggcgggg cggggcgagg    780
cggagaggtg cggcggcagc caatcagagc ggcgcgctcc gaaagtttcc ttttatggcg    840
aggcggcggc ggcggcggcc ctataaaaag cgaagcgcgc ggcgggcggg agcgggatca    900
gccaccgcgg tggcggccct agagtcgatc gaggaactga aaaaccagaa agttaactgg    960
taagtttagt cttttttgtct tttatttcag gtcccggatc cggtggtggt gcaaatcaaa   1020
gaactgctcc tcagtggatg ttgcctttac ttctaggcct gtacggaagt gttacttctg    1080
ctctaaaagc tgcggaattg tacccgcggc cgatccaccg gtcgccacca tggtgagcaa    1140
gggcgaggag ctgttcaccg gggtggtgcc catcctggtc gagctggacg gcgacgtaaa    1200
cggccacaag ttcagcgtgt ccggcgaggg cgagggcgat gccacctacg gcaagctgac    1260
cctgaagttc atctgcacca ccggcaagct gcccgtgccc tggcccaccc tcgtgaccac    1320
cctgacctac ggcgtgcagt gcttcagccg ctaccccgac cacatgaagc agcacgactt    1380
cttcaagtcc gccatgcccg aaggctacgt ccaggagcgc accatcttct tcaaggacga    1440
cggcaactac aagacccgcg ccgaggtgaa gttcgagggc gacaccctgg tgaaccgcat    1500
cgagctgaag ggcatcgact tcaaggagga cggcaacatc ctggggcaca gctggagta    1560 caactacaac agccacaacg tctatatcat ggccgacaag cagaagaacg gcatcaaggt    1620
gaacttcaag atccgccaca acatcgagga cggcagcgtg cagctcgccg accactacca    1680
gcagaacacc cccatcggcg acggccccgt gctgctgccc gacaaccact acctgagcac    1740
ccagtccgcc ctgagcaaag accccaacga gaagcgcgat cacatggtcc tgctggagtt    1800
cgtgaccgcc gccgggatca ctctcggcat ggacgagctg tacaagtaaa gcggccatca    1860
agcttatcga taccgtcgac tagagctcgc tgatcagcct cgactgtgcc ttctagttgc    1920
cagccatctg ttgtttgccc ctcccccgtg ccttccttga ccctggaagg tgccactccc    1980
actgtccttt cctaataaaa tgaggaaatt gcatcgcatt gtctgagtag gtgtcattct    2040
attctggggg gtggggtggg gcaggacagc aaggggggagg attgggaaga caattaggta    2100
gataagtagc atggcgggtt aatcattaac tacaaggaac ccctagtgat ggagttggcc    2160
actccctctc tgcgcgctcg ctcgctcact gaggccagat atctatttta gatatctggc    2220
agaatcccga aacgggattc tggcctcagt gagcgagcga gcgcgcagtt aattaaccta    2280
attcactggc cgtcgtttta caacgtcgtg actgggaaaa ccctggcgtt acccaactta    2340
atcgccttgc agcacatccc cctttcgcca gctggcgtaa tagcgaagag gcccgcaccg    2400
atcgcccttc ccaacagttg cgcagcctga atggcgaatg gacgcgcccc tgtagcggcg    2460
cattaagcgc ggcgggtgtg gtggttacgc gcagcgtgac cgctacactt gccagcgccc    2520
tagcgcccgc tcctttcgct ttcttccctt cctttctcgc cacgttcgcc ggctttcccc    2580
gtcaagctct aaatcggggg ctccctttag ggttccgatt tagtgcttta cggcacctcg    2640
accccaaaaa acttgattag ggtgatggtt cacgtagtgg gccatcgccc tgatagacgg    2700
tttttcgccc tttgacgttg gagtccacgt tctttaatag tggactcttg ttccaaactg    2760
gaacaacact caaccctatc tcggtctatt cttttgattt ataagggatt ttgccgattt    2820
cggcctattg gttaaaaaat gagctgattt aacaaaaatt taacgcgaat tttaacaaaa    2880
tattaacgct tacaatttag gtggcacttt tcggggaaat gtgcgcggaa ccctatttg     2940
```

```
tttattttc   taaatacatt   caaatatgta   tccgctcatg   agacaataac   cctgataaat      3000
gcttcaataa   tattgaaaaa   ggaagagtat   gagtattcaa   catttccgtg   tcgcccttat      3060
tccctttttt   gcggcatttt   gccttcctgt   ttttgctcac   ccagaaacgc   tggtgaaagt      3120
aaaagatgct   gaagatcagt   tgggtgcacg   agtgggttac   atcgaactgg   atctcaacag      3180
cggtaagatc   cttgagagtt   ttcgccccga   agaacgtttt   ccaatgatga   gcacttttaa      3240
agttctgcta   tgtggcgcgg   tattatcccg   tattgacgcc   gggcaagagc   aactcggtcg      3300
ccgcatacac   tattctcaga   atgacttggt   tgagtactca   ccagtcacag   aaaagcatct      3360 tacgatggc    atgacagtaa   gagaattatg   cagtgctgcc   ataaccatga   gtgataacac      3420
tgcggccaac   ttacttctga   caacgatcgg   aggaccgaag   gagctaaccg   cttttttgca      3480
caacatgggg   gatcatgtaa   ctcgccttga   tcgttgggaa   ccggagctga   atgaagccat      3540
accaaacgac   gagcgtgaca   ccacgatgcc   tgtagcaatg   gcaacaacgt   tgcgcaaact      3600
attaactggc   gaactactta   ctctagcttc   ccggcaacaa   ttaatagact   ggatggaggc      3660
ggataaagtt   gcaggaccac   ttctgcgctc   ggcccttccg   gctggctggt   ttattgctga      3720
taaatctgga   gccggtgagc   gtgggtctcg   cggtatcatt   gcagcactgg   ggccagatgg      3780
taagccctcc   cgtatcgtag   ttatctacac   gacggggagt   caggcaacta   tggatgaacg      3840
aaatagacag   atcgctgaga   taggtgcctc   actgattaag   cattggtaac   tgtcagacca      3900
agtttactca   tatatacttt   agattgattt   aaaacttcat   ttttaattta   aaaggatcta      3960
ggtgaagatc   ctttttgata   atctcatgac   caaaatccct   taacgtgagt   tttcgttcca      4020
ctgagcgtca   gaccccgtag   aaaagatcaa   aggatcttct   tgagatcctt   ttttttctgcg     4080 cgtaatctgc   tgcttgcaaa   caaaaaaacc   accgctacca   gcggtggttt   gtttgccgga      4140
tcaagagcta   ccaactcttt   ttccgaaggt   aactggcttc   agcagagcgc   agataccaaa      4200
tactgttctt   ctagtgtagc   cgtagttagg   ccaccacttc   aagaactctg   tagcaccgcc      4260
tacatacctc   gctctgctaa   tcctgttacc   agtggctgct   gccagtggcg   ataagtcgtg      4320
tcttaccggg   ttggactcaa   gacgatagtt   accggataag   gcgcagcggt   cgggctgaac      4380
ggggggttcg   tgcacacagc   ccagcttgga   gcgaacgacc   tacaccgaac   tgagatacct      4440
acagcgtgag   ctatgagaaa   gcgccacgct   tcccgaaggg   agaaaggcgg   acaggtatcc      4500
ggtaagcggc   agggtcggaa   caggagagcg   cacgaggag    cttccagggg   gaaacgcctg      4560
gtatctttat   agtcctgtcg   ggtttcgcca   cctctgactt   gagcgtcgat   ttttgtgatg      4620
ctcgtcaggg   gggcggagcc   tatggaaaaa   cgccagcaac   gcggcctttt   tacgttcct       4680 ggccttttgc   tggccttttg   ctcacatgtt   ctttcctgcg   ttatcccctg   attctgtgga      4740
taaccgtatt   accgcctttg   agtgagctga   taccgctcgc   cgcagccgaa   cgaccgagcg      4800
cagcgagtca   gtgagcgagg   aagcggaaga   gcgcccaata   cgcaaaccgc   ctctccccgc      4860
gcgttggccg   attcattaat   gcagctggca   cgacaggttt   cccgactgga   aagcgggcag      4920
tgagcgcaac   gcaattaatg   tgagttagct   cactcattag   gcaccccagg   ctttacactt      4980
tatgcttccg   gctcgtatgt   tgtgtggaat   tgtgagcgga   taacaatttc   acacaggaaa      5040
cagctatgac   catgattacg   ccagatttaa   ttaaggcctt   a                           5081
```

<210> SEQ ID NO 12
<211> LENGTH: 5041
<212> TYPE: DNA
<213> ORGANISM: Artificial Sequence
<220> FEATURE:

<223> OTHER INFORMATION: Synthetic Polynucleotide

<400> SEQUENCE: 12

```
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctactcg aggccacgtt ctgcttcact ctccccatct cccccccctc cccacccca      360
attttgtatt tatttatttt ttaattattt tgtgcagcga tgggggcggg ggggggggg      420
ggggggcgc gcgccaggcg gggcggggcg gggcgagggg cggggcgggg cgaggcggag     480
aggtgcggcg gcagccaatc agagcggcgc gctccgaaag tttccttta tggcgaggcg     540
gcggcggcgg cggccctata aaagcgaag cgcgcggcgg gcgggagcgg gatcagccac     600
cgcggtggcg gccctagagt cgatcgagga actgaaaaac cagaaagtta actggtaagt     660
ttagtctttt tgtcttttat ttcagtagca attcgaacgc tgacgtcatc aacccgctcc     720
aaggaatcgc gggcccagtg tcactaggcg ggaacaccca gcgcgcgtgc gccctggcag     780
gaagatggct gtgagggaca ggggagtggc gccctgcaat atttgcatgt cgctatgtgt     840
tctgggaaat caccataaac gtgaaatgtc tttggatttg ggaatcttat aagttctgta     900
tgagaccaca gatctcccga tccctatgg tgcactctca gtacaatctg ctctgatgcc     960
gcataactag tctgcaggaa gacaatgtcc cggatccggt ggtggtgcaa atcaaagaac    1020
tgctcctcag tggatgttgc ctttacttct aggcctgtac ggaagtgtta cttctgctct    1080
aaaagctgcg gaattgtacc cgcggccgat ccaccggtcg ccaccatggt gagcaagggc    1140
gaggagctgt tcaccggggt ggtgcccatc ctggtcgagc tggacggcga cgtaaacggc    1200
cacaagttca gcgtgtccgg cgagggcgag ggcgatgcca cctacggcaa gctgaccctg    1260
aagttcatct gcaccaccgg caagctgccc gtgccctggc ccaccctcgt gaccaccctg    1320
acctacggcg tgcagtgctt cagccgctac cccgaccaca tgaagcagca cgacttcttc    1380
aagtccgcca tgcccgaagg ctacgtccag gagcgcacca tcttcttcaa ggacgacggc    1440
aactacaaga cccgcgccga ggtgaagttc gagggcgaca ccctggtgaa ccgcatcgag    1500
ctgaagggca tcgacttcaa ggaggacggc aacatcctgg ggcacaagct ggagtacaac    1560
tacaacagcc acaacgtcta tatcatggcc gacaagcaga agaacggcat caaggtgaac    1620
ttcaagatcc gccacaacat cgaggacggc agcgtgcagc tcgccgacca ctaccagcag    1680
aacaccccca tcggcgacgg ccccgtgctg ctgcccgaca ccactacct gagcacccag    1740
tccgccctga gcaaagaccc caacgagaag cgcgatcaca tggtcctgct ggagttcgtg    1800
accgccgccg ggatcactct cggcatggac gagctgtaca gtaaagcgg ccatcaagct    1860
tatcgatacc gtcgactaga gctcgctgat cagcctcgac tgtgccttct agttgccagc    1920
catctgttgt ttgcccctcc cccgtgcctt ccttgaccct ggaaggtgcc actcccactg    1980
tcctttccta ataaaatgag gaaattgcat cgcattgtct gagtaggtgt cattctattc    2040
tggggggtgg ggtggggcag gacagcaagg gggaggattg ggaagacaat taggtagata    2100
agtagcatgg cgggttaatc attaactaca aggaacccct agtgatggag ttggccactc    2160
cctctctgcg cgctcgctcg ctcactgagg ccttcaagag aggcctcagt gagcgagcga    2220
gcgcgcagtt aattaaccta attcactggc cgtcgtttta caacgtcgtg actgggaaaa    2280
```

```
ccctggcgtt acccaactta atcgccttgc agcacatccc cctttcgcca gctggcgtaa    2340
tagcgaagag gcccgcaccg atcgcccttc ccaacagttg cgcagcctga atggcgaatg    2400
ggacgcgccc tgtagcggcg cattaagcgc ggcgggtgtg gtggttacgc gcagcgtgac    2460
cgctacactt gccagcgccc tagcgcccgc tcctttcgct ttcttccctt cctttctcgc    2520
cacgttcgcc ggctttcccc gtcaagctct aaatcggggg ctccctttag ggttccgatt    2580
tagtgcttta cggcacctcg accccaaaaa acttgattag ggtgatggtt cacgtagtgg    2640
gccatcgccc tgatagacgg ttttcgccc tttgacgttg gagtccacgt tctttaatag    2700
tggactcttg ttccaaactg gaacaacact caaccctatc tcggtctatt cttttgattt    2760
ataagggatt ttgccgattt cggcctattg gttaaaaaat gagctgattt aacaaaaatt    2820
taacgcgaat tttaacaaaa tattaacgct tacaatttag gtggcacttt tcggggaaat    2880
gtgcgcggaa cccctatttg tttatttttc taaatacatt caaatatgta tccgctcatg    2940
agacaataac cctgataaat gcttcaataa tattgaaaaa ggaagagtat gagtattcaa    3000
catttccgtg tcgcccttat tcccttttt gcggcatttt gccttcctgt ttttgctcac    3060
ccagaaacgc tggtgaaagt aaaagatgct gaagatcagt tgggtgcacg agtgggttac    3120
atcgaactgg atctcaacag cggtaagatc cttgagagtt ttcgccccga agaacgtttt    3180
ccaatgatga gcacttttaa agttctgcta tgtggcgcgg tattatcccg tattgacgcc    3240
gggcaagagc aactcggtcg ccgcatacac tattctcaga atgacttggt tgagtactca    3300
ccagtcacag aaaagcatct tacgatggc atgacagtaa gagaattatg cagtgctgcc    3360
ataaccatga gtgataacac tgcggccaac ttacttctga caacgatcgg aggaccgaag    3420
gagctaaccg cttttttgca acatgggg gatcatgtaa ctcgccttga tcgttgggaa    3480
ccggagctga atgaagccat accaaacgac gagcgtgaca ccacgatgcc tgtagcaatg    3540
gcaacaacgt tgcgcaaact attaactggc gaactactta ctctagcttc ccggcaacaa    3600
ttaatagact ggatggaggc ggataaagtt gcaggaccac ttctgcgctc ggcccttccg    3660
gctggctggt ttattgctga taaatctgga gccggtgagc gtgggtctcg cggtatcatt    3720
gcagcactgg ggccagatgg taagccctcc cgtatcgtag ttatctacac gacggggagt    3780
caggcaacta tggatgaacg aaatagacag atcgctgaga taggtgcctc actgattaag    3840
cattggtaac tgtcagacca agtttactca tatatacttt agattgattt aaaacttcat    3900
ttttaattta aaaggatcta ggtgaagatc ctttttgata atctcatgac caaaatccct    3960
taacgtgagt tttcgttcca ctgagcgtca gaccccgtag aaaagatcaa aggatcttct    4020
tgagatcctt ttttctgcg cgtaatctgc tgcttgcaaa caaaaaaacc accgctacca    4080
gcggtggttt gtttgccgga tcaagagcta ccaactcttt ttccgaaggt aactggcttc    4140
agcagagcgc agataccaaa tactgttctt ctagtgtagc cgtagttagg ccaccacttc    4200
aagaactctg tagcaccgcc tacatacctc gctctgctaa tcctgttacc agtggctgct    4260
gccagtggcg ataagtcgtg tcttaccggg ttggactcaa gacgatagtt accggataag    4320
gcgcagcggt cgggctgaac ggggggttcg tgcacacagc ccagcttgga gcgaacgacc    4380
tacaccgaac tgagatacct acagcgtgag ctatgagaaa gcgccacgct tcccgaaggg    4440
agaaaggcgg acaggtatcc ggtaagcggc agggtcggaa caggagagcg cacgagggag    4500
cttccagggg gaaacgcctg gtatctttat agtcctgtcg gtttcgcca cctctgactt    4560 gagcgtcgat ttttgtgatg ctcgtcaggg gggcggagcc tatggaaaaa cgccagcaac    4620
```

```
gcggccttttt tacggttcct ggccttttgc tggccttttg ctcacatgtt ctttcctgcg   4680
ttatcccctg attctgtgga taaccgtatt accgcctttg agtgagctga taccgctcgc   4740
cgcagccgaa cgaccgagcg cagcgagtca gtgagcgagg aagcggaaga gcgcccaata   4800
cgcaaaccgc ctctccccgc gcgttggccg attcattaat gcagctggca cgacaggttt   4860
cccgactgga aagcgggcag tgagcgcaac gcaattaatg tgagttagct cactcattag   4920 gcacccagg  ctttacactt tatgcttccg gctcgtatgt tgtgtggaat tgtgagcgga   4980
taacaatttc acacaggaaa cagctatgac catgattacg ccagatttaa ttaaggcctt   5040
a                                                                   5041

<210> SEQ ID NO 13
<211> LENGTH: 5077
<212> TYPE: DNA
<213> ORGANISM: Artificial Sequence
<220> FEATURE:
<223> OTHER INFORMATION: Synthetic Polynucleotide

<400> SEQUENCE: 13
cgcgtcgaca ttgattattg actctggtcg ttacataact tacggtaaat ggcccgcctg     60
gctgaccgcc caacgacccc gcccattgac gtcaataatg acgtatgttc ccatagtaac    120
gccaataggg actttccatt gacgtcaatg ggtggagtat ttacggtaaa ctgcccactt    180
ggcagtacat caagtgtatc atatgccaag tacgccccct attgacgtca atgacggtaa    240
atggcccgcc tggcattatg cccagtacat gaccttatgg gactttccta cttggcagta    300
catctactcg aggccacgtt ctgcttcact ctccccatct ccccccctc cccacccca    360 attttgtatt tatttatttt ttaattattt tgtgcagcga tggggcggg ggggggggg    420 gggggggcgc gcgccaggcg gggcggggcg gggcgagggg cggggcgggg cgaggcggag    480
aggtgcggcg gcagccaatc agagcggcgc gctccgaaag tttccttta tggcgaggcg    540 gcggcggcg cggccctata aaaagcgaag cgcgcggcgg gcgggagcgg gatcagccac    600
cgcggtggcg gccctagagt cgatcgagga actgaaaaac cagaaagtta actggtaagt    660
ttagtctttt tgtcttttat ttcagtagca attcgaacgc tgacgtcatc aacccgctcc    720
aaggaatcgc gggcccagtg tcactaggcg ggaacaccca gcgcgcgtgc gccctggcag    780
gaagatggct gtgagggaca ggggagtggc gccctgcaat atttgcatgt cgctatgtgt    840
tctgggaaat caccataaac gtgaaatgtc tttggatttg ggaatcttat aagttctgta    900
tgagaccaca gatctcccga tcccctatgg tgcactctca gtacaatctg ctctgatgcc    960
gcataactag tctgcaggaa gacaatgtcc cggatccggt ggtggtgcaa atcaaagaac   1020
tgctcctcag tggatgttgc ctttacttct aggcctgtac ggaagtgtta cttctgctct   1080
aaaagctgcg gaattgtacc cgcggccgat ccaccggtcg ccaccatggt gagcaagggc   1140
gaggagctgt tcaccggggt ggtgcccatc ctggtcgagc tggacggcga cgtaaacggc   1200
cacaagttca gcgtgtccgg cgagggcgag ggcgatgcca cctacggcaa gctgaccctg   1260
aagttcatct gcaccaccgg caagctgccc gtgccctggc ccaccctcgt gaccaccctg   1320
acctacggcg tgcagtgctt cagccgctac cccgaccaca tgaagcagca cgacttcttc   1380
aagtccgcca tgcccgaagg ctacgtccag gagcgcacca tcttcttcaa ggacgacggc   1440
aactacaaga cccgcgccga ggtgaagttc gagggcgaca cctggtgaa ccgcatcgag   1500 ctgaagggca tcgacttcaa ggaggacggc aacatcctgg ggcacaagct ggagtacaac   1560
tacaacagcc acaacgtcta tatcatggcc gacaagcaga agaacggcat caaggtgaac   1620
```

```
ttcaagatcc gccacaacat cgaggacggc agcgtgcagc tcgccgacca ctaccagcag   1680
aacaccccca tcggcgacgg ccccgtgctg ctgcccgaca accactacct gagcacccag   1740
tccgccctga gcaaagaccc caacgagaag cgcgatcaca tggtcctgct ggagttcgtg   1800
accgccgccg ggatcactct cggcatggac gagctgtaca agtaaagcgg ccatcaagct   1860
tatcgatacc gtcgactaga gctcgctgat cagcctcgac tgtgccttct agttgccagc   1920
catctgttgt ttgcccctcc cccgtgcctt ccttgaccct ggaaggtgcc actcccactg   1980
tcctttccta ataaaatgag gaaattgcat cgcattgtct gagtaggtgt cattctattc   2040
tggggggtgg ggtggggcag gacagcaagg gggaggattg ggaagacaat taggtagata   2100
agtagcatgg cgggttaatc attaactaca aggaacccct agtgatggag ttggccactc   2160
cctctctgcg cgctcgctcg ctcactgagg cctactttca gtttctgaaa gtaggcacat   2220
gatgtaaaac atcatgtggc ctcagtgagc gagcgagcgc gcagttaatt aacctaattc   2280
actggccgtc gttttacaac gtcgtgactg ggaaaaccct ggcgttaccc aacttaatcg   2340
ccttgcagca catccccctt cgccagctg gcgtaatagc gaagaggccc gcaccgatcg   2400
cccttcccaa cagttgcgca gcctgaatgg cgaatgggac gcgccctgta gcggcgcatt   2460
aagcgcggcg ggtgtggtgg ttacgcgcag cgtgaccgct acacttgcca gcgccctagc   2520
gcccgctcct ttcgctttct tcccttcctt tctcgccacg ttcgccggct ttccccgtca   2580
agctctaaat cggggctcc ctttagggtt ccgatttagt gctttacggc acctcgaccc   2640
caaaaaactt gattagggtg atggttcacg tagtgggcca tcgccctgat agacggtttt   2700
tcgccctttg acgttggagt ccacgttctt taatagtgga ctcttgttcc aaactggaac   2760
aacactcaac cctatctcgg tctattcttt tgatttataa gggattttgc cgatttcggc   2820
ctattggtta aaaaatgagc tgatttaaca aaaatttaac gcgaatttta acaaaatatt   2880
aacgcttaca atttaggtgg cacttttcgg ggaaatgtgc gcggaacccc tatttgttta   2940
tttttctaaa tacattcaaa tatgtatccg ctcatgagac aataaccctg ataaatgctt   3000
caataatatt gaaaaaggaa gagtatgagt attcaacatt tccgtgtcgc ccttattccc   3060
ttttttgcgg cattttgcct tcctgttttt gctcacccag aaacgctggt gaaagtaaaa   3120
gatgctgaag atcagttggg tgcacgagtg ggttacatcg aactggatct caacagcggt   3180
aagatccttg agagttttcg ccccgaagaa cgttttccaa tgatgagcac ttttaaagtt   3240
ctgctatgtg gcgcggtatt atcccgtatt gacgccgggc aagagcaact cggtcgccgc   3300
atacactatt ctcagaatga cttggttgag tactcaccag tcacagaaaa gcatcttacg   3360
gatggcatga cagtaagaga attatgcagt gctgccataa ccatgagtga taacactgcg   3420
gccaacttac ttctgacaac gatcggagga ccgaaggagc taaccgcttt tttgcacaac   3480 atggggatc atgtaactcg ccttgatcgt tgggaaccgg agctgaatga agccatacca   3540
aacgacgagc gtgacaccac gatgcctgta gcaatgcaa caacgttgcg caaactatta   3600
actggcgaac tacttactct agcttcccgg caacaattaa tagactggat ggaggcggat   3660
aaagttgcag gaccacttct gcgctcggcc cttccggctg ctggttat tgctgataaa   3720 tctggagccg gtgagcgtgg gtctcgcggt atcattgcag cactgggcc agatggtaag   3780 ccctcccgta tcgtagttat ctacacgacg gggagtcagg caactatgga tgaacgaaat   3840
agacagatcg ctgagatagg tgcctcactg attaagcatt ggtaactgtc agaccaagtt   3900
tactcatata ctttagat tgatttaaaa cttcatttt aatttaaaag gatctaggtg   3960
```

```
aagatccttt ttgataatct catgaccaaa atcccttaac gtgagttttc gttccactga   4020
gcgtcagacc ccgtagaaaa gatcaaagga tcttcttgag atccttttt tctgcgcgta    4080 atctgctgct tgcaaacaaa aaaccaccg ctaccagcgg tggtttgttt gccggatcaa    4140
gagctaccaa ctcttttcc gaaggtaact ggcttcagca gagcgcagat accaaatact   4200
gttcttctag tgtagccgta gttaggccac cacttcaaga actctgtagc accgcctaca   4260
tacctcgctc tgctaatcct gttaccagtg gctgctgcca gtggcgataa gtcgtgtctt   4320
accgggttgg actcaagacg atagttaccg gataaggcgc agcggtcggg ctgaacgggg   4380
ggttcgtgca cacagcccag cttggagcga acgacctaca ccgaactgag atacctacag   4440
cgtgagctat gagaaagcgc cacgcttccc gaagggagaa aggcggacag gtatccggta   4500
agcggcaggg tcggaacagg agagcgcacg agggagcttc caggggggaaa cgcctggtat   4560 ctttatagtc ctgtcgggtt cgccacctc tgacttgagc gtcgattttt gtgatgctcg    4620 tcagggggc ggagcctatg gaaaaacgcc agcaacgcgg ccttttacg gttcctggcc    4680 ttttgctggc cttttgctca catgttcttt cctgcgttat cccctgattc tgtggataac   4740
cgtattaccg cctttgagtg agctgatacc gctcgccgca gccgaacgac cgagcgcagc   4800
gagtcagtga gcgaggaagc ggaagagcgc ccaatacgaa aaccgcctct ccccgcgcgt   4860
tggccgattc attaatgcag ctggcacgac aggtttcccg actggaaagc gggcagtgag   4920
cgcaacgcaa ttaatgtgag ttagctcact cattaggcac cccaggcttt acactttatg   4980
cttccggctc gtatgttgtg tggaattgtg agcggataac aatttcacac aggaaacagc   5040
tatgaccatg attacgccag atttaattaa ggcctta                            5077

<210> SEQ ID NO 14
<211> LENGTH: 5077
<212> TYPE: DNA
<213> ORGANISM: Artificial Sequence
<220> FEATURE:
<223> OTHER INFORMATION: Synthetic Polynucleotide

<400> SEQUENCE: 14
cgcgtcgaca ttgattattg actctggtcg ttacataact tacggtaaat ggcccgcctg     60
gctgaccgcc caacgacccc gcccattgac gtcaataatg acgtatgttc ccatagtaac    120
gccaataggg actttccatt gacgtcaatg ggtggagtat ttacggtaaa ctgcccactt    180
ggcagtacat caagtgtatc atatgccaag tacgccccct attgacgtca atgacggtaa    240
atggcccgcc tggcattatg cccagtacat gaccttatgg gactttccta cttggcagta    300
catctactcg aggccacgtt ctgcttcact ctccccatct ccccccctc ccacccca      360 attttgtatt tatttatttt ttaattattt tgtgcagcga tggggcggg ggggggggg     420 gggggggcgc gcgccaggcg gggcggggcg gggcgagggg cggggcgggg cgaggcggag    480
aggtgcggcg gcagccaatc agagcggcgc gctccgaaag tttccttta tggcgaggcg    540 gcggcggcg cggccctata aaaagcgaag cgcgcggcgg gcgggagcgg gatcagccac     600
cgcggtggcg gccctagagt cgatcgagga actgaaaaac cagaaagtta actggtaagt    660
ttagtctttt tgtctttat ttcagtagca attcgaacgc tgacgtcatc aacccgctcc    720
aaggaatcgc gggcccagtg tcactaggcg ggaacaccca gcgcgcgtgc gccctggcag    780
gaagatggct gtgagggaca ggggagtggc gccctgcaat atttgcatgt cgctatgtgt    840
tctgggaaat caccataaac gtgaaatgtc tttggatttg ggaatcttat aagttctgta    900
tgagaccaca gatctcccga tccctatgg tgcactctca gtacaatctg ctctgatgcc    960
```

```
gcataactag tctgcaggaa gacaatgtcc cggatccggt ggtggtgcaa atcaaagaac    1020
tgctcctcag tggatgttgc ctttacttct aggcctgtac ggaagtgtta cttctgctct    1080
aaaagctgcg gaattgtacc cgcggccgat ccaccggtcg ccaccatggt gagcaagggc    1140
gaggagctgt tcaccggggt ggtgcccatc ctggtcgagc tggacggcga cgtaaacggc    1200
cacaagttca gcgtgtccgg cgagggcgag ggcgatgcca cctacggcaa gctgaccctg    1260
aagttcatct gcaccaccgg caagctgccc gtgccctggc ccaccctcgt gaccaccctg    1320
acctacggcg tgcagtgctt cagccgctac cccgaccaca tgaagcagca cgacttcttc    1380
aagtccgcca tgcccgaagg ctacgtccag gagcgcacca tcttcttcaa ggacgacggc    1440
aactacaaga cccgcgccga ggtgaagttc gagggcgaca ccctggtgaa ccgcatcgag    1500
ctgaagggca tcgacttcaa ggaggacggc aacatcctgg ggcacaagct ggagtacaac    1560
tacaacagcc acaacgtcta tatcatggcc gacaagcaga agaacggcat caaggtgaac    1620
ttcaagatcc gccacaacat cgaggacggc agcgtgcagc tcgccgacca ctaccagcag    1680
aacaccccca tcggcgacgg ccccgtgctg ctgcccgaca accactacct gagcacccag    1740
tccgccctga gcaaagaccc caacgagaag cgcgatcaca tggtcctgct ggagttcgtg    1800
accgccgccg ggatcactct cggcatggac gagctgtaca agtaaagcgg ccatcaagct    1860
tatcgatacc gtcgactaga gctcgctgat cagcctcgac tgtgccttct agttgccagc    1920
catctgttgt ttgcccctcc cccgtgcctt ccttgaccct ggaaggtgcc actcccactg    1980
tcctttccta ataaaatgag gaaattgcat cgcattgtct gagtaggtgt cattctattc    2040
tggggggtgg ggtggggcag gacagcaagg gggaggattg ggaagacaat taggtagata    2100
agtagcatgg cgggttaatc attaactaca aggaacccct agtgatggag ttggccactc    2160
cctctctgcg cgctcgctcg ctcactgagg ccagatatct attttagata tctggcagaa    2220
tcccgaaacg ggattctggc ctcagtgagc gagcgagcgc gcagttaatt aacctaattc    2280
actggccgtc gttttacaac gtcgtgactg ggaaaaccct ggcgttaccc aacttaatcg    2340
ccttgcagca catcccccct tcgccagctg gcgtaatagc gaagaggccc gcaccgatcg    2400
cccttcccaa cagttgcgca gcctgaatgg cgaatgggac gcgccctgta gcggcgcatt    2460
aagcgcggcg ggtgtggtgg ttacgcgcag cgtgaccgct acacttgcca gcgccctagc    2520
gcccgctcct ttcgctttct tcccttcctt tctcgccacg ttcgccggct ttccccgtca    2580
agctctaaat cgggggctcc ctttagggtt ccgatttagt gctttacggc acctcgaccc    2640
caaaaaactt gattagggtg atggttcacg tagtgggcca tcgccctgat agacggtttt    2700
tcgccctttg acgttggagt ccacgttctt taatagtgga ctcttgttcc aaactggaac    2760
aacactcaac cctatctcgg tctattcttt tgatttataa gggattttgc cgatttcggc    2820
ctattggtta aaaaatgagc tgatttaaca aaaatttaac gcgaatttta acaaaatatt    2880
aacgcttaca atttaggtgg cacttttcgg ggaaatgtgc gcggaacccc tatttgttta    2940
tttttctaaa tacattcaaa tatgtatccg ctcatgagac aataaccctg ataaatgctt    3000
caataatatt gaaaaaggaa gagtatgagt attcaacatt tccgtgtcgc ccttattccc    3060
ttttttgcgg cattttgcct tcctgttttt gctcacccag aaacgctggt gaaagtaaaa    3120
gatgctgaag atcagttggg tgcacgagtg ggttacatcg aactggatct caacagcggt    3180
aagatccttg agagttttcg ccccgaagaa cgttttccaa tgatgagcac ttttaaagtt    3240
ctgctatgtg gcgcggtatt atcccgtatt gacgccgggc aagagcaact cggtcgccgc    3300
```

```
atacactatt ctcagaatga cttggttgag tactcaccag tcacagaaaa gcatcttacg    3360
gatggcatga cagtaagaga attatgcagt gctgccataa ccatgagtga taacactgcg    3420
gccaacttac ttctgacaac gatcggagga ccgaaggagc taaccgcttt tttgcacaac    3480 atggggatc atgtaactcg ccttgatcgt tgggaaccgg agctgaatga agccatacca     3540
aacgacgagc gtgacaccac gatgcctgta gcaatggcaa caacgttgcg caaactatta    3600
actggcgaac tacttactct agcttcccgg caacaattaa tagactggat ggaggcggat    3660
aaagttgcag gaccacttct gcgctcggcc cttccggctg gctggtttat tgctgataaa    3720
tctggagccg gtgagcgtgg gtctcgcggt atcattgcag cactgggcc agatggtaag     3780 ccctcccgta tcgtagttat ctacacgacg gggagtcagg caactatgga tgaacgaaat    3840
agacagatcg ctgagatagg tgcctcactg attaagcatt ggtaactgtc agaccaagtt    3900
tactcatata tactttagat tgatttaaaa cttcattttt aatttaaaag gatctaggtg    3960
aagatccttt ttgataatct catgaccaaa atcccttaac gtgagttttc gttccactga    4020
gcgtcagacc ccgtagaaaa gatcaaagga tcttcttgag atcctttttt tctgcgcgta    4080
atctgctgct tgcaaacaaa aaaaccaccg ctaccagcgg tggtttgttt gccggatcaa    4140
gagctaccaa ctcttttcc gaaggtaact ggcttcagca gagcgcagat accaaatact     4200
gttcttctag tgtagccgta gttaggccac cacttcaaga actctgtagc accgcctaca    4260
tacctcgctc tgctaatcct gttaccagtg ctgctgcca gtggcgataa gtcgtgtctt     4320
accgggttgg actcaagacg atagttaccg gataaggcgc agcggtcggg ctgaacgggg    4380
ggttcgtgca cacagcccag cttggagcga acgacctaca ccgaactgag atacctacag    4440
cgtgagctat gagaaagcgc cacgcttccc gaagggagaa aggcggacag gtatccggta    4500
agcggcaggg tcggaacagg agagcgcacg agggagcttc cagggggaaa cgcctggtat    4560
ctttatagtc ctgtcgggtt tcgccacctc tgacttgagc gtcgattttt gtgatgctcg    4620 tcagggggc ggagcctatg gaaaaacgcc agcaacgcgg cctttttacg gttcctggcc     4680
ttttgctggc cttttgctca catgttcttt cctgcgttat cccctgattc tgtggataac    4740
cgtattaccg cctttgagtg agctgatacc gctcgccgca gccgaacgac cgagcgcagc    4800
gagtcagtga gcgaggaagc ggaagagcgc ccaatacgca aaccgcctct ccccgcgcgt    4860
tggccgattc attaatgcag ctggcacgac aggtttcccg actggaaagc gggcagtgag    4920
cgcaacgcaa ttaatgtgag ttagctcact cattaggcac cccaggcttt acactttatg    4980
cttccggctc gtatgttgtg tggaattgtg agcggataac aatttcacac aggaaacagc    5040
tatgaccatg attacgccag atttaattaa ggcctta                             5077
```

<210> SEQ ID NO 15
<211> LENGTH: 5045
<212> TYPE: DNA
<213> ORGANISM: Artificial Sequence
<220> FEATURE:
<223> OTHER INFORMATION: Synthetic Polynucleotide

<400> SEQUENCE: 15

```
tagcaattcg aacgctgacg tcatcaaccc gctccaagga atcgcgggcc cagtgtcact      60
aggcgggaac acccagcgcg cgtgcgccct ggcaggaaga tggctgtgag ggacagggga    120
gtggcgccct gcaatatttg catgtcgcta tgtgttctgg gaaatcacca taaacgtgaa    180
atgtctttgg atttgggaat cttataagtt ctgtatgaga ccacagatct gactttcatc    240
tgtactacat tcaagagatg tagtacagat gaaagtcttt ttctagtctg caggaagaca    300
```

```
atagccgcgt cgacattgat tattgactct ggtcgttaca taacttacgg taaatggccc    360
gcctggctga ccgcccaacg accccgccca ttgacgtcaa taatgacgta tgttcccata    420
gtaacgccaa tagggacttt ccattgacgt caatgggtgg agtatttacg gtaaactgcc    480
cacttggcag tacatcaagt gtatcatatg ccaagtacgc ccctattga cgtcaatgac    540
ggtaaatggc ccgcctggca ttatgcccag tacatgacct tatgggactt tcctacttgg    600
cagtacatct actcgaggcc acgttctgct tcactctccc catctccccc cctccccac    660
ccccaatttt gtatttattt attttttaat tattttgtgc agcgatgggg gcggggggg    720
ggggggggg ggcgcgcgcc aggcggggcg gggcggggcg aggggcgggg cggggcgagg    780
cggagaggtg cggcggcagc caatcagagc ggcgcgctcc gaaagtttcc ttttatggcg    840
aggcggcggc ggcggcggcc ctataaaaag cgaagcgcgc ggcgggcggg agcgggatca    900
gccaccgcgg tggcggccct agagtcgatc gaggaactga aaaccagaa agttaactgg    960
taagtttagt cttttgtct tttatttcag gtcccggatc cggtggtggt gcaaatcaaa   1020
gaactgctcc tcagtggatg ttgcctttac ttctaggcct gtacggaagt gttacttctg   1080
ctctaaaagc tgcggaattg tacccgcggc cgatccaccg gtcgccacca tggtgagcaa   1140
gggcgaggag ctgttcaccg ggtggtgcc atcctggtc gagctggacg gcgacgtaaa   1200
cggccacaag ttcagcgtgt ccggcgaggg cgagggcgat gccacctacg gcaagctgac   1260
cctgaagttc atctgcacca ccggcaagct gcccgtgccc tggcccaccc tcgtgaccac   1320
cctgacctac ggcgtgcagt gcttcagccg ctaccccgac cacatgaagc agcacgactt   1380
cttcaagtcc gccatgcccg aaggctacgt ccaggagcgc accatcttct tcaaggacga   1440
cggcaactac aagacccgcg ccgaggtgaa gttcgagggc gacaccctgg tgaaccgcat   1500
cgagctgaag ggcatcgact tcaaggagga cggcaacatc ctggggcaca agctggagta   1560
caactacaac agccacaacg tctatatcat ggccgacaag cagaagaacg gcatcaaggt   1620
gaacttcaag atccgccaca acatcgagga cggcagcgtg cagctcgccg accactacca   1680
gcagaacacc cccatcggcg acggccccgt gctgctgccc gacaaccact acctgagcac   1740
ccagtccgcc ctgagcaaag accccaacga gaagcgcgat cacatggtcc tgctggagtt   1800
cgtgaccgcc gccgggatca ctctcggcat ggacgagctg tacaagtaaa gcggccatca   1860
agcttatcga taccgtcgac tagagctcgc tgatcagcct cgactgtgcc ttctagttgc   1920
cagccatctg ttgtttgccc ctcccccgtg ccttccttga ccctggaagg tgccactccc   1980
actgtccttt cctaataaaa tgaggaaatt gcatcgcatt gtctgagtag gtgtcattct   2040
attctggggg gtggggtggg gcaggacagc aaggggagg attgggaaga caattaggta   2100
gataagtagc atggcgggtt aatcattaac tacaaggaac ccctagtgat ggagttggcc   2160
actccctctc tgcgcgctcg ctcgctcact gaggccttca agagaggcct cagtgagcga   2220
gcgagcgcgc agttaattaa cctaattcac tggccgtcgt tttacaacgt cgtgactggg   2280
aaaaccctgg cgttacccaa cttaatcgcc ttgcagcaca tcccccttc gccagctggc   2340
gtaatagcga agaggcccgc accgatcgcc cttcccaaca gttgcgcagc ctgaatggcg   2400
aatgggacgc gccctgtagc ggcgcattaa gcgcggcggg tgtggtggtt acgcgcagcg   2460
tgaccgctac acttgccagc gccctagcgc ccgctccttt cgctttcttc ccttcctttc   2520
tcgccacgtt cgccggcttt ccccgtcaag ctctaaatcg gggctccct ttagggttcc   2580
gatttagtgc tttacggcac ctcgacccca aaaaacttga ttagggtgat ggttcacgta   2640
```

```
gtgggccatc gccctgatag acggttttc gcccttgac gttggagtcc acgttcttta      2700
atagtggact cttgttccaa actgaacaa cactcaaccc tatctcggtc tattcttttg     2760
atttataagg gattttgccg atttcggcct attggttaaa aaatgagctg atttaacaaa   2820
aatttaacgc gaattttaac aaaatattaa cgcttacaat ttaggtggca cttttcgggg    2880
aaatgtgcgc ggaacccta tttgtttatt tttctaaata cattcaaata tgtatccgct      2940
catgagacaa taaccctgat aaatgcttca ataatattga aaaggaaga gtatgagtat      3000
tcaacatttc cgtgtcgccc ttattccctt ttttgcggca ttttgccttc ctgttttgc     3060
tcacccagaa acgctggtga agtaaaaga tgctgaagat cagttgggtg cacgagtggg     3120
ttacatcgaa ctggatctca acagcggtaa gatccttgag agttttcgcc ccgaagaacg    3180
ttttccaatg atgagcactt ttaaagttct gctatgtggc gcggtattat cccgtattga    3240
cgccgggcaa gagcaactcg gtcgccgcat acactattct cagaatgact tggttgagta    3300
ctcaccagtc acagaaaagc atcttacgga tggcatgaca gtaagagaat tatgcagtgc    3360
tgccataacc atgagtgata acactgcggc caacttactt ctgacaacga tcggaggacc    3420
gaaggagcta accgcttttt tgcacaacat gggggatcat gtaactcgcc ttgatcgttg    3480
ggaaccggag ctgaatgaag ccataccaaa cgacgagcgt gacaccacga tgcctgtagc    3540
aatggcaaca acgttgcgca aactattaac tggcgaacta cttactctag cttcccggca    3600
acaattaata gactggatgg aggcggataa agttgcagga ccacttctgc gctcggccct    3660
tccggctggc tggtttattg ctgataaatc tggagccggt gagcgtgggt ctcgcggtat    3720
cattgcagca ctggggccag atggtaagcc ctcccgtatc gtagttatct acacgacggg    3780
gagtcaggca actatggatg aacgaaatag acagatcgct gagataggtg cctcactgat    3840
taagcattgg taactgtcag accaagttta ctcatatata ctttagattg atttaaaact    3900
tcatttttaa tttaaaagga tctaggtgaa gatcctttt gataatctca tgaccaaaat    3960
cccttaacgt gagttttcgt tccactgagc gtcagacccc gtagaaaaga tcaaaggatc    4020
ttcttgagat cctttttttc tgcgcgtaat ctgctgcttg caaacaaaaa aaccaccgct    4080
accagcggtg gtttgtttgc cggatcaaga gctaccaact ctttttccga aggtaactgg    4140
cttcagcaga gcgcagatac caaatactgt tcttctagtg tagccgtagt taggccacca    4200
cttcaagaac tctgtagcac cgcctacata cctcgctctg ctaatcctgt taccagtggc    4260
tgctgccagt ggcgataagt cgtgtcttac cgggttggac tcaagacgat agttaccgga    4320
taaggcgcag cggtcgggct gaacggggg ttcgtgcaca cagcccagct tggagcgaac    4380
gacctacacc gaactgagat acctacagcg tgagctatga gaaagcgcca cgcttcccga    4440
agggagaaag gcggacaggt atccggtaag cggcagggtc ggaacaggag agcgcacgag    4500
ggagcttcca gggggaaacg cctggtatct ttatagtcct gtcgggtttc gccacctctg    4560
acttgagcgt cgatttttgt gatgctcgtc aggggggcgg agcctatgga aaaacgccag    4620
caacgcggcc ttttacggt tcctggcctt ttgctggcct tttgctcaca tgttctttcc    4680
tgcgttatcc cctgattctg tggataaccg tattaccgcc tttgagtgag ctgataccgc    4740
tcgccgcagc cgaacgaccg agcgcagcga gtcagtgagc gaggaagcgg aagagcgccc    4800
aatacgcaaa ccgcctctcc ccgcgcgttg gccgattcat taatgcagct ggcacgacag    4860
gtttcccgac tggaaagcgg gcagtgagcg caacgcaatt aatgtgagtt agctcactca    4920
ttaggcaccc caggctttac actttatgct tccggctcgt atgttgtgtg gaattgtgag    4980
cggataacaa tttcacacag gaaacagcta tgaccatgat tacgccagat ttaattaagg    5040
``` cctta                                                                  5045

<210> SEQ ID NO 16
<211> LENGTH: 5081
<212> TYPE: DNA
<213> ORGANISM: Artificial Sequence
<220> FEATURE:
<223> OTHER INFORMATION: Synthetic Polynucleotide

<400> SEQUENCE: 16
tagcaattcg aacgctgacg tcatcaaccc gctccaagga atcgcgggcc cagtgtcact      60
aggcgggaac acccagcgcg cgtgcgccct ggcaggaaga tggctgtgag ggacagggga     120
gtggcgccct gcaatatttg catgtcgcta tgtgttctgg gaaatcacca taaacgtgaa     180
atgtctttgg atttgggaat cttataagtt ctgtatgaga ccacagatct gactttcatc     240
tgtactacat tcaagagatg tagtacagat gaaagtcttt ttctagtctg caggaagaca     300
atagccgcgt cgacattgat tattgactct ggtcgttaca taacttacgg taaatggccc     360
gcctggctga ccgcccaacg accccgccca ttgacgtcaa taatgacgta tgttcccata     420
gtaacgccaa tagggacttt ccattgacgt caatgggtgg agtatttacg gtaaactgcc     480
cacttggcag tacatcaagt gtatcatatg ccaagtacgc ccctattga cgtcaatgac      540
ggtaaatggc ccgcctggca ttatgcccag tacatgacct tatgggactt tcctacttgg     600
cagtacatct actcgaggcc acgttctgct tcactctccc catctccccc cctccccac      660
ccccaatttt gtatttattt attttttaat tattttgtgc agcgatgggg gcggggggg      720
ggggggggg gcgcgcgcc aggcggggcg gggcggggcg agggcgggg cggggcgagg        780
cggagaggtg cggcggcagc caatcagagc ggcgcgctcc gaaagtttcc ttttatggcg     840
aggcggcggc ggcggcggcc ctataaaaag cgaagcgcgc ggcgggcggg agcgggatca     900
gccaccgcgg tggcggccct agagtcgatc gaggaactga aaaaccagaa agttaactgg     960
taagtttagt cttttttgtct ttatttcag gtcccggatc cggtggtggt gcaaatcaaa    1020
gaactgctcc tcagtggatg ttgcctttac ttctaggcct gtacgaagt gttacttctg     1080
ctctaaaagc tgcggaattg tacccgcggc cgatccaccg gtcgccacca tggtgagcaa     1140
gggcgaggag ctgttcaccg gggtggtgcc catcctggtc gagctggacg gcgacgtaaa    1200
cggccacaag ttcagcgtgt ccggcgaggg cgagggcgat gccacctacg gcaagctgac    1260
cctgaagttc atctgcacca ccggcaagct gcccgtgccc tggcccaccc tcgtgaccac    1320
cctgacctac ggcgtgcagt gcttcagccg ctacccgac cacatgaagc agcacgactt    1380
cttcaagtcc gccatgcccg aaggctacgt ccaggagcgc accatcttct tcaaggacga    1440
cggcaactac aagacccgcg ccgaggtgaa gttcgagggc gacaccctgg tgaaccgcat    1500
cgagctgaag ggcatcgact tcaaggagga cggcaacatc ctggggcaca agctggagta    1560
caactacaac agccacaacg tctatatcat ggccgacaag cagaagaacg gcatcaaggt    1620
gaacttcaag atccgccaca acatcgagga cggcagcgtg cagctcgccg accactacca    1680
gcagaacacc cccatcggcg acggccccgt gctgctgccc gacaaccact acctgagcac    1740
ccagtccgcc ctgagcaaag accccaacga gaagcgcgat cacatggtcc tgctggagtt    1800
cgtgaccgcc gccgggatca ctctcggcat ggacgagctg tacaagtaaa gcggccatca    1860
agcttatcga taccgtcgac tagagctcgc tgatcagcct cgactgtgcc ttctagttgc    1920
cagccatctg ttgtttgccc ctccccgtg ccttccttga ccctggaagg tgccactccc     1980

```
actgtccttt cctaataaaa tgaggaaatt gcatcgcatt gtctgagtag gtgtcattct    2040
attctggggg gtggggtggg gcaggacagc aaggggagg attgggaaga caattaggta     2100
gataagtagc atggcgggtt aatcattaac tacaaggaac ccctagtgat ggagttggcc    2160
actccctctc tgcgcgctcg ctcgctcact gaggcctact ttcagtttct gaaagtaggc    2220
acatgatgta aaacatcatg tggcctcagt gagcgagcga gcgcgcagtt aattaaccta    2280
attcactggc cgtcgtttta caacgtcgtg actgggaaaa ccctggcgtt acccaactta    2340
atcgccttgc agcacatccc cctttcgcca gctggcgtaa tagcgaagag gcccgcaccg    2400 atcgccttc ccaacagttg cgcagcctga atggcgaatg ggacgcgccc tgtagcggcg    2460
cattaagcgc ggcgggtgtg gtggttacgc gcagcgtgac cgctacactt gccagcgccc    2520
tagcgcccgc tcctttcgct ttcttccctt cctttctcgc cacgttcgcc ggctttcccc    2580
gtcaagctct aaatcggggg ctccctttag ggttccgatt tagtgcttta cggcacctcg    2640
accccaaaaa acttgattag ggtgatggtt cacgtagtgg gccatcgccc tgatagacgg    2700
tttttcgccc tttgacgttg gagtccacgt tctttaatag tggactcttg ttccaaactg    2760
gaacaacact caaccctatc tcggtctatt cttttgattt ataagggatt ttgccgattt    2820
cggcctattg gttaaaaaat gagctgattt aacaaaaatt taacgcgaat tttaacaaaa    2880
tattaacgct tacaatttag gtggcacttt tcggggaaat gtgcgcggaa cccctatttg    2940
tttatttttc taaatacatt caaatatgta tccgctcatg agacaataac cctgataaat    3000
gcttcaataa tattgaaaaa ggaagagtat gagtattcaa catttccgtg tcgcccttat    3060
tccctttttt gcggcatttt gccttcctgt ttttgctcac ccagaaacgc tggtgaaagt    3120
aaaagatgct gaagatcagt tgggtgcacg agtgggttac atcgaactgg atctcaacag    3180
cggtaagatc cttgagagtt ttcgccccga agaacgtttt ccaatgatga gcacttttaa    3240
agttctgcta tgtggcgcgg tattatcccg tattgacgcc gggcaagagc aactcggtcg    3300
ccgcatacac tattctcaga atgacttggt tgagtactca ccagtcacag aaaagcatct    3360
tacggatggc atgacagtaa gagaattatg cagtgctgcc ataaccatga gtgataacac    3420
tgcggccaac ttacttctga caacgatcgg aggaccgaag gagctaaccg cttttttgca    3480
caacatgggg gatcatgtaa ctcgccttga tcgttgggaa ccggagctga atgaagccat    3540
accaaacgac gagcgtgaca ccacgatgcc tgtagcaatg gcaacaacgt tgcgcaaact    3600
attaactggc gaactactta ctctagcttc ccggcaacaa ttaatagact ggatggaggc    3660
ggataaagtt gcaggaccac ttctgcgctc ggcccttccg gctggctggt ttattgctga    3720
taaatctgga gccggtgagc gtgggtctcg cggtatcatt gcagcactgg ggccagatgg    3780
taagccctcc cgtatcgtag ttatctacac gacggggagt caggcaacta tggatgaacg    3840
aaatagacag atcgctgaga taggtgcctc actgattaag cattggtaac tgtcagacca    3900
agtttactca tatatacttt agattgattt aaaacttcat ttttaattta aaaggatcta    3960
ggtgaagatc cttttgata atctcatgac caaaatccct taacgtgagt tttcgttcca    4020
ctgagcgtca gaccccgtag aaaagatcaa aggatcttct tgagatcctt ttttctgcg    4080 cgtaatctgc tgcttgcaaa caaaaaaacc accgctacca gcggtggttt gtttgccgga    4140
tcaagagcta ccaactcttt ttccgaaggt aactggcttc agcagagcgc agataccaaa    4200
tactgttctt ctagtgtagc cgtagttagg ccaccacttc aagaactctg tagcaccgcc    4260
tacatacctc gctctgctaa tcctgttacc agtggctgct gccagtggcg ataagtcgtg    4320
tcttaccggg ttggactcaa gacgatagtt accggataag cgcagcggt cgggctgaac    4380
```

```
gggggggttcg tgcacacagc ccagcttgga gcgaacgacc tacaccgaac tgagatacct    4440
acagcgtgag ctatgagaaa gcgccacgct tcccgaaggg agaaaggcgg acaggtatcc    4500
ggtaagcggc agggtcggaa caggagagcg cacgagggag cttccagggg gaaacgcctg    4560
gtatctttat agtcctgtcg ggtttcgcca cctctgactt gagcgtcgat ttttgtgatg    4620
ctcgtcaggg gggcggagcc tatggaaaaa cgccagcaac gcggcctttt tacggttcct    4680
ggccttttgc tggccttttg ctcacatgtt ctttcctgcg ttatcccctg attctgtgga    4740
taaccgtatt accgcctttg agtgagctga taccgctcgc cgcagccgaa cgaccgagcg    4800
cagcgagtca gtgagcgagg aagcggaaga gcgcccaata cgcaaaccgc ctctccccgc    4860
gcgttggccg attcattaat gcagctggca cgacaggttt cccgactgga aagcgggcag    4920
tgagcgcaac gcaattaatg tgagttagct cactcattag gcaccccagg ctttacactt    4980
tatgcttccg gctcgtatgt tgtgtggaat tgtgagcgga taacaatttc acacaggaaa    5040
cagctatgac catgattacg ccagatttaa ttaaggcctt a                        5081

<210> SEQ ID NO 17
<211> LENGTH: 5138
<212> TYPE: DNA
<213> ORGANISM: Artificial Sequence
<220> FEATURE:
<223> OTHER INFORMATION: Synthetic Polynucleotide

<400> SEQUENCE: 17
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctactcg aggccacgtt ctgcttcact ctccccatct cccccccctc cccaccccca     360
attttgtatt tatttatttt ttaattatt tgtgcagcga tggggcgggg ggggggggg     420 gggggggcgc gcgccaggcg gggcggggcg gggcgagggg cggggcgggg cgaggcggag     480
aggtgcggcg gcagccaatc agagcggcgc gctccgaaag tttccttttta tggcgaggcg     540 gcggcggcgc cggccctata aaaagcgaag cgcgcggcgg gcgggagcgg gatcagccac     600
cgcggtggcg gccctagagt cgatcgagga actgaaaaac cagaaagtta actggtaagt     660
ttagtctttt tgtctttat ttcagaattc cccagtggaa agacgcgcag gcaaaacgca     720
ccacgtgacg gagcgtgacc gcgcgccgag cgcgcgccaa ggtcgggcag gaagagggcc     780
tatttcccat gattccttca tatttgcata tacgatacaa ggctgttaga gagataatta     840
gaattaattt gactgtaaac acaaagatat tagtacaaaa tacgtgacgt agaaagtaat     900
aatttcttgg gtagtttgca gttttaaaat tatgttttaa aatggactat catatgctta     960
ccgtaacttg aaagtatttc gatttcttgg gtttatatat cttgtggaaa ggacgcggga    1020
tcccgcttac gctgagtact tcgattcaag agatcgaagt actcagcgta agttttttcc    1080
aaagtcccgg atccggtggt ggtgcaaatc aaagaactgc tcctcagtgg atgttgcctt    1140
tacttctagg cctgtacgga agtgttactt ctgctctaaa agctgcggaa ttgtacccgc    1200
ggccgatcca ccggtcgcca ccatggtgag caagggcgag gagctgttca ccggggtggt    1260
gcccatcctg gtcgagctgg acggcgacgt aaacggccac aagttcagcg tgtccggcga    1320
```

```
gggcgagggc gatgccacct acggcaagct gaccctgaag ttcatctgca ccaccggcaa    1380
gctgcccgtg ccctggccca ccctcgtgac caccctgacc tacggcgtgc agtgcttcag    1440
ccgctacccc gaccacatga agcagcacga cttcttcaag tccgccatgc ccgaaggcta    1500
cgtccaggag cgcaccatct tcttcaagga cgacggcaac tacaagaccc gcgccgaggt    1560
gaagttcgag ggcgacaccc tggtgaaccg catcgagctg aagggcatcg acttcaagga    1620
ggacggcaac atcctggggc acaagctgga gtacaactac aacagccaca acgtctatat    1680
catggccgac aagcagaaga acggcatcaa ggtgaacttc aagatccgcc acaacatcga    1740
ggacggcagc gtgcagctcg ccgaccacta ccagcagaac ccccatcg gcgacggccc     1800
cgtgctgctg cccgacaacc actacctgag cacccagtcc gccctgagca agacccaa     1860
cgagaagcgc gatcacatgg tcctgctgga gttcgtgacc gccgccggga tcactctcgg    1920
catggacgag ctgtacaagt aaagcggcca tcaagcttat cgataccgtc gactagagct    1980
cgctgatcag cctcgactgt gccttctagt tgccagccat ctgttgtttg cccctccccc    2040
gtgccttcct tgaccctgga aggtgccact cccactgtcc tttcctaata aaatgaggaa    2100
attgcatcgc attgtctgag taggtgtcat tctattctgg ggggtggggt gggcaggac    2160
agcaagggg aggattggga agacaattag gtagataagt agcatggcgg ttaatcatt    2220
aactacaagg aacccctagt gatggagttg gccactccct ctctgcgcgc tcgctcgctc    2280
actgaggcct tcaagagagg cctcagtgag cgagcgagcg cgcagttaat taacctaatt    2340
cactggccgt cgttttacaa cgtcgtgact gggaaaaccc tggcgttacc caacttaatc    2400
gccttgcagc acatccccct ttcgccagct ggcgtaatag cgaagaggcc cgcaccgatc    2460
gcccttccca acagttgcgc agcctgaatg gcgaatggga cgcgccctgt agcggcgcat    2520
taagcgcggg gggtgtggtg gttacgcgca gcgtgaccgc tacacttgcc agcgccctag    2580
cgcccgctcc tttcgctttc ttcccttcct ttctcgccac gttcgccggc tttccccgtc    2640
aagctctaaa tcgggggctc cctttagggt tccgatttag tgctttacgg cacctcgacc    2700
ccaaaaaact tgattagggt gatggttcac gtagtgggcc atcgccctga tagacggttt    2760
ttcgcccttt gacgttggag tccacgttct ttaatagtgg actcttgttc caaactggaa    2820
caacactcaa ccctatctcg gtctattctt ttgatttata agggattttg ccgatttcgg    2880
cctattggtt aaaaaatgag ctgatttaac aaaaatttaa cgcgaatttt aacaaaatat    2940
taacgcttac aatttaggtg cacttttcg gggaaatgtg cgcggaaccc ctatttgttt    3000
attttttctaa atacattcaa atatgtatcc gctcatgaga caataaccct gataaatgct    3060
tcaataatat tgaaaaagga agagtatgag tattcaacat ttccgtgtcg cccttattcc    3120
cttttttgcg cattttgcc ttcctgtttt tgctcaccca gaaacgctgg tgaaagtaaa    3180
agatgctgaa gatcagttgg gtgcacgagt gggttacatc gaactggatc tcaacagcgg    3240
taagatcctt gagagttttc gccccgaaga acgttttcca atgatgagca cttttaaagt    3300
tctgctatgt ggcgcggtat tatcccgtat tgacgccggg caagagcaac tcggtcgccg    3360
catacactat tctcagaatg acttggttga gtactcacca gtcacagaaa agcatcttac    3420
ggatggcatg acagtaagag aattatgcag tgctgccata accatgagtg ataacactgc    3480
ggccaactta cttctgacaa cgatcggagg accgaaggag ctaaccgctt ttttgcacaa    3540
catgggggat catgtaactc gccttgatcg ttgggaaccg gagctgaatg aagccatacc    3600
aaacgacgag cgtgacacca cgatgcctgt agcaatggca acaacgttgc gcaaactatt    3660
aactggcgaa ctacttactc tagcttcccg gcaacaatta atagactgga tggaggcgga    3720
```

```
taaagttgca ggaccacttc tgcgctcggc ccttccggct ggctggttta ttgctgataa    3780
atctggagcc ggtgagcgtg ggtctcgcgg tatcattgca gcactggggc cagatggtaa    3840
gccctcccgt atcgtagtta tctacacgac ggggagtcag gcaactatgg atgaacgaaa    3900
tagacagatc gctgagatag gtgcctcact gattaagcat tggtaactgt cagaccaagt    3960
ttactcatat atactttaga ttgatttaaa acttcatttt taatttaaaa ggatctaggt    4020
gaagatcctt tttgataatc tcatgaccaa atcccttaa cgtgagtttt cgttccactg     4080
agcgtcagac cccgtagaaa agatcaaagg atcttcttga tcctttttt ttctgcgcgt     4140
aatctgctgc ttgcaaacaa aaaaaccacc gctaccagcg gtggtttgtt tgccggatca    4200
agagctacca actcttttc cgaaggtaac tggcttcagc agagcgcaga taccaaatac     4260
tgttcttcta gtgtagccgt agttaggcca ccacttcaag aactctgtag caccgcctac    4320
atacctcgct ctgctaatcc tgttaccagt ggctgctgcc agtggcgata gtcgtgtct    4380
taccggttg gactcaagac gatagttacc ggataaggcg cagcggtcgg gctgaacggg     4440
gggttcgtgc acacagccca gcttggagcg aacgacctac accgaactga gatacctaca    4500
gcgtgagcta tgagaaagcg ccacgcttcc cgaagggaga aaggcggaca ggtatccggt    4560
aagcggcagg gtcggaacag gagagcgcac gagggagctt ccagggggaa acgcctggta    4620
tctttatagt cctgtcgggt ttcgccacct ctgacttgag cgtcgatttt tgtgatgctc    4680
gtcagggggg cggagcctat ggaaaaacgc cagcaacgcg gcctttttac ggttcctggc    4740
cttttgctgg ccttttgctc acatgttctt cctgcgtta tcccctgatt ctgtggataa    4800
ccgtattacc gcctttgagt gagctgatac cgctcgccgc agccgaacga ccgagcgcag    4860
cgagtcagtg agcgaggaag cggaagagcg cccaatacgc aaaccgcctc tccccgcgcg    4920
ttggccgatt cattaatgca gctggcacga caggtttccc gactggaaag cgggcagtga    4980
gcgcaacgca attaatgtga gttagctcac tcattaggca ccccaggctt tacactttat    5040
gcttccggct cgtatgttgt gtggaattgt gagcggataa caatttcaca caggaaacag    5100
ctatgaccat gattacgcca gatttaatta aggcctta                            5138
```

<210> SEQ ID NO 18
<211> LENGTH: 5174
<212> TYPE: DNA
<213> ORGANISM: Artificial Sequence
<220> FEATURE:
<223> OTHER INFORMATION: Synthetic Polynucleotide

<400> SEQUENCE: 18

```
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacgtaa     240
atggcccgcc tggcattatg cccagtacat gaccttatgg actttcctta cttggcagta    300
catctactcg aggccacgtt ctgcttcact ctccccatct ccccccctc cccaccccca     360
attttgtatt tatttatttt ttaattattt tgtgcagcga tggggggcggg gggggggggg    420
ggggggcgc gcgccaggcg gggcggggcg gggcgagggg cggggcgggg cgaggcggag     480
aggtgcggcg gcagccaatc agagcggcgc gctccgaaag tttccttta tggcgaggcg    540
gcggcggcgg cggccctata aaaagcgaag cgcgcggcgg gcgggagcgg gatcagccac    600
```

```
cgcggtggcg gccctagagt cgatcgagga actgaaaaac cagaaagtta actggtaagt       660 ttagtcttttt tgtctttat ttcagaattc cccagtggaa agacgcgcag gcaaaacgca        720
ccacgtgacg gagcgtgacc gcgcgccgag cgcgcgccaa ggtcgggcag gaagagggcc        780
tatttcccat gattccttca tatttgcata tacgatacaa ggctgttaga gagataatta        840
gaattaattt gactgtaaac acaaagatat tagtacaaaa tacgtgacgt agaaagtaat        900
aatttcttgg gtagtttgca gttttaaaat tatgttttaa aatggactat catatgctta        960
ccgtaacttg aaagtatttc gatttcttgg gtttatatat cttgtggaaa ggacgcggga       1020
tcccgcttac gctgagtact tcgattcaag agatcgaagt actcagcgta agttttttcc       1080
aaagtcccgg atccggtggt ggtgcaaatc aaagaactgc tcctcagtgg atgttgcctt       1140
tacttctagg cctgtacgga agtgttactt ctgctctaaa agctgcggaa ttgtacccgc       1200
ggccgatcca ccggtcgcca ccatggtgag caagggcgag gagctgttca ccggggtggt       1260
gcccatcctg gtcgagctgg acggcgacgt aaacggccac aagttcagcg tgtccggcga       1320
gggcgagggc gatgccacct acggcaagct gaccctgaag ttcatctgca ccaccggcaa       1380
gctgcccgtg ccctggccca ccctcgtgac caccctgacc tacggcgtgc agtgcttcag       1440
ccgctacccc gaccacatga agcagcacga cttcttcaag tccgccatgc ccgaaggcta       1500
cgtccaggag cgcaccatct tcttcaagga cgacggcaac tacaagaccc gcgccgaggt       1560
gaagttcgag ggcgacaccc tggtgaaccg catcgagctg aagggcatcg acttcaagga       1620
ggacggcaac atcctggggc acaagctgga gtacaactac aacagccaca acgtctatat       1680
catggccgac aagcagaaga acggcatcaa ggtgaacttc aagatccgcc acaacatcga       1740
ggacggcagc gtgcagctcg ccgaccacta ccagcagaac ccccccatcg gcgacggccc       1800
cgtgctgctg cccgacaacc actacctgag cacccagtcc gccctgagca agacccccaa       1860
cgagaagcgc gatcacatgg tcctgctgga gttcgtgacc gccgccggga tcactctcgg       1920
catggacgag ctgtacaagt aaagcggcca tcaagcttat cgataccgtc gactagagct       1980
cgctgatcag cctcgactgt gccttctagt tgccagccat ctgttgtttg cccctcccc       2040 gtgccttcct tgaccctgga aggtgccact cccactgtcc tttcctaata aaatgaggaa       2100
attgcatcgc attgtctgag taggtgtcat tctattctgg ggggtggggt ggggcaggac       2160 agcaagggg aggattggga agacaattag gtagataagt agcatggcgg gttaatcatt       2220
aactacaagg aaccctagt gatggagttg gccactccct ctctgcgcgc tcgctcgctc       2280
actgaggcct acttttcagtt tctgaaagta ggcacatgat gtaaaacatc atgtggcctc       2340
agtgagcgag cgagcgcgca gttaattaac ctaattcact ggccgtcgtt ttacaacgtc       2400
gtgactggga aaaccctggc gttacccaac ttaatcgcct tgcagcacat ccccctttcg       2460
ccagctggcg taatagcgaa gaggcccgca ccgatcgccc ttcccaacag ttgcgcagcc       2520
tgaatggcga atgggacgcg ccctgtagcg gcgcattaag cgcggcgggt gtggtggtta       2580
cgcgcagcgt gaccgctaca cttgccagcg ccctagcgcc cgctccttc gctttcttcc       2640 cttcctttct cgccacgttc gccggctttc cccgtcaagc tctaaatcgg ggctcccttt       2700 agggttccg atttagtgct ttacggcacc tcgacccaa aaaacttgat tagggtgatg       2760
gttcacgtag tgggccatcg ccctgataga cggttttcg ccctttgacg ttggagtcca       2820
cgttctttaa tagtggactc ttgttccaaa ctggaacaac actcaaccct atctcggtct       2880
attcttttga tttataaggg attttgccga tttcggccta ttggttaaaa aatgagctga       2940
tttaacaaaa atttaacgcg aattttaaca aaatattaac gcttacaatt taggtggcac       3000
```

```
ttttcgggga aatgtgcgcg gaacccctat tgtttatttt ttctaaatac attcaaatat    3060
gtatccgctc atgagacaat aaccctgata aatgcttcaa taatattgaa aaaggaagag    3120
tatgagtatt caacatttcc gtgtcgccct tattcccttt tttgcggcat tttgccttcc    3180
tgtttttgct cacccagaaa cgctggtgaa agtaaaagat gctgaagatc agttgggtgc    3240
acgagtgggt tacatcgaac tggatctcaa cagcggtaag atccttgaga gttttcgccc    3300
cgaagaacgt tttccaatga tgagcacttt taaagttctg ctatgtggcg cggtattatc    3360
ccgtattgac gccgggcaag agcaactcgg tcgccgcata cactattctc agaatgactt    3420
ggttgagtac tcaccagtca cagaaaagca tcttacggat ggcatgacag taagagaatt    3480
atgcagtgct gccataacca tgagtgataa cactgcggcc aacttacttc tgacaacgat    3540
cggaggaccg aaggagctaa ccgcttttttt gcacaacatg ggggatcatg taactcgcct    3600
tgatcgttgg gaaccggagc tgaatgaagc cataccaaac gacgagcgtg acaccacgat    3660
gcctgtagca atggcaacaa cgttgcgcaa actattaact ggcgaactac ttactctagc    3720
ttcccggcaa caattaatag actggatgga ggcggataaa gttgcaggac cacttctgcg    3780
ctcggccctt ccggctggct ggtttattgc tgataaatct ggagccggtg agcgtgggtc    3840
tcgcggtatc attgcagcac tggggccaga tggtaagccc tcccgtatcg tagttatcta    3900
cacgacgggg agtcaggcaa ctatggatga acgaaataga cagatcgctg agataggtgc    3960
ctcactgatt aagcattggt aactgtcaga ccaagtttac tcatatatac tttagattga    4020
tttaaaactt catttttaat ttaaaaggat ctaggtgaag atcctttttg ataatctcat    4080
gaccaaaatc ccttaacgtg agttttcgtt ccactgagcg tcagaccccg tagaaaagat    4140
caaaggatct tcttgagatc ctttttttct gcgcgtaatc tgctgcttgc aaacaaaaaa    4200
accaccgcta ccagcggtgg tttgtttgcc ggatcaagag ctaccaactc tttttccgaa    4260
ggtaactggc ttcagcagag cgcagatacc aaatactgtt cttctagtgt agccgtagtt    4320
aggccaccac ttcaagaact ctgtagcacc gcctacatac ctcgctctgc taatcctgtt    4380
accagtggct gctgccagtg gcgataagtc gtgtcttacc gggttggact caagacgata    4440
gttaccggat aaggcgcagc ggtcgggctg aacggggggt tcgtgcacac agcccagctt    4500
ggagcgaacg acctacaccg aactgagata cctacagcgt gagctatgag aaagcgccac    4560
gcttcccgaa gggagaaagg cggacaggta tccggtaagc ggcagggtcg gaacaggaga    4620
gcgcacgagg gagcttccag ggggaaacgc ctggtatctt tatagtcctg tcgggtttcg    4680
ccacctctga cttgagcgtc gatttttgtg atgctcgtca ggggggcgga gcctatggaa    4740
aaacgccagc aacgcggcct ttttacggtt cctggccttt tgctggcctt ttgctcacat    4800
gttctttcct gcgttatccc ctgattctgt ggataaccgt attaccgcct ttgagtgagc    4860
tgataccgct cgccgcagcc gaacgaccga gcgcagcgag tcagtgagcg aggaagcgga    4920
agagcgccca atacgcaaac cgcctctccc cgcgcgttgg ccgattcatt aatgcagctg    4980
gcacgacagg tttcccgact ggaaagcggg cagtgagcgc aacgcaatta atgtgagtta    5040
gctcactcat taggcacccc aggctttaca ctttatgctt ccggctcgta tgttgtgtgg    5100
aattgtgagc ggataacaat ttcacacagg aaacagctat gaccatgatt acgccagatt    5160
taattaaggc ctta                                                      5174

<210> SEQ ID NO 19
<211> LENGTH: 5174
<212> TYPE: DNA
```

<213> ORGANISM: Artificial Sequence
<220> FEATURE:
<223> OTHER INFORMATION: Synthetic Polynucleotide

<400> SEQUENCE: 19

```
cgcgtcgaca ttgattattg actctggtcg ttacataact tacggtaaat ggcccgcctg      60
gctgaccgcc caacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctactcg aggccacgtt ctgcttcact ctccccatct ccccccctc cccaccccca      360
attttgtatt tatttatttt ttaattattt tgtgcagcga tggggcggg ggggggggg       420
gggggggcgc gcgccaggcg gggcggggcg gggcgagggg cggggcgggg cgaggcggag     480
aggtgcggcg gcagccaatc agagcggcgc gctccgaaag tttcctttta tggcgaggcg     540
gcggcggcgg cggccctata aaagcgaag cgcgcggcgg gcgggagcgg gatcagccac      600
cgcggtggcg gccctagagt cgatcgagga actgaaaaac cagaaagtta actggtaagt     660
ttagtctttt tgtcttttat ttcagaattc cccagtggaa agacgcgcag gcaaaacgca     720
ccacgtgacg gagcgtgacc gcgcgccgag cgcgcgccaa ggtcgggcag gaagagggcc     780
tatttcccat gattccttca tatttgcata tacgatacaa ggctgttaga gagataatta     840
gaattaattt gactgtaaac acaaagatat tagtacaaaa tacgtgacgt agaaagtaat     900
aatttcttgg gtagtttgca gttttaaaat tatgttttaa aatggactat catatgctta     960
ccgtaacttg aaagtatttc gatttcttgg gtttatatat cttgtggaaa ggacgcggga    1020
tcccgcttac gctgagtact tcgattcaag agatcgaagt actcagcgta agttttttcc    1080
aaagtcccgg atccggtggt ggtgcaaatc aaagaactgc tcctcagtgg atgttgcctt    1140
tacttctagg cctgtacgga agtgttactt ctgctctaaa agctgcggaa ttgtacccgc    1200
ggccgatcca ccggtcgcca ccatggtgag caagggcgag gagctgttca ccggggtggt    1260
gcccatcctg gtcgagctgg acggcgacgt aaacggccac aagttcagcg tgtccggcga    1320
gggcgagggc gatgccacct acggcaagct gaccctgaag ttcatctgca ccaccggcaa    1380
gctgcccgtg ccctggccca ccctcgtgac caccctgacc tacggcgtgc agtgcttcag    1440
ccgctacccc gaccacatga agcagcacga cttcttcaag tccgccatgc cgaaggcta     1500
cgtccaggag cgcaccatct tcttcaagga cgacggcaac tacaagaccc gcgccgaggt    1560
gaagttcgag ggcgacaccc tggtgaaccg catcgagctg aagggcatcg acttcaagga    1620
ggacggcaac atcctggggc acaagctgga gtacaactac aacagccaca acgtctatat    1680
catggccgac aagcagaaga acggcatcaa ggtgaacttc aagatccgcc acaacatcga    1740
ggacggcagc gtgcagctcg ccgaccacta ccagcagaac acccccatcg gcgacggccc    1800
cgtgctgctg cccgacaacc actacctgag cacccagtcc gccctgagca agacccaa     1860
cgagaagcgc gatcacatgg tcctgctgga gttcgtgacc gccgccggga tcactctcgg    1920
catgacgag ctgtacaagt aaagcggcca tcaagcttat cgataccgtc gactagagct     1980
cgctgatcag cctcgactgt gccttctagt tgccagccat ctgttgtttg ccctccccc     2040
gtgccttcct tgaccctgga aggtgccact cccactgtcc tttcctaata aaatgaggaa    2100
attgcatcgc attgtctgag taggtgtcat tctattctgg ggggtggggt ggggcaggac    2160
agcaagggggg aggattggga agacaattag gtagataagt agcatggcgg ttaatcatt    2220
```

```
aactacaagg aaccnctagt gatggagttg gccactccct ctctgcgcgc tcgctcgctc   2280
actgaggcca gatatctatt ttagatatct ggcagaatcc cgaaacggga ttctggcctc   2340
agtgagcgag cgagcgcgca gttaattaac ctaattcact ggccgtcgtt ttacaacgtc   2400
gtgactggga aaaccctggc gttacccaac ttaatcgcct tgcagcacat cccccttcg    2460 ccagctggcg taatagcgaa gaggcccgca ccgatcgccc ttcccaacag ttgcgcagcc   2520
tgaatggcga atgggacgcg ccctgtagcg gcgcattaag cgcggcgggt gtggtggtta   2580
cgcgcagcgt gaccgctaca cttgccagcg ccctagcgcc cgctcctttc gctttcttcc   2640
cttcctttct cgccacgttc gccggctttc cccgtcaagc tctaaatcgg gggctccctt   2700
tagggttccg atttagtgct ttacggcacc tcgaccccaa aaaacttgat tagggtgatg   2760
gttcacgtag tgggccatcg ccctgataga cggttttcg cccttgacg ttggagtcca    2820 cgttctttaa tagtggactc ttgttccaaa ctggaacaac actcaaccct atctcggtct   2880
attcttttga tttataaggg attttgccga tttcggccta ttggttaaaa aatgagctga   2940
tttaacaaaa atttaacgcg aattttaaca aaatattaac gcttacaatt taggtggcac   3000
ttttcgggga aatgtgcgcg gaaccctat ttgttattt ttctaaatac attcaaatat      3060
gtatccgctc atgagacaat aaccctgata aatgcttcaa taatattgaa aaaggaagag   3120
tatgagtatt caacatttcc gtgtcgccct tattccctt tttgcggcat tttgccttcc     3180 tgttttgct cacccagaaa cgctggtgaa agtaaaagat gctgaagatc agttgggtgc    3240 acgagtggg tacatcgaac tggatctcaa cagcggtaag atccttgaga gttttcgccc    3300
cgaagaacgt tttccaatga tgagcacttt taaagttctg ctatgtggcg cggtattatc   3360
ccgtattgac gccgggcaag agcaactcgg tcgccgcata cactattctc agaatgactt   3420
ggttgagtac tcaccagtca cagaaaagca tcttacggat ggcatgacag taagagaatt   3480
atgcagtgct gccataacca tgagtgataa cactgcggcc aacttacttc tgacaacgat   3540
cggaggaccg aaggagctaa ccgcttttt gcacaacatg ggggatcatg taactcgcct    3600
tgatcgttgg gaaccggagc tgaatgaagc cataccaaac gacgagcgtg acaccacgat   3660
gcctgtagca atggcaacaa cgttgcgcaa actattaact ggcgaactac ttactctagc   3720
ttcccggcaa caattaatag actggatgga ggcggataaa gttgcaggac cacttctgcg   3780
ctcggccctt ccggctggct ggtttattgc tgataaatct ggagccggtg agcgtgggtc   3840
tcgcggtatc attgcagcac tggggccaga tggtaagccc tcccgtatcg tagttatcta   3900
cacgacgggg agtcaggcaa ctatggatga acgaaataga cagatcgctg agataggtgc   3960
ctcactgatt aagcattggt aactgtcaga ccaagtttac tcatatatac tttagattga   4020
tttaaaactt catttttaat ttaaaaggat ctaggtgaag atccttttg ataatctcat     4080 gaccaaaatc ccttaacgtg agttttcgtt ccactgagcg tcagaccccg tagaaaagat   4140
caaaggatct tcttgagatc cttttttct gcgcgtaatc tgctgcttgc aaacaaaaaa    4200
accaccgcta ccagcggtgg tttgtttgcc ggatcaagag ctaccaactc ttttccgaa    4260 ggtaactggc ttcagcagag cgcagatacc aaatactgtt cttctagtgt agccgtagtt   4320
aggccaccac ttcaagaact ctgtagcacc gcctacatac ctcgctctgc taatcctgtt   4380
accagtggct gctgccagtg gcgataagtc gtgtcttacc gggttggact caagacgata   4440
gttaccggat aaggcgcagc ggtcgggctg aacggggggt tcgtgcacac agcccagctt   4500
ggagcgaacg acctacaccg aactgagata cctacagcgt gagctatgag aaagcgccac   4560
```

```
gcttcccgaa gggagaaagg cggacaggta tccggtaagc ggcagggtcg gaacaggaga    4620
gcgcacgagg gagcttccag ggggaaacgc ctggtatctt tatagtcctg tcgggtttcg    4680
ccacctctga cttgagcgtc gattttgtg atgctcgtca gggggcgga gcctatggaa     4740 aaacgccagc aacgcggcct ttttacggtt cctggccttt tgctggcctt ttgctcacat    4800
gttctttcct gcgttatccc ctgattctgt ggataaccgt attaccgcct ttgagtgagc    4860
tgataccgct cgccgcagcc gaacgaccga gcgcagcgag tcagtgagcg aggaagcgga    4920
agagcgccca atacgcaaac cgcctctccc cgcgcgttgg ccgattcatt aatgcagctg    4980
gcacgacagg tttcccgact ggaaagcggg cagtgagcgc aacgcaatta atgtgagtta    5040
gctcactcat taggcacccc aggctttaca ctttatgctt ccggctcgta tgttgtgtgg    5100
aattgtgagc ggataacaat ttcacacagg aaacagctat gaccatgatt acgccagatt    5160
taattaaggc ctta                                                      5174
```

<210> SEQ ID NO 20
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 20

```
cgcctcgaga aattgaagaa gatctgttaa c                                    31
```

<210> SEQ ID NO 21
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 21

```
cgcgcggccg ctcttctctg gaggggactg t                                    31
```

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22

```
gtccaggttg aatcacgggt                                                 20
```

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23

```
aggatcctgc aaggtcaagc                                                 20
```

<210> SEQ ID NO 24
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 24

```
atgccaacac agtgctgtct gg                                            22

<210> SEQ ID NO 25
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 25
tgcttgctga tccacatctg ct                                            22

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
gcagcttttn gagcagaagt                                               20

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 27
tctagttgcc agccatctgt tgt                                           23

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
agcaaagacc ccaacgagaa                                               20

<210> SEQ ID NO 29
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 29
ggcggcggtc acgaa                                                    15

<210> SEQ ID NO 30
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with 6FAM
<220> FEATURE:
<221> NAME/KEY: misc_feature
<222> LOCATION: (22)..(22)
<223> OTHER INFORMATION: Modified with TAMRA
```

<400> SEQUENCE: 30
cgcgatcaca tggtcctgct gg                                      22

<210> SEQ ID NO 31
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 31
gactttcatc tgtactaca                                          19

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 32
ctctgtatcg ttccaatttt agtata                                  26

<210> SEQ ID NO 33
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 33
gactttcatc tgtactacat tcaagagatg tagtacagat gaaagtcttt tt     52

<210> SEQ ID NO 34
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 34
gcttacgctg agtacttcga ttcaagagat cgaagtactc agcgtaagtt tttt   54

<210> SEQ ID NO 35
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 35
tcctttcaga tgtcataact tcaagagatg tagtacagat gaaagtc            47

<210> SEQ ID NO 36
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 36
tcctttcaga tgtcatacat tcaagagatg tagtacagat gaaagtc            47

<210> SEQ ID NO 37
<211> LENGTH: 47

```
<212> TYPE: DNA
<213> ORGANISM: Artificial Sequence
<220> FEATURE:
<223> OTHER INFORMATION: Synthetic Polynucleotide

<400> SEQUENCE: 37
tcctttcatc tgtcataact tcaagagatg tagtacagat gaaagtc        47

<210> SEQ ID NO 38
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 38
gactttcaga tgtcataact tcaagagatg tagtacagat gaaagtc        47

<210> SEQ ID NO 39
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 39
tcctttcaga tgtactacat tcaagagatg tagtacagat gaaagtc        47

<210> SEQ ID NO 40
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 40
gactggcaga tgtactacat tcaagagatg tagtacagat gaaagtc        47

<210> SEQ ID NO 41
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 41
tcctttcatc tgtcatacat tcaagagatg tagtacagat gaaagtc        47

<210> SEQ ID NO 42
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 42
gactttcaga tgtcatacat tcaagagatg tagtacagat gaaagtc        47

<210> SEQ ID NO 43
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 43
```

```
tcctttcatc tgtactaact tcaagagatg tagtacagat gaaagtc        47
```

```
<210> SEQ ID NO 44
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 44
gactggcatc tgtactaact tcaagagatg tagtacagat gaaagtc        47
```

```
<210> SEQ ID NO 45
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 45
gactttcaga tgtactaact tcaagagatg tagtacagat gaaagtc        47
```

```
<210> SEQ ID NO 46
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 46
gactttcatc tgtcataact tcaagagatg tagtacagat gaaagtc        47
```

```
<210> SEQ ID NO 47
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 47
gactttcatc tgtactacat tcaagagatg tagtacagat gaaagag        47
```

```
<210> SEQ ID NO 48
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 48
ctctttcatc tgtactacat tcaagagatg tagtacagat gaaagtc        47
```

```
<210> SEQ ID NO 49
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 49
tcctttcatc tgtactacat tcaagagatg tagtacagat gaaagtc        47
```

```
<210> SEQ ID NO 50
<211> LENGTH: 47
<212> TYPE: DNA
<213> ORGANISM: Artificial Sequence
```

```
<220> FEATURE:
<223> OTHER INFORMATION: Synthetic Polynucleotide

<400> SEQUENCE: 50
gactggcatc tgtactacat tcaagagatg tagtacagat gaaagtc              47

<210> SEQ ID NO 51
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 51
gactttcaga tgtactacat tcaagagatg tagtacagat gaaagtc              47

<210> SEQ ID NO 52
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 52
gactttcatc tgtcatacat tcaagagatg tagtacagat gaaagtc              47

<210> SEQ ID NO 53
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 53
gactttcatc tgtactaact tcaagagatg tagtacagat gaaagtc              47

<210> SEQ ID NO 54
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 54
gactttcatc tgtactacat tcaagagatg tagtacagat gaaagtc              47

<210> SEQ ID NO 55
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 55
gactttcatc tgtactacat tcaagagatg tagtacagat gaaagtctttt tt       52

<210> SEQ ID NO 56
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 56
gactttcatc tgtactacaa agttcaagag actttgtagt acagatgaaa gtctttttt    58
```

<210> SEQ ID NO 57
<211> LENGTH: 71
<212> TYPE: RNA
<213> ORGANISM: Artificial Sequence
<220> FEATURE:
<223> OTHER INFORMATION: Synthetic Polynucleotide

<400> SEQUENCE: 57
gcgacuguaa acauccucga cuggaagcug ugaagccaca aaugggcuuu cagucggaug    60
uuugcagcug c                                                         71

<210> SEQ ID NO 58
<211> LENGTH: 92
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (85)..(87)
<223> OTHER INFORMATION: n is a, c, g, or t

<400> SEQUENCE: 58
nnnagtgagc gacctttgta gtacagatga aagtcctgtg aagccacaag tagggacttt    60
catctactac aaaggctgcc cactnnnttt tt                                  92

<210> SEQ ID NO 59
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 59
cagatctgac tttcatctgt actacattcg ctcactgagg ccgggcgacc aaaggtcgcc    60
cgacgcccgg gctttgcccg ggcggcctca gtgagcgagc                          100

<210> SEQ ID NO 60
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 60
cagatctgac tttcatctgt actacaggtc gcccgacgcc cgggctttgc ccgggcggcc    60
tcagtgagcg agc                                                       73

<210> SEQ ID NO 61
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 61
cagatctgac tttcatctgt actacattca ccgggcaaag cccgggcgtc gggcgaccttt    60 tgcccgggcg gcctcagtga gcgagc                                         86

-continued

```
<210> SEQ ID NO 62
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 62
cagatctgac tttcatccgg gcggcctcag tgagcgagc                    39

<210> SEQ ID NO 63
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 63
cagatctgac tttcatctgt actagcggcc tcagtgagcg agc               43

<210> SEQ ID NO 64
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 64
cagatctgac tttcatctgt actattcgcg gcctcagtga gcgagc            46

<210> SEQ ID NO 65
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 65
cagatctgac tttcatctgt actacatctc caaaggtcgc cgacgcccg ggctttgccc    60 gggcggcctc agtgagcgag c                                       81

<210> SEQ ID NO 66
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 66
ctcgctcact gaggccgccc gggcaaagcc cgggcgtcgg gcgacctttg gtcgcccggc   60
ctcagtgtag tacagatgaa agtcttttc tagtctgcag g                  101

<210> SEQ ID NO 67
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 67
ctcgctcact gaggccgccc cgatgaaagt cttttctag tctgcagg           48

<210> SEQ ID NO 68
<211> LENGTH: 61
<212> TYPE: DNA
```

```
<213> ORGANISM: Artificial Sequence
<220> FEATURE:
<223> OTHER INFORMATION: Synthetic Polynucleotide

<400> SEQUENCE: 68
ctcgctcact gaggccgggg cgacttgtag tacagatgaa agtcttttc tagtctgcag    60 g                                                                   61

<210> SEQ ID NO 69
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 69
ctcgctcact gaggccgccg agatgtagta cagatgaaag tcttttcta gtctgcagg     59

<210> SEQ ID NO 70
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 70
ctcgctcact gaggccgccc gggcaaagcc cgggcgtcgg gcgaccaatg tagtacagat   60
gaaagtcttt ttctagtctg cagg                                          84

<210> SEQ ID NO 71
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 71
ctcgctcttt ttctagtctg cagg                                          24

<210> SEQ ID NO 72
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 72
gacgcgcgag cgagcgagtg actccggccc gctggtttcc agcgggctgc gggcccgaaa   60
cgggcccgcc ggagtcactc gctcgctcgc gcgtctctcc ctcaccggtt gaggtagtga  120
tccccaagga                                                         130

<210> SEQ ID NO 73
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 73 gaccccccgcc cattgacgtc aataatgacg tatgttccca tagtaacgcc aatagggact  60
ttccattcac gtcaatgggt ggactat                                       87
```

```
<210> SEQ ID NO 74
<211> LENGTH: 107
<212> TYPE: DNA
<213> ORGANISM: Artificial Sequence
<220> FEATURE:
<223> OTHER INFORMATION: Synthetic Polynucleotide

<400> SEQUENCE: 74
ctttccattg acgtcaatgg gtggagtatt tacggtaaac tgcccacttg gcagtacatc      60
aagtgtacat ttagccaagt acgccccta ttgacgtcaa tgacggt                    107

<210> SEQ ID NO 75
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 75
catctccccc ccctccccac ccccaatttt gtatttattt attttttaat tattttgtgc      60
agcgatgggg gcggggggggg gggggcgcgc                                      90

<210> SEQ ID NO 76
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 76
tgtccggcga gggcgagggc gatgccacct acggcaagct gaccctgaag ttcatctgca      60
ccaccggcaa gctgcccgtg ccctggccca ccc                                   93

<210> SEQ ID NO 77
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 77
gcctggcgcg cgcccccccc cctccccacc cccaattttg tatttattta ttttttaatt      60
attttgtgca gcgatggggg cggggggggg ggggcgcgcg ccagg                     105

<210> SEQ ID NO 78
<211> LENGTH: 104
<212> TYPE: DNA
<213> ORGANISM: Artificial Sequence
<220> FEATURE:
<223> OTHER INFORMATION: Synthetic Polynucleotide

<400> SEQUENCE: 78
ttaccgtaaa tactccgccc attgacgtca ataatgacgt atgttcccat agtaacgcca      60
atgggacttt ccattgacgt caatgggtgg agtatttacg gtaa                      104

<210> SEQ ID NO 79
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 79
```

```
ccatttaccg tcattgacgt caatgggtgg agtatttacg gtaaactgcc cacttggcag      60
tacatcaagt gtacatttag ccaagtacgc cccctattga cgtcaatgac ggtaaatgg      119

<210> SEQ ID NO 80
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 80
acgagggtgg gcgagggcga gggcgatgcc acctacggca agctgaccct gaagttcatc      60
tgcaccaccg gcaagctgcc cgtgccctgg cccaccctcg t                         101
```

MODIFIED AAV CONSTRUCTS AND USES THEREOF

RELATED APPLICATIONS

This application is a Continuation of U.S. application Ser. No. 15/568,650, filed Oct. 23, 2017, entitled "MODIFIED AAV CONSTRUCTS AND USES THEREOF", which is a national stage application under 35 U.S.C. 371 of International Patent Application Serial No. PCT/US2016/027848, filed Apr. 15, 2016, entitled "MODIFIED AAV CONSTRUCTS AND USES THEREOF", which claims the benefit under 35 USC 119(e)) of U.S. Provisional Application Ser. No. 62/152,602, filed Apr. 24, 2015, entitled "MODIFIED AAV CONSTRUCTS AND USES THEREOF", the entire contents of each of which are incorporated herein by reference.

FIELD OF THE INVENTION

Some aspects of the invention relate to the field of gene expression constructs. Some aspects of the invention relate to viral expression constructs, for example, adeno-associated virus (AAV)-related expression constructs. Some aspects of the invention relate to the field of RNAi.

BACKGROUND OF INVENTION

Recombinant AAV (rAAV) vectors are useful for the delivery of transgenes into a variety of cell types and tissues. In particular, rAAV vector-delivered RNAi molecules (e.g., shRNA, miRNA, and AmiRNA) are a valuable tool for gene function studies and have many gene therapy applications. For example, shRNA cassettes can be cloned into rAAV vector genomes to achieve a high efficacy of gene silencing in vivo. However, the replication and packing efficiency of rAAV vectors containing nucleic acids encoding hairpin-forming RNA cassettes is significantly lower than rAAV vectors without hairpin-forming RNA cassettes. Accordingly, methods and compositions that increase the replication and packaging efficiency of rAAV vectors containing hairpin-forming RNA cassettes is needed.

SUMMARY OF INVENTION rAAV vector-delivered RNAi molecules are a valuable tool for gene function studies and have many gene therapy applications. In some embodiments, microRNA (miRNA) and artificial miRNA (AmiRNA) are useful therapeutic molecules because they overcome cellular toxicity issues related to the saturation of RNAi machinery by short-hairpin RNA (shRNA). However, in some cases, introduction of nucleic acid sequences encoding hairpin-forming RNA (e.g., shRNA, miRNA, and AmiRNA) may have deleterious effects on rAAV genome replication and rAAV yield, resulting in the generation of a heterogeneous population of rAAVs having either full length or truncated vector genomes.

The instant disclosure provides compositions and methods that overcome these issues and allow efficient, safe and sustained in vivo gene silencing. The instant invention is based, in part, on a surprising discovery that DNA fragments encoding RNA hairpin structures (e.g., shRNA, miRNA, and AmiRNA) can serve a function similar to a mutant inverted terminal repeat (ITR) during viral genome replication, generating self-complementary vector genomes.

Accordingly, in some aspects, the disclosure provides an rAAV vector comprising a single-stranded self-complementary nucleic acid with inverted terminal repeats (ITRs) at each of two ends and an inner portion comprising a hairpin-forming nucleic acid.

In some aspects, the disclosure provides an isolated nucleic acid having one inverted terminal repeat at a first terminus and a promoter operably linked with a sequence encoding a hairpin-forming RNA at a second terminus, wherein the isolated nucleic acid is configured for forming a self-complementary AAV (scAAV) vector.

In some embodiments, an isolated nucleic acid is present on a plasmid. Plasmids can be circular plasmids or linearized plasmids.

In some embodiments, hairpin-forming nucleic acid comprises a sequence encoding an hairpin-forming RNA. In some embodiments, sequence encoding the hairpin-forming RNA is operably linked with a promoter.

In some embodiments, hairpin-forming nucleic acid is substituted at a position of the self-complementary nucleic acid normally occupied by a mutant ITR. In some embodiments, sequence encoding a hairpin-forming RNA forms a shRNA, miRNA, or AmiRNA.

In some embodiments, an AmiRNA construct comprises: a nucleic acid sequence encoding a pri-miRNA scaffold; a nucleic acid sequence encoding a guide strand; and, a nucleic acid sequence encoding a passenger strand, wherein, the pri-miRNA scaffold is derived from a naturally-occurring pri-miRNA and comprises at least one flanking sequence and a loop-forming sequence comprising at least 4 nucleotides.

In some embodiments, the guide strand of an AmiRNA and the passenger strand of an AmiRNA share at least 50% complementarity to a target nucleic acid sequence but are not 100% complementary to one another. In some embodiments, the nucleic acid sequence encoding the guide strand and the nucleic acid sequence encoding the passenger strand are inserted into the pri-miRNA scaffold between the flanking sequence and the loop-forming sequence, thereby forming a stem.

In some embodiments, the nucleic acid sequence encoding the guide strand of an AmiRNA and the nucleic acid sequence encoding the passenger strand of an AmiRNA have at least one base pair mismatch. In some embodiments, the nucleic acid sequence encoding the guide strand and the nucleic acid sequence encoding the passenger strand have two base pair mismatches, three base pair mismatches, four base pair mismatches, five base pair mismatches, six base pair mismatches, seven base pair mismatches, eight base pair mismatches, nine base pair mismatches, ten base pair mismatches, eleven base pair mismatches, twelve base pair mismatches, thirteen base pair mismatches, fourteen base pair mismatches or fifteen base pair mismatches. In some embodiments, the nucleic acid sequence encoding the guide strand and the nucleic acid sequence encoding the passenger strand have mismatches at no more than ten consecutive base pairs. In some embodiments, at least one base pair mismatch is located at an anchor position. In some embodiments, at least one base pair mismatch is located in a center portion of the stem.

In some embodiments, the pri-miRNA scaffold is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

In some embodiments, the guide strand of an AmiRNA targets a gene associated with a gain of function mutation disease, an oncogene, or a gene associated with a metabolic disorder. In some embodiments, the guide strand of an AmiRNA targets SOD1, Huntington gene, p53, HER2/neu, LDLR, or beta-glucosidase.

In some embodiments, the size of a single stranded nucleic acid is in a range of 300 bp to 10 kb.

In some embodiments, ITRs of rAAV vectors described herein are AAV1, AAV2, AAV3, AAV4, AAV5, or AAV6 ITRs.

In some aspects, the disclosure provides an rAAV vector comprising an artificial miRNA (AmiRNA) construct.

In some aspects, the disclosure provides a preparation comprising a plurality of rAAVs, wherein at least 80% of the rAAVs comprise a non-truncated genome having a sequence encoding an artificial miRNA (AmiRNA).

In some embodiments, a non-truncated genome comprises two ITRs flanking the sequence encoding an artificial miRNA (AmiRNA). In some embodiments, at least 90% of the rAAVs comprise a non-truncated genome having a sequence encoding an artificial miRNA (AmiRNA). In some embodiments, at least 95% of the rAAVs comprise a non-truncated genome having a sequence encoding an artificial miRNA (AmiRNA). In some embodiments, at least 99% of the rAAVs comprise a non-truncated genome having a sequence encoding an artificial miRNA (AmiRNA).

In some aspects, the disclosure provides a self-complementary adeno-associated virus (scAAV) comprising: a viral genome comprising a nucleic acid sequence encoding at least one inverted terminal repeat and a promoter operably linked with a nucleic acid sequence encoding a hairpin-forming RNA; and at least one AAV capsid protein serotype.

In some embodiments, the nucleic acid sequence encoding a hairpin-forming RNA is between two inverted terminal repeats.

In some embodiments, the size of a scAAV viral genome is between about 150 bp and 5 kb.

In some embodiments, the disclosure relates to a host cell comprising an rAAV vector, nucleic acid encoding an rAAV vector, or a scAAV as described by the disclosure.

In some aspects, the disclosure provides a kit comprising a container housing an rAAV vector, nucleic acid encoding an rAAV vector, or a scAAV as described by the disclosure. In some embodiments, the container is a syringe.

BRIEF DESCRIPTION OF DRAWINGS

FIG. 1A, depicts the structure of a scAAV vector carrying shRNA cassette next to wild-type ITR. FIG. 1B shows the AAV yield analyzed by quantitative-PCR.

FIG. 2A depicts the scAAV plasmids harboring the shRNA cassette near the mutated ITR, in the intron, and near the wild-type ITR. FIG. 2B shows the levels of Firefly luciferase (Fluc) and Relina luciferase activity 48 hours after equal amounts of scAAV-shFluc plasmids were co-transfected with psiCheck-2 plasmid into 293HEK cells. FIG. 2C shows EGFP expression of scAAV vectors. FIG. 2D shows vector yield of scAAV plasmids harboring shRNA against Fluc or Apob at different positions that were packaged into AAV9, as determined by qPCR.

FIG. 3A shows SYBR gold staining of full length and truncated viral genomes from scAAV9-shFluc vectors. FIG. 3B shows southern blot analysis of Hirt's DNA from 293HEK cells after triple-transfection with scAAV9-shFluc vectors for 48 or 72 hours was probed by an EGFP fragment. FIG. 3C shows SYBR gold staining of full length and truncated viral genomes from a scAAV9-shApob vectors. FIG. 3D shows southern blot analysis of Hirt's DNA from 293HEK cells after triple-transfection with scAAV9-shApob for 48 or 72 hours was probed by an EGFP fragment.

FIG. 5A depicts the locations of shFluc in the ssAAV genome. FIG. 5B shows the viral genome DNA. FIG. 5C shows vector yield from ssAAV-shFluc.

FIG. 6A shows a model for a shRNA sequence on AAV genome replication. G. 6B shows DNA extracted from AAV vectors was examined on alkaline agarose gel. FIG. 6C shows restriction enzyme digestion of genome of AAV vectors carrying shApob cassettes in the intron. DNA isolated from AAV vectors was probed with an EGFP fragment with or without Msc I digestion.

FIGS. 7A-7C show shRNA-encoding DNA functions as a mutant ITR in AAV genome replication and vector production. FIG. 7A depicts constructs used in the study. shApob or shFluc cassettes were integrated into the intron or upstream of CB promoter in the absence of mutant ITR. scAAV plasmids without mITR or Wt-ITR were used as controls. SEQ ID NO:2 is scAAV-CBEGFP; SEQ ID NO: 1 is Intron-D; SEQ ID NO: 7 is NoshRNA; SEQ ID NO: 8 is pshRNA+wtTR−; SEQ ID NO: 4 is pH1-shApob1.3; SEQ ID NO: 3 is pH1-shApob1.5; SEQ ID NO: 6 is pH1-shApob2.2; SEQ ID NO: 5 is pH1-shApob2.0; and SEQ ID NO: 9 is pU6-shFluc1.3. FIG. 7B shows a Southern blot analysis of Hirt's DNA from 293HEK cells transfected with the constructs in FIG. 7A, adeno-helper plasmid, and Rep2/Cap9 plasmid for 48 hours. The EGFP fragments were labelled by P32 as probe using a random labelling kit from Takara. FIG. 7C depicts viral genome DNA from AAV vectors containing WT FR and hairpin DNA at two ends.

FIGS. 8A-8F show the thermodynamic stability of the DNA encoding shRNAs determine the truncation of AAV genome. FIG. 8A depicts the rational design of shApob. The guide strand of shApob remains unchanged and singular or multiple bulges were introduced into different positions. The sequences, from top to bottom, correspond to SEQ ID NOs: 35-54. FIG. 8B shows a Southern blot analysis of Hirt's DNA from 293HEK cells co-transfected with a scAAV-shApob plasmid, pAdeno-helper plasmid, and pRep2/Cap9 plasmid. The intensity of the truncated and full-length genomes was measured using Image J. FIG. 8C shows the correlation between the portion of the AAV truncated genome and the short hairpin DNA thermodynamic stability. The dG was calculated by RNAfold. FIG. 8D illustrates the ratio of Gal and Fluc in 293EK cells co-transfected with shApob constructs and a pmiCHECK-Apob sensor plasmid. FIG. 8E presents the small RNA Northern blot analysis of pre-shApob and antisense-Apob in 293HEK cells transfected with the indicated shApob constructs. FIG. 8F shows the Apob silencing efficacy of shApob contains certain bulges at a lower ratio of shApob plasmids and the sensor plasmid.

FIG. 9A depicts the viral genome of scAAV8 vectors carrying the pri-miRNA fragment. The pri-miRNA fragment was amplified by PCR from the C57/B6 mouse genome DNA, including the pre-miRNA flanked with about 100 bps up- and down-stream nucleotides and integrated into the intron between the Gluc reporter gene and CB promoter in the scAAV plasmid. The constructs were packaged into AAV8 vectors and viral genome DNA was run on a 1% agarose gel. FIG. 9B shows the design of AAV-compatible gene silencing constructs. The guide strand of the miRNA was replaced with the shApob guide strand, and the passenger strand and flanking sequence were changed based on the structure of the pre-miRNA in the design of AAV-compatible gene silencing constructs. The sequences, from top to bottom, correspond to SEQ ID NOs: 55-58. FIG. 9C illustrates gene silencing constructs that were co-transfected with pmiCHECK-Apob sensor plasmid at a 1:3 ratio into 293HEK and Huh7.5 cells. After 48 hours, Fluc and Gal levels were measured and the ratio between Gal and Fluc was calculated. FIG. 9D shows the ratio of Gal and Fluc levels in 293HEK cells co-transfected pri-miR-451, pri-miR-26a, and pri-miR-33 scaffolds with pmiCHECK-Apob plasmid at the ratio of 1:3, 1:1, and 1:0.33. FIG. 9E depicts a Northern blot analysis of Apob antisense small RNA in 293HEK cells transfected with shRNA or miRNA scaffold constructs. U6 RNA was used as a loading control. FIGS. 9F and 9G show that miRNA scaffolds improve the integrity of the scAAV genome. scAAV plasmids carrying shApob or miApob scaffolds were transfected with pAdeno-helper and Rep2/Cap9 plasmids into 293HEK cells. Southern blot analysis was performed on the Hirt's DNA after 48 hours of triple-transfection using a Gluc probe (FIG. 9F). FIG. 9G shows the agarose gel of viral genome extracted from the AAV preps.

FIGS. 10A-10B present comparisons of reporter gene expression and target gene silencing efficacy between shApob and miR-33 Apob in mice. FIG. 10A shows the *Gaussia* luciferase expression in mouse serum from mice that received IV-delivered AAV9 carrying shApob or miR-33 Apob at the indicated doses. FIG. 10B shows the relative quantification of Apob rnRNA in mouse livers by gRT-PCR.

FIGS. 11A-11F show in vivo performance of scAAV-shApob vectors and analysis of the truncated AAV molecules. $1\times10^{12}$ GCs scAAV9-shApob was administrated to 6-8 week old C57/B6 mice through tail vein. After 3 weeks, serum ALT was measured (FIG. 11A), relative Apob expression was analyzed by qRT-PCR (FIG. 11B), EGFP expression in liver was observed (FIG. 11C). Six mice were used in each group. (FIG. 11D) Southern blot analysis of AAV molecular forms using EGFP probe in liver. The liver DNA was digested with EcoR I or Msc I before hybridization. There is one Msc I site in the wtTR region and no EcoR I site in the vector genome. (FIG. 11E) Amplification of the junction connected to wtITR by Inverted PCR. (FIG. 11F) Sequence of TOPO colonies from PCR products by inverted PCR. The sequences, from top to bottom, correspond to SEQ ID NOs: 59-71. Values are mean±s.d.

FIG. 13A shows the strategy for the preparation of library for SMRT sequencing and data process. Model guided AAV sequence prediction (FIG. 13B) and sequence of scAAV and truncated AAV genomes (FIG. 13C) are also shown. RBE, Rep binding element. B-B' and C-C' are two palindromes in TR. A, replicated A in vector genome.

FIG. 14A shows pC is constructs used for AAV production. SEQ ID NO: 10 is U6-shFluc1.3. FIG. 14B shows prediction of packaged genome size based on the hairpin DNA position. FIG. 14C shows Southern blot analysis of the Hirt DNA from triple-transfection using EGFP probe. FIG. 14D shows viral genome DNA from purified vectors in native agarose gel and alkaline gel. FIG. 14E shows EGFP expression in the liver of mice received $3\times10^{11}$ GCs of AAV vectors from tail vein for 3 weeks. FIG. 14F shows Southern blot analysis of the EcoR I or Msc I digested liver DNA using EGFP probe. FIG. 14G shows qRT-PCR analysis of Apob mRNA and small RNA Northern blot analysis in mouse liver. FIG. 14H shows alkaline gel analysis of H1-shApob1.3 and H1-shApob1.5 shAAV genomes. FIG. 14I shows an illustration of the production of shRNA from AAV vectors. Values are mean±s.d. Four mice were used in each group.

FIG. 15A shows a prediction of the secondary structure from CB promoter sequence by RNAfold. FIG. 15B shows AAV yield of scAAV9 and shAAV9 vectors. The titers were determined by qPCR. FIG. 15C shows re-engineering of wtTR in scAAV genome (SEQ ID NO: 72). In the reservation of RBE, A, trs and D elements, RBE-D-A element was created by replacing the B-B' and C-C' with a shRNA loop (TT-CAAGAGA), T-Apob and T-PC1 were made by replacing the B-B' and C-C' with non-relevant sequence which can maintain the T-shape structure. The Cis plasmids with modified wtTR were co-transfected with pAd and pRep/Cap plasmids into HEK293 cells for 48 hours. Hirt DNA was extracted and probed with EGFP fragment. SEQ ID NO: 12 is shApob1.3-(RBE-A-D); SEQ ID NO: 17 is shFluc1.3-(RBE-A-D); SEQ ID NO: 15 is shApob2.0-(RBE-A-D); SEQ ID NO: 13 is shApob1.3-TApob; SEQ ID NO: 18 is shFluc1.3-TApob; SEQ ID NO: 16 is shApob2.0-TApob; SEQ ID NO: 14 is shApob1.3-TApob; SEQ ID NO: 19 is shFluc1.3-TPC1; and SEQ ID NO: 11 is shApob2.0-TPC1. FIG. 15D shows SMRT sequence analysis of H1-Apob1.3 and H1-shApob1.5 shAAV vector genomes.

FIG. 16A shows yield comparison of independent scAAV8 preparations with (n=15) or without (n=11) shRNA cassettes designed proximal to the wtTR. FIG. 16B shows a schematic of scAAV plasmids consisting of a CMV enhancer/Chicken β-actin promoter (CB), an EGFP reporter gene, and a beta-globin polyA sequence (PA). shRNA cassettes against Apob, driven by the H1 promoter; or the Firefly luciferase gene (Fluc), driven by the U6 promoter was inserted adjacent to the mTR (m-P and m-D), within the intron (Intron-P and Intron-D), or adjacent to the wtTR (Wt-D and Wt-P). FIG. 16C shows vectors depicted in FIG. 16B were packaged into AAV9 capsids and assessed for yield by quantitating genome copy number (GC) using an EGFP primer/probe set.

FIG. 17A shows qPCR analysis of hepatic Apob expression 3 weeks after injection of PBS or scAAV9-shApob vectors ($5 \times 10^{13}$ GCs/kg) into 6- to 8-week old C57/B6 mice. Expression levels are represented as relative apob mRNA levels normalized to actin levels. FIG. 17B shows EGFP expression in livers as determined by fluorescence microscopy. Bar=100 µM. FIG. 17C shows Southern blot analysis of AAV molecular forms in livers by probing against EGFP sequence. Liver DNAs were digested with EcoRI (non-cutter), or MscI (single cutter within the wtTR) prior to hybridization FIG. 17D shows a diagram showing the detection of wtTR junctions in circular AAV molecules by inverse PCR. Intron-Rev and PA-For primers are designed in opposing directions to span only circularized DNA templates. Total DNA from the livers of mice receiving AAV-shApob vectors was used as template. FIG. 17E shows TOPO sequences of the inverse PCR products from mice that received Intron-P and Intron-D vectors using total liver DNA as template. The shRNA cassette depicted here comprises an H1 promoter and an shRNA sequence, which consists of a passenger strand, and a guide strand, connected by a loop sequence. The sequences, from top to bottom, correspond to SEQ ID NOs: 59-71. Values are mean±s.d. Six mice were used in each group.

FIG. 18A shows agarose gel analysis of scAAV vector genomes carrying shApob, driven by the H1 promoter; or shFluc, driven by the U6 promoter at different positions. FIG. 18B shows AAV vector genomes (AAV8, AAV9, AAVrh10, and AAV2) carrying intronic shRNA cassettes against different genes. FIG. 18C shows AAV9 genomes carrying different shRNA sequence inserted between the EGFP transgene and the wtTR. FIG. 18D shows AAV6 and AAV8 genomes harboring shRNA cassettes inserted between the mTR and the CB promoter. Vector DNA equivalents of $0.1-1 \times 10^{11}$ GC viral genomes was loaded on 1% agarose gels and stained with SYBR Gold. sh-1 to sh-26 represents 26 different shDNA sequences. FIG. 18E shows the molar ratio of truncated genomes to full-length genomes in AAV vectors carrying shDNA at different positions. Ratios were calculated by normalizing their band intensities by densitometry to their molecular sizes. The ratio of truncated to full-length genomes of Wt-P (n=5), Wt-D (n=5), Intron-D (n=12), Intron-P (n=2), m-D (n=9), and m-P (n=2) preparations are reported on a log scale. Values are mean±s.d.

FIG. 19A shoes scAAV Constructs carrying shApob or shFluc were co-transfected with pAd helper plasmid and pRep2/Cap9 or pRep2/Cap8 plasmid into 293 cells. After 48 or 72 hours, Hirt DNA was extracted and probed with EGFP fragment. FIG. 19B shows a schematic of ssAAV constructs carrying shFluc cassette at different locations. The black solid circles indicate the shFluc locations. FIG. 19C shows Southern blot analysis of the Hirt DNA samples from 293 cells co-transfected with pAd helper plasmid, pRep2/Cap9 plasmid and pCis plasmids (Indicated in FIG. 19B) for 48 hours with GFP or Neo probe. Unlike scAAV, the replication of ssAAV genomes can start from either left or right TR.

FIG. 20A shows a model of conventional scAAV genome replication. AAV genome replication initiates from the wtTR and generates intra-molecular double-stranded genomes. FIG. 20B shows a model of AAV genome replication detoured by a short DNA hairpin. FIG. 20C shows DNAs extracted from AAV vectors were examined on an alkaline agarose gel. FIG. 19D shows a schematic diagram showing the strategy of library preparation for SMRT sequencing and data processing. FIG. 20E shows model-guided sequence prediction of truncated AAV genomes. Functional segments of the mTR are displayed: Rep binding element (RBE), the B-B' hairpin, and the C-C' hairpin. "A", represents the replicated A domain in the vector genome. FIG. 20F shows SMRT sequencing reads aligned to custom references that represent self-complementary sequence resulting from template-switching events at the mTR (top panel), and the shApob-encoding sequences (middle panel, Intron-D; and bottom panel, Intron-P).

FIG. 21A shows the location of restriction enzymes (RE) in the Intron-P and Intron-D vectors. Three restriction enzymes (MluI, XhoI and BstXI) that recognize the sites located upstream of shDNA were chosen to excise only the full-length AAV genomes, while three other restriction enzymes (EagI, HindIII and MscI) that recognize the sites located downstream of shDNA were selected to digest both full-length and truncated genomes. FIG. 21B shows restriction enzyme mapping on the vector genome. MluI, XhoI and BstXI that recognize the upstream of the shApob encoding sequence only digest the full-length genome. EagI, HindIII and MscI that recognize the downstream digest both full-length and truncated genome. FIG. 21C shows agarose gel analysis of vector genome of the Intron-P and Intron-D vectors after digestion by the REs as indicated.

FIG. 22A shows a schematic of pCis constructs used for AAV production. FIG. 22B shows Southern blot analysis of the Hirt DNA from transfected HEK293 cells using an EGFP probe. FIG. 22C shows viral genome DNA from purified of vectors (~$1.0 \times 10^{10}$ GCs) in native (left panel) and alkaline (right panel) agarose gels. FIG. 22D shows EGFP expression in the livers of adult mice i.v. treated with AAV ($1.6 \times 1013$ GCs/kg) for 3 weeks. FIG. 22E shows Southern blot analysis of the EcoRI or MscI digested liver DNA using an EGFP probe. FIG. 22F shows qRT-PCR analysis of Apob mRNA and small RNA Northern blot analysis of mouse livers. Mice were administrated with AAV vectors ($1.6 \times 10^{13}$ GCs/kg) for three weeks. FIG. 22G shows alkaline agarose gel analysis of H1-shApob1.3 and H1-shApob1.5 shAAV genomes. DNA extracted from AAV vectors (~$1.5 \times 10^{10}$ GCs) were digested with PstI, BglII, or BstBI, separated on a 0.8% alkaline agarose gel, and stained with SYBR Gold. FIG. 22H shows a diagram of replication products from the H1-shApob1.3 shAAV vector, illustrating re-direction at the shRNA expression cassette to produce 1.3-kb species, or read through products. The percentages of read-through genomes and shAAV genomes were calculated by their band intensities by densitometry, normalized to their molecular sizes. FIG. 22I shows a schematic of pCis constructs lacking PolIII promoters. FIG. 22J shows EGFP expression and FIG. 22K shows qPCR analysis of Apob mRNA and Northern blot analysis of Apob antisense small RNA from mouse liver at 3 weeks post injection with $1.6 \times 10^{13}$ GCs/kg shAAV9 vectors that packaged constructs from FIG. 22I. Bar=100 µm. Values are mean±s.d. Four mice were used in each group.

FIG. 26A shows aggregation plots of alignment termination positions along the pH1-shAPob1.3 construct (top panel), or the scAAV-EGFP construct (bottom panel) as assessed by direct SMRT sequencing of AAV genomes. Positional tags were distributed into intervals of 10 nt bins and the density of tags were plotted along the H1-shApob1.3 vector sequence. Peaks indicate regions along the genome where termination hotspots occur. Sequences of discovered hotspots are flanked by inverted repeats (IR). The linear sequences in the CMV enhancer (IR-1 and IR-2), CB promoter (IR-3), and the EGFP reporter gene (IR-4) are displayed below. FIG. 26B shows the secondary structures of IR1-4 using RNA Fold. Sequences in grey highlight the inverted repeat sequences. Underlined sequences reside outside of the inverted repeat region. The sequences are as follows: IR-1 (SEQ ID NO: 73), IR-2 (SEQ ID NO: 74), IR-3 (SEQ ID NO: 75), and IR-4 (SEQ ID NO: 76). FIG. 26C shows sequence alignments of AAV genomes to a reference consisting of self-complementary strands flanking the IR-3 sequence (Top). The bottom panel details the loop sequence that connects the partial CB-promoter and its reverse complementary sequence. The sequence corresponds to SEQ ID NO: 77.

DETAILED DESCRIPTION OF INVENTION

Figure 1A:
FIGS. 1A-1B show the yield of scAAV vectors embedded with or without shRNA cassettes.

Adeno-associated virus (AAV) is a small (~26 nm) replication-defective, non-enveloped virus, that generally depends on the presence of a second virus, such as adenovirus or herpes virus, for its growth in cells. AAV is not known to cause disease and induces a very mild immune response. AAV can infect both dividing and non-dividing cells and may incorporate its genome into that of the host cell. These features make AAV a very attractive candidate for creating viral vectors for gene therapy. Modified AAV-based vectors, referred to as recombinant AAV (rAAV) vectors, generally comprise two AAV inverted terminal repeat (ITR) sequences separated by a transgene. Transgenes capable of being delivered by rAAV vectors include, but are not limited to, nucleic acids encoding peptides and polypeptides, and RNAi molecules (e.g., dsRNA, siRNA, shRNA, miRNA, AmiRNA, etc.). However, the introduction of nucleic acid sequences encoding hairpin-forming RNA (e.g., shRNA, miRNA, and AmiRNA) has deleterious effects on rAAV genome replication and rAAV yield. Accordingly, new rAAV vectors that allow efficient replication and generate improved rAAV yield are needed.

In some aspects, the instant disclosure provides rAAV (e.g., self-complementary AAV; scAAV) vectors comprising a single-stranded self-complementary nucleic acid with inverted terminal repeats (ITRs) at each of two ends and a central portion comprising a promoter operably linked with a sequence encoding a hairpin-forming RNA. In some embodiments, the sequence encoding a hairpin-forming RNA is substituted at a position of the self-complementary nucleic acid normally occupied by a mutant ITR. In some embodiments, the disclosure provides an isolated nucleic acid having one inverted terminal repeat at a first terminus and a promoter operably linked with a sequence encoding a hairpin-forming RNA at a second terminus, wherein the isolated nucleic acid forms a self-complementary AAV (scAAV) vector.

Self-Complementary AAV (scAAV)Vectors

As used herein, the term "self-complementary AAV vector" (scAAV) refers to a vector containing a double-stranded vector genome generated by the absence of a terminal resolution site (TR) from one of the ITRs of the AAV. The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle. The instant invention is based, in part, on the recognition that DNA fragments encoding RNA hairpin structures (e.g., shRNA, miRNA, and AmiRNA) can serve a function similar to a mutant inverted terminal repeat (mITR) during viral genome replication, generating self-complementary AAV vector genomes. For example, in some embodiments, the disclosure provides rAAV (e.g., self-complementary AAV; scAAV) vectors comprising a single-stranded self-complementary nucleic acid with inverted terminal repeats (ITRs) at each of two ends and a central portion comprising a promoter operably linked with a sequence encoding a hairpin-forming RNA. In some embodiments, the sequence encoding a hairpin-forming RNA is substituted at a position of the self-complementary nucleic acid normally occupied by a mutant ITR.

Recombinant AAV Vectors

In some aspects, the disclosure provides an rAAV vector comprising a single-stranded self-complementary nucleic acid with inverted terminal repeats (ITRs) at each of two ends and a central portion comprising a promoter operably linked with a sequence encoding a hairpin-forming RNA.

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR. Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, and/or AAVrh10 ITR sequence.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-

8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene (e.g., hairpin forming nucleic acid) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al; Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some aspects, the disclosure relates to a host cell comprising an rAAV vector. Generally, host cells are useful for amplifying and/or packaging rAAV vectors. The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. In some embodiments, a host cell is a 293 cell, HeLa cell, A549 cell, or a SF9 cell. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). In some embodiments, a single nucleic acid encoding all three capsid proteins (e.g., VP1, VP2 and VP3) is delivered into the packaging host cell in a single vector. In some embodiments, nucleic acids encoding the capsid proteins are delivered into the packaging host cell by two vectors; a first vector comprising a first nucleic acid encoding two capsid proteins (e.g., VP1 and VP2) and a second vector comprising a second nucleic acid encoding a single capsid protein (e.g., VP3). In some embodiments, three vectors, each comprising a nucleic acid encoding a different capsid protein, are delivered to the packaging host cell. The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

Isolated Nucleic Acids

In some aspects, the disclosure relates to an isolated nucleic acid having one inverted terminal repeat at a first terminus and a promoter operably linked with a sequence encoding a hairpin-forming RNA at a second terminus, wherein the isolated nucleic acid forms a self-complementary AAV (scAAV) vector. In some embodiments, the sequence encoding a hairpin-forming RNA is substituted at a position of the scAAV vector normally occupied by a mutant ITR.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al; eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein. Furthermore, nucleic acids can be tailored for optimal gene expression based on optimization of nucleotide sequence to reflect the codon bias of a host cell. The skilled artisan appreciates that gene expression may be improved if codon usage is biased towards those codons favored by the host.

A "self-complementary nucleic acid" refers to a nucleic acid capable of hybridizing with itself (i.e., folding back upon itself) to form a single-stranded duplex structure, due to the complementarity (e.g., base-pairing) of the nucleotides within the nucleic acid strand. Self-complementary nucleic acids can form a variety of secondary structures, such as hairpin loops, loops, bulges, junctions and internal bulges. Certain self-complementary nucleic acids (e.g., miRNA, shRNA, AmiRNA) perform regulatory functions, such as gene silencing. Self-complementary nucleic acids having AAV ITRs can form self-complementary AAVs.

The degree of complementarity between the nucleotide bases of a self-complementary nucleic acid affects the stability (e.g., thermodynamic stability) of the molecule's secondary structure. For example, mismatches present in the duplex region of the self-complementary nucleic acid can form additional bulges or loops, thereby lowering the thermodynamic stability of the structure formed by the nucleic acid. In some aspects, the instant disclosure is based, in part, on the recognition that lowering the thermodynamic stability of a hairpin-forming self-complementary nucleic acid allows the nucleic acid to function as a mutant ITR in a self-complementary AAV vector. In some embodiments, the thermostability of a self-complementary nucleic acid is lowered by mutating the nucleic acid to introduce at least 1, at least 2, at least 3, at least 4, at least 5, at least 6, at least 7 at least 8, at least 9, or at least 10 mismatches in the duplex forming region. In some embodiments, the nucleic acid is mutated to introduce more than 10 mismatches in the duplex region. Mismatches can also be introduced into the non-duplex-forming region of the nucleic acid.

Transgenes

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

The disclosure is based, in part, on the discovery that transgenes comprising hairpin-forming nucleic acids with decreased thermostability are useful for replacing mutant ITRs in self-complementary AAV vectors. In some embodiments, nucleic acids described herein increase scAAV vector replication and packaging efficiency. In some aspects, the disclosure relates to rAAVs and rAAV vectors comprising a transgene, wherein the transgene is a hairpin-forming RNA. Non-limiting examples of hairpin-forming RNA include short hairpin RNA (shRNA), microRNA (miRNA) and artificial microRNA (AmiRNA). In some embodiments, nucleic acids are provided herein that contain or encode the target recognition and binding sequences (e.g., a seed sequence or a sequence complementary to a target) of any one of the inhibitory RNAs (e.g., shRNA, miRNA, AmiRNA) disclosed herein.

Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

The following non-limiting list of miRNA genes, and their homologues, which are also useful in certain embodiments of the vectors provided herein: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR- 1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-12′7-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR- 519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*. In some embodiments, the above miRNAs may be encoded for in a vector provided herein (e.g., in a hairpin nucleic acid that replaces a mutant ITR). In some embodiments, sequences of the foregoing miRNAs may be useful as scaffolds or as targeting regions (e.g., seed regions of AmiRNA).

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

In some embodiments, the rAAV vectors described herein further comprise a protein-encoding transgene. In some embodiments, the protein coding gene located upstream of the hairpin forming nucleic acid of the rAAV vector. For example, rAAV vectors described herein can further comprise a therapeutic protein or a reporter protein. Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some embodiments, the rAAV vectors described herein further comprise a therapeutic protein. Such rAAV may be useful for preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

In some aspects, the disclosure relates to rAAV comprising a combination of hairpin-forming nucleic acid and a protein coding gene. rAAV vectors comprising an interfering nucleic acid and a protein coding gene are useful for simultaneously performing gene silencing and gene substitution. For example, rAAV vectors described herein can be used to silence a defective gene (e.g., mutated SOD1) while simultaneously delivering a non-mutated or functional copy of the defective gene (e.g., wild-type SOD1).

Certain transgenes may exceed the cloning capacity of traditional rAAV vectors (e.g., transgenes larger than about 4.8 kb). However, methods for the delivery of large therapeutic proteins by rAAV vectors, for example as disclosed by Lai et al., Nat Biotechnol., 23(11): 1435-1439, 2005; Flotte, Respir. Res., 1: 16-18, 2000; Duan et al., Nat. Med., 6(5): 595-598, 2000; Sun et al., Nat. Med., 6(5): 599-602; each of which references is incorporated herein by reference in its entirety, have been developed. These methods rely on the capability of rAAV vectors to undergo genome concatenation and trans-splicing in host cells. For example, fragments of a large gene (e.g., >4.8 kb) may be encoded on several rAAV vectors and delivered to a host cell. Upon entry into the host cell, the rAAV vector genomes concatenate and trans-splice the fragments of the transgene, resulting in reconstitution of the full-length transgene. Therefore, in some embodiments, the disclosure relates to a composition comprising a plurality of rAAV vectors, wherein each rAAV vector of the plurality encodes a fragment of a transgene such that introduction of the composition to a host cell will result in the production of the full-length transgene encoded by the fragments.

In some embodiments, rAAV vectors comprise a transgene to be transferred to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

In some embodiments, the disclosure relates to an AAV comprising a nucleic acid encoding a protein or functional RNA useful for the treatment of a condition, disease or disorder associated with the central nervous system (CNS). The following is a non-limiting list of genes associated with CNS disease: DRD2, GRIA1, GRIA2,GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy. In some embodiments, the disclosure relates to recombinant AAVs comprising nucleic acids that express one or more of the foregoing genes or fragments thereof. In some embodiments, the disclosure relates to recombinant AAVs comprising nucleic acids that express one or more functional RNAs that inhibit expression of one or more of the foregoing genes.

In some embodiments, rAAV vectors described by the disclosure comprise AmiRNA having a guide strand that targets genes related to diseases caused by gain of function mutations. Generally, gain of function mutations confer new or enhanced activity on a protein. Examples of genes in which a gain of function mutation causes disease include SOD1 (Amyotrophic lateral sclerosis, ALS), huntington (Huntington's disease, HD) and beta globulin (sickle cell disease). In some embodiments, rAAV vectors described by the disclosure comprise AmiRNA having a guide strand that targets one or more oncogenes. Oncogenes are gene that has the potential to cause cancer, and are often mutated or expressed at high levels. Examples of oncogenes include p53, HER2/neu, and c-Myc. In some embodiments, rAAV vectors described by the disclosure comprise AmiRNA having a guide strand that targets genes involved in metabolic pathways (e.g., lipogenesis). Dysfunction of metabolic genes is associated with several diseases, including Gaucher disease (beta-glucosidase), Tay-Sachs disease (beta-hexosaminidase A), and familial hypercholesterolemia (low-density lipoprotein receptor, LDLR).

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Recombinant AAV Administration Methods

The rAAVs may be delivered to a subject in compositions according to any appropriate methods known in the art. The rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for constructing an AAV vector as described herein. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Novel rAAV Genome Designs Using Artificial Hairpin Loop Structures to Replace at Least One AAV Inverted Terminal Repeat (ITR)

Figure 1B:
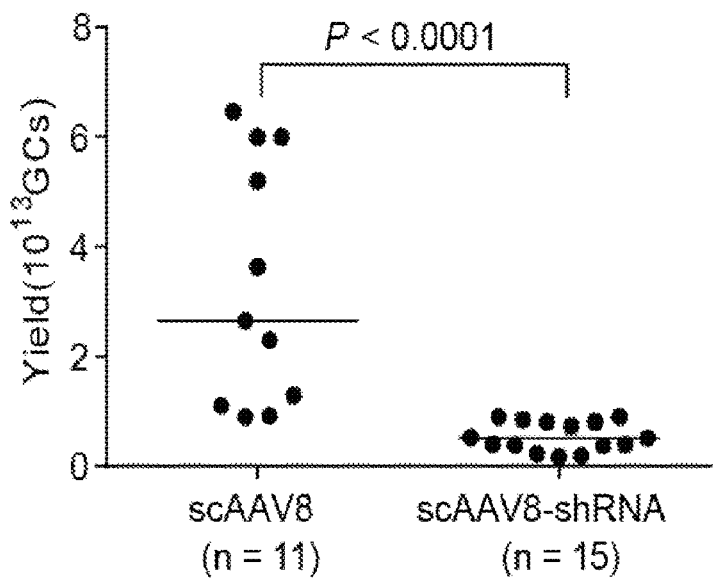

When scAAV vectors carrying shRNA cassettes are produced next to wild type ITRs in the genome, the yield is much lower than scAAV vectors without shRNA cassettes (FIGS. 1A and 1B). In the production process, the vector genome flanked with two ITRs is excised from the rAAV vector plasmid (FIG. 1A), replicated, and packaged into AAV capsids. scAAV genome replication can only start from the wild-type ITR (Wt-ITR) due to the mutation in the other ITR (mITR). The tight hairpin structure of shRNA-encoding DNA next to the Wt-ITR inhibits AAV genome replication and leads to the poor vector yield.

Figure 2A:
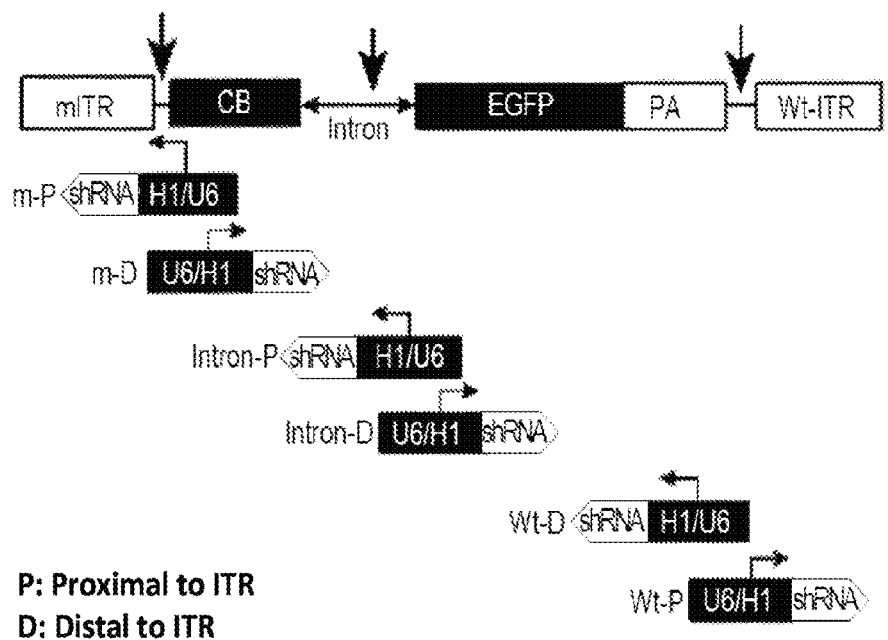
FIGS. 2A-2D show the effects of the shRNA cassette position within scAAV plasmids on RNAi efficacy, reporter gene expression and AAV production.
Figure 2B:
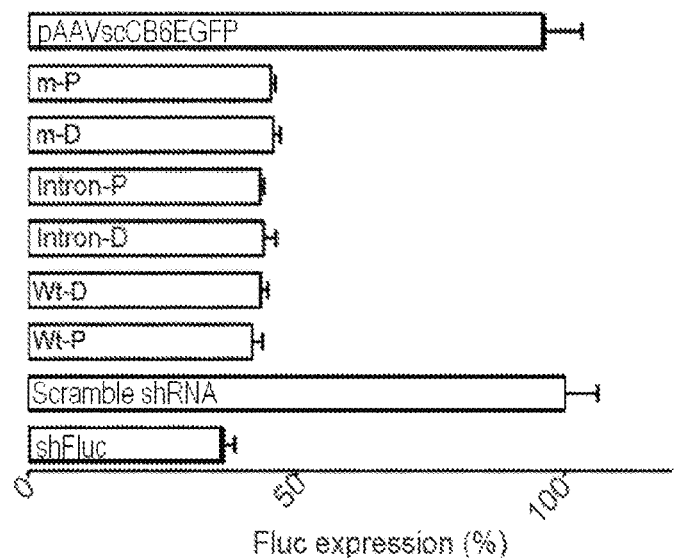
Figure 2C:
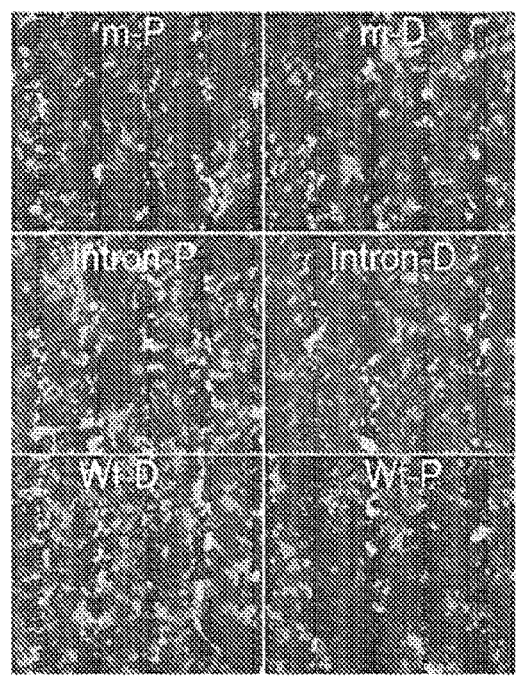
Figure 2D:
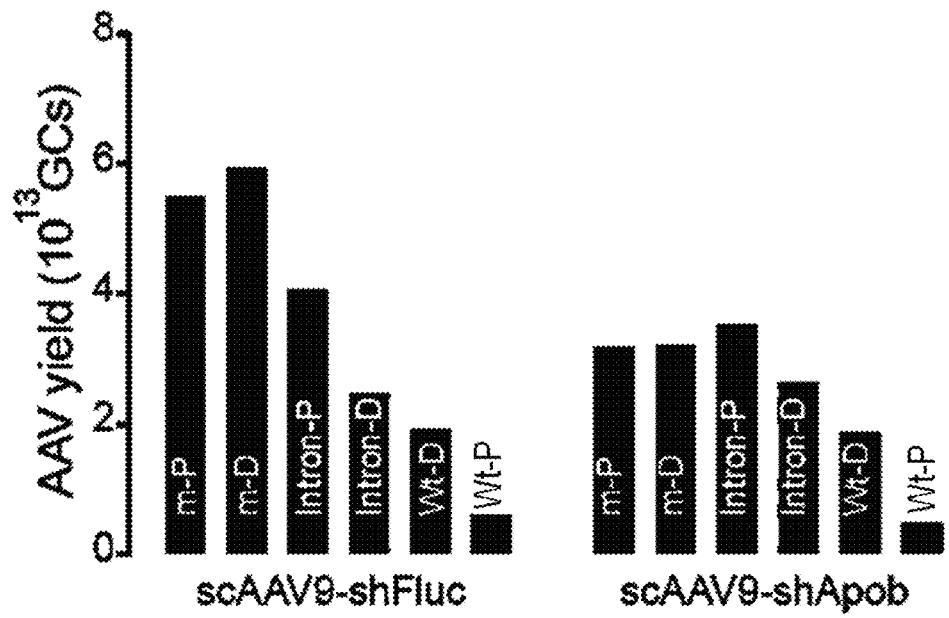
Figure 2E:
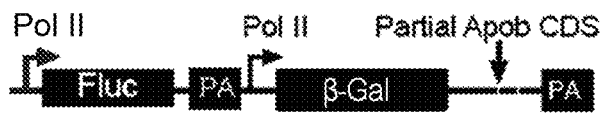
FIG. 2E shows the comparison of RNAi efficacy from scAAV plasmids carrying shApob at different locations. After 48 hours, EGFP expression was observed and the cell lysis was used for firefly luciferase and beta-gal activity assay. The pmiCheck-Apob plasmid was constructed by incorporating partial Apob cDNA after β-Galactosidase gene in pmiCheck plasmid. Fluc reporter gene was served as control for transfection efficacy. The ratio between β-Galactosidase and Fluc activity reflects the shApob activity in cells. Values are mean±s.d.
Figure 2E:
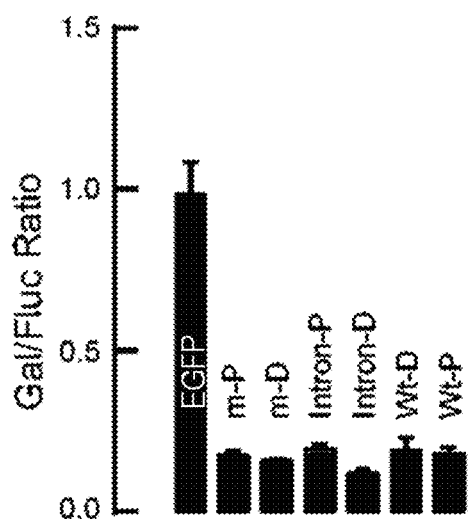

The location of the shRNA cassette in the AAV genome was changed to avoid the positioning effect on genome replication. Two shRNA cassettes, H1-shApob and U6-shFluc, expressing shRNAs that target endogenous the mouse Apob gene and firefly luciferase transgene, respectively, were used to test positional effects. The shRNA cassettes were cloned into different locations in the scAAV vector plasmid as shown in FIG. 2A. Relocated shRNA cassettes in the vector genome did not affect the RNAi efficacy or control transgene EGFP expression in 293HEK cells (FIGS. 2B and 2C), but did improve the vector yield 5-10 fold (FIG. 2D).

Figures 3A, 3B:
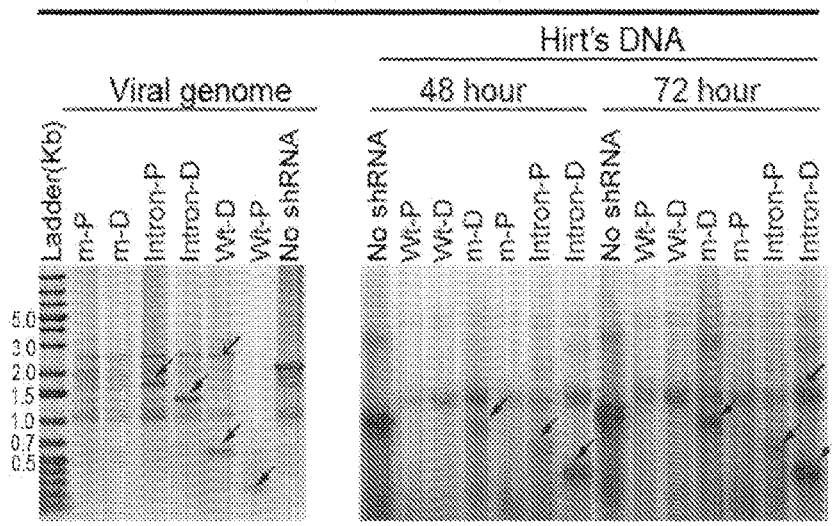
FIGS. 3A-3D show the analysis of truncated AAV genomes in viral vector DNA and Hirt's DNA from 293HEK cells after triple transfection.
Figures 3C, 3D:
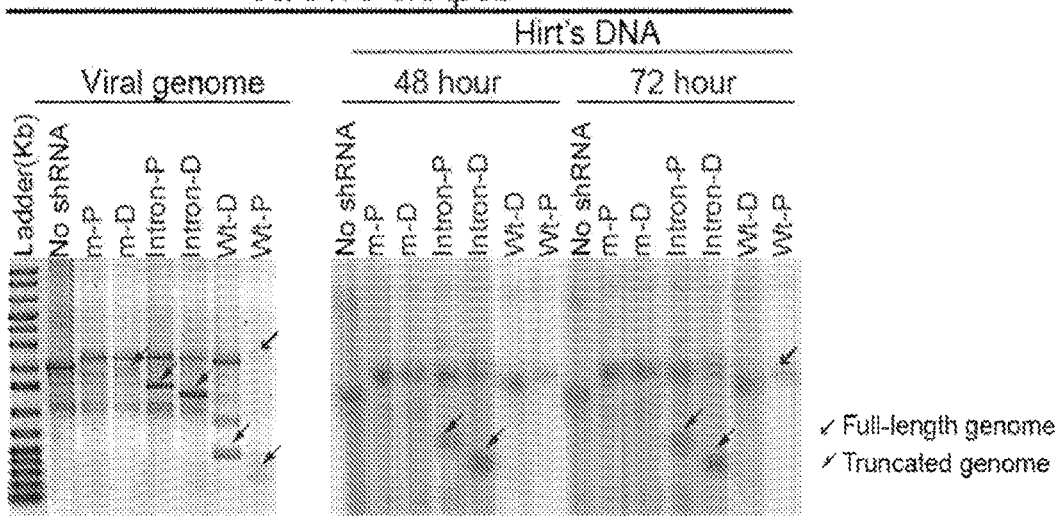

In the genome DNA extracted from the purified viral vector preparations, in addition to the expected full-length genome, truncated vector genomes were found to be packaged in sizes that correlated with the distance from the Wt-ITR to the location of the shRNA cassettes in the vector genome (FIGS. 3A and 3C). Non-genomic Hirt's DNAs prepared from triple transfected 293 cells in a small scale rAAV production experiment were analyzed by Southern blot using an EGFP probe (FIGS. 3B and 3D). Consistent with the AAV vector genome designs (FIGS. 2A and 2B), the truncated AAV molecules were found in the AAV genome replication stage (FIGS. 3B and 3D), indicating the shRNA-encoding DNA is a barrier to genome replication during scAAV vector production. Fewer rescued, replicated, and packaged AAV genomes were detected in the constructs with shRNA cassettes proximal to Wt-ITR, which is consistent with the lower vector yields in the purified preparations from these particular scAAV-shRNA constructs (FIGS. 3A and 3C). Both H1-shApob and U6-shFluc cassettes led to the truncation of vector genomes, suggesting that the negative impact on rAAV production is not shRNA sequence-specific (FIG. 3).

Figure 4A:
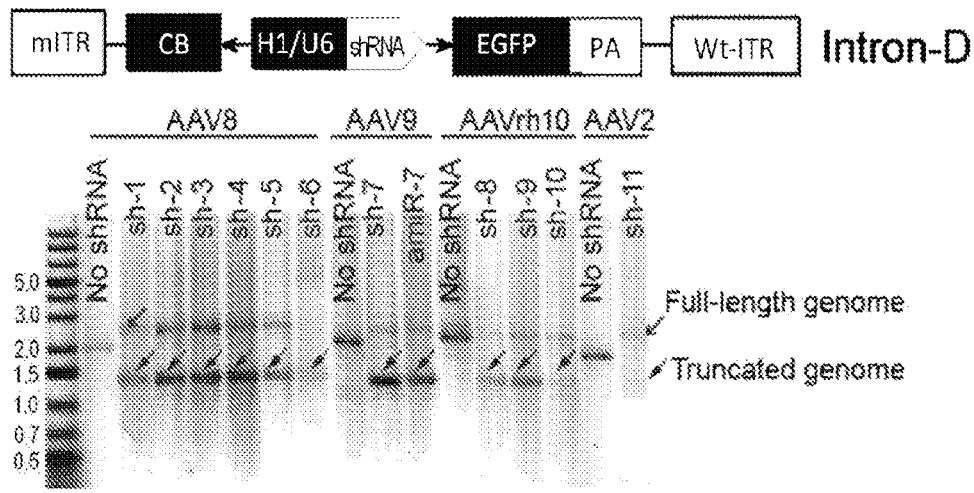
FIGS. 4A-4C show an examination of the AAV viral genomes from AAV8, AAV9, AAVrh10, and AAV2 carrying shRNA or artificial miRNA cassettes against different genes in the intron region (FIG. 4A); AAV9 carrying different shRNA sequence proximal or distal to wild-type ITR (FIG. 4B); and AAV6, AAV8, and AAV9 harboring shRNA or artificial miRNA distal to mutant ITR (FIG. 4C). Vector DNA equivalent to 0.1-1×E11 GC viral genomes was loaded in 1% agarose gel and stained with SYBR Gold.H1/U6, H1, or U6 promoter.
Figure 4B:
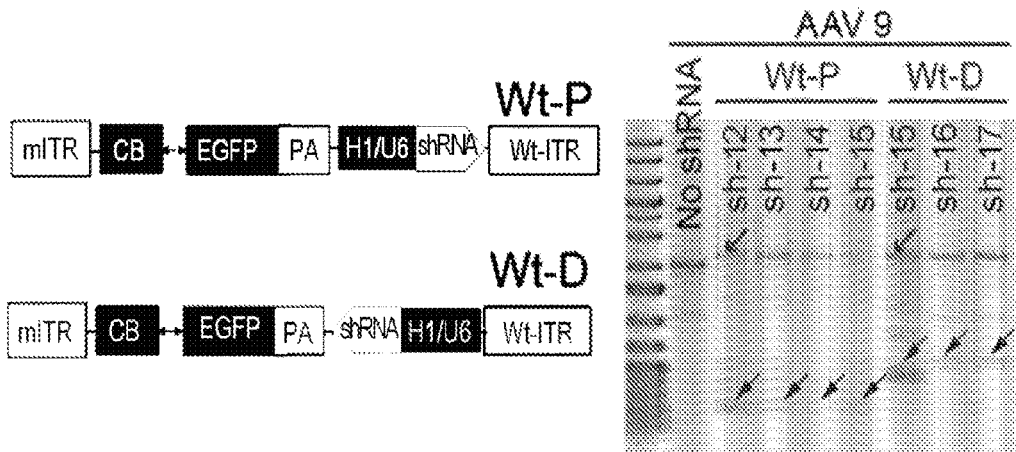
Figure 4C:
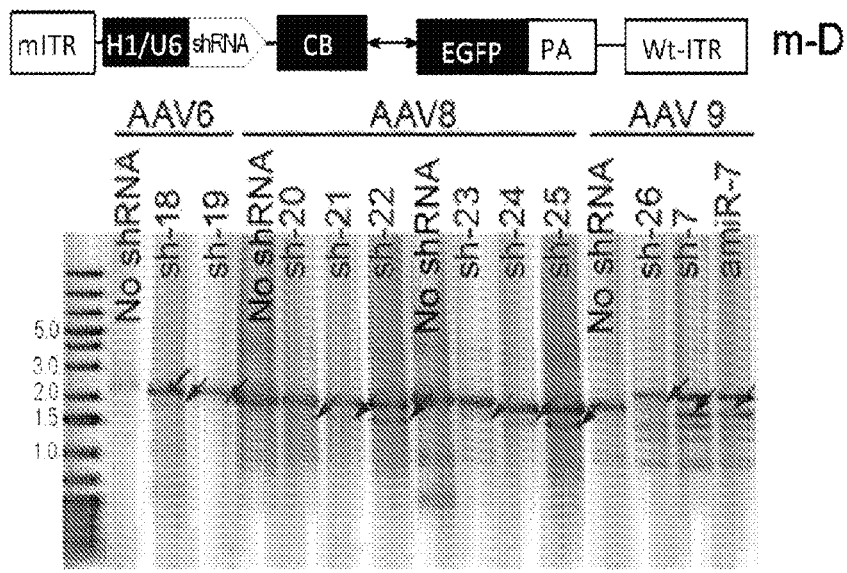

Genomes of scAAV vectors carrying different shRNA cassettes at different positions and packaged with different AAV serotypes were next investigated. When shRNA cassettes were located in the intron between the EGFP gene and CB promoter of scAAV genomes, AAV vectors including AAV8, AAV9, AAVrh10, and AAV2 all generated truncated genomes (FIG. 4A). scAAV genomes containing shRNA embedded into a miR-30 shuttle also produced the shortened genome (FIG. 4A). When shRNA cassettes were cloned into sites distal or proximal to Wt-ITR, shRNA cassettes were found closer to the wild-type ITR generated smaller truncated genomes (FIG. 4B). When shRNA cassettes were positioned distal to a mITR, more intact genomes were found; however there was still a noticeable amount of truncated genomes (FIG. 4C).

Figure 5A:
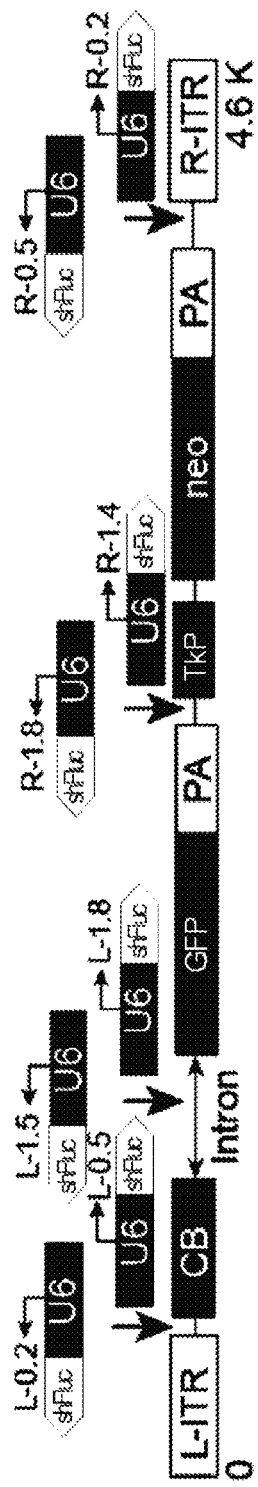
FIGS. 5A-5C show the impacts of shFluc cassettes on single-stranded AAV vector genome truncation and production.
Figure 5C:
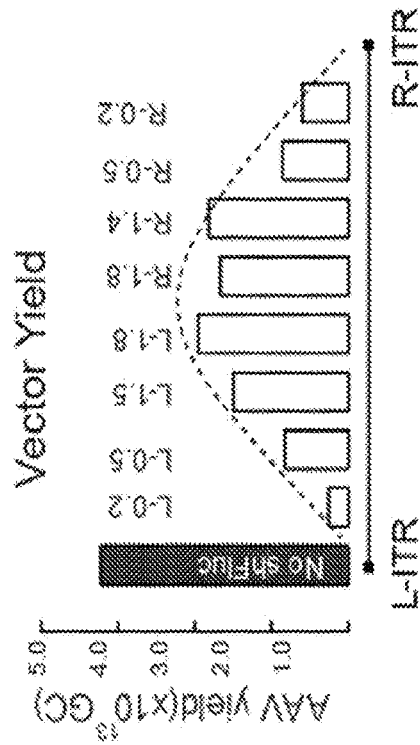
Figure 5B:
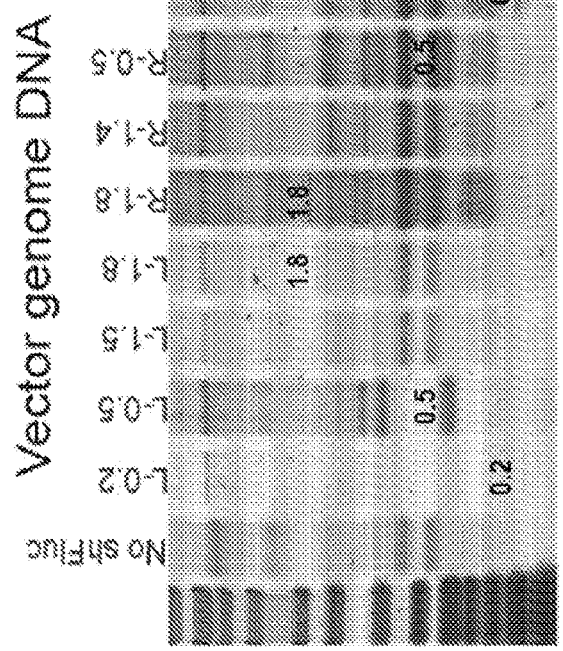

To clarify if only a self-complementary vector genome phenomenon was observed, vector genomes of conventional single-stranded (ss) AAV vectors in purified ssAAVshRNA preparations were examined. Both full length and truncated vector genomes as seen in the scAAV preparations were identified, as well as the negative impact on the yield of vectors with shRNA cassettes close to either 5' or 3' Wt-ITR (FIG. 5). Taken together, shRNA cassettes hinder replication of both ss and scAAV genomes and cause vector genome truncations. Both the intact and truncated genomes with a linear single-stranded genome size <4.7 kb are packaged into AAV vectors. Truncation of shRNA cassettes containing AAV genomes is a universal phenomenon, it is not AAV serotype, shRNA cassette, or genome format (ss versus sc) specific.

Figure 6A:
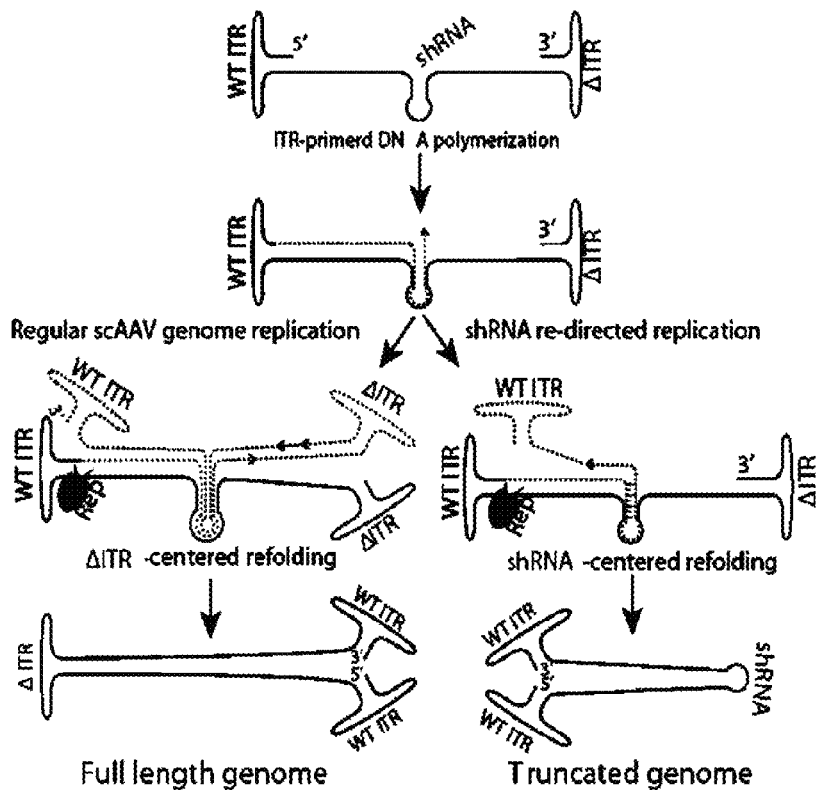
FIGS. 6A-6D show that short hairpin DNA compromises the scAAV genome integrity.
Figure 6B:
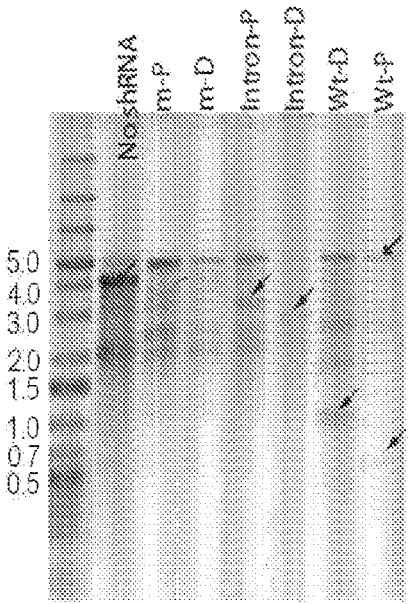
Figure 6C:
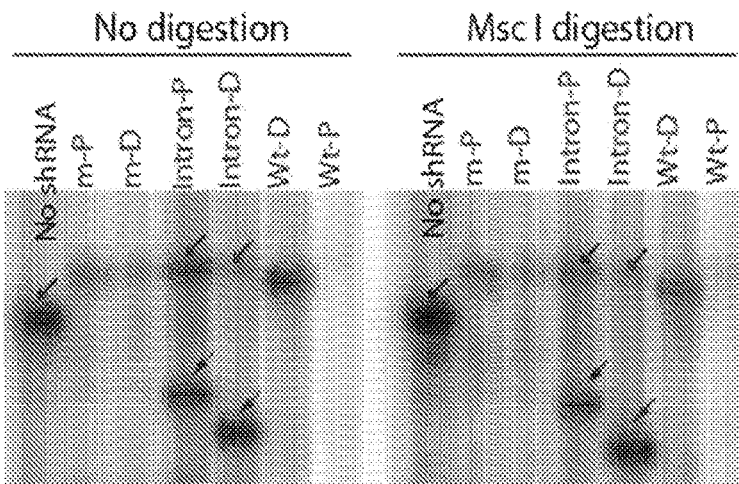

Based on this data, a model illustrating the impact of shRNA cassettes on AAV genome replication was formed (FIG. 6A). Genome replication starts from the Wt-ITR during scAAV vector production and forms an intra-molecular double-stranded DNA with an mITR loop when a normal scAAV genome without a shRNA cassette is used. However, for the scAAV-shRNA construct, when AAV genome replication reaches to the shRNA cassette, the base-paring shRNA stem redirects the orientation of replication and uses the newly synthesized genome as a template to form the truncated genome. If the replication overcomes the complementarity of shRNA's secondary structure, it will generate the full-length scAAV genome for packaging. Therefore, replication of the scAAVshRNA genome has two possible fates: a complete replication to produce a full length genome, or a partial replication to generate a truncated genome. Viral genomes extracted from purified viral preparations were run in an alkaline gel and the sizes of both intact and truncated genomes were found to double (FIG. 6B). The result indicated the truncated genome is an intra-molecular double-stranded DNA-like scAAV genome at a smaller size (FIG. 6B). The Southern blot analysis of the viral genomes with and without digestion with an Wt-ITR-specific restriction enzyme confirmed the truncated genomes contain an EGFP fragment and that the Wt-ITR is where the replication starts (FIG. 6C).

Figure 6D:
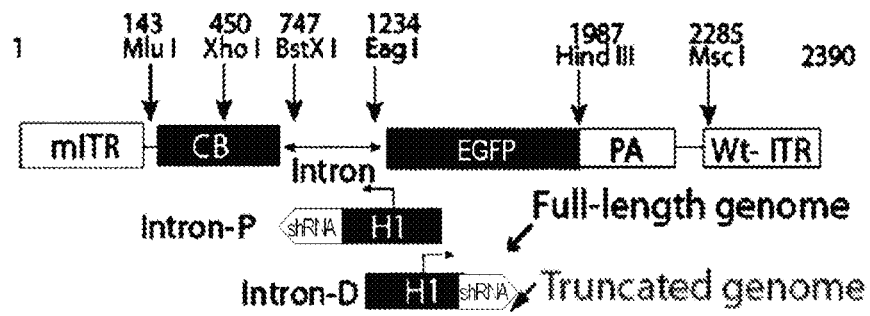
Figure 6D:
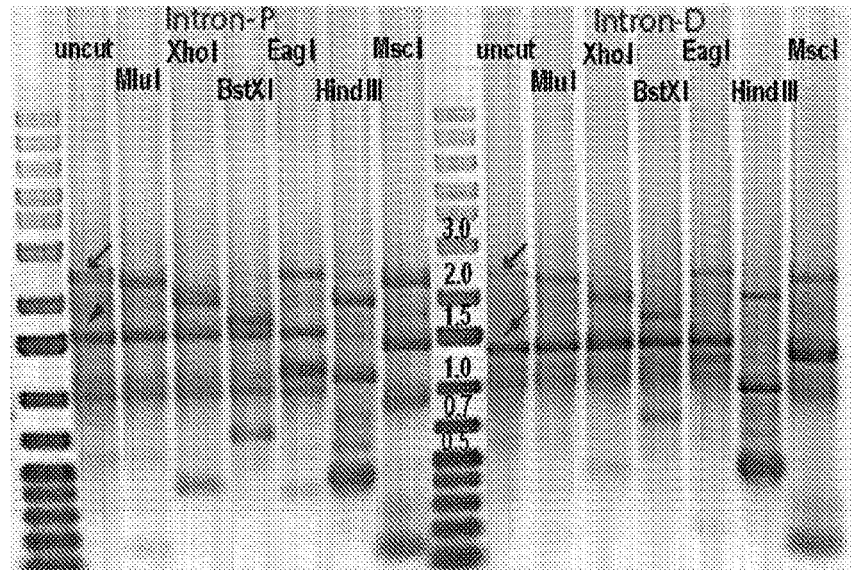
Figure 7A:
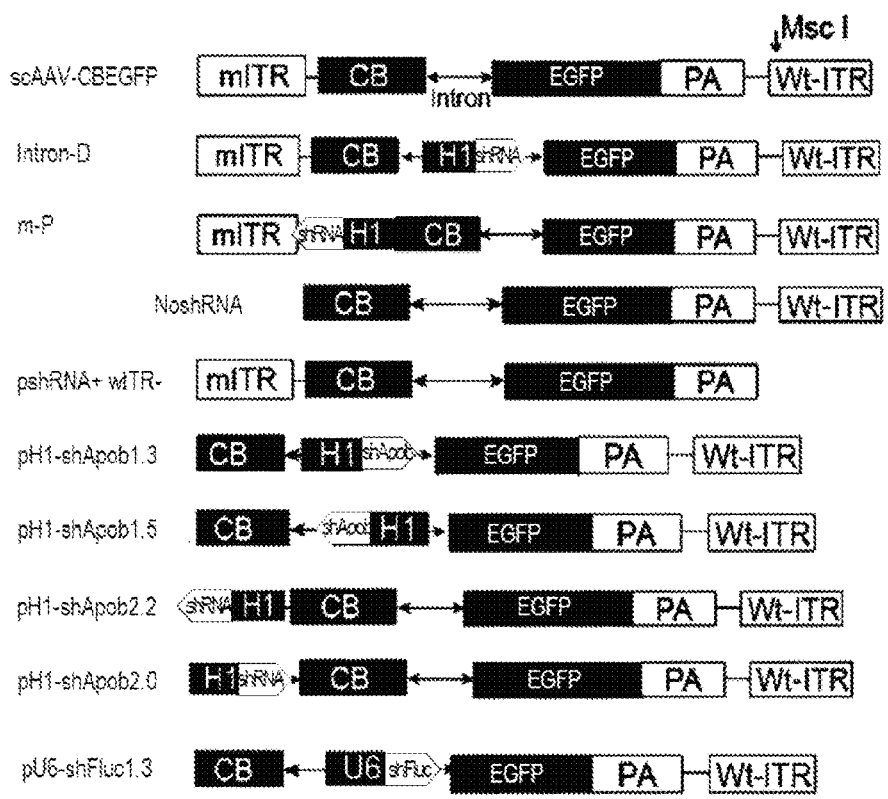
Figure 7B:
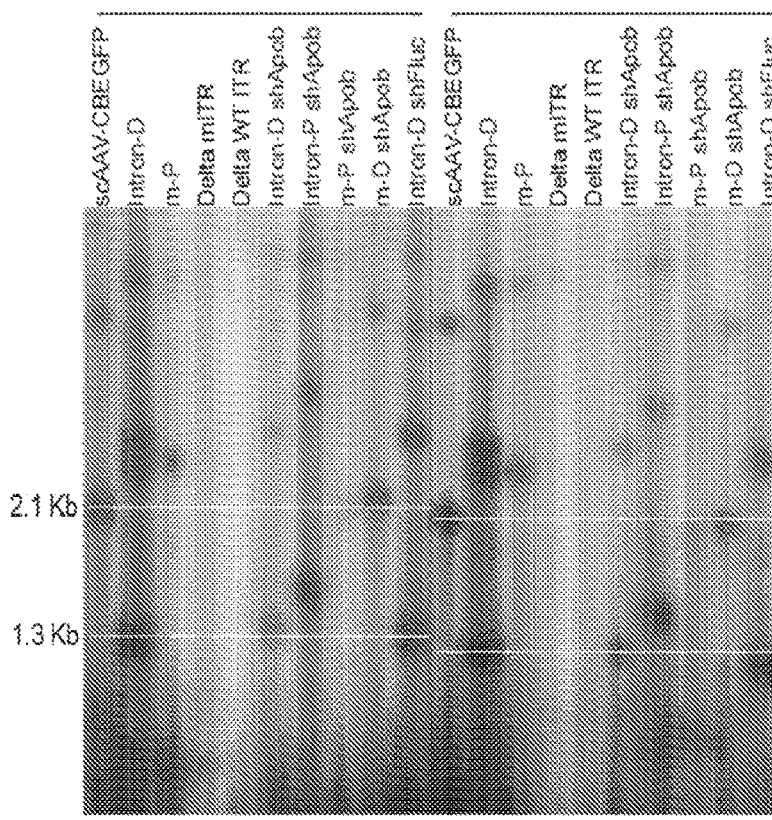

To further characterize the truncated AAV genomes, restriction enzyme mapping was performed on the DNA from a scAAV9 vector carrying the shApob in the intron. Three restriction enzymes (Mlu I, Xho I, and BstX I) with reorganization sites upstream of shRNA-encoding DNA only digested full-length AAV genomes, but the other three restriction enzymes (Eag I, Hind III, and Msc I) which recognize the downstream shRNA-encoding DNA region can digest both full-length and truncated genomes (FIG. 6D). The digestion results suggest the shRNA sequence is a dividing line for the full-length and truncated genomes. More importantly, the short hairpin DNA seems to serve as another mutant ITR during the AAV genome replication. To test this concept, the mITR was replaced with a DNA fragment encoding shApob or shFluc in the scAAV constructs (FIG. 7A). When the hybrid shDNA-ITR plasmid was co-transfected with adeno helper plasmid and Rep/Cap trans-plasmid, the rescued AAV genomes could be detected from Hirt's DNA (FIG. 7B), which was confirmed by large scale rAAV production and purification (FIG. 7C). In summary, a DNA fragment with a hairpin structure can serve as an alternative mutant ITR for rAAV vector production.

Example 2: Development of Efficient and Safe rAAV Compatible Silencing Construct Reports show that AAV-delivered shRNAs may cause cellular toxicity by saturating the RNAi machinery. To overcome this issue, scientists have embedded antisense RNA into endogenous miRNA scaffolds to improve small RNA processing and reduce toxicity. However, the artificial miRNAs are not as potent as shRNAs in gene silencing. The principle of artificial miRNA design is to replace the natural miRNA with the desired antisense RNA and to keep approximately 100 bases of flanking sequences at both ends.

It is therefore necessary to design rAAV-compatible molecules for efficient, safe, and sustained in vivo gene silencing. Example 1 demonstrates a strategy to overcome the negative impact of shRNA cassettes on the vector genome replication and homogeneity and yield of AAV vectors. This example provides data demonstrating the advantages of replacing currently utilized artificial miRNAs (AmiRNAs), which harbor a shRNA stem sequence consisting of 100% complementary passenger and guide strands, with a novel design that mimics the natural structures of native miRNAs (i.e. having reduced complementarities between passage and guide strands). The new design is more compatible with rAAV genome structures and AAV replication biology, leading to a more homogenous rAAV-AmiRNA genome population from the rAAV production process.

After screening and characterizing a panel of rAAV vectors carrying 14 different pri-miRNA structures for the homogeneity of rAAV genome populations, nine pre-miRNA structures, namely miR-21, miR-375, miR-30a, miR-26a, miR-451, miR-33, pri-miR-99, pri-miR-194, and pri-miR-155 were selected as the AmiRNA backbones to create a panel of mouse Apob specific AmiRNAs. The selected AmiRNAs were tested for their silencing efficiency and As-RNA processing in vitro in comparison with the classic shRNA design. The constructs were also packaged in small and large scale rAAV production and their ratios of truncated to full length vector genomes were compared. When the leading constructs were tested in vivo, it was found that the novel AmiRNA design can achieve the same silencing efficiency as the classic shRNA design.

Design and Generation of rAAV Compatible shRNA Expression Cassettes

The base pairing in the shRNA stem appears to be critical for the AAV genome replication. Lowering the thermodynamic stability of the DNA fragment that encodes the shRNA improves AAV genome integrity.

Figure 8B:
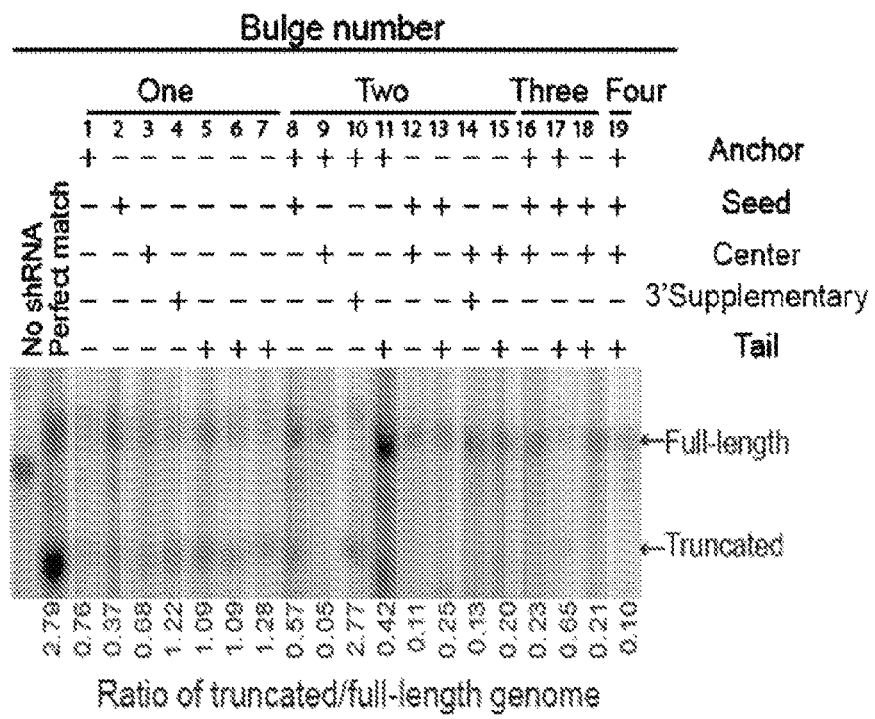
Figure 8C:
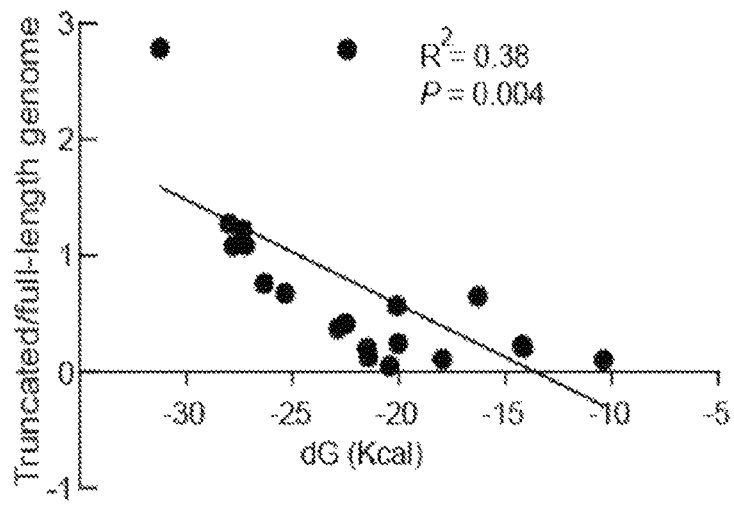
Figure 8D:
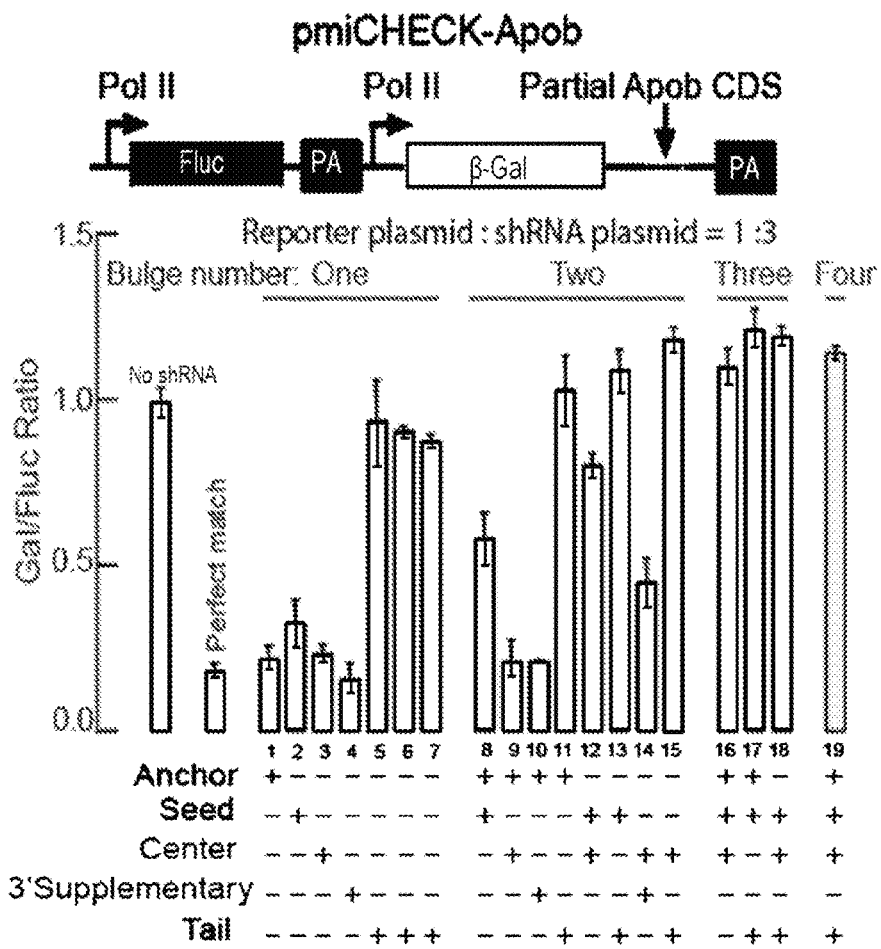
Figure 8E:
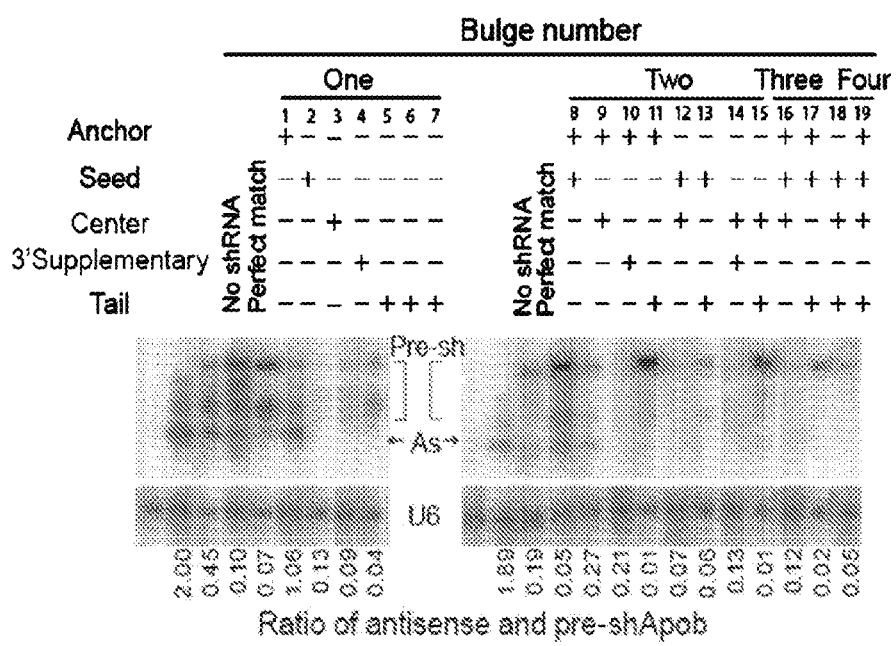
Figure 8F:
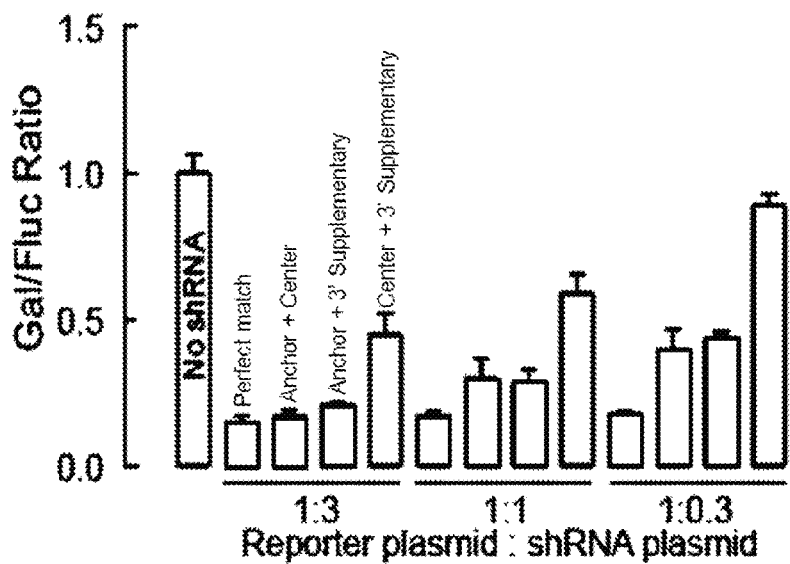

This phenomenon was examined by keeping the guide strand of shApob unchanged and introducing one to four bulges at different positions in the passenger strand (FIG. 8A). The shApob cassettes carrying bulges were incorporated into the intron between the EGFP and CB promoter in scAAV genome plasmids. The scAAV-shApob plasmid was co-transfected with pAdeno-helper plasmid and pRep2/Cap9 plasmid into 293HEK cells, and it was found that the truncated genomes in shApob with bulges are significantly less than a perfect match with shApob, except for one outliner (FIG. 8B, lane 10). The shApob constructs with lower thermodynamic stability correlate with less truncated genomes (FIG. 8C). To quantitatively compare the gene silencing efficacy of the shApobs carrying bulges in the passenger strand, they were co-transfected with the pmi-CHECK-Apob sensor plasmid, which contains part of the Apob cDNA fragment targeted by the shRNAs in the 3'UTR of the Gal reporter gene (FIG. 8D). Among the scAAV plasmids that generate much less truncated vector genomes (FIG. 8D), shApob carrying bulges at the anchor and center achieved a silencing effect comparable to the shApob with a perfectly matched stem (FIG. 8D, lane 9). However, the small RNA Northern blot analysis showed massive unprocessed pre-shApob from the bulged-shApob as compared to conventional shApob (FIG. 8E). It was also determined that the silencing effect from bulged-shApob is not as potent as the conventional shApob when lower doses of shApob plasmids are transfected according to the reporter gene sensor assay (FIG. 8F).

Artificial miRNAs mimicking the natural miRNA structure are as potent as conventional shRNAs in target gene silencing, but more compatible with rAAV genomes for efficient, safe, and sustained in vivo gene silencing As demonstrated by the above, lowering the shRNA thermodynamic stability by introducing bulges in the passenger strand reduced the portion of truncated genomes in rAAV preparations, but the gene silencing capability was greatly compromised as compared to the classic shRNA design. To improve pre-shRNA processing, the Apob antisense RNA was embedded into miRNA scaffolds which use the endogenous RNAi machinery. First, a panel of 14 rAAV-pri-miRNA expression constructs was screened, and the impact of natural pri-miRNAs which contain bulges in their stem on the scAAV genome integrity was analyzed.

Figure 9A:
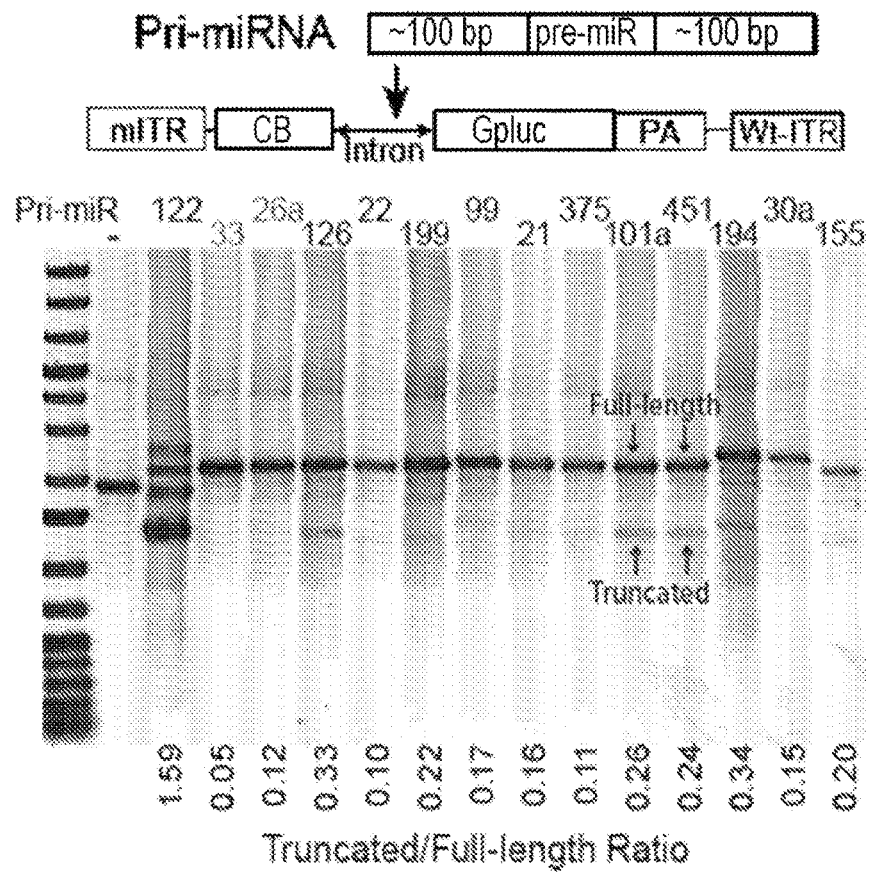
FIGS. 9A-9G show the development of AAV-compatible gene silencing construct using pri-miRNA scaffold.

Overall, all endogenous pri-miRNAs expressing rAAV constructs also generated truncated vector genomes but the proportions of the truncated vector genomes were smaller than those in rAAVshRNA constructs. Some pri-miRs such as pri-miR-33, pri-miR-26a, and pri-miR-22 generated minimal truncated genomes; however, rAAV pri-miR-122 generated approximately the same amount of truncated genomes as rAAVshRNAs, likely due to the high complementarity between the passenger and guide strands of the miR-122 stem sequence (FIG. 9A). This observation suggests that the current principles in the AmiRNA design, including formation of perfect, 100% pairing between the passenger and guide strands in the stem sequence, is incompatible with rAAV replication biology and may not be suitable for rAAV-mediated in vivo gene silencing. This observation has led to a novel design concept for rAAV-compatible AmiRNAs.

Figure 9B:
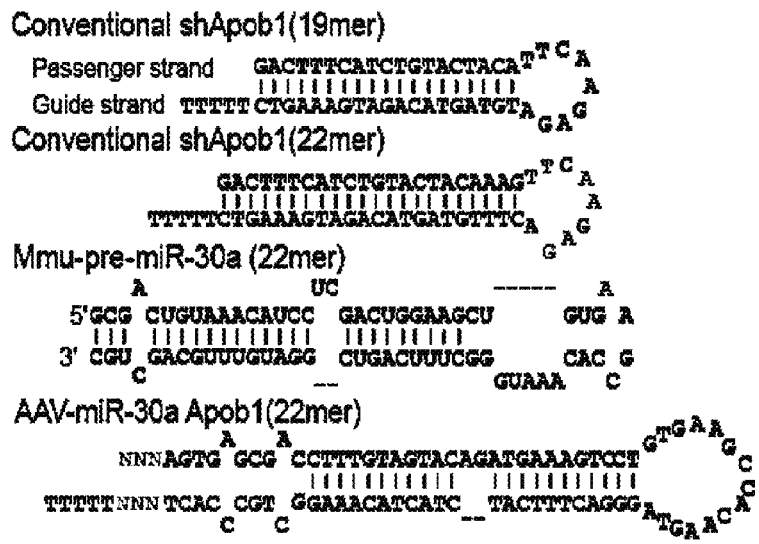
Figure 9C:
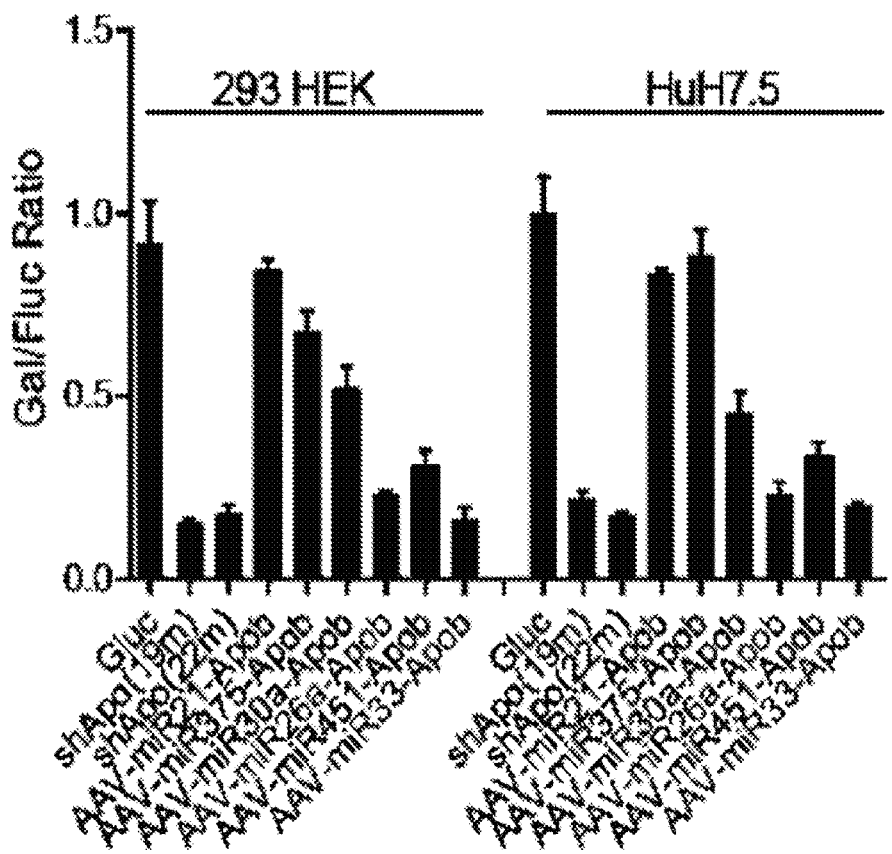
Figure 9D:
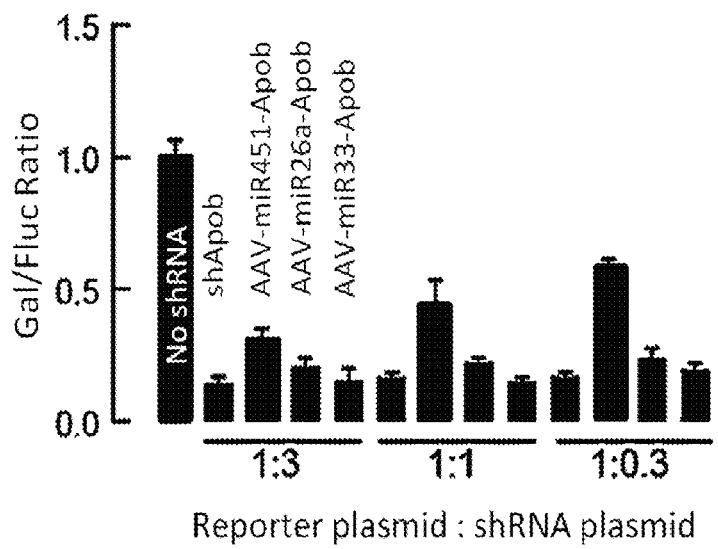
Figure 9E:
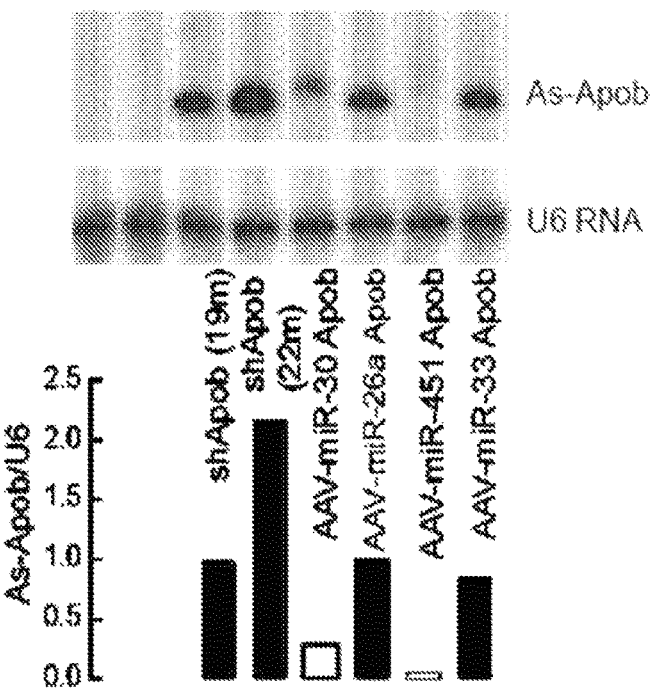
Figures 9F, 9G:
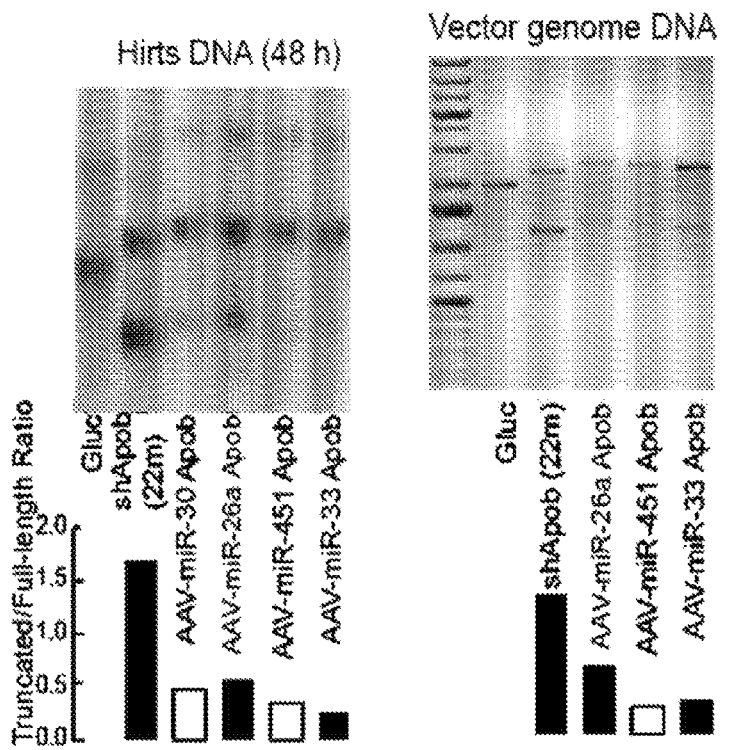

Second, pri-miR-21, pri-miR-375, pri-miR-30a, pri-miR-26a, pri-miR-451, pri-miR-33, pri-miR-99, pri-miR-194, and pri-miR-155 were selected as scaffolds to embed the Apob antisense. To mimic the native structures of corresponding pri-miRs, the stem sequence of the miRNA was replaced with the Apob shRNA guide strand and bulged passenger strand as naturally present in the original pri-miRNA (FIG. 9B). In addition, the flanking sequences were arranged as those in the natural pri-miR structure (FIG. 9B). The RNAi efficacy of those miRNA scaffolds carrying the Apob antisense RNA were compared with the conventional shApob in 293HEK and Huh7.5 cells (FIG. 9C). Using the novel AmiRNA design, even when the ratio between the miRNA scaffolds and Apob sensor plasmid were lowered by one log, the miR-33 and miR-26a scaffolds still showed robust gene silencing capability (FIGS. 9C and 9D). No pre-Apobs were detected by small RNA Northern blot (FIG. 9E). The amounts of mature antisense Apob RNAs from these two scaffolds are comparable with the conventional shApob construct (FIG. 9E). The constructs were packaged into AAV9 vectors in small and large scale vector production, and fewer truncated forms of viral vector genomes in both crude Hirt's DNA and purified viral preparations were found (FIGS. 9F and 9G).

Figure 10A:
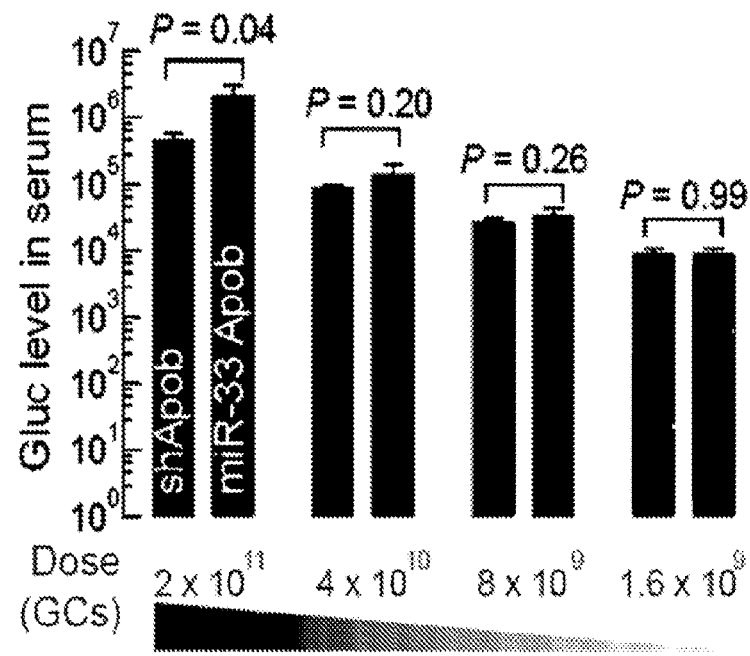

The silencing efficiencies of those novel rAAV-AmiRNAs in vivo and the classic rAAV-shRNA construct were compared. There were improvements in reporter gene expression (i.e., more intact vector genomes) in mice receiving vectors carrying miR-33 Apob as compared to conventional shApob at the dose of $2 \times 10^{11}$ (FIG. 10A) and comparable gene silencing effects (FIG. 10B). In summary, studies using natural miRNA scaffolds with lower complementarity in the stem and flaking sequences as the carrier for target specific antisense RNA improve AAV genome integrity and achieve gene silencing capability comparable to conventional shRNAs, but better than the current artificial miRNA design. Further studies are under way to further characterize RNAi machinery involved with the processing of those novel AmiRNAs and evaluate potential toxicity that may or may not be caused by long term expression of those silencing molecules from rAAV etc.

Figure 11C:
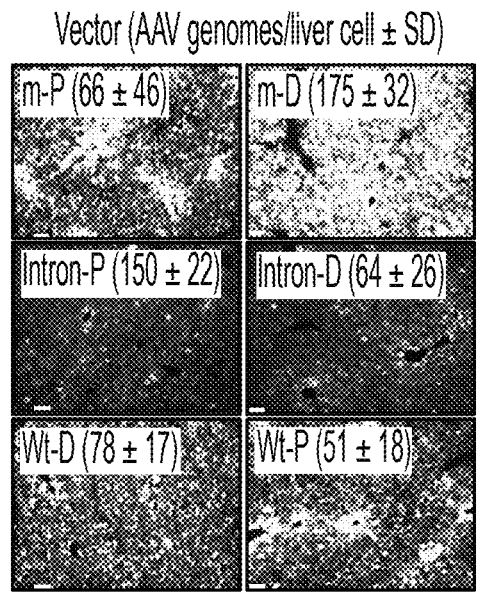
Figure 11D:
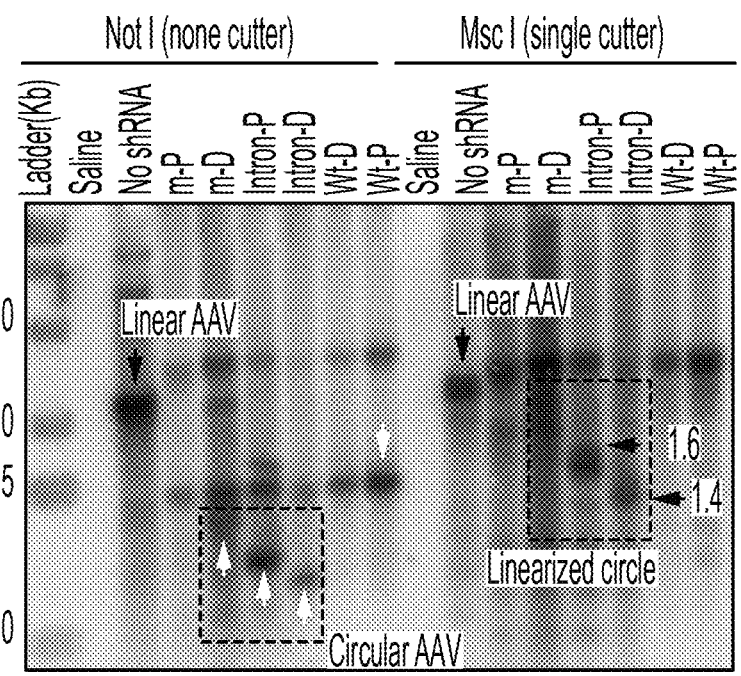
Figure 11D:
Figure 11D:

Example 3: Short DNA Hairpins Function as the Mutated Terminal Repeat of Adeno-Associated Virus Vectors Truncated AAV Genomes were Found in Mice Received scAAV9-shApob To compare the functionality of scAAV carrying shRNA cassettes in different position, the scAAV9-shApob vectors were administered intravenously with $5 \times 10^{13}$ genome copies per kg each to adult male C57B/6 mice. The vector titer was determined by Taqman quantitative PCR using EGFP probe[15]. Three weeks after the injection, no significant increase was detected in serum alanine aminotransferase (ALT), indicating no AAV-delivered shRNA related liver toxicity (FIG. 11A). Efficient gene silencing was observed in Apob gene in the liver of mice received the scAAV9 carrying shApob cassette at different position shown in FIG. 2A, compared to vector expressing no shRNA or saline control (FIG. 11B). In contrast to EGFP expression from scAAV-shApob plasmids in 293HEK cells, EGFP expression was much lower in the liver of mice received scAAV9 carrying shApob in the intron (Intron-P and Intron-D groups), even the transduced AAV genomes are comparable which was analyzed by Taqman quantitative PCR using EGFP probe (FIG. 11C). AAV vector genome will form linear and circular monomers and concatemers which have different transduction potency after vector metabolism in cells[12]. To characterize the molecular structures of AAV genomes in liver, Southern blot analyses was performed. Total liver DNA was digested with Not I which does not cut the AAV genome and Msc I which is a single cutter in AAV genome, respectively. In the Not I digested liver DNA, a probe binding to the EGFP transgene detected not only the linear and circular AAV molecules at expected size but also smaller molecules in mice received scAAV9 carrying shApob in the intron. After Msc I digestion, the small molecules migrated up, indicating the small molecules are in circle. The sizes of linearized bands are 1.5 kb and 1.3 kb equal to the distance from wtTR to the location of shApob (FIG. 11D). Results indicate that small circular molecules consist of EGFP transgene and wtTR. To explore the unknown junction with wtTR, PCR primers targeting the upstream of EGFP and downstream of wtTR were designed which can only amplify circular DNA template (FIG. 11E). From the genome DNA from mice received scAAV9 carrying shApob in the intron, the fragments were amplified at expected sizes (FIG. 11E), cloned into TOPO vector and sequenced them (FIG. 11F). The sequence data showed the junction to wtTR in Intron-P treated mouse is the sequence of shApob passenger strand and H1 promoter and the junction to wtTR in Intron-D treated mouse is the sequence of shApob guide strand and intron (FIG. 11F). In these two different truncated AAV molecules, the EGFP transgene is in the lack of Chicken β-actin (CB) promoter which explains the lower EGFP expression. The results suggest the shApob cassettes lead to the AAV genome truncations and compromise the EGFP reporter gene expression in vivo.

Figure 12:
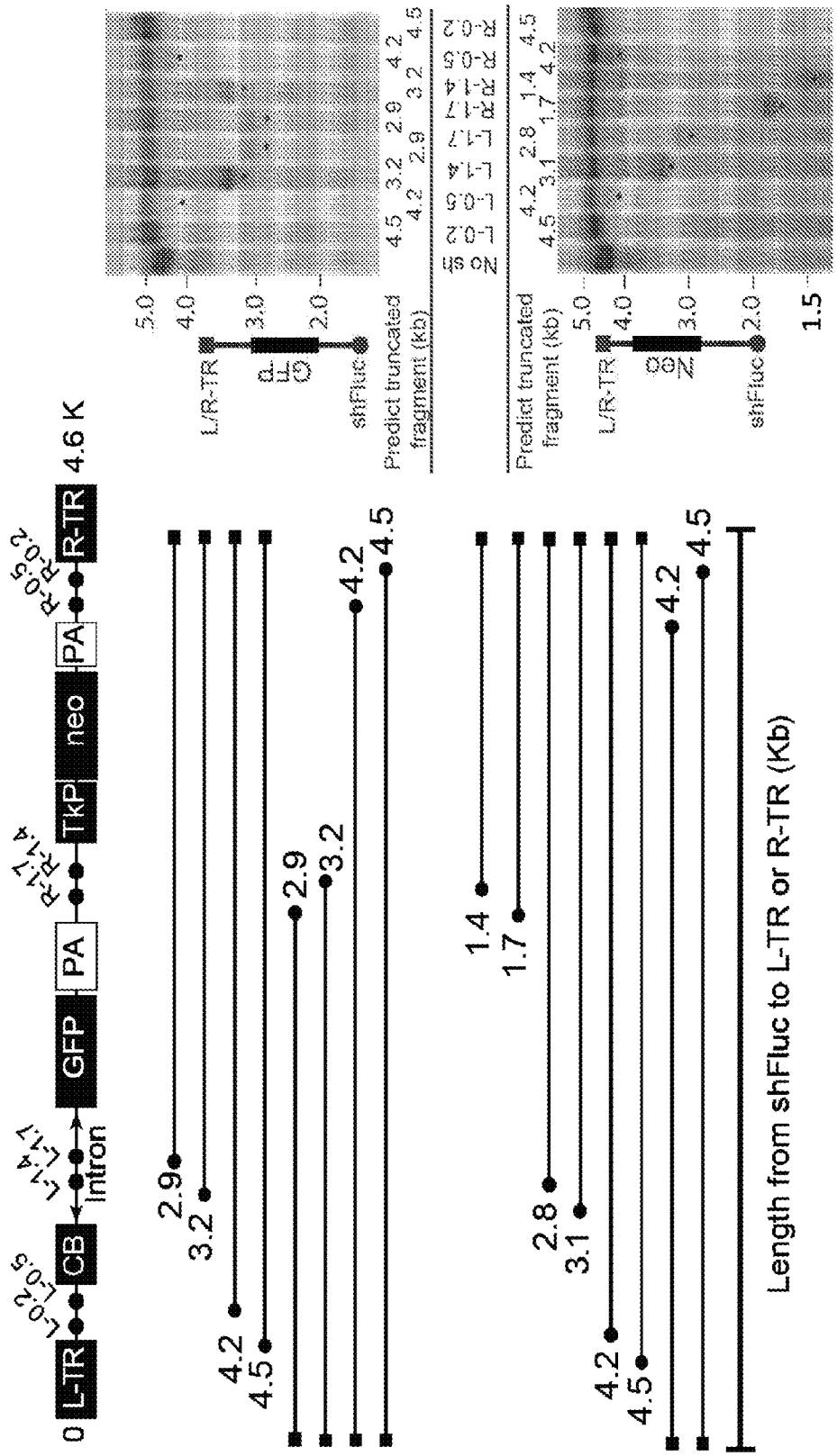
FIG. 12 shows a ssAAV construct incorporating shFluc cassette at different locations co-transfected with pAd and pRep/Cap into HEK293 cells. After 48 hours of transfection, Hirt DNA was extracted and probed with the GFP or Neo probes, respectively. The black solid circles indicate the shFluc locations. L0.2 represents the shRNA is 0.2 kb away to the L-TR. R0.2 represents the shRNA is 0.2 kb away to the R-TR.

To clarify if what was observed is not only a self-complementary vector genome phenomenon, the Hirt DNA from HEK293 cells transfected with pAd, pRep/Cap and conventional single stranded AAV vector (ssAAV) plasmids harboring shFluc-encoding DNA at different locations (FIG. 12) were also examined. Different from scAAV, the replication of ssAAV can start from left TR or right TR. After the hybridization with GFP and Neo probes, all the truncations except the 4.5 kb fragments (FIG. 12) were detected. No detection of these 4.5 kb fragments might be due to their small size difference with 4.6 kb full-length genome in regular agarose gel. This Southern blot data further confirmed that shRNA-encoding DNA is a barrier of genome replication for both ssAAV and scAAV.

Short DNA Hairpins Function as the Mutated Terminal Repeat

Figure 13A:
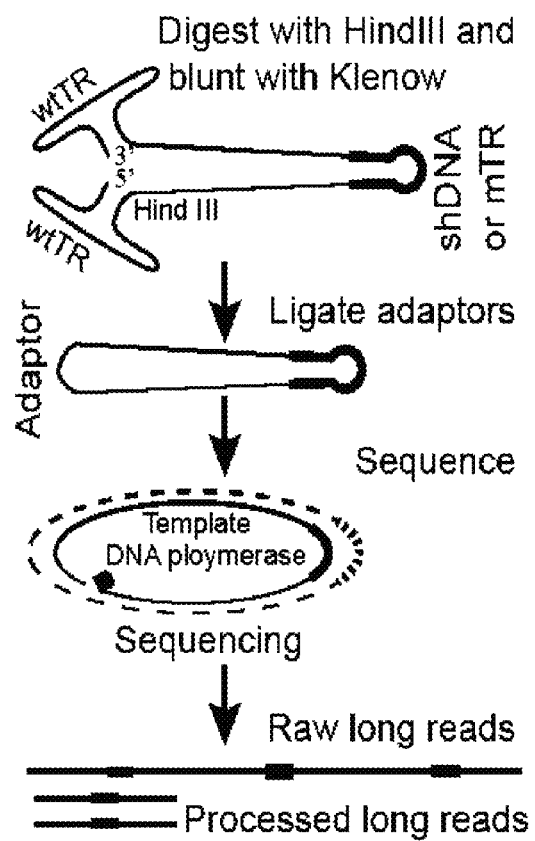
FIGS. 13A-C show the characterization of the truncated AAV genomes.
Figure 13B:
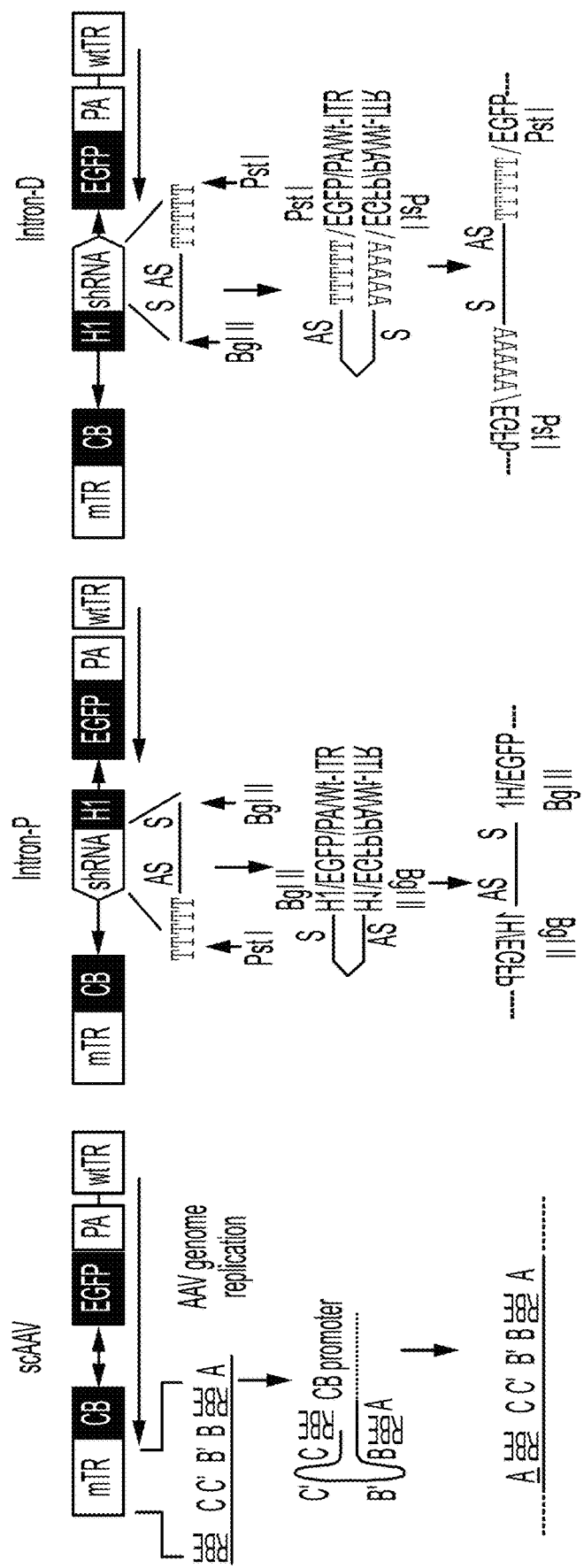
Figure 13C:
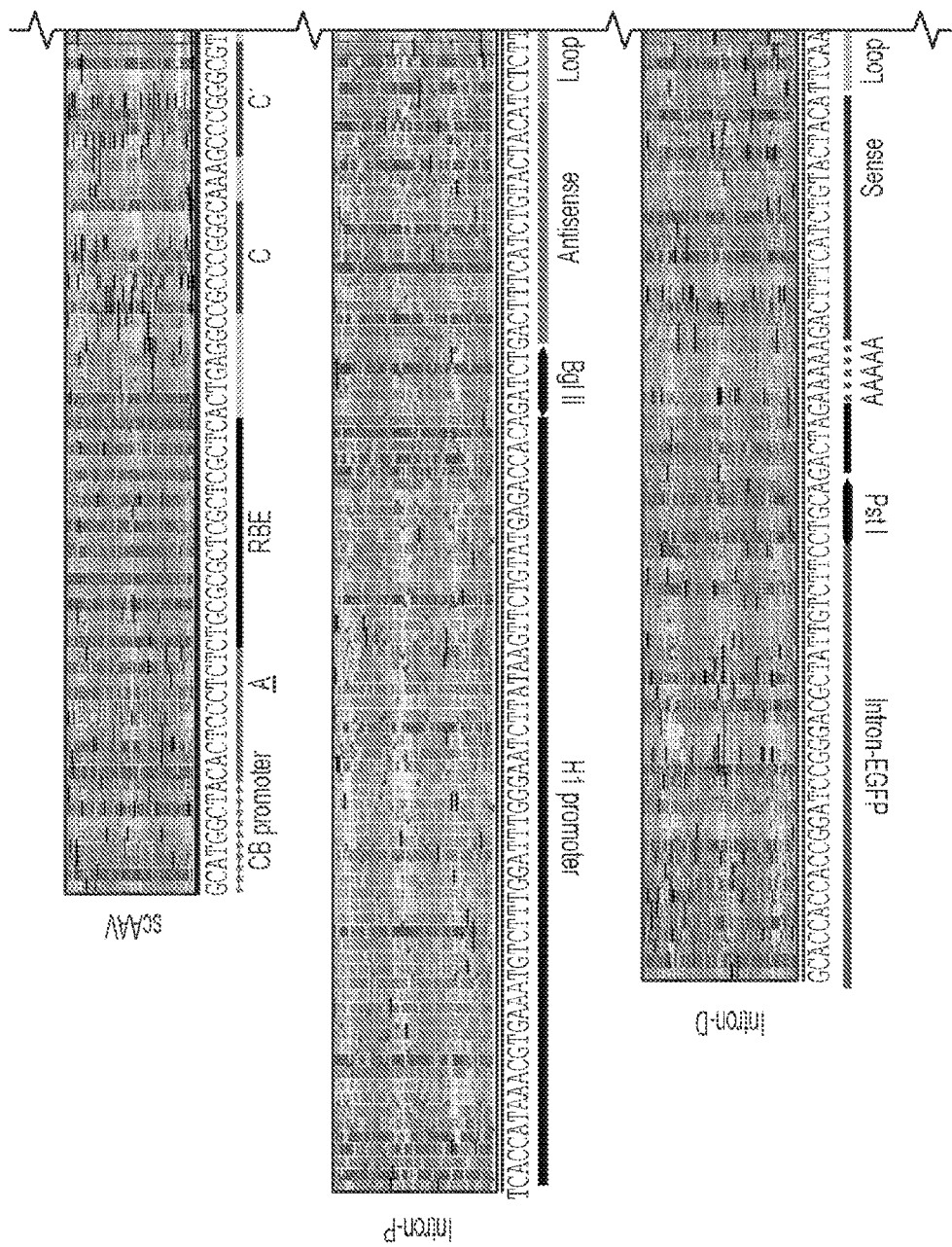
Figure 13C:
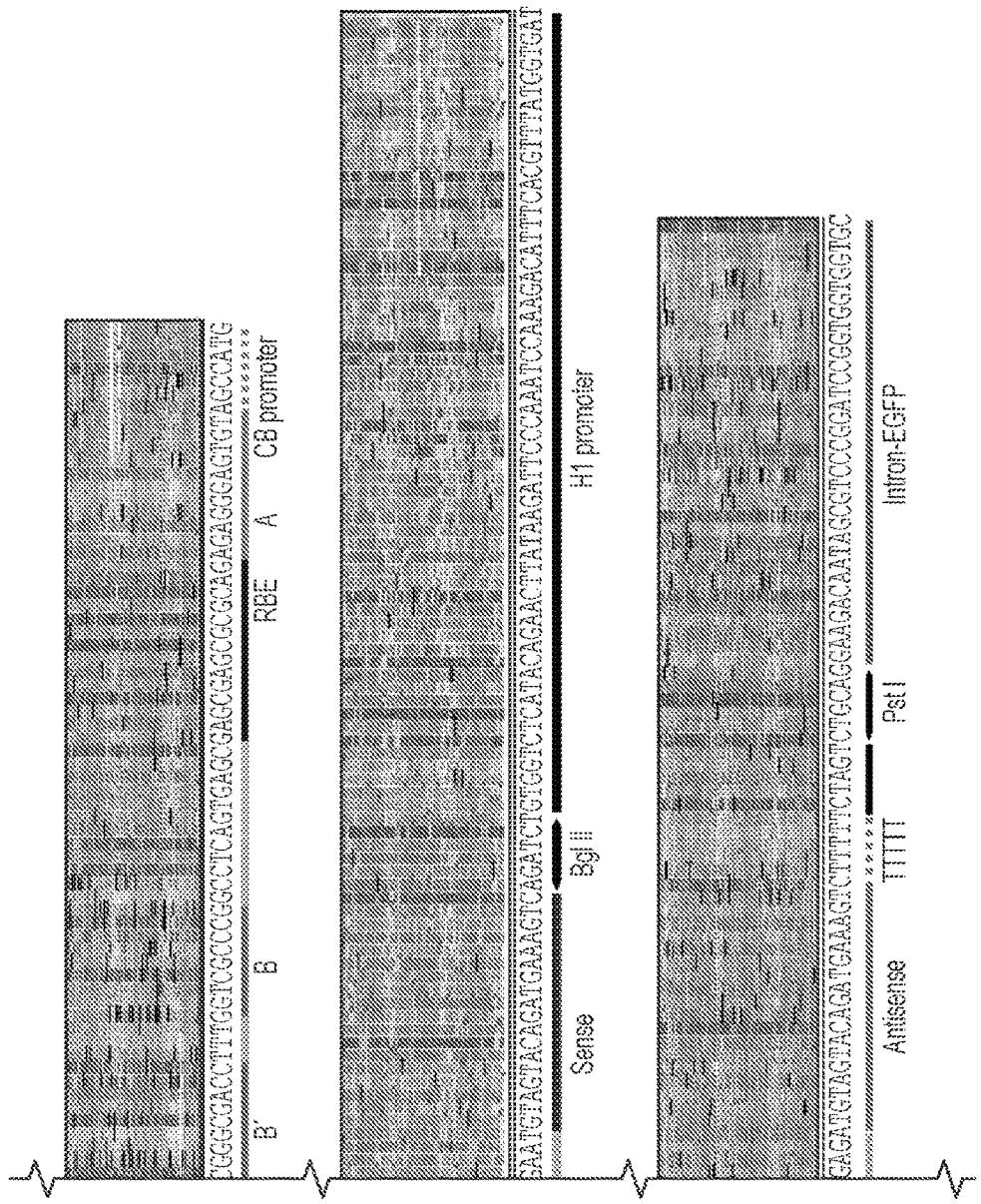

A model to illustrate how short DNA hairpins impact AAV genome replication (FIG. 6A) is provided. In a normal scAAV genome without shRNA cassette, its genome replication starts from the wtTR and forms an intra-molecular double-stranded DNA with mTR as a loop. However, for the scAAV construct bearing short DNA hairpin, when AAV genome replication reaches to the hairpin, the base-pairing of the hairpin stem switches the template from parental strand (FIG. 6A, solid line) to the daughter strand (FIG. 6A, dotted line). As a consequence of redirected genome replication, truncated genome will be produced. If the replication overcomes the complementarity of hairpin structure, it will generate the full-length scAAV genome for packaging. In both cases, the Rep will nick the wtITR to release the newly synthesized genomes for next round of replication. Viral genomes extracted from purified viral vectors were examined in an alkaline gel and the sizes of both intact and truncated genomes were doubled (FIG. 6B). The results indicate the truncated genome is an intra-molecular double-stranded DNA like scAAV genome at smaller size (FIG. 6B). To characterize the truncated AAV genomes, restriction enzyme mapping was performed on the DNAs from two scAAV9 vector carrying shApob in the intron (Intron-P and Intron-D). Three restriction enzymes (Mlu I, Xho I and BstX I) with reorganization sites upstream of shRNA-encoding DNA only digested the full-length AAV genomes, but the other three restriction enzymes (Eag I, Hind III and Msc I) which recognize the downstream of shRNA-encoding DNA can digest both full-length and truncated genomes (FIG. 6D). The result showed the shRNA sequence is a dividing line for the full-length and truncated genomes. Taken the alkaline gel and restriction enzyme mapping data together, the truncated genomes are intra-molecular double-stranded DNA with shRNA at one end. To further characterize the truncated molecules, they were sequenced by single molecule real-time sequencing (SMRT, Pacific Biosciences) platform. In standard SMRT library preparation, adaptors will be added to both ends of one DNA molecule form a circular template for sequencing. In library preparation, adaptor is added to one end of the intra-molecular DNA. To avoid the potential sequencing difficulty from the strong secondary structure of wtTR at the end, the viral genome DNA with Hind III was digested to remove the wtTR fragment and performed SMRT-CCS (FIG. 13A). After sequencing, the adaptors were removed from the raw long reads and the processed long reads will be the sequence of denatured AAV genomes. Because of lacking of the Rep nicking sites in the mTR, scAAV genome continues its replication after mTR, forms molecules with mTR in the middle and complementary sequences at two ends, and generates intra-molecular double-stranded genomes after folding back (FIG. 13B left). Based on the model, in Intron-P vector, when the genome replication reaches to the antisense strand of shRNA, the base-pairing from the shRNA stem re-directs the orientation of replication, the five thymine and Pst I site right after shRNA antisense strand will not the replicated and the sequence of Bgl II site and H1 promoter located before the shRNA sense strand will be duplicated in the truncated genomes (FIG. 13B middle). In Intron-D vector, the genome replication turns back before the Bgl II site which is next to the shRNA sense strand, the Bgl II site will be not replicated, but the five thymine and Pst I site will be replicated (FIG. 1B3 right). In the scAAV-CBEGFP plasmid, there is only one "A" site in the inner border of mTR. But in the scAAV-CBEGFP vector genome, one more "A" (A) after RBE site was found, indicating the re-directed and continued genome replication by mTR. It is the first time to sequence the mTR loop in the scAAV vector since it has been developed (FIG. 13C top). In the sequencing data, the molecules with predicted hairpin DNA centered structures (FIG. 13C middle and bottom) were also detected.

The truncated AAV genomes are intra-molecular double-stranded DNA with short hairpin DNA in the middle.

Figures 14A, 14B:
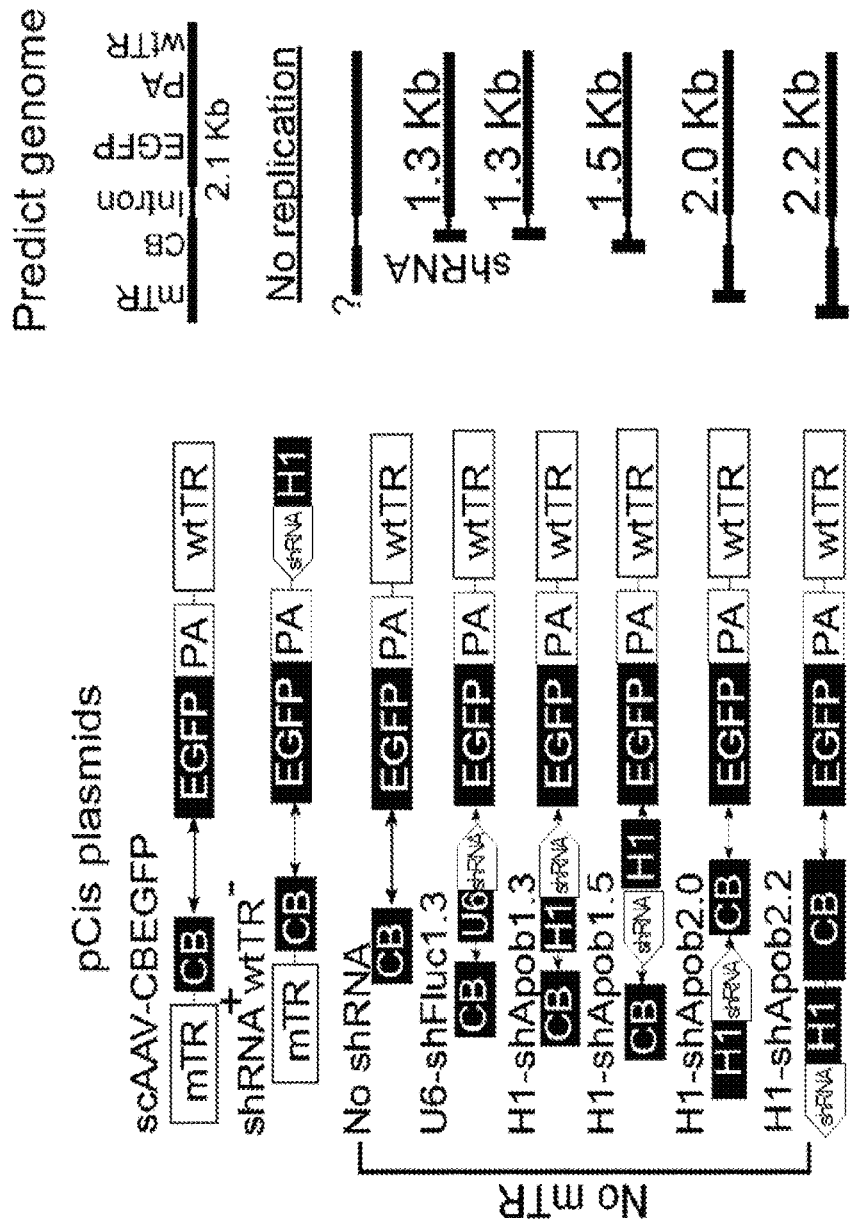
FIGS. 14A-14I show the production of AAV vectors flanked one wtTR and one hairpin DNA at two ends and the functionality evaluation in mice.
Figure 14D:
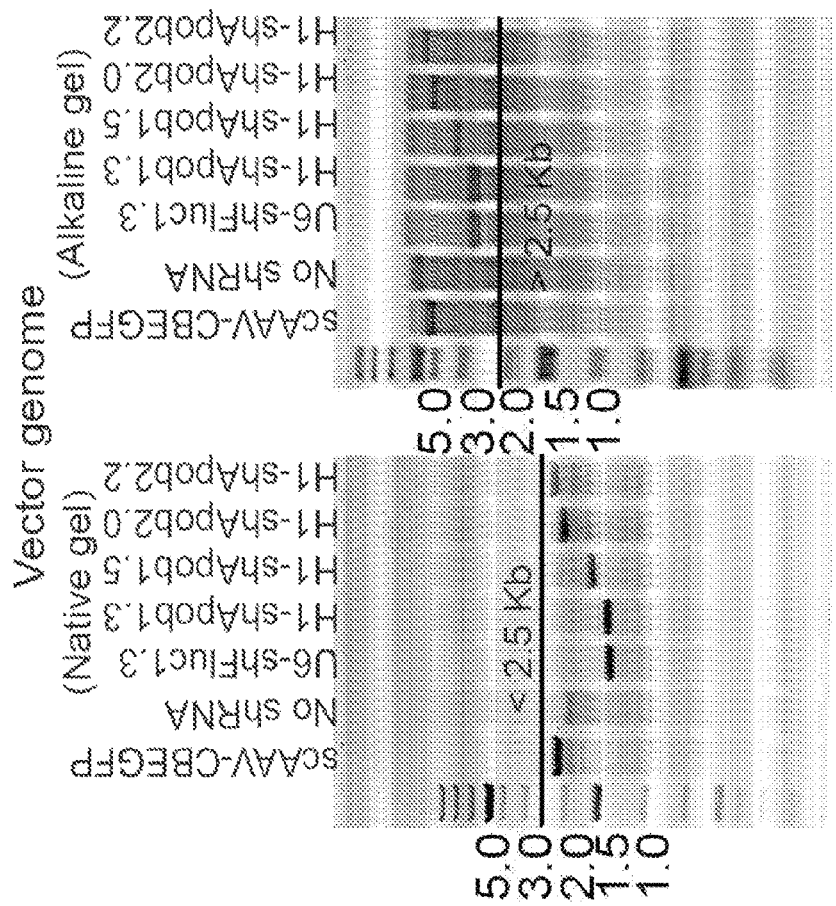
Figure 14C:
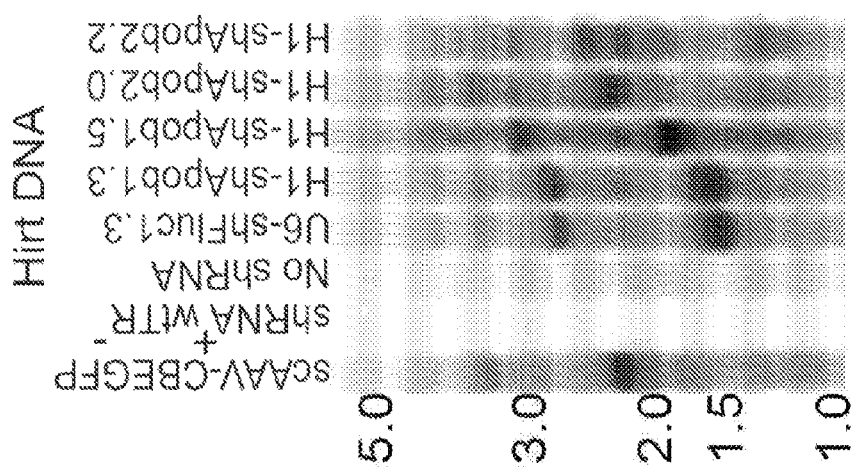
Figure 14E:
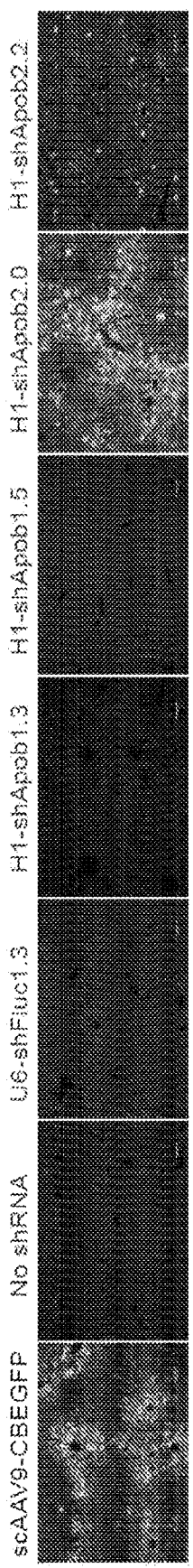
Figure 15A:
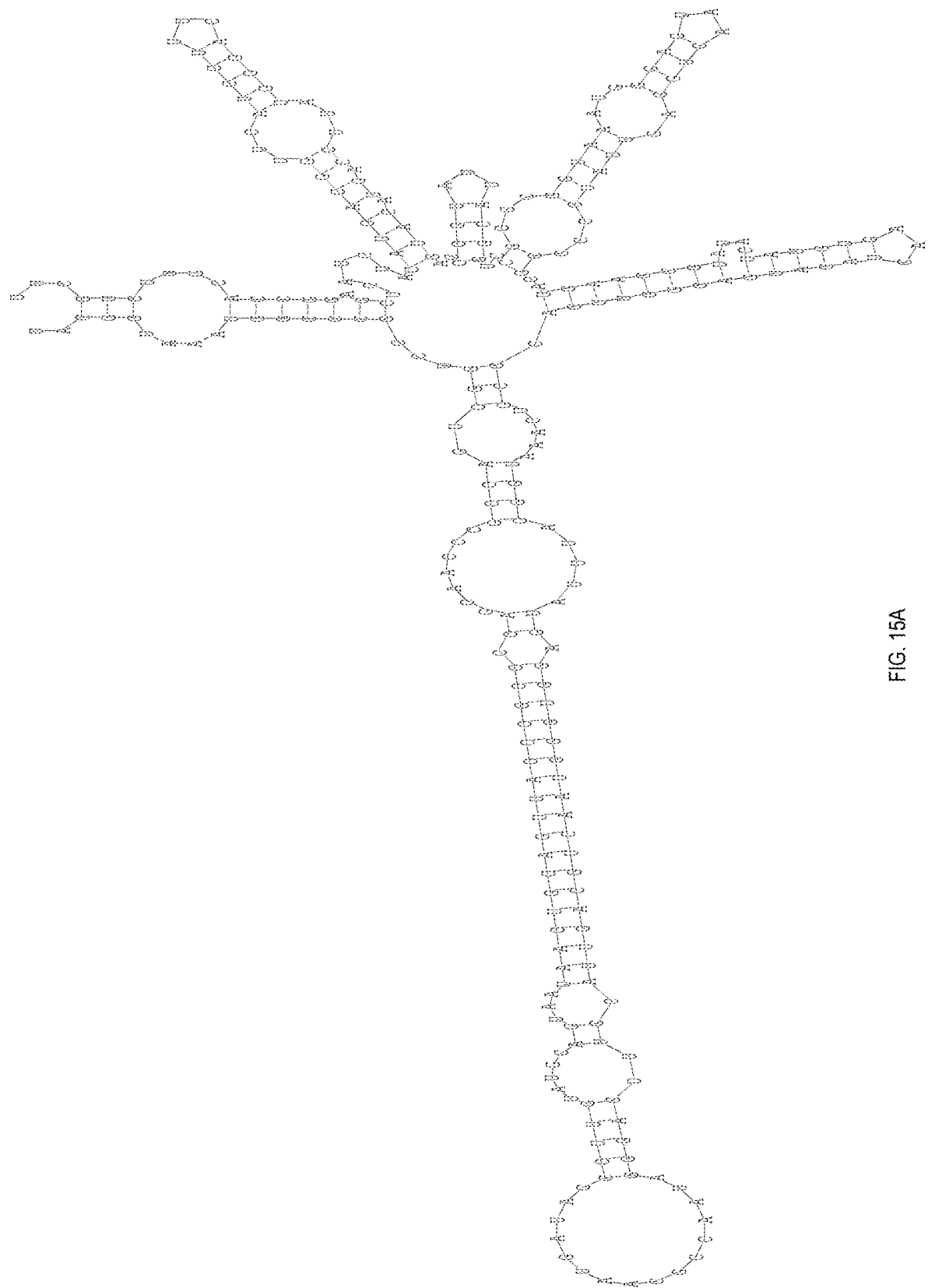
FIGS. 15A-15D show hairpin DNA function as mutant TR in AAV package and in vivo transduction.
Figure 15C:
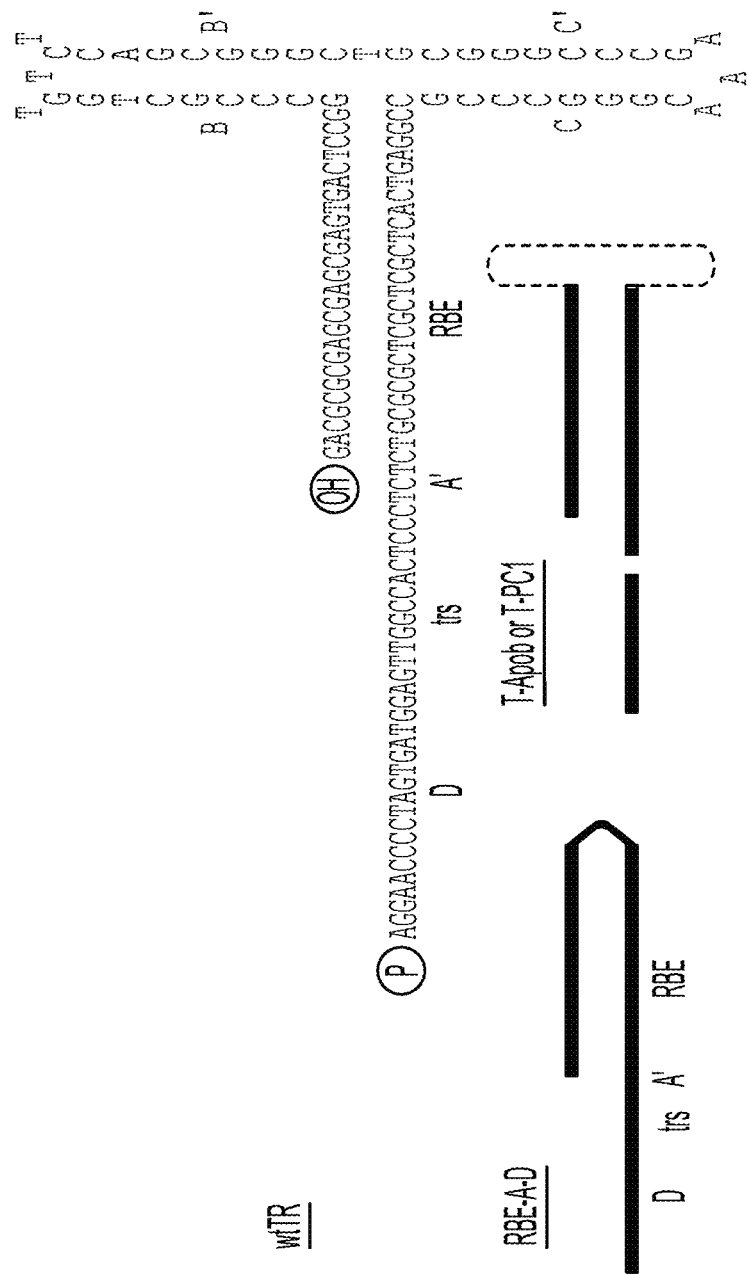
Figure 15B:
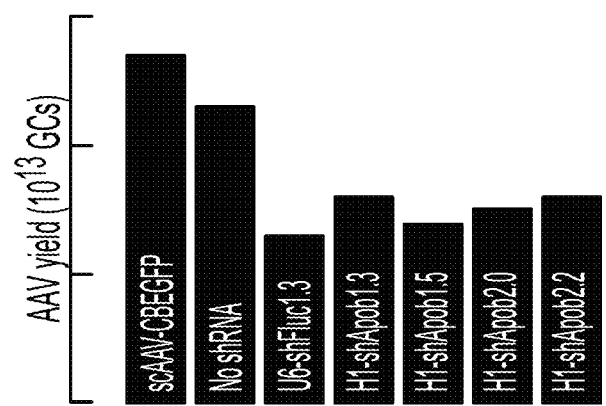
Figure 15C:
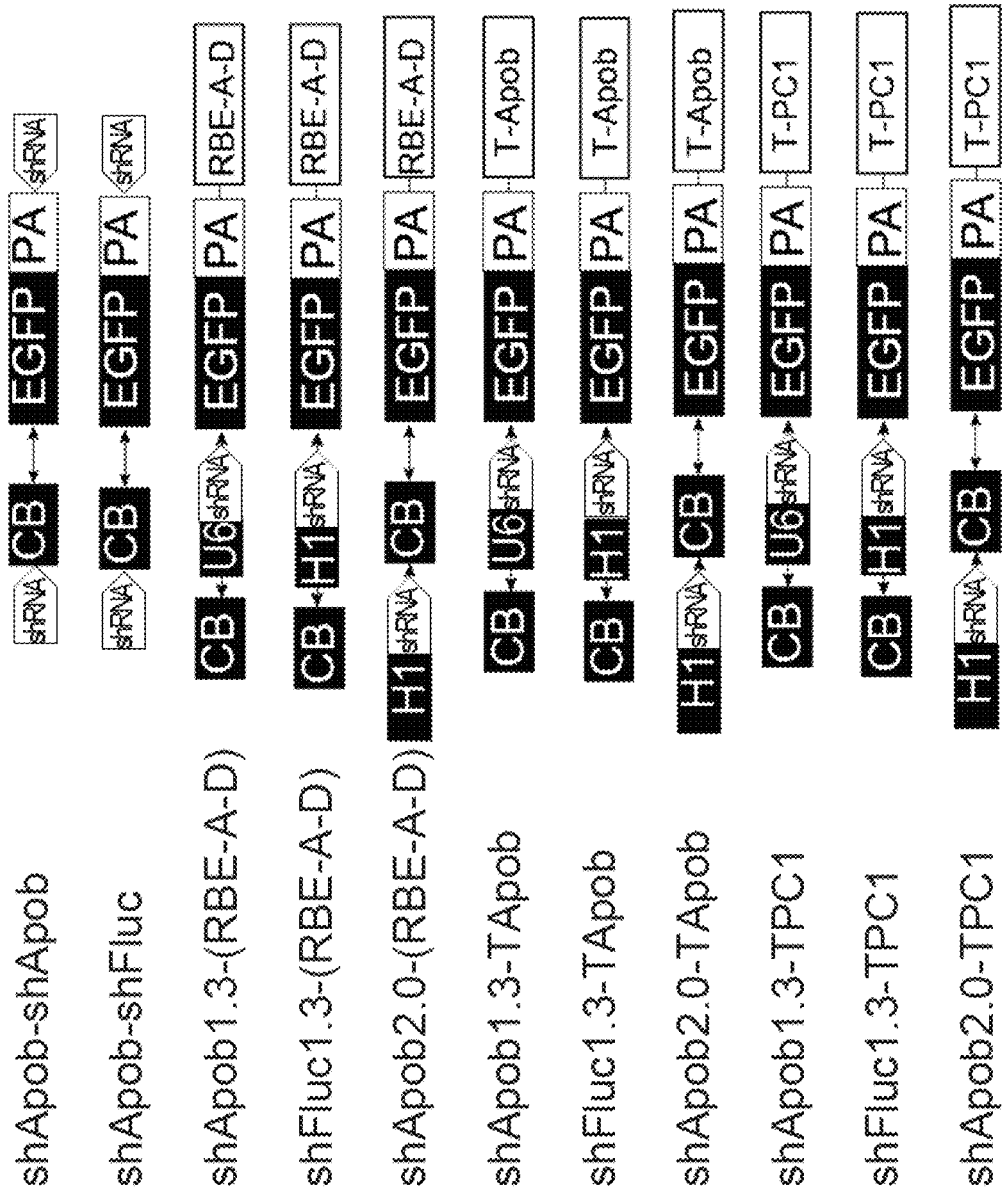
Figure 15C:
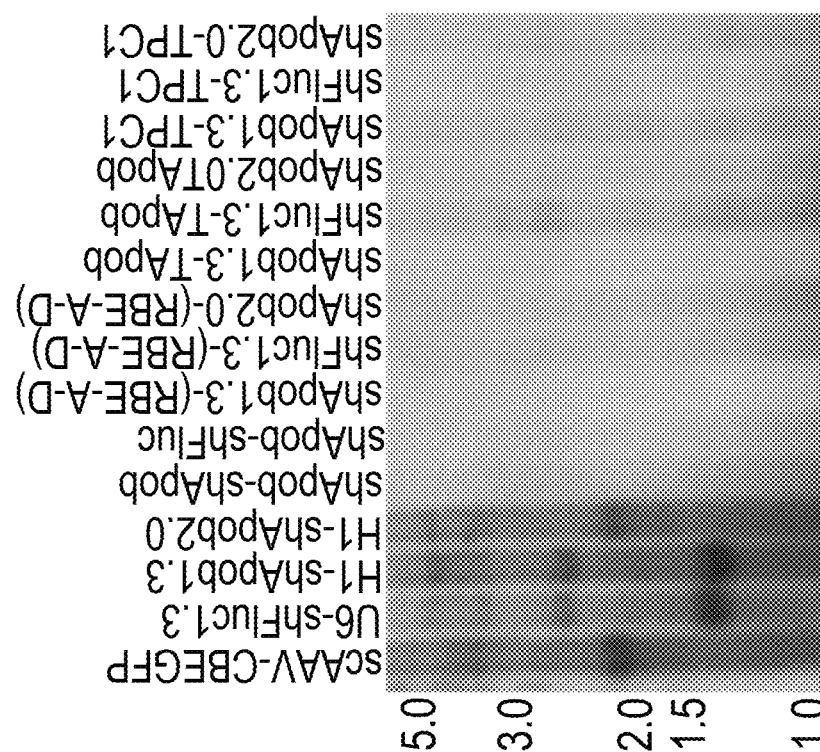
Figure 15D:
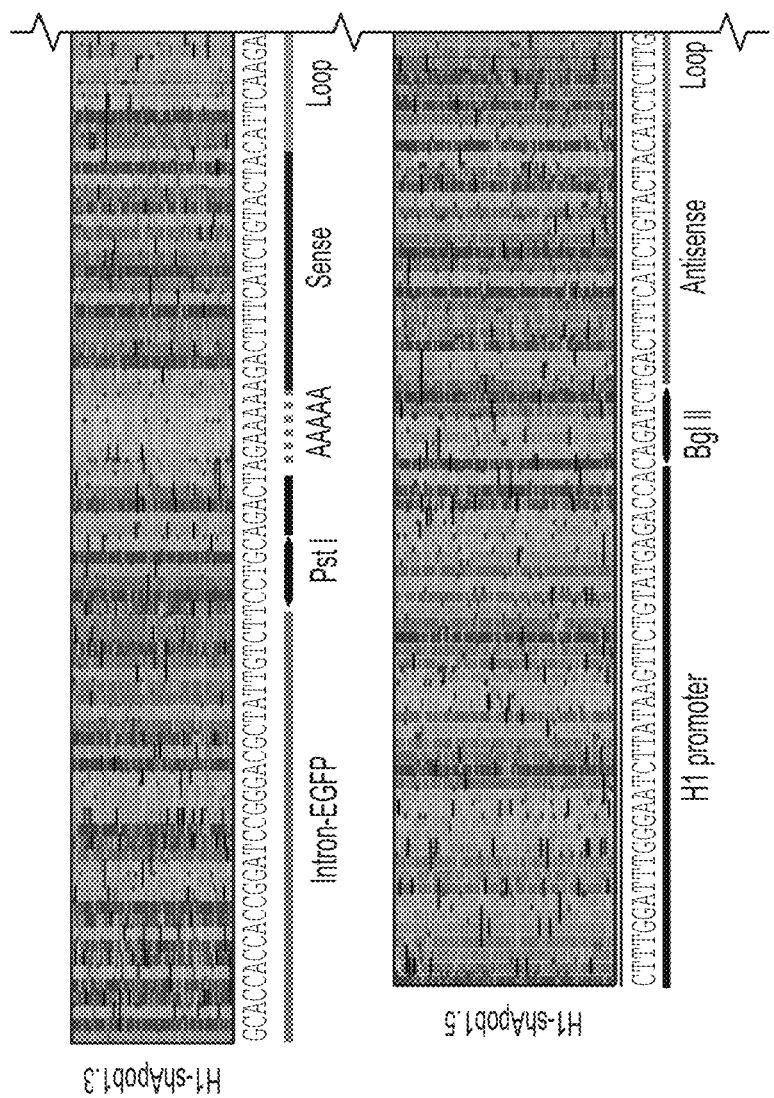
Figure 15D:
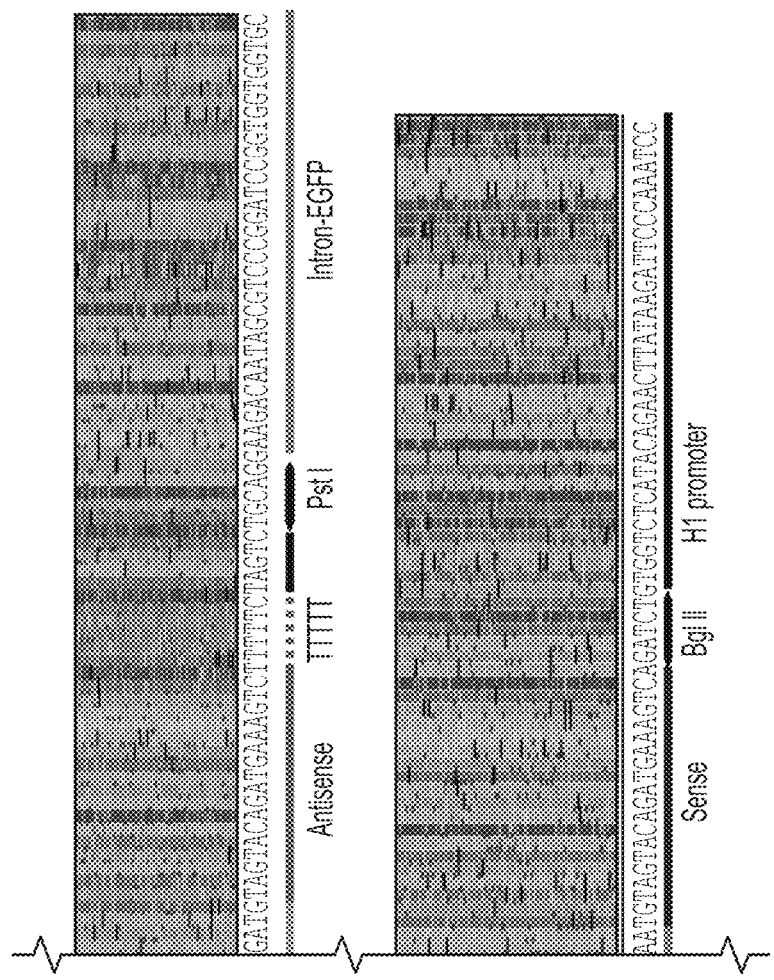

Results indicated that short hairpin DNA at least functions as an alternative mTR in the truncated AAV genomes. To further characterize, the mTR was replaced with DNA fragments encoding shRNA against Apob or Fluc gene in the scAAV constructs (FIG. 14A-14B, showing constructs and predicted lengths). In the absence of mTR, and the presence of wtTR and hairpin DNA (U6-shFluc1.3, H1-shApob1.3, H1-shApob1.5, H1-shApob2.0 and H1-shApob2.2), AAV genomes can be rescued and existed as monomers and dimers (FIG. 14C). The genome can be rescued from construct carrying only one wtTR (pmD−). The sequence which can form hairpin structure within the CB promoter may serve as mTR for the genome replication (FIG. 15A). When wtTR was replaced with hairpin DNA (pshRNA+wtTR−), no AAV genomes were able to be rescued from the triple-transfected HEK293 cells (FIG. 14C). The original elements (D, RBE, trs and A) were observed in the wtTR and maintain the same T-shape structure by replacing the B-B' and C-C' with the other palindromes, no AAV genome can be rescued either (FIG. 15B). Then these pCis plasmids were packaged into AAV9 and the purified rAAV genomes in both native and alkaline gels were analyzed. The molecular weight of AAV vectors containing wtTR and hairpin DNA at two ends was doubled in alkaline gel comparing to the size in native gel, indicating the vector genomes are also intra-molecular double-stranded DNA like scAAV genome (FIG. 14D). The vector yield is comparable to the scAAV control (FIG. 15C). SMRT sequencing revealed the symmetrical structure of AAV genome, hairpin DNA in the center and complementary sequences at two sides (FIG. 15D). These AAV vectors were named shAAV.

Figures 14F, 14G:
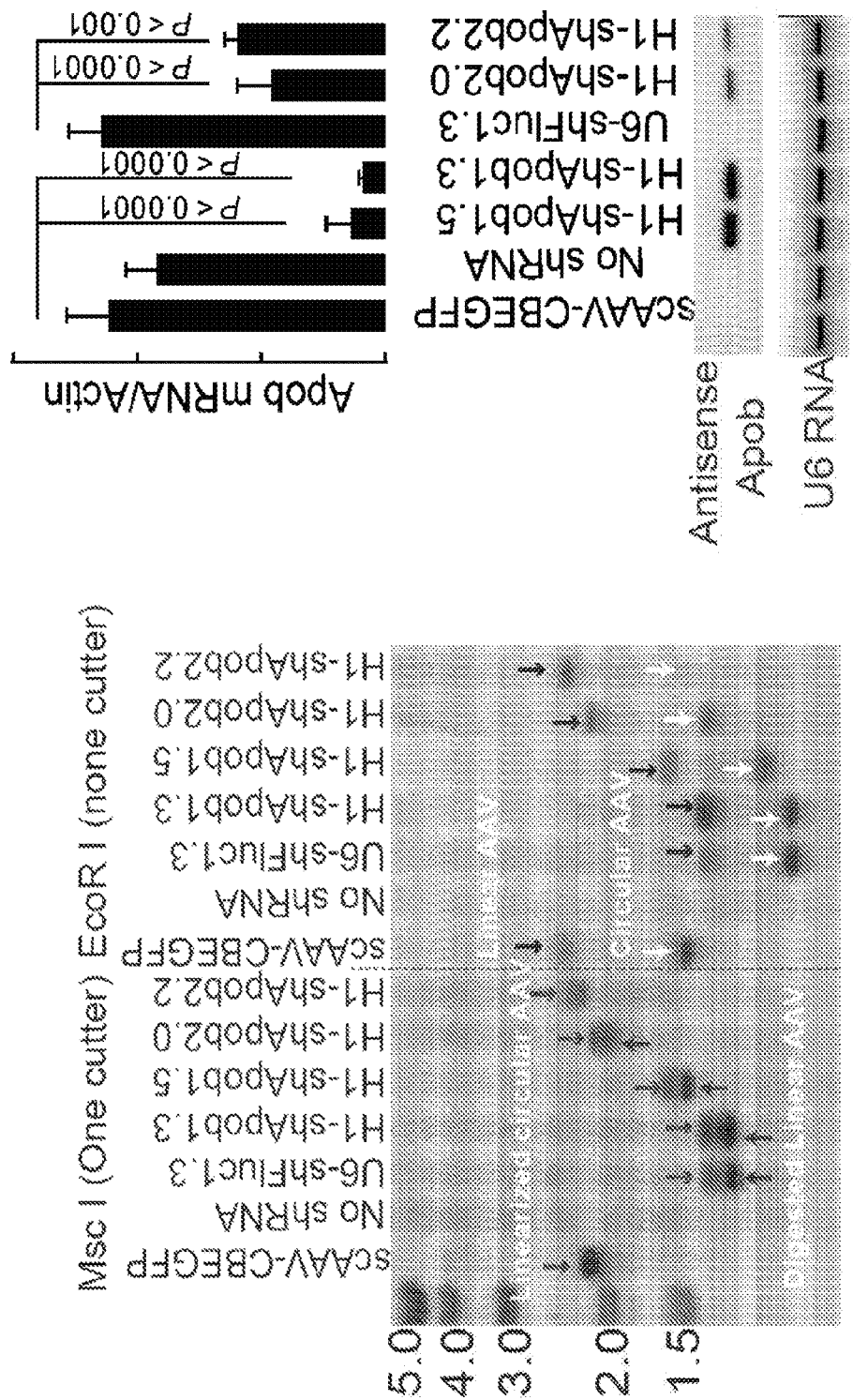
Figures 14H, 14I:
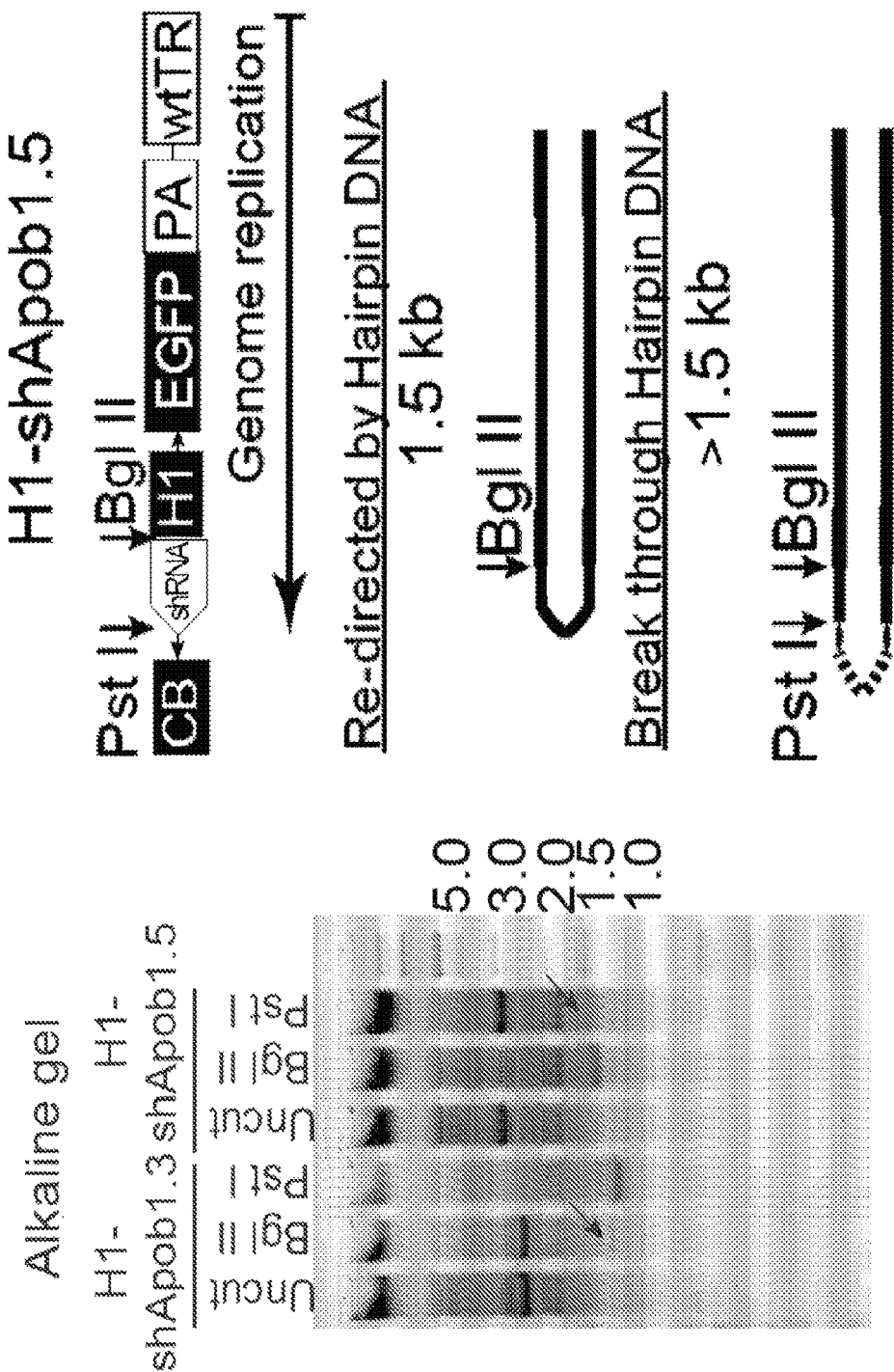

To test their functionalities in vivo, shAAV9 was intravenously injected carrying EGFP gene into adult C57/B6 mice at the dose of $1.6\times10^{13}$ GCs/kg and harvested liver tissues 3 weeks later. Because of the lack of CB promoter for EGFP reporter gene in the viral genomes, U6-shFluc1.3, H1-shApob1.3 and H1-shApob1.5 shAAVs produced few green cells in the liver. Compared to regular scAAVEGFP vector, the H1-shApob2.0 shAAV vectors achieved comparable EGFP transduction efficacy, but the EGFP expression was much less in the H1-shApob2.2 shAAV. To characterize the molecular forms of shAAV in vivo, the same Southern blot analysis as FIG. 11C was performed. The Southern blot data showed shAAV vectors exist as both linear and circular forms like scAAV vectors in vivo. Dominant AAV molecular H1-shApob2.2 is in linear form may be the reason of the low EGFP expression in vivo (FIG. 14F). ApoB gene expression was down-regulated by shAAV vector carrying shApob cassette and the RNAi phenomenon was confirmed by small RNA Northern blot (FIG. 14G). These results are unexpected because the shRNA cassettes in the shAAV vector genomes are not intact to produce functional shRNA (FIG. 4g and FIG. 15D). Based on the SMRT sequence data, both H1 promoter and passenger strand RNA-encoding sequence are missing in H1-shApob1.3 shAAV genome. Also there are no five thymine terminal signal and guide strand RNA-encoding DNA in the H1-shApob1.5 shAAV genome (FIG. 15D). To validate the SMRT sequence result, the H1-shApob1.3 and H1-shApob 1.5 shAAV vector genomes were digested with Bgl II and Pst I and checked the size in the alkaline gel. The size of uncut H1-Apob1.3 shAAV genome became 2.6 kb because of the denaturing of the intra-molecular double-stranded DNA in alkaline gel. Based on the SMRT sequence data, Pst I digests the middle of H1-Apob1.3 and the size of Pst I digested genome should remain as 1.3 kb. The Bgl II digested genome should be doubled because there is no Bgl II site in the H1-Apob1.3 genome. The Pst I digestion confirmed the presence of Pst I site in the genome, but except the dominant 2.6 kb fragment from Bgl II digestion, the additional fragment (>1.3 kb), indicating the Bgl II digested some of shAAV genomes (FIG. 14H) was seen. In H1-Apob1.5 shAAV, there is one Bgl II site and no Pst I site in the genome based on the SMRT sequence data. The Bgl II site was confirmed and the extra >1.5 kb fragment in the Pst I digestion (FIG. 14H) was also found. In the AAV package, except producing the dominant shAAVs, the AAV genome replication broke through the hairpin barrier and generated intact shRNA expression cassettes (FIG. 14I and FIG. 6A). Then the PolII promoters were deleted for the shRNAs in the shAAV plasmids, packaged them into AAV9 vectors and inject the mice again. After 3 weeks of the injection, neither the reduction of Apob gene nor the Apob antisense in the liver of mice was detected. The EGFP expression and AAV molecular forms were not affected by the deletion of Pol III promoter.

Materials and Methods:

Vector Design, Construction, and Production

The shFluc fragment in pRNA-U6.1/Neo-siFluc (GenScript, Piscataway, NJ) was integrated into the MluI, PpuMI and Bbs I site of pscAAVCBEGFP plasmid to generate pscAAV-shFluc plasmids bearing shFluc in different locations. And also the shFluc fragment was cloned into pUF11 plasmid at the Kpn I, SgrAI, Xho I and Bbs I sites to generate pUF11-shFluc serial plasmids. The mutant TR in pscAAVCBEGFP was deleted by Pac I and Mlu I digestion to pmTR− plasmid. The pshRNA+wtTR− was made by replacing the Msc I-Pac I fragment in wtTR with shApob-encoding DNA. Pac I and Mlu I digestions was also used to delete the mTR from the original plasmids of pU6-shFluc1.3, pH1-shApob1.3 and pH1-shApob1.5. ShApob-encoding DNA was incorporated into the Sal site of pmTR- to generated plasmids pH1-shApob2.0 and pH1-shApob2.2. The RBE-D-A, T-shApob and T-PC1 adaptors were cloned between the Pac I and Msc I sites of wtTR to reconstruct the wtTR. To delete the H1 promoters from pshAAV plasmids, Bgl II and BstX I fragment was removed from p pH1-shApob1.3, pH1-shApob1.5, pH1-shApob2.0 and pH1-shApob2.2 plasmids. The shFluc fragment was integrated into the BamH I of pmTR− to make pshFluc1.3 plasmid without U6 promoter. Partial Apob cDNA was amplified from mouse liver RNA and incorporated between the Not I and Xho I site of pmiCHECK to generate shApob activity sensor plasmid. Vectors used in this study were generated, purified, and titered as described[21]. All the constructs will be deposited to Addgene.

Vector DNA Analysis

Viral DNA was extracted from purified vector following the protocol for extraction of recombinant adenovirus genomic DNA. Vector DNA equivalent to $0.1-1\times10^{11}$ genomes was loaded into agarose gel or alkaline gel and stained with SYBR gold.

Southern Blot Analysis for Hirt DNA and Liver DNA.

Low molecular weight Hirt DNA extracted from triple-transfected Hek293 cells and digested with Dpn I before hybridization. To analyze the AAV genome in mouse, three microgram of total liver DNA was digested with EcoR I (none cutter) or Msc I (single cutter) for hybridization. The results were visualized using a FLA-7000 Imager (FUJIFILM). All the probes were labeled by $P^{32}$ using random primer labeling kit (Takara).

SMRT Sequencing and Data Analysis

Vector DNA was digested with Hind III to remove the wtTR and agarose gel purified. Around 500 ng viral DNA was submitted for SMRT sequencing. Library preparation and sequencing were done following standard Pacific Biosciences protocols PacBio raw reads processed into circular consensus (CCS) reads using the PacBio pipeline. CCS reads were aligned to the reference sequence using Bowtie. Data was visualized using IGV. Sequence data are available from the NCBI Short Read Archive (www.ncbi.nlm.nih.gov/sites/sra) as GSExxxx.

Mouse Studies

Male C57BL/6 mice (Harlan, IN) were obtained and maintained and all animal procedures performed according to the guidelines of the Institutional Animal Care and Use Committee of the University of Massachusetts Medical School. After injection of the vectors at indicated dose, the mice were sacrificed 3 weeks later and liver was harvested for cryosectioning using a Nikon TE-20005 inverted microscope. Serum samples were collected and analyzed for ALT using a COBAS C 111 analyzer (Roche Diagnostics, Lewes, UK). Total liver RNA was extracted using Trizol (Invitrogen). qRT-PCR and small RNA Northern blot were performed as reported before[23]. rAAV genome copy numbers in total liver DNA were determined.

Statistical Analysis

All results are given as mean±standard deviation and compared between groups using the two-tailed Student's t-test.

Figure 16A:
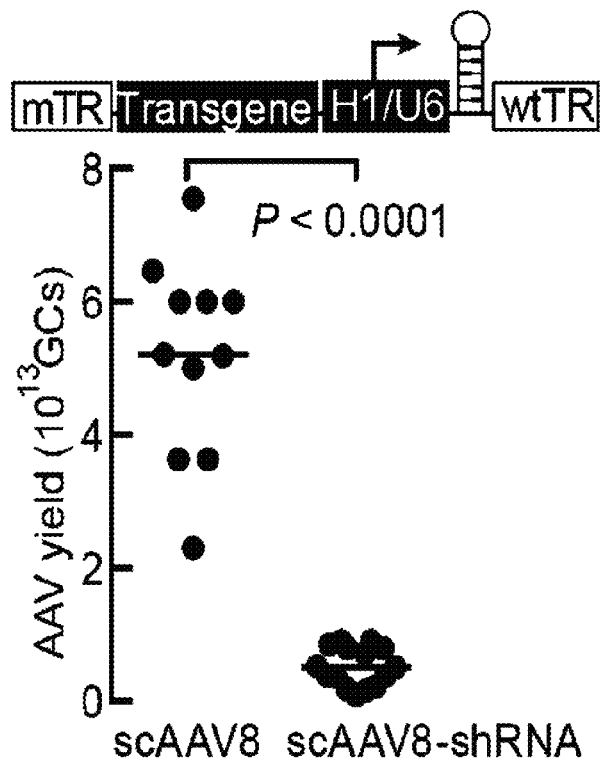
FIGS. 16A-16C show positioning of shRNA cassettes within scAAV constructs impacts vector yield.
Figure 16B:
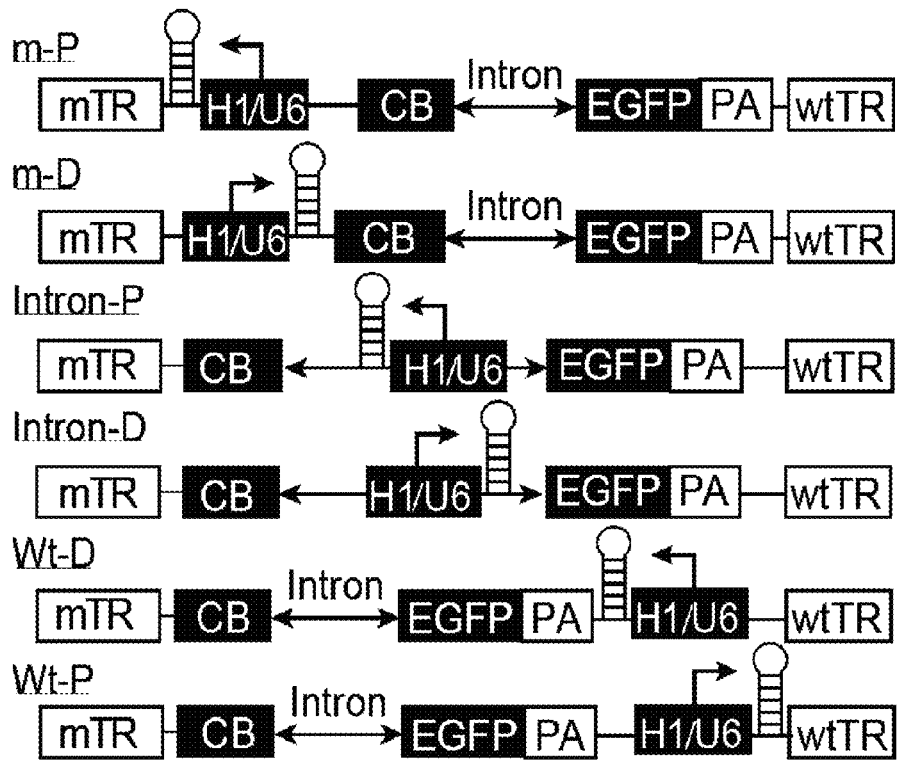
Figure 16C:
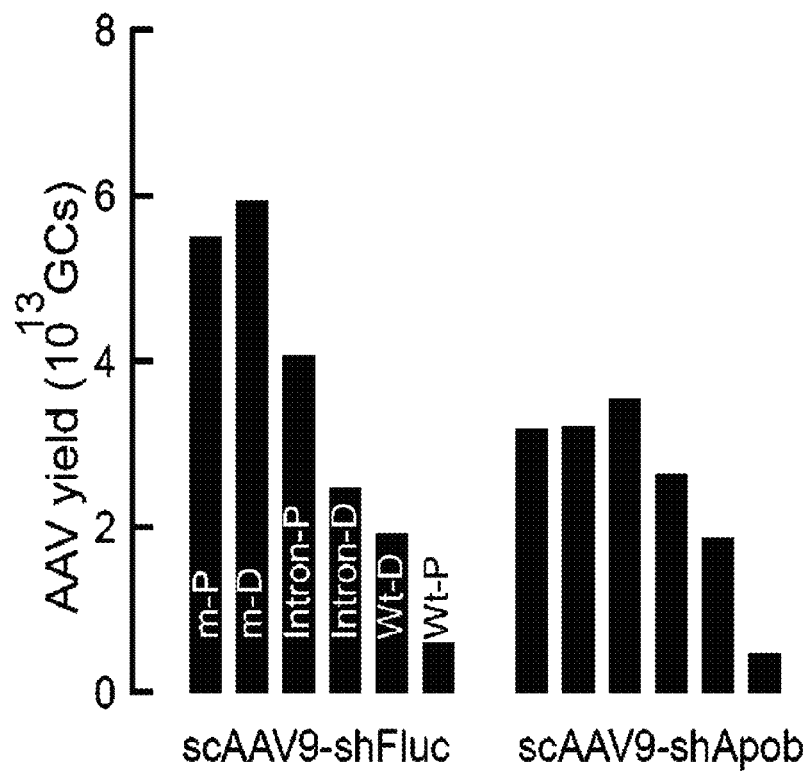

Example 4: Short DNA Hairpins Generate Self-Complementary Adeno-Associated Virus Genomes by a Template-Switching Mechanism Placement of shDNA Sequences Proximal to the Wild-Type TR Reduces scAAV Vector Yield During the manufacturing of scAAV vectors, it was found that the yield of scAAV vectors carrying shRNA expression cassettes proximal to the wild-type terminal repeat (wtTR) was consistently lower than that of scAAV vectors without shRNA cassettes. This difference occurred independent of transgene or shDNA sequences (FIG. 16A). Since the replication of scAAV genomes can only initiate from the wtTR, due to a lack of replication initiation sites in the mTR, whether the hairpin structure of the shDNA sequence interferes with AAV genome replication when placed proximal to the wtTR resulting in poor vector yield was investigated. scAAV vectors that consist of an eGFP reporter gene driven by the CMV enhancer/chicken β-actin promoter (CB) and an shRNA cassette placed at different positions along the scAAV genome were produced. By using two different shRNA expression cassettes, the first encoding an shRNA against mouse Apob driven by the H1 promoter (H1-shApob), and the second encoding an shRNA against firefly luciferase driven by the U6 promoter (U6-shFLuc) (FIG. 16B), it was observed that the yield of scAAV-shRNA vectors is reduced when shRNA cassettes are proximal to the wtTR (Wt-P) (FIG. 16C).

Figure 17A:
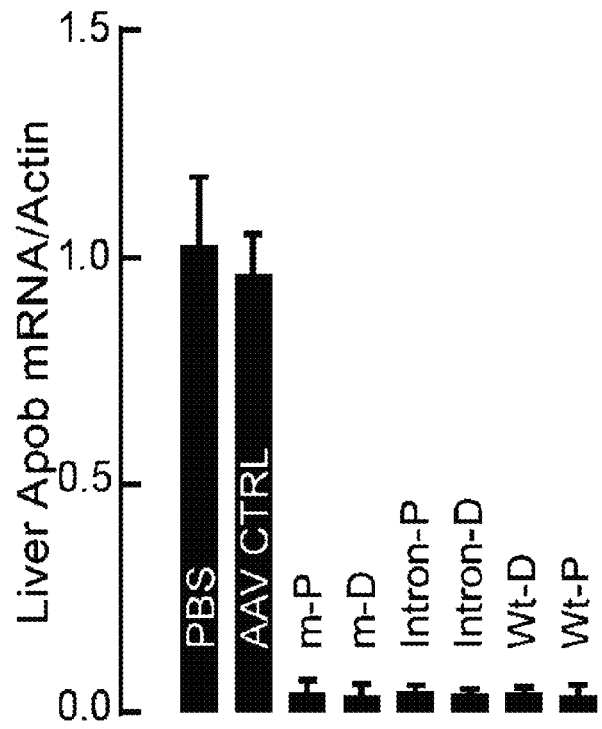
FIGS. 17A-17E show in vivo performances of scAAV-shApob vectors and analysis of small AAV molecules.
Figure 17B:
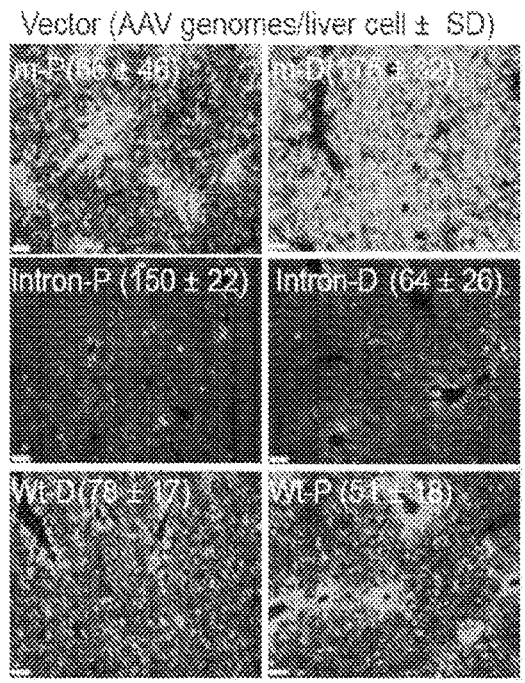
Figure 17C:
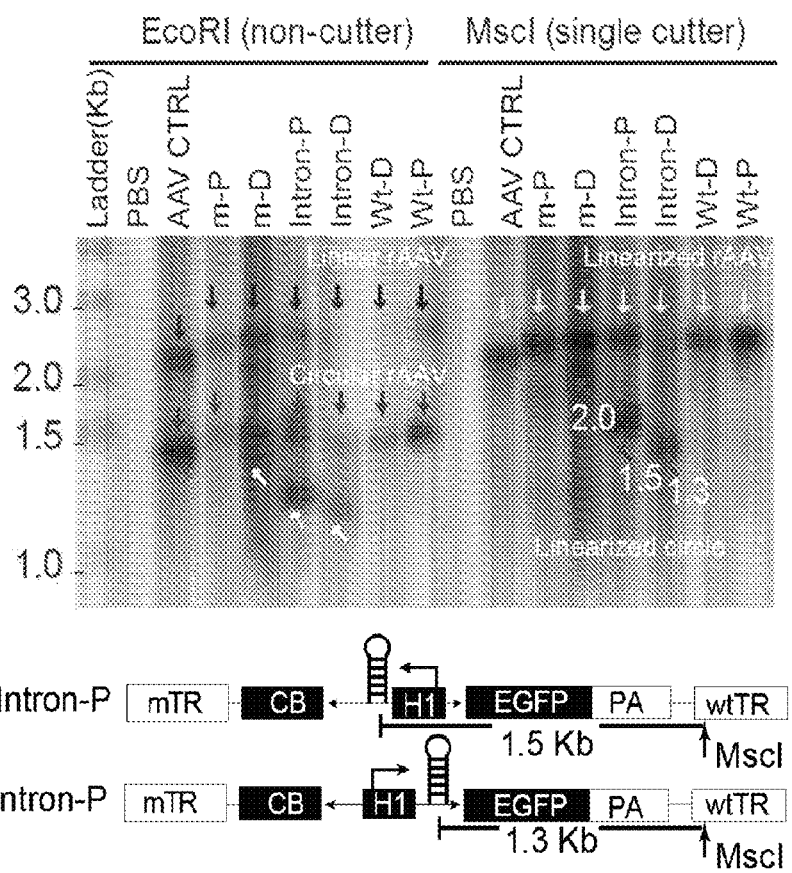

Truncated Vector Genomes are Produced from In Vivo Gene Transferred rAAVs Containing shDNA RNAi efficacies and EGFP reporter gene expressions of scAAVs carrying shApob cassettes at different positions were compared in mouse liver. Three weeks after vector infusion, similar levels of Apob gene silencing were observed with all six vectors (FIG. 17A). Despite treating with equal dosages and detecting comparable vector genomes after transduction, mice treated with scAAV9 carrying shApob cassettes within the intron (Intron-P and Intron-D) produced much lower EGFP levels compared to other groups (FIG. 17B). In contrast, scAAV vector plasmids all displayed uniform and robust expression of EGFP when transiently transfected into HEK293 cells. To understand the cause for low EGFP expression in Intron-D and Intron-P treatment groups, the vector genomes of treated mouse livers were characterized by Southern blot analysis. While both linear and circular monomers were detected at their expected sizes in liver DNA digested with EcoRI (which does not cut the rAAV genome), additional smaller bands were also observed with m-D, Intron-P, and Intron-D vector treatment (FIG. 17C, arrows). After digesting with MscI, which cuts the rAAV genome once, circular monomers of all vector genomes co-migrated with their linear counterparts (FIG. 17C, arrows). The smaller molecules from the m-D, Intron-P, and Intron-D treatment groups co-migrated up with linear molecules, indicating that these molecules were also circularized. Interestingly, the sizes of the linearized fragments (2.0 kb, m-D; 1.5 kb, intron-D; and 1.3 kb, intron-P) were well correlated with nucleotide lengths ascribed to the distance between MscI sites and the shDNA sequence (FIG. 17C, arrows). These findings suggest that inclusion of shRNA cassettes leads to genome truncations near shDNA sequences.

Figure 17D:
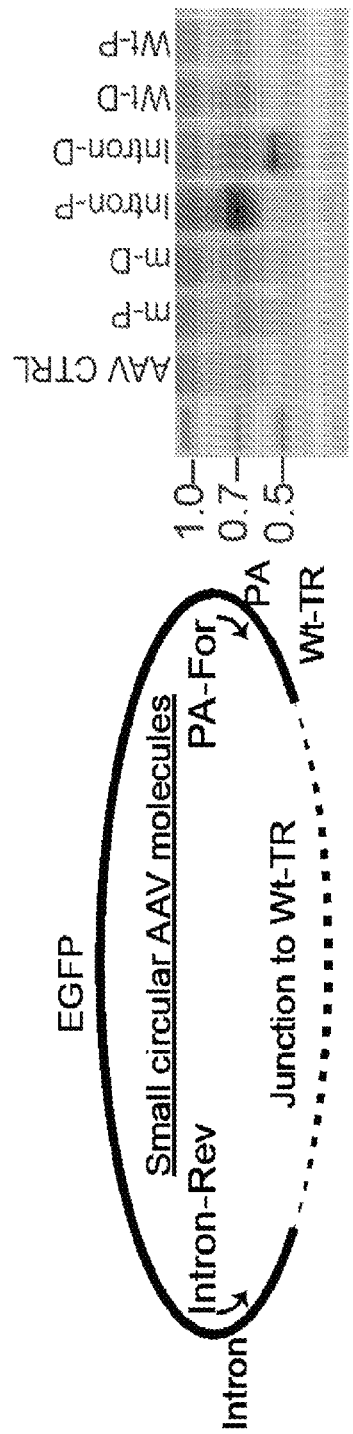
Figure 17E:
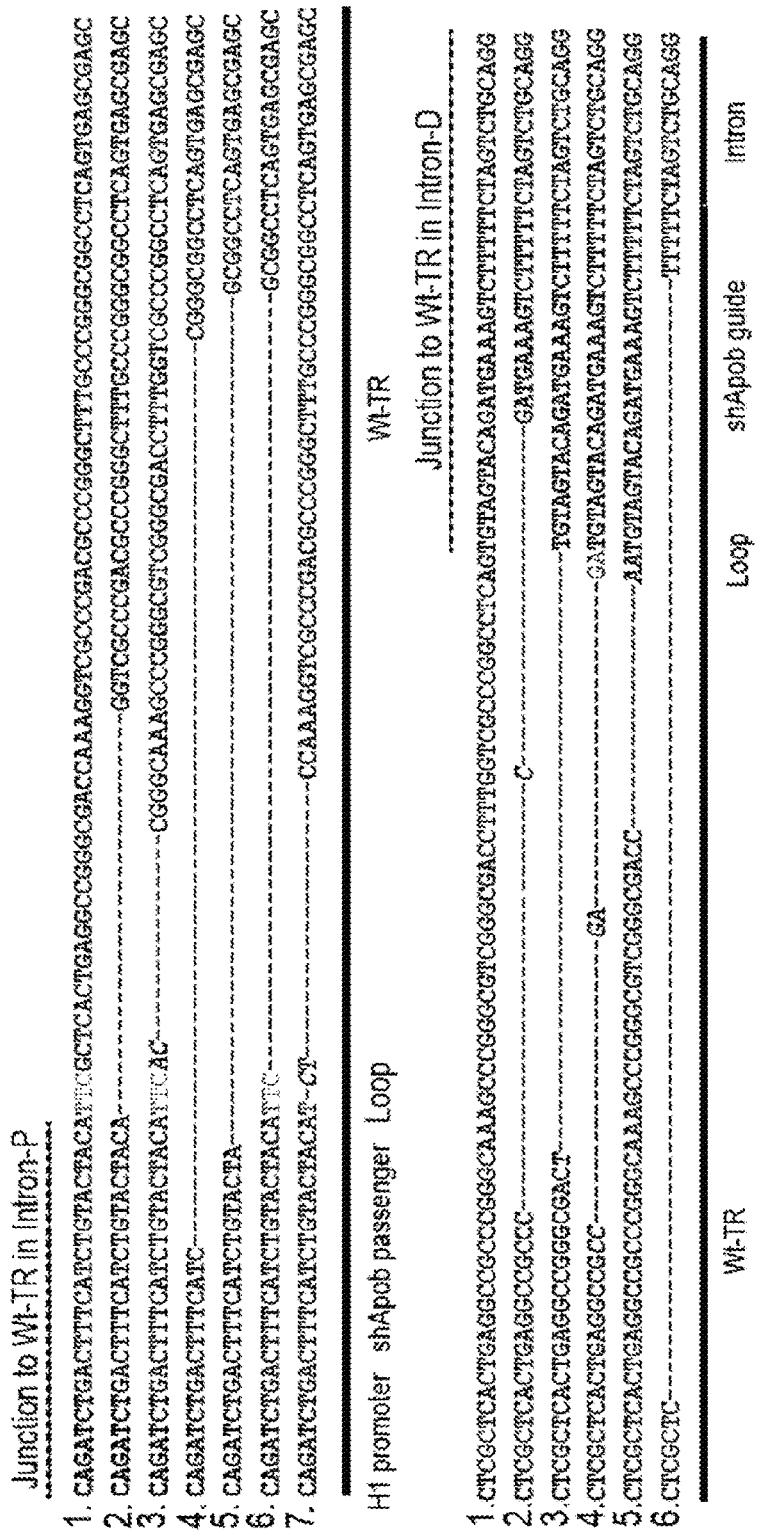

Southern blot data demonstrate that these smaller molecular forms are circularized vectors that contain EGFP transgenes (detected by an EGFP probe) and wtTR sequences (sensitive to MscI digestion) (FIG. 17C). An inverse-PCR primer set unique to these features was designed to specifically amplify circular DNA templates to query fusion events between shDNA sequences and wtTR regions (FIG. 17D). Sequence analyses of these specific amplicons support the formation of these smaller circularized AAV molecules (FIG. 17E). In the truncated genomes from Intron-P vector treated mice, wtTR was fused with the shRNA guide strand. While in the Intron-D group, wtTR was fused to the shRNA passenger strand. Notably, data show that fusion events in both cases resulted in the loss of the CMV enhancer/chicken β-actin (CB) promoter (FIG. 17E), offering an explanation for the reduction in EGFP expression in the livers of mice treated with Intron-D and Intron-P vectors (FIG. 17B).

Figure 18A:
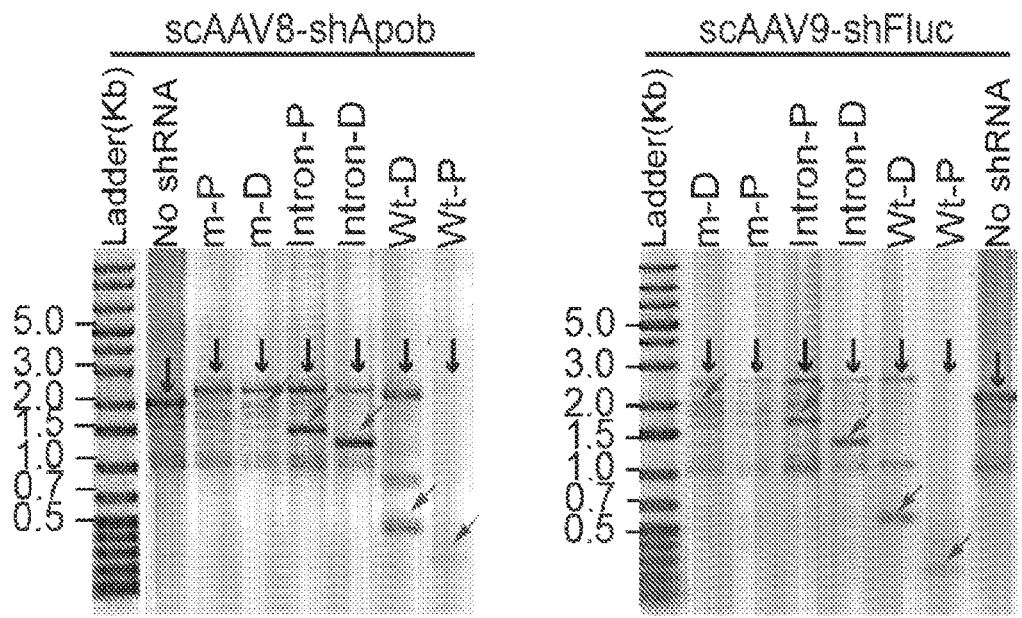
FIGS. 18A-18E show profiling of truncated genomes produced by AAV vectors containing shRNA cassettes.

Truncation Events Mediated by shDNA Sequences are not Specific to AAV Serotype, Sequence Composition, or Position within the Vector Genome To investigate whether shDNA-associated vector genome truncation occurs during the rAAV production stage or after in vivo transduction, vector DNA from preparations of purified rAAVs was examined. In addition to the full-length genomes, truncated genomes with molecular sizes that correlate well with the nucleotide distance between the wtTR and shDNA sequences were also detected (FIG. 18A). Importantly, the same pattern of genomic species was detected from rAAVs carrying either H1-shApob or U6-shFluc cassettes (FIG. 18A), suggesting that shDNA-associated AAV vector genome truncations are not shRNA sequence-specific.

Figure 18B:
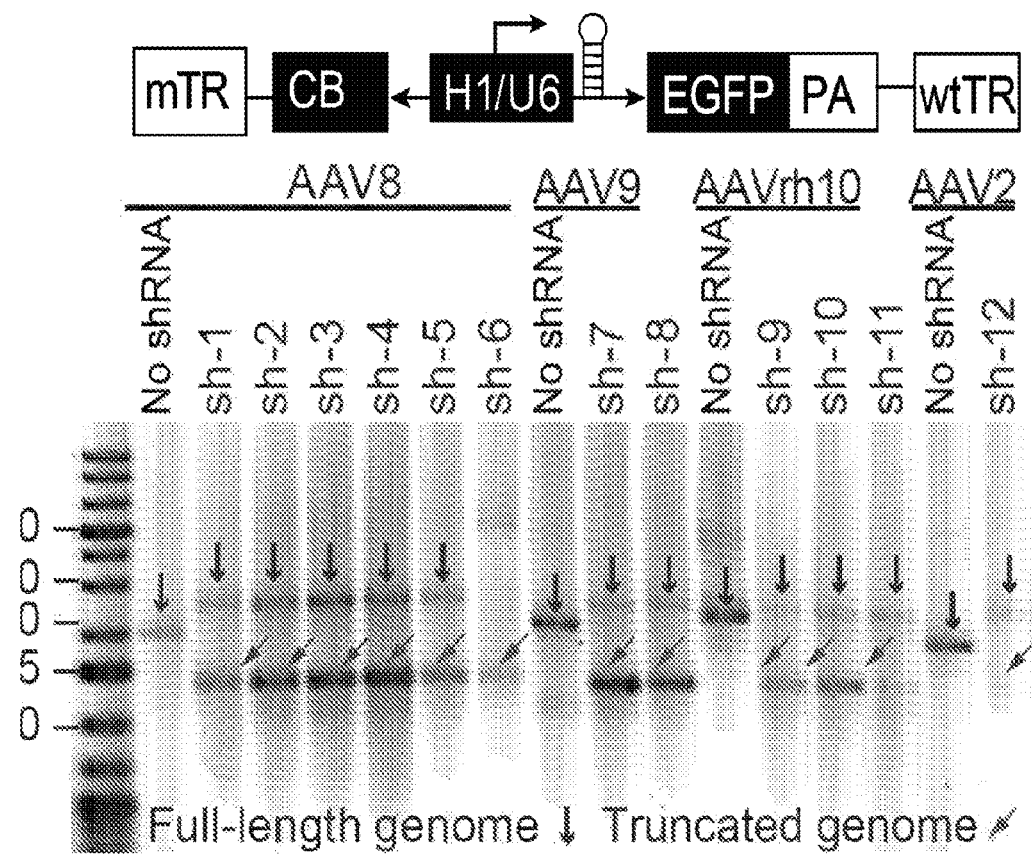
Figure 18C:
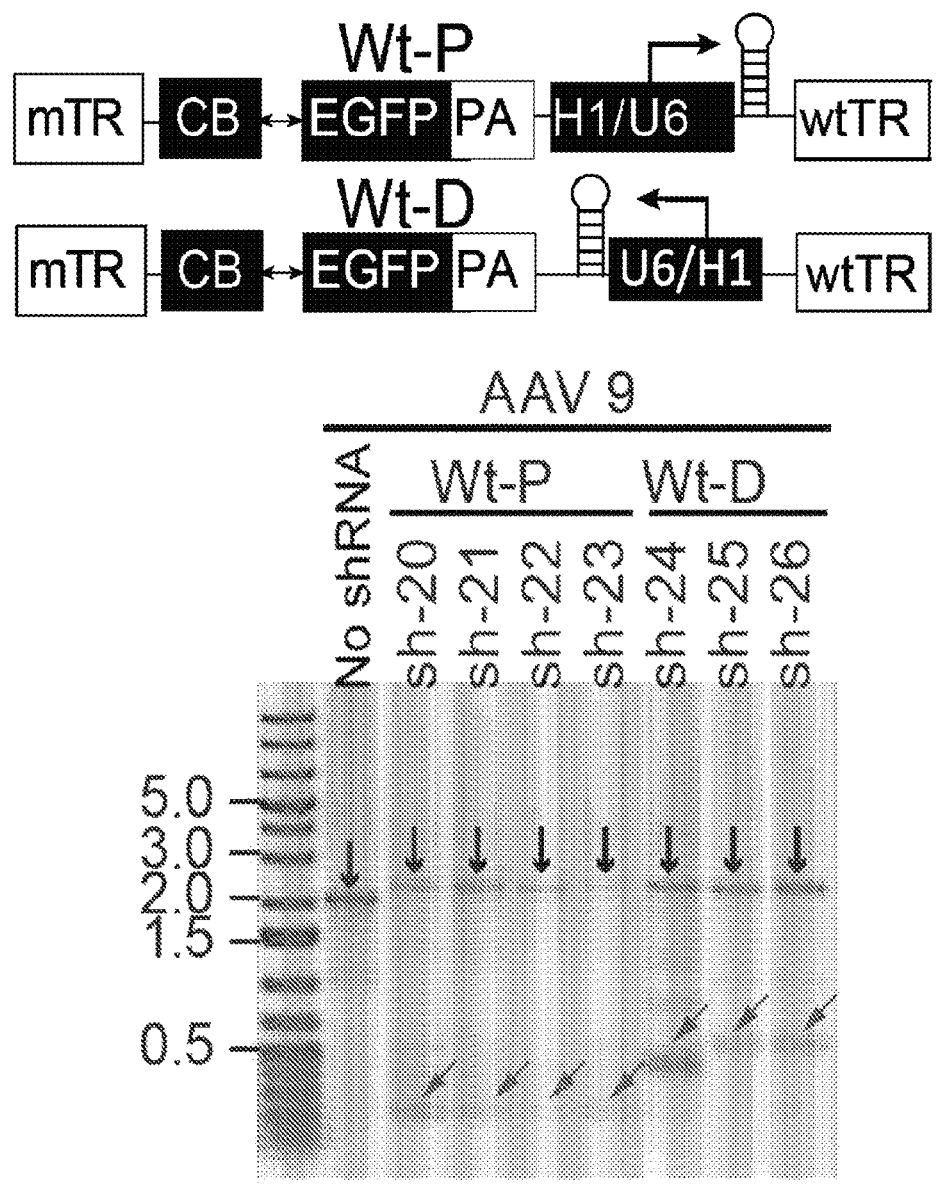
Figure 18D:
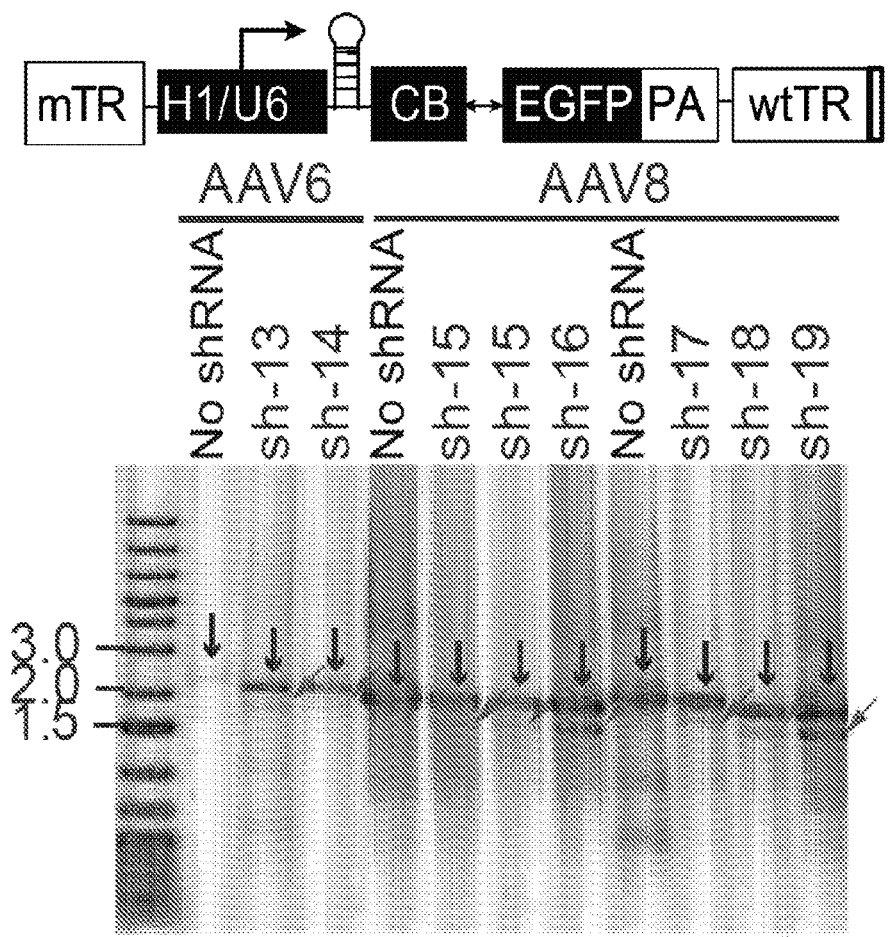
Figure 18E:
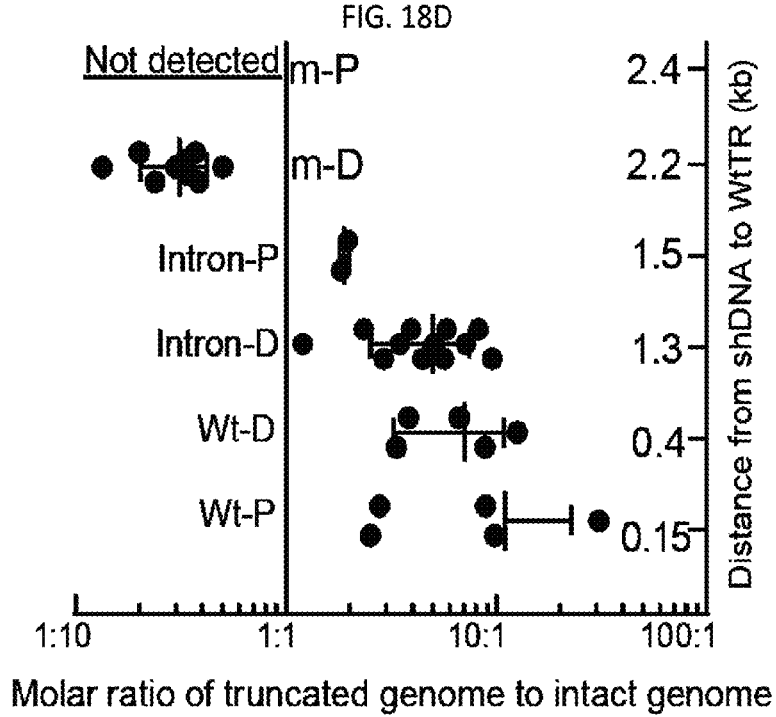

The position effects of shRNA cassette on truncation frequency was examined: within intronic sequence (FIG. 18B), proximal to the wTR (FIG. 18C), or proximal to the mTR (FIG. 18D). Constructs targeting 26 different genes were packaged into five different capsid serotypes (AAV2, AAV6, AAV8, AAV9, and AAVrh10). All constructs that carrying shRNA cassettes (33 total vector preparations), regardless of serotype or position within the vector genome, generated truncated vector genomes (FIGS. 18B-18D). The sizes of truncated genomes in these preparations correlate with the placement of the shRNA cassette within each vector. Interestingly, the closer the shDNA sequence was to the wtTR, the higher the molar ratio of truncated vector genomes to intact genomes (FIG. 18E). Taken together, data indicate that shDNA sequences drive AAV vector genome truncation in a manner that is independent of serotype, sequence, and position and that one good option for achieving shRNA cassette design compatibility with rAAVs is to place shRNA cassettes proximal to mTR sequences.

Figure 19A:
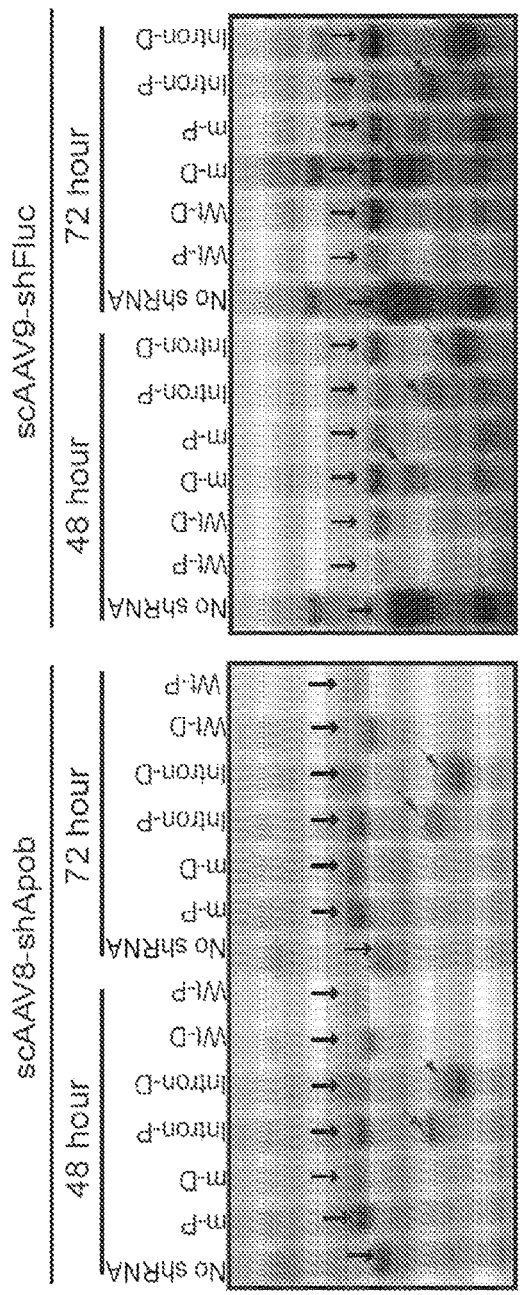
FIGS. 19A-19C show truncated genomes in Hirt DNA from 293 cells transfected with scAAV or ssAAV constructs.
Figure 19B:
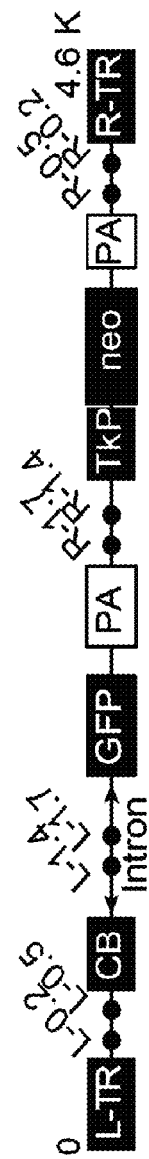
Figure 19C:
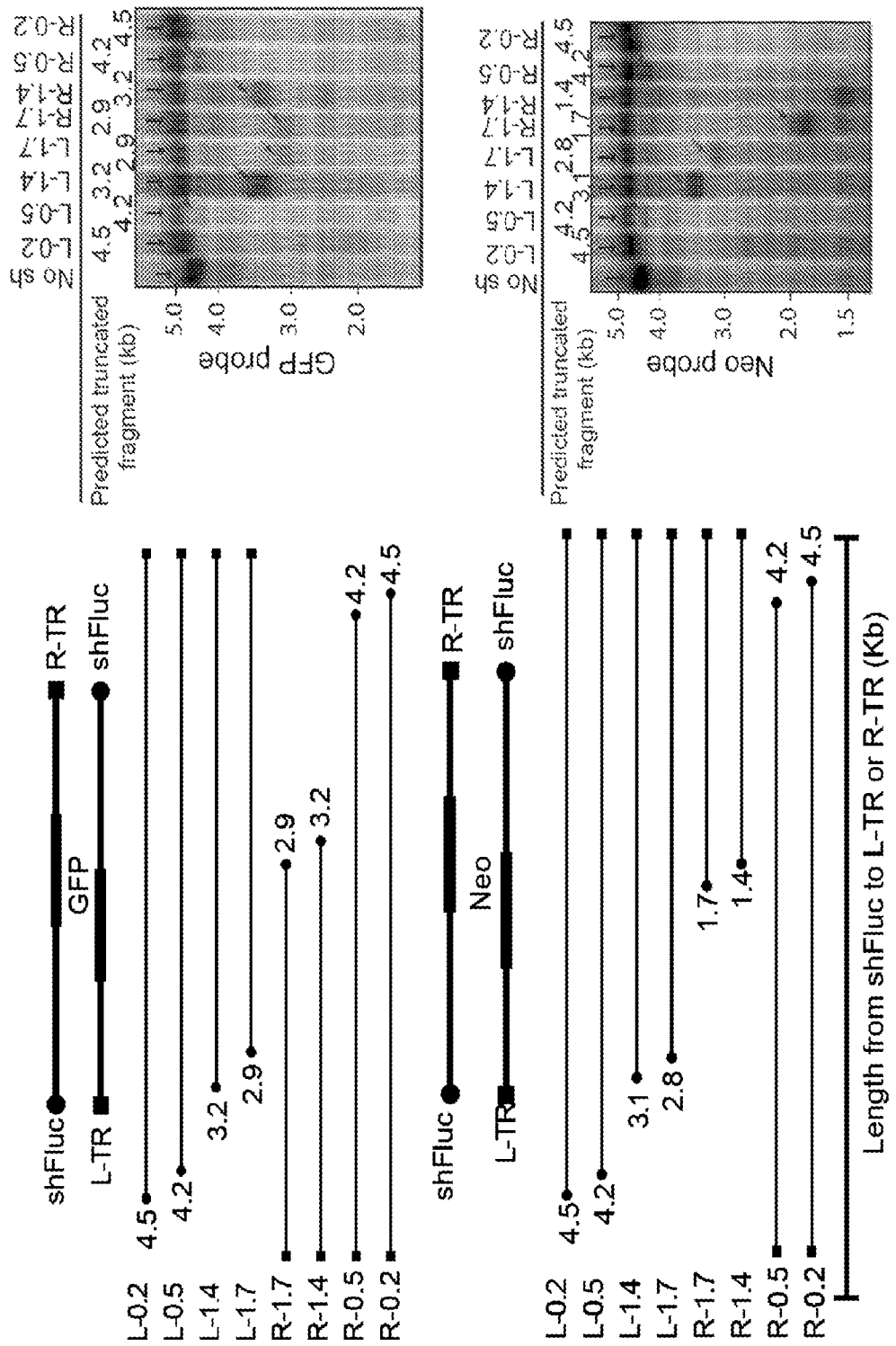

To determine whether genome truncations occur during genome rescue/replication or the packaging phase of viral production, low molecular-weight Hirt DNAs extracted from HEK293 cells after triple plasmid transfection for rAAV production was examined. Southern blot analysis of Hirt DNA revealed detectable amounts of truncated rAAV genomes, suggesting that truncations take place during rAAV genome replication (FIGS. 19A-19B). Notably, fewer rescued and replicated AAV genomes were detected from constructs with shDNA sequences placed next to the wtTR (Wt-P)(FIG. 19A). This observation was consistent with the low vector yields associated with these constructs (FIGS. 19A and 19C). Truncated genomes were also detected in Hirt DNA extracted from cells producing ssAAV vectors harboring shRNA cassettes (FIGS. 19B and 19C).

Figure 20A:
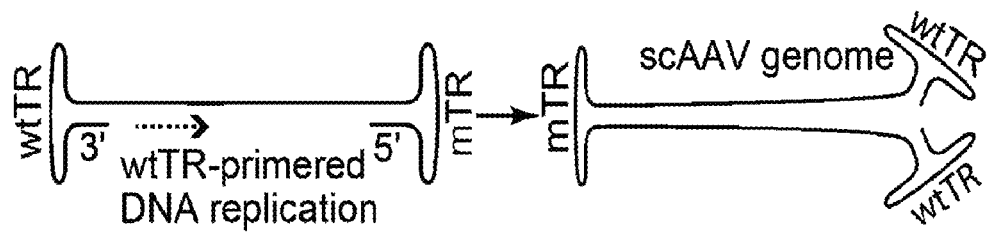
FIGS. 20A-20F show characterization of truncated AAV genomes.
Figure 20B:
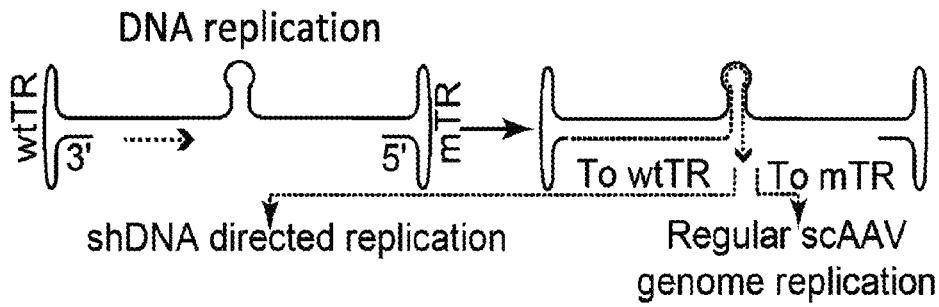
Figure 20B:
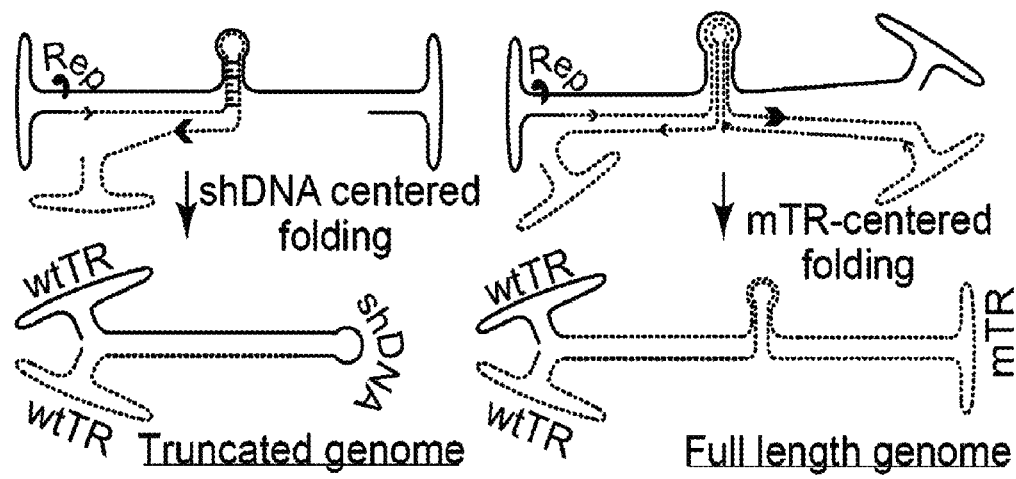
Figure 20C:
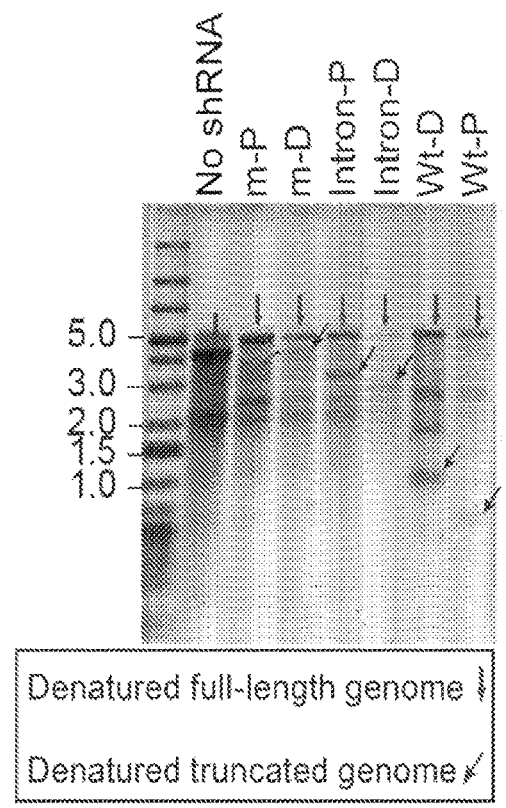
Figure 21A:
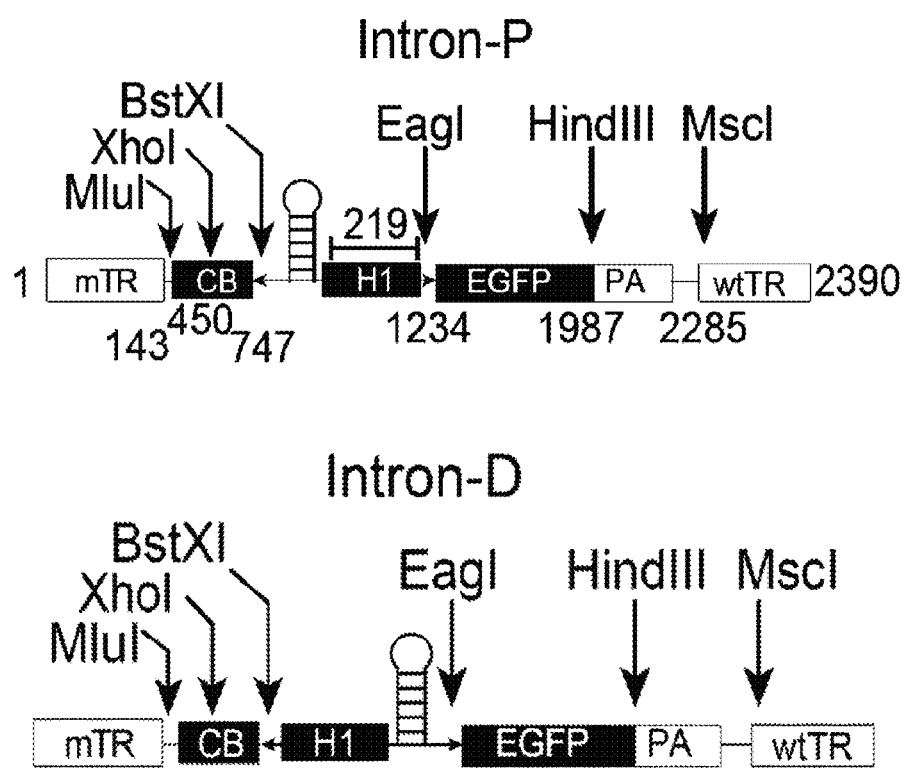
FIGS. 21A-21C show restriction enzyme digestion of the AAV genomes carrying shApob cassette in the intron (Intron-P and Intron-D).
Figure 21B:
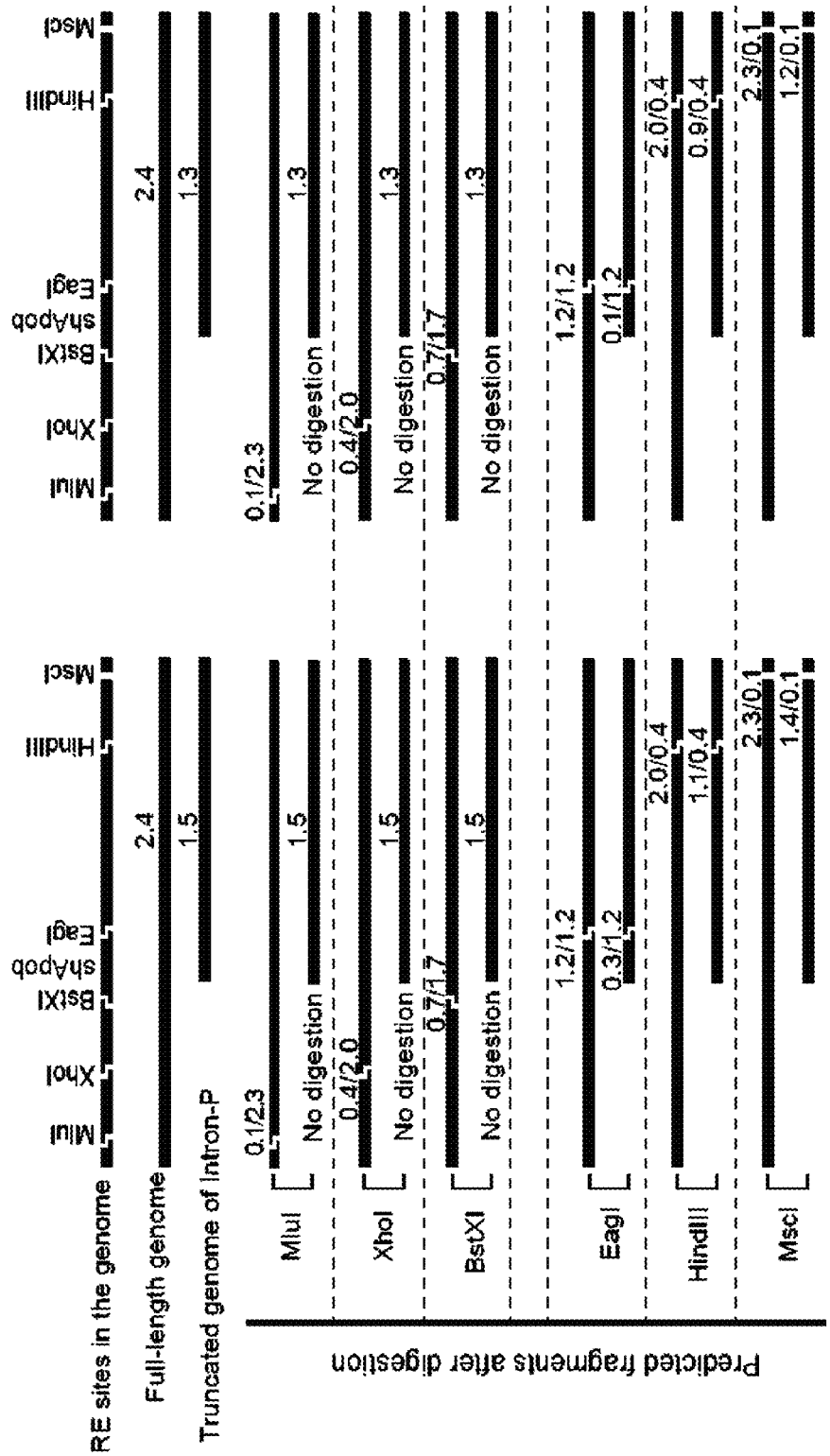
Figure 21C:
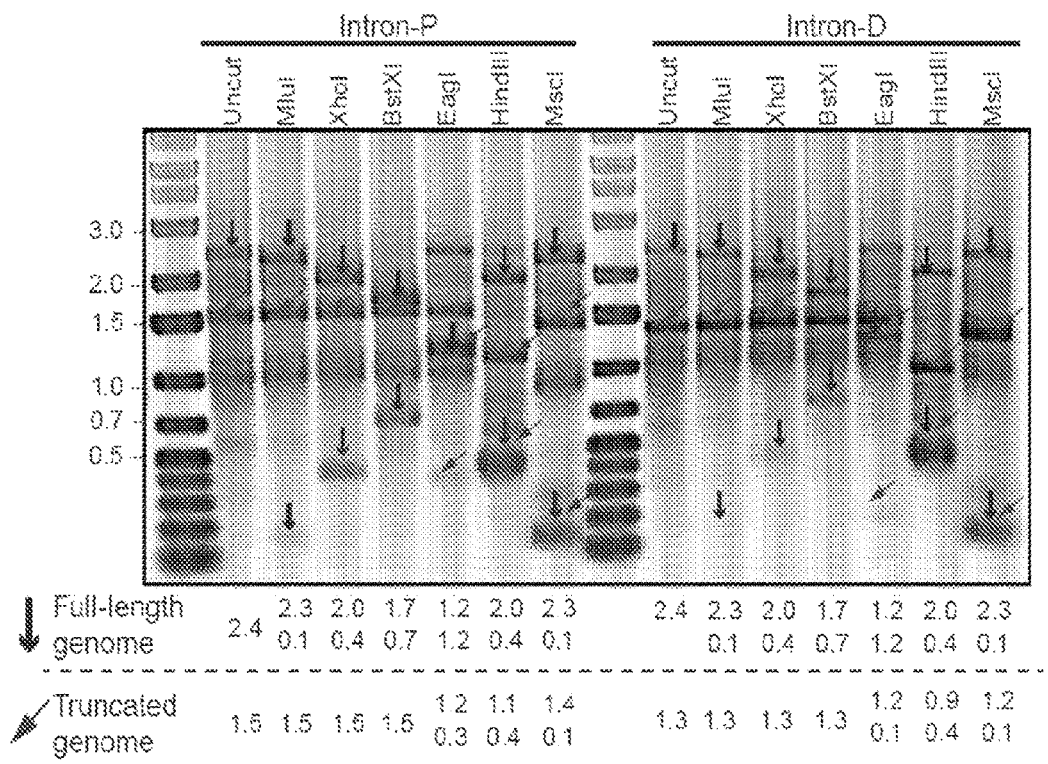

Short DNA Hairpins Cause rAAV Genome Truncation Via Template-Switching During Viral DNA Replication Data suggest that shDNA sequences promote the generation of truncated AAV vectors by impacting viral genome replication. Typically, scAAV replication begins at the wtTR and extends along the length of the rAAV genome. Once replication reaches the mTR, the newly synthesized mTR strand folds into a hairpin, and replication continues with the new strand as template. The resulting intra-molecular, double-stranded DNA consists of an mTR hairpin loop that connects two complementary sequences, each terminating with wtTR ends 17 (FIG. 20A). Here it is described that shDNA sequences behave as template switching scaffolds in a manner similar to the mTR region in scAAV vectors (FIG. 20B). rAAV genome replication starts from the wtTR, but faces two choices when reaching the hairpin. If base pairing of the hairpin stem switches templates from the parental strand for replication (FIG. 20B, solid line) to the newly synthesized daughter strand (FIG. 20B, dotted line), then replication makes a U-turn back towards the wtTR without synthesizing sequence beyond the hairpin structure. As a result, truncated, intra-molecular double-stranded genomes with loop regions centered at the shDNA sequence are generated for packaging (FIG. 20B, left). If replication overcomes the complementarity of the hairpin structure, it continues to replicate the parental strand to completion, producing full-length scAAV genomes (FIG. 20B, right). To test this idea, denaturing alkaline-agarose gel electrophoresis was used to examine genomic DNAs extracted from purified viral vector preparations. The sizes of both intact and truncated genomes were doubled as compared to their sizes revealed by native agarose gels (compare FIGS. 18A and 20C), suggesting that the truncated genomes are indeed intra-molecular double-stranded DNA molecules, similar to scAAV genomes. The composition of truncated AAV genomes was examined by restriction enzyme mapping of two scAAV9 vectors that carry shApob cassettes within intronic sequence (FIG. 21). These data indicate that truncated AAV genomes primarily encompass sequence between the wtTR and the shDNA sequence.

Figure 20D:
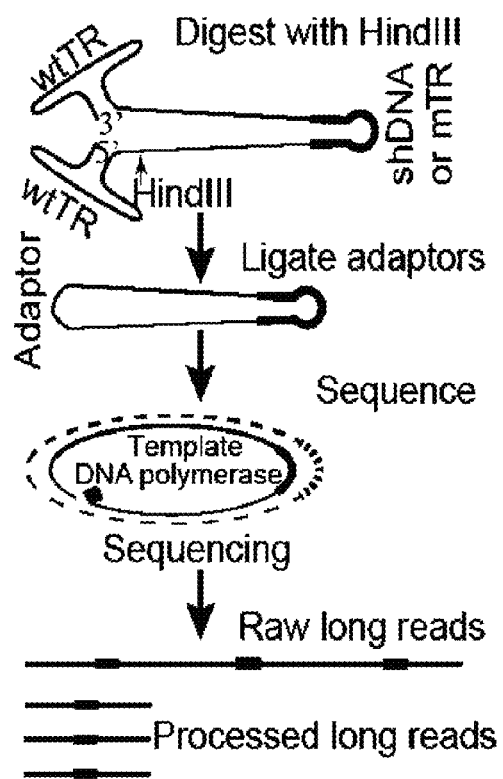
Figure 20E:
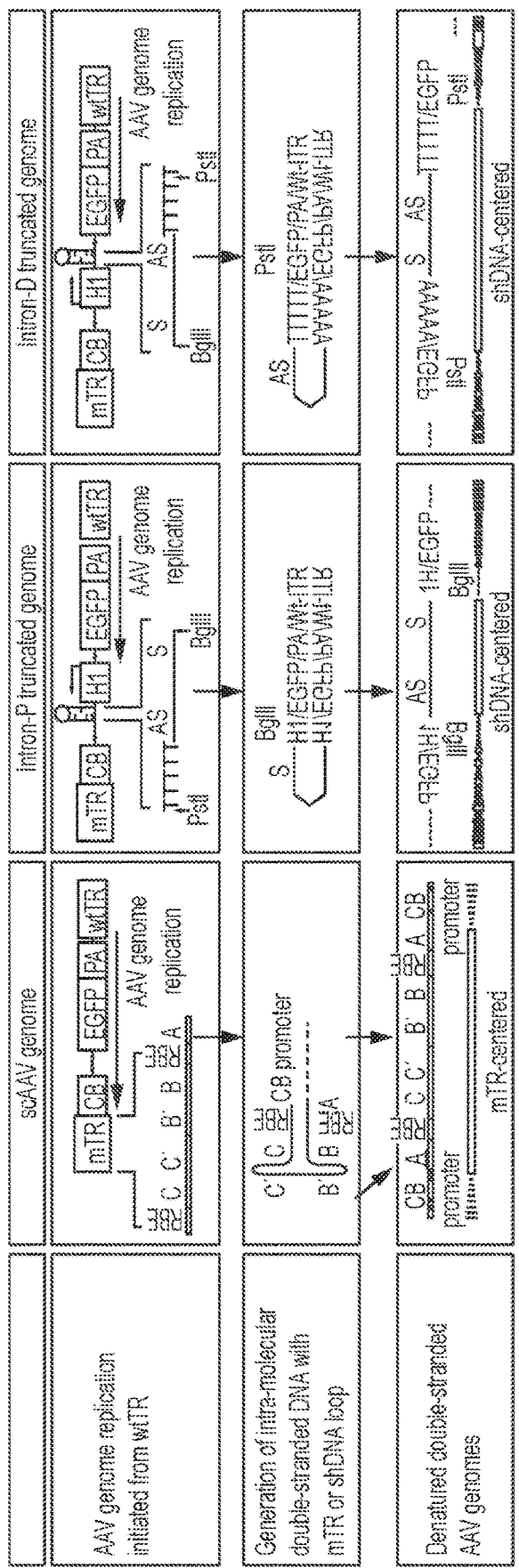
Figure 20F:
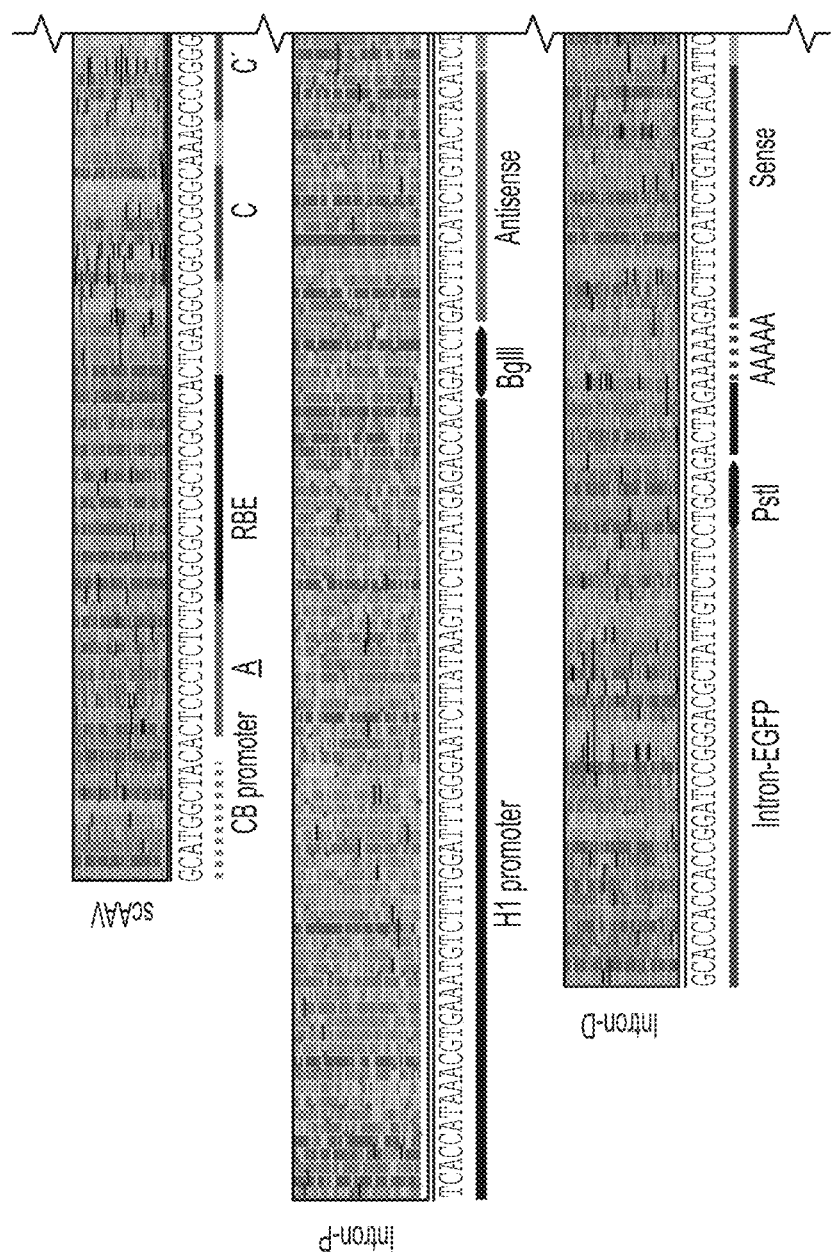
Figure 20F:
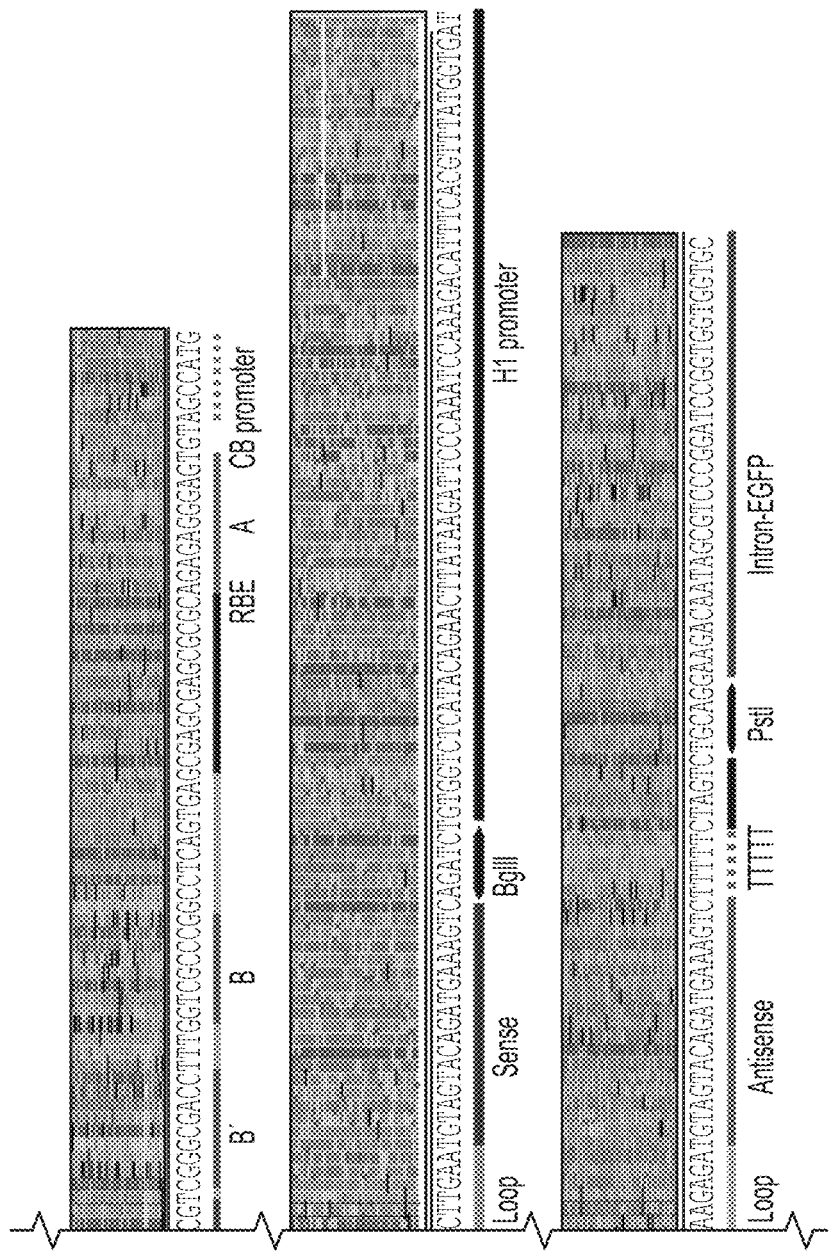

High-throughput sequencing was used to analyze the composition of the template switch position. The predicted structure of the self-complementary truncated vector genome is a double-stranded molecule with a single closed end. When the open end of the molecule is adapted using a single-stranded DNA loop, the resulting molecule is a circular single-stranded DNA template, ideal for single molecule real-time sequencing (SMRT). To further improve sequencing processivity, wtTR sequences were removed from vector genomes by digesting viral DNA with HindIII. After purification, the resulting molecules were subjected to single-SMRT-bell adapting to the open end of the truncated genomes to form single-stranded circular templates. The resulting processed long reads, in essence, represent the linear sequences of denatured AAV genomes minus the wtTR regions (FIG. 20D). Vector genomes from scAAV, Intron-P, and Intron-D were sequenced and reads were aligned to custom references based on the predicted outcomes illustrated in FIG. 20E. These references are tandemized forward and reverse strands of vector genome sequence linked together by mTR or shApob hairpin regions (FIG. 20F). Notably, the scAAV-CB EGFP plasmid used in this study contains only one "A" element at the border of the mTR region (FIG. 20E). During vector production, the A-element (FIG. 20F) was observed to be replicated on the reverse strand, suggesting that the template-switching event occurs at the hairpin terminus. More importantly, the sequences of the shDNA loops within truncated Intron-P and Intron-D genomes (FIG. 20E) are corroborated by SMRT sequencing analysis (FIG. 20F, middle, and bottom panel). In summary, shDNA causes rAAV genome truncation by re-direction of DNA polymerization via template switching during DNA replication. These events generate intra-molecular double-stranded AAV genomes with a terminal shDNA loop. It is worth noting that neither Intron-D nor Intron-P vectors contain intact shRNA expression cassettes. They either lack the antisense strand and the five-thymine termination signal (Intron-P, FIG. 20E middle, and FIG. 20F middle), or the H1 promoter and the sense strand (Intron-D, FIG. 20E right, and FIG. 20F bottom),respectively.

Figure 22A:
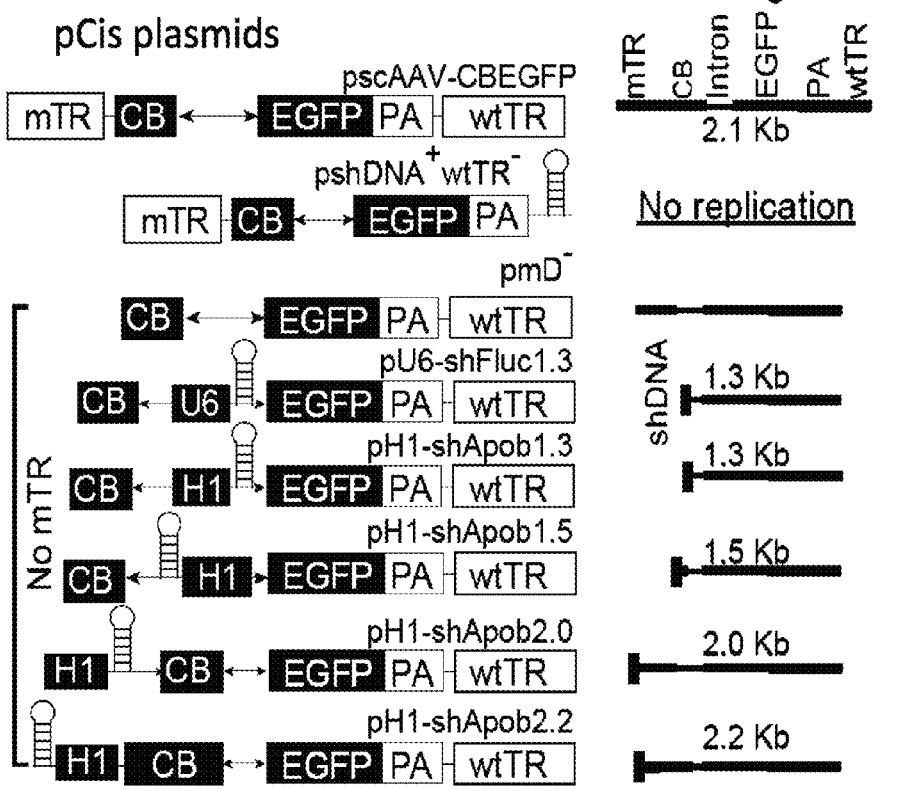
FIGS. 22A-22K show characterization of shAAV genome and in vivo evaluation of shAAV vectors.
Figure 22B:
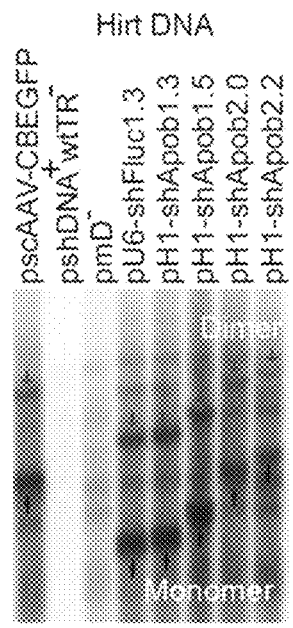
Figure 22C:
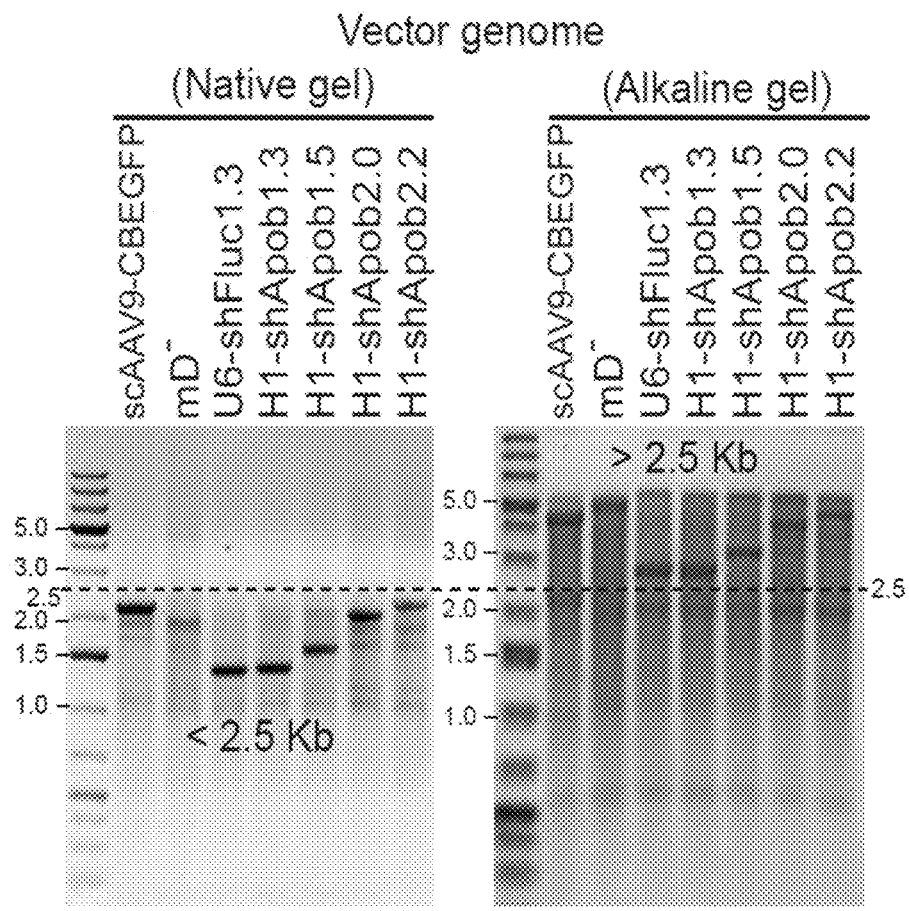
Figure 22D:
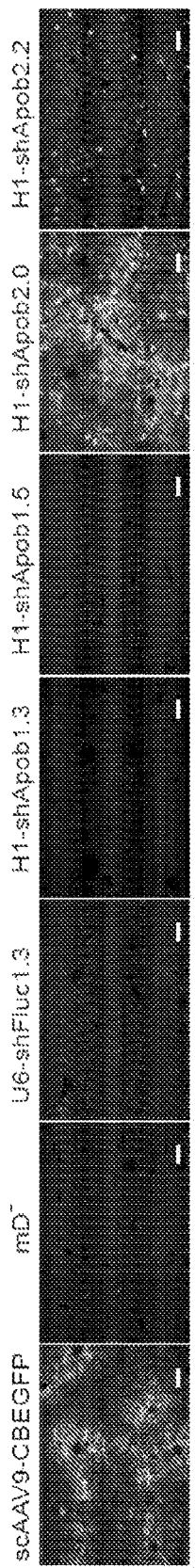
Figure 23A:
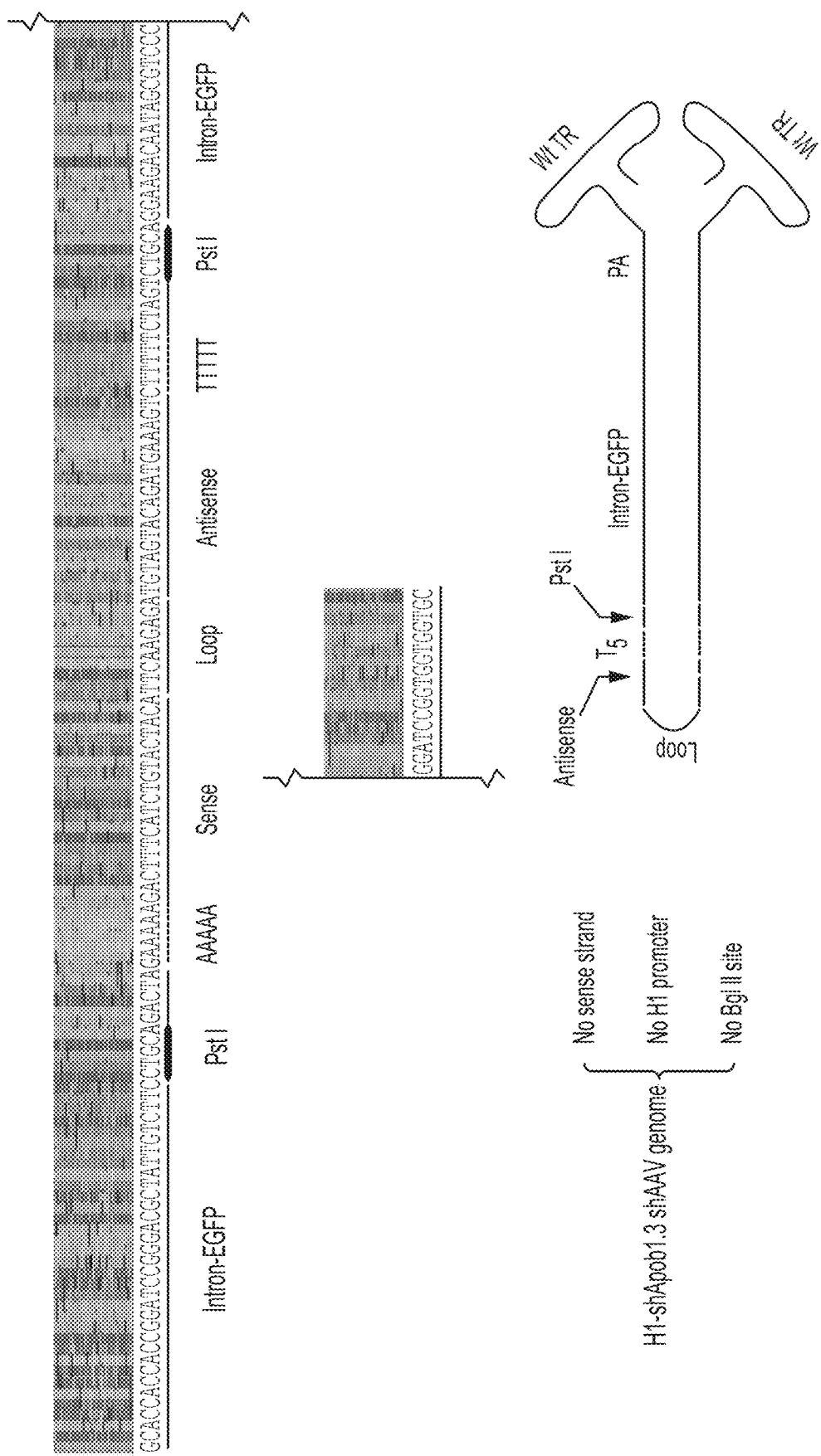
FIGS. 23A-23B show sequence analysis of H1-Apob1.3 (FIG. 23A) and H1-Apob1.5 (FIG. 23B) shAAV vector genomes. The intra-molecular double-stranded genomes and the missing sequences were indicated for both shAAV genomes.
Figure 23B:
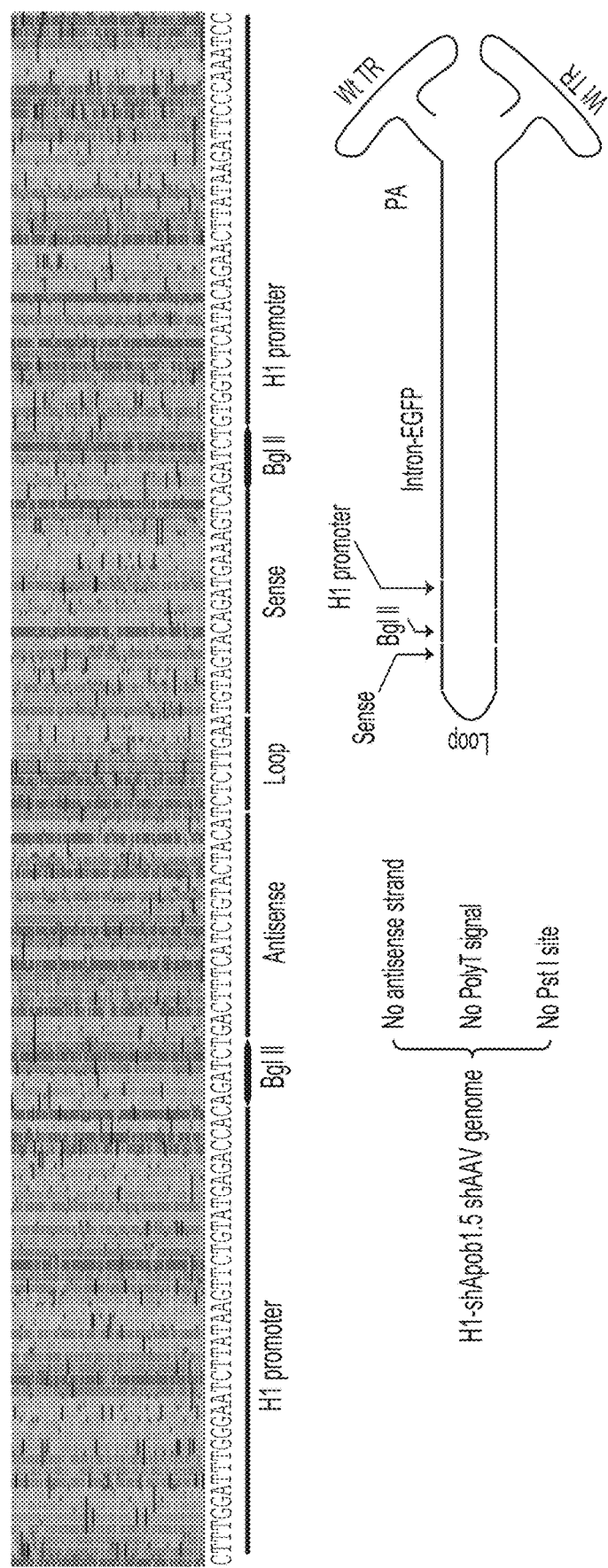

Replacement of the mTR with shDNA Sequences Produces Novel Functional Double-Stranded rAAVs Replacing mTR with shDNA to create a novel AAV vector genome was investigated. The mTR was removed from scAAV constructs containing shRNA cassettes at different positions (FIG. 22A), and evaluated these constructs for in vitro genome rescue and replication, vector production, and in vivo transduction. In the absence of the mTR sequence, scAAV genomes were efficiently rescued from all constructs containing shRNA cassettes (FIG. 22B). However, when the wtTR was replaced with shDNA sequence (pshDNA+ wtTR−), no AAV genomes were rescued or replicated (FIG. 22B). The latter observation confirms the importance of the wtTR for AAV replication. Native agarose gel analysis demonstrates that the genome sizes of these vectors produced from constructs in the absence of mTR are equivalent to sequence lengths spanning from the wtTR to the shDNA sequence. The molecular sizes are also doubled in alkaline gels, indicating that these vector genomes are intra-molecular double-stranded DNAs similar to scAAV genomes (FIG. 22C). SMRT sequencing confirmed the presence of these self-complimentary AAV genomes (FIGS. 23A-23B). This novel class of rAAVs is termed short-hairpin AAVs (shAAVs).

shAAV vectors were packaged with AAV9 capsid and administrated intravenously to adult mice. The three constructs that harbor shDNA sequences inserted between the CB promoter and the EGFP transgene (U6-shFluc1.3, H1-shApob1.3, and H1-shApob1.5 shAAV) were package shAAV genomes that lack the promoter for EGFP expression. Animals treated with these vectors produced few EGFP positive cells in the liver (FIG. 22D). While the H1-shApob2.0 shAAV vector achieved EGFP transduction at efficiency comparable to the transduction achieved by the scAAV-EGFP vector, the H1-shApob2.2 shAAV generated much less EGFP expression (FIG. 22D).

Figure 22F:
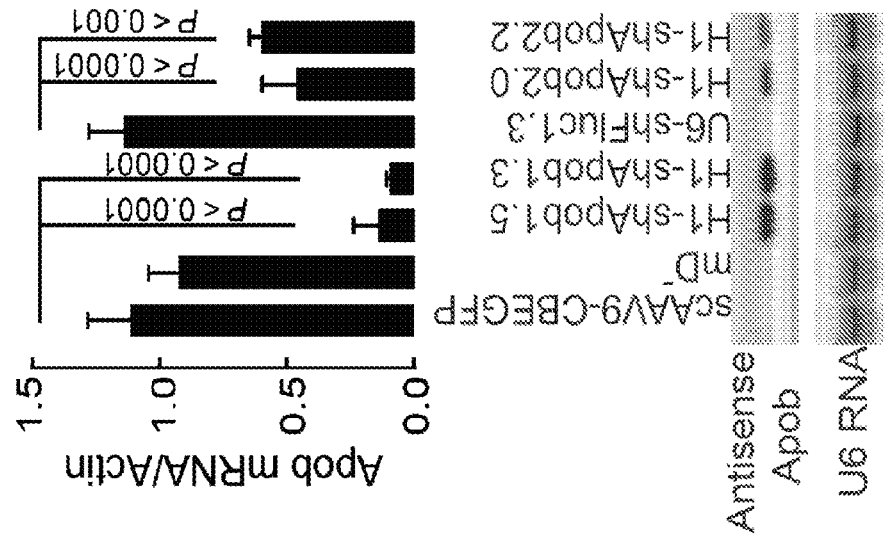
Figure 22E:
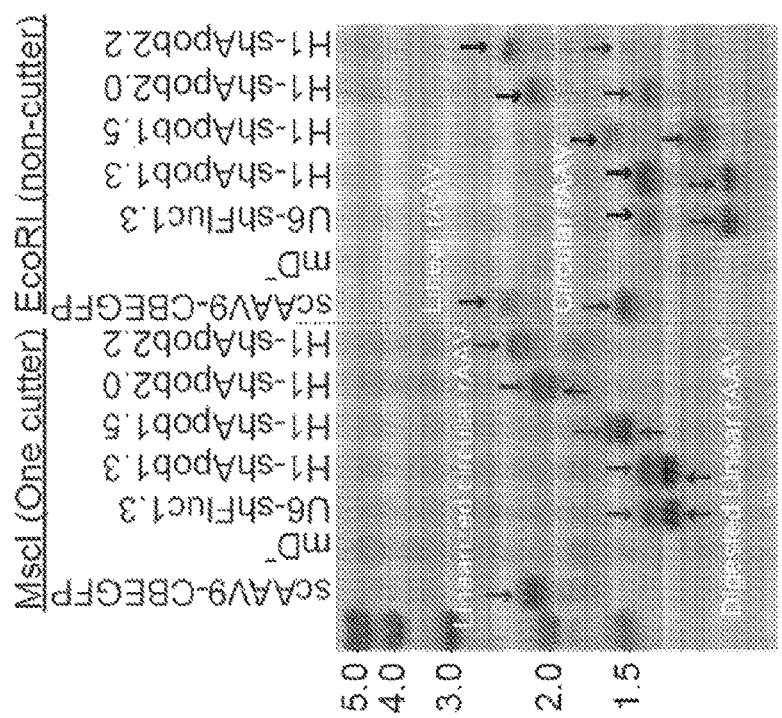

Southern blot analysis of total liver DNA showed that shAAV vector genomes persist as both linear and circular forms, similar to scAAV vectors in vivo (FIG. 22E). Interestingly, a dominant portion of shAAV-H1-shApob2.2 vector genomes was linear (FIG. 22E). This result indicates that circular shAAV genomes are primarily responsible for in vivo transduction and linear shAAV genomes are less potent and/or stable, which could explain the poor EGFP expression in the shAAV H1-shApob2.2 treated livers (FIG. 22D). In summary, by mimicking the mTR, shDNA sequences can generate intra-molecular double stranded genomes similar to classical rAAV vectors to produce novel shAAVs with the capacity for in vivo gene transfer.

Figure 22H:
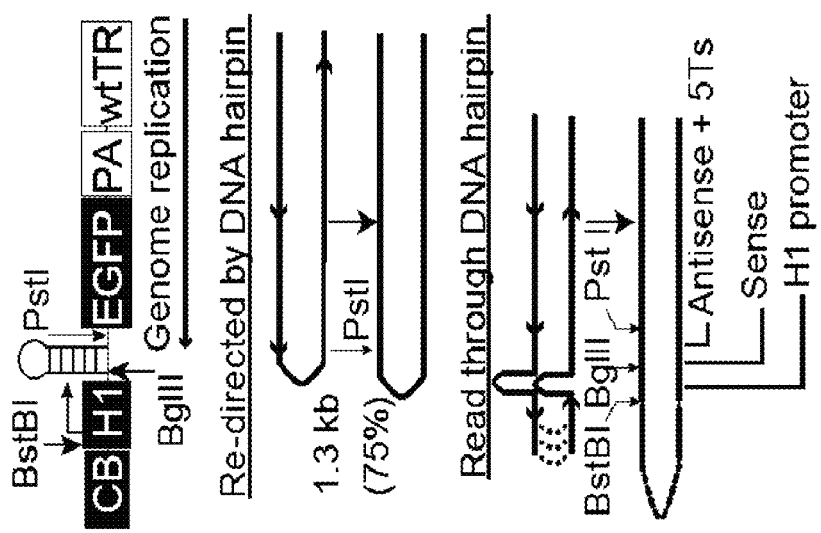
Figure 22G:
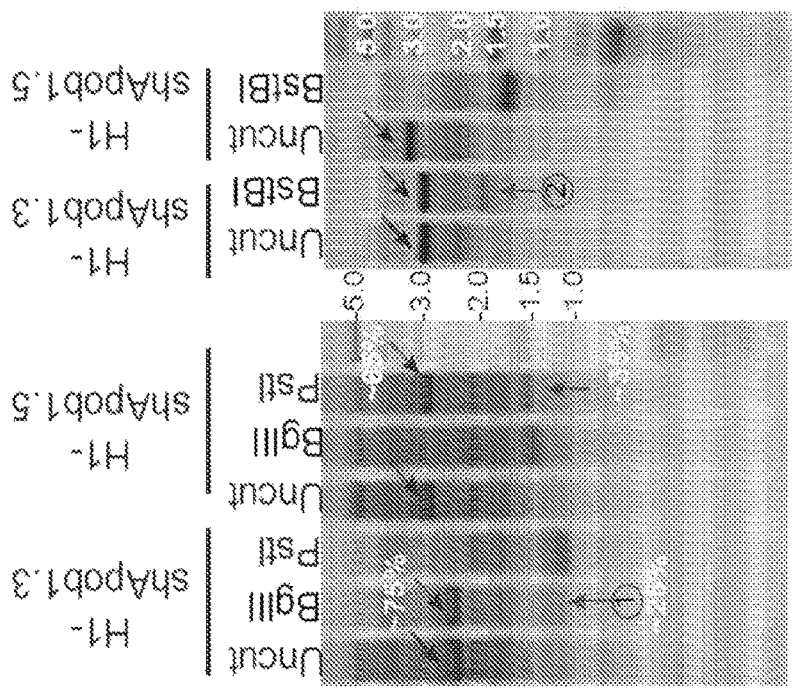
Figure 24:
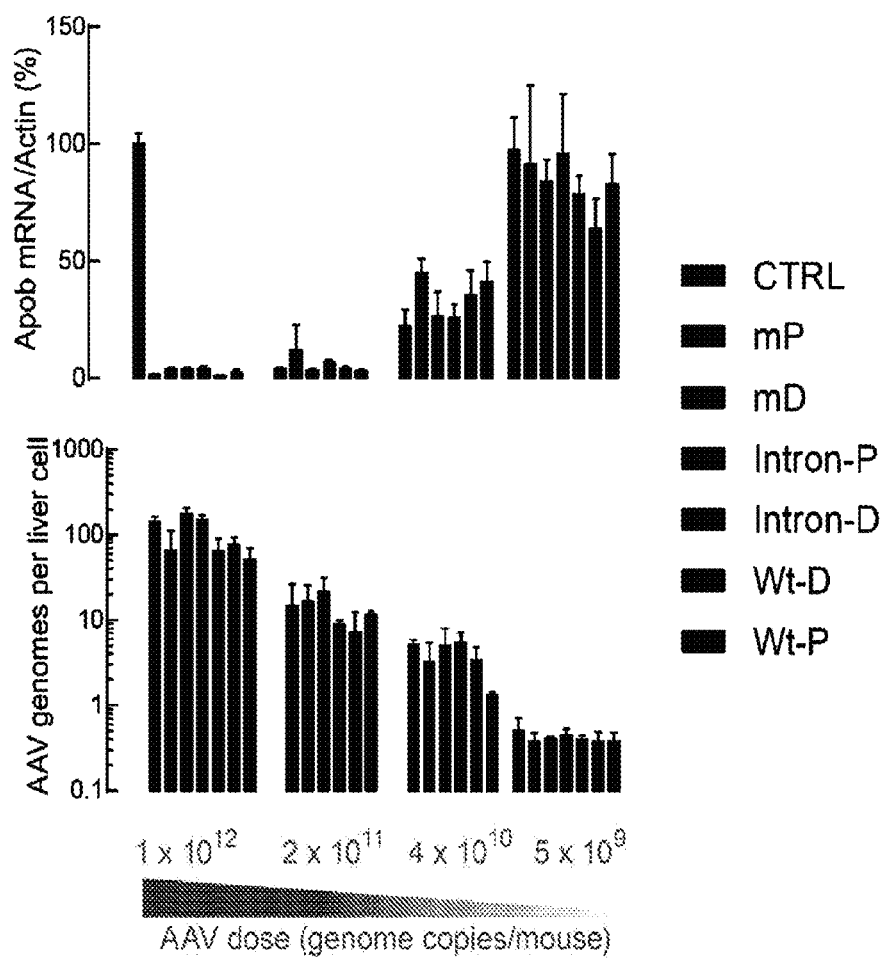
FIG. 24 shows comparisons of the gene silencing efficacy of scAAV9 vectors carrying shApob-encoding sequence in different positions. Six to eight weeks old C57/B6 mice were intravenously injected with scAAV9-shApob vectors at the indicating doses. The mice were sacrificed three weeks later and expression of Apob gene and transduced AAV genome copies in liver were analyzed by qRT-PCR and qPCR, respectively. Three mice were used in each group treated with $1 \times 10^{12}$, $2 \times 10^{11}$ and $4 \times 10^{10}$ GCs per mouse. Five mice were used in each group treated with $5 \times 10^{9}$ GCs/mouse. Values are mean±s.d.

Unexpectedly, it was observed that ApoB gene expression was reduced in the livers of mice receiving shAAV vectors that carry shRNA cassettes targeting Apob (FIG. 22F). Gene silencing by shAAV vectors was unexpected, because SMRT sequencing data showed that these two shAAV vectors lack intact shApoB expression cassettes FIGS. 23A-23B). To validate SMRT sequencing results and to identify vector genomes that contained intact shRNA cassettes, the vector genomes of the H1-shApob1.3 and H1-shApob 1.5 constructs were analyzed by diagnostic enzymatic digestion using BglII (single cutter between H1 promoter and the sense strand of shDNA) or PstI (single cutter after the five-thymine termination signal) (FIG. 22G). Bands of 2.6-kb and 3.0-kb were detected for H1-shApob1.3 and H1-shApob 1.5 genomes, respectively. These bands represent the denatured intra-molecular double-stranded DNA genomes (FIG. 22G). SMRT sequencing data indicates that PstI digestion of H1-shApob 1.3 genomes removes the shDNA loop and results in ~1.3 kb DNA fragments with open ends, while BglII should not cut in the H1-shApob1.3 genome (FIGS. 23A-23B). However, an additional fragment (>1.3 kb) was observed with BglII digestion, indicating the presence of vector genomes carrying the BglII site within the vector, and the successful replication through the shDNA sequence (arrow 1 in FIG. 22G). To substantiate the presence of such genomes, the vector DNA was digested with BstBI, which has a recognition site within the 5'-end of the H1 promoter. This treatment resulted in a reduction of the 3.0-kb band and an appearance of a new 1.5-kb band (arrow 2 in FIG. 22G). Together, this set of data indicates that packaged H1-Apob1.3 genomes are a mixture of vectors that possess intact H1-promoter-shRNA expression cassettes (~25%), and shAAV genomes that lack functional shRNA expression cassettes (~75%). A similar distribution of intact (~35%, purple arrow in FIG. 5g) and incomplete (~65%) shRNA cassettes among shAAV9-H1-shApob1.5 genomes (FIG. 22G) was also observed. Data indicate that despite the high prevalence of truncation events as a consequence of shRNA cassettes within rAAV genomes, a portion of genomes still harbor intact sequences as a result of complete replication through shDNA sequences (FIG. 22H). These "read-through" genomes generate enough functional shRNA to silence target gene expression, compensating the loss of RNAi functions from truncated genomes (FIG. 24).

Figure 22I:
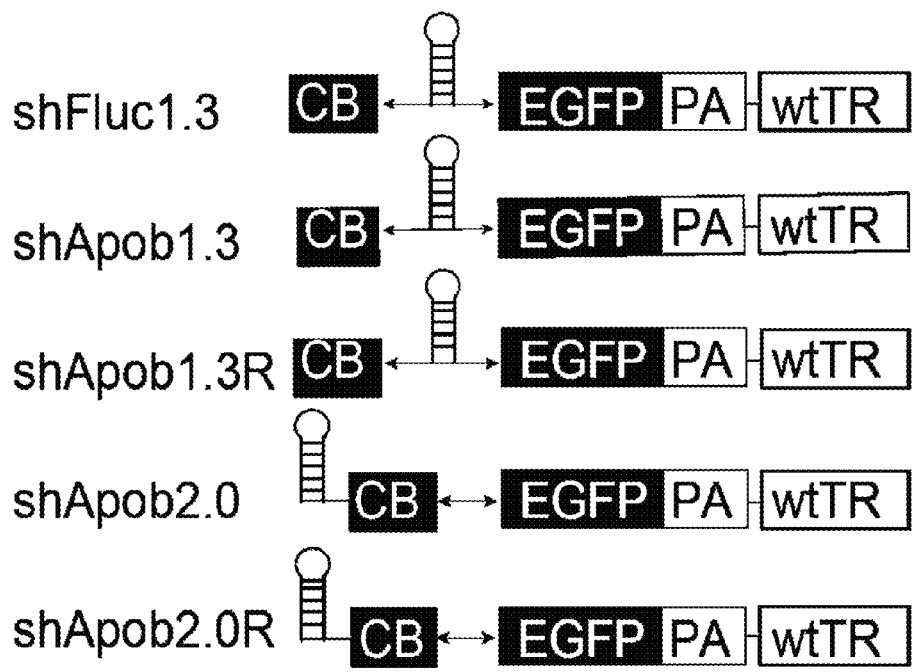
Figure 22J:
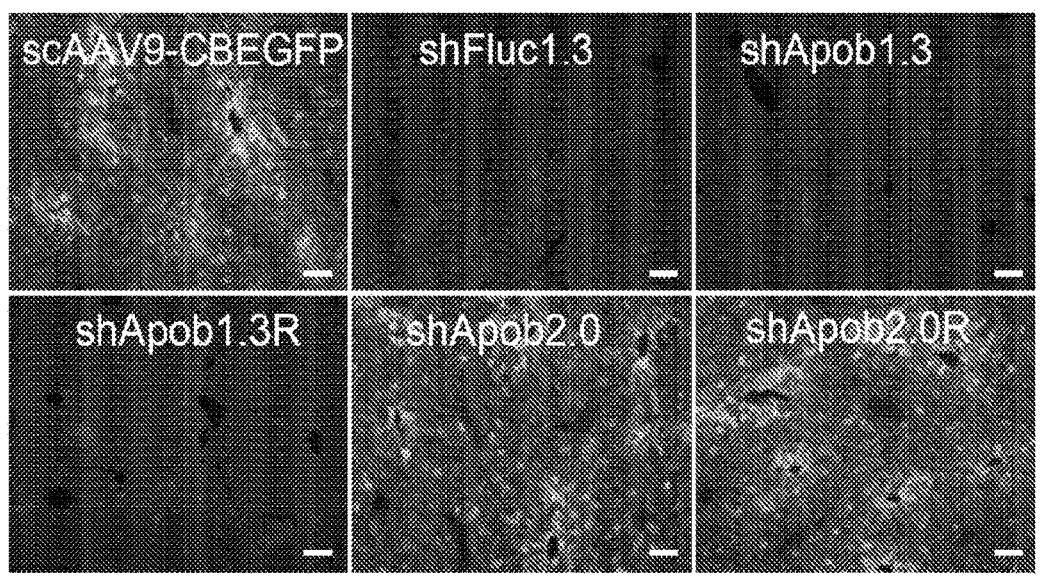
Figure 22K:
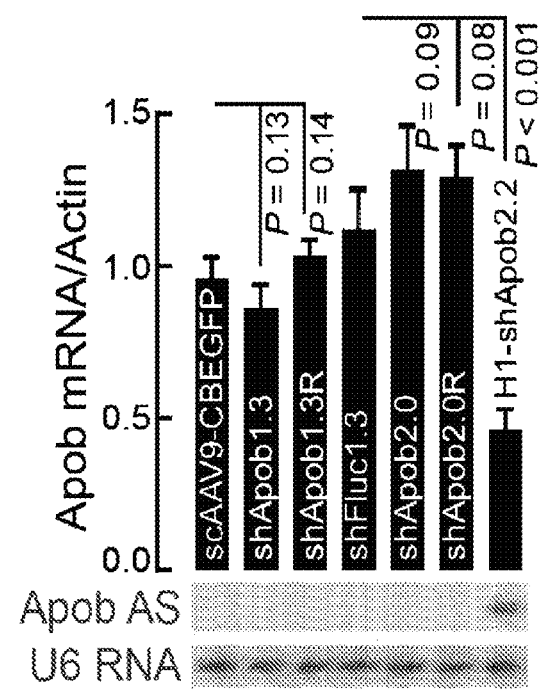

The H1 or U6 promoter from the shAAV constructs (FIG. 22I) and characterized these constructs in mouse livers. Comparable EGFP expression was only seen in the livers treated with shApob2.0, shApob2.0R, and control vectors (FIG. 22J). Neither the reduction of ApoB gene expression nor shRNA transcripts was detected in these livers (FIG. 22K), indicating that the complete shRNA expression cassette is necessary for functional silencing of Apob. This data also demonstrates that shDNA sequences alone, not other cassette elements, can promote the formation of shAAV genomes.

Figure 25A:
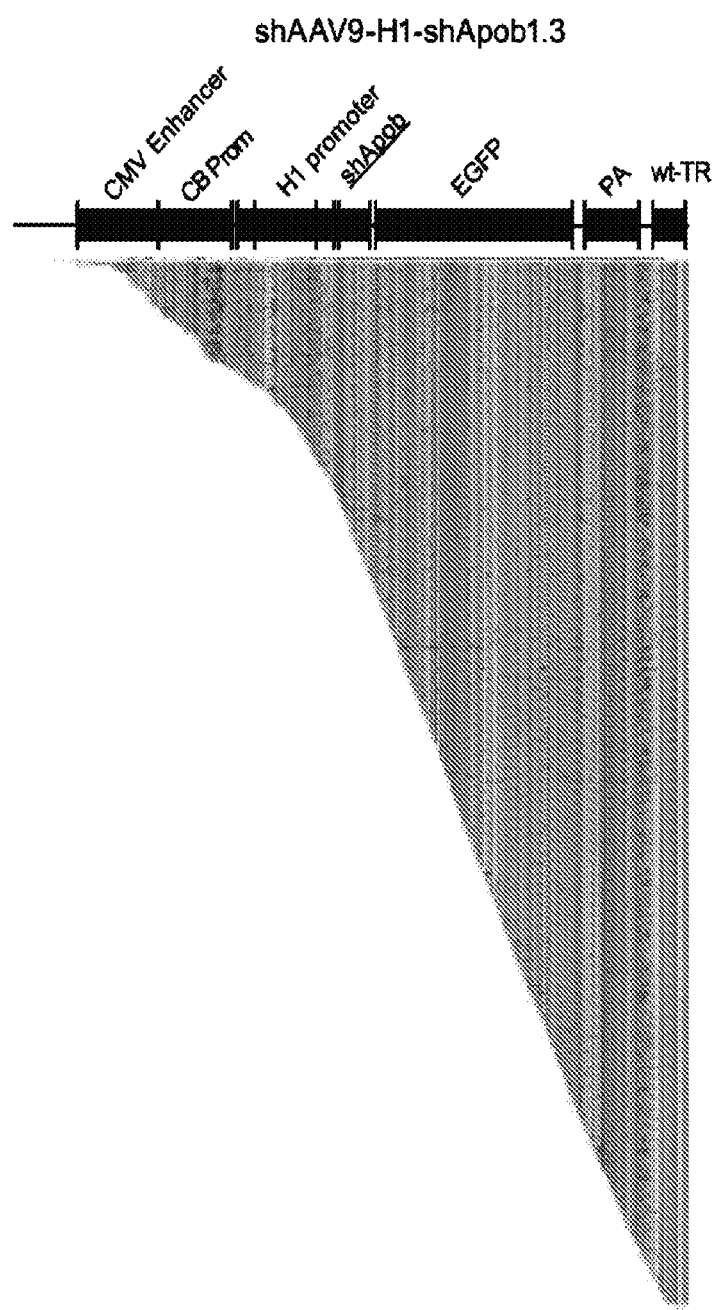
FIGS. 25A-25B show SMRT sequencing reads of whole-vector genomes of the Intron-D construct, or the scAAV0CB6-PI-EGFP construct mapped to their respective references, related to FIGS. 26A-26C. Reads in fastq format where halved to map only the sense strand of self-complementary molecules. Reads mapped by BWA-MEM were visualized with IGV to display only a subset of genomes to illustrate the full distribution of genome heterogeneity. Alignments were thus downsized to display a single representative read per sequence length. IGV display is set to show the base pair compositions of reads.
Figure 25B:
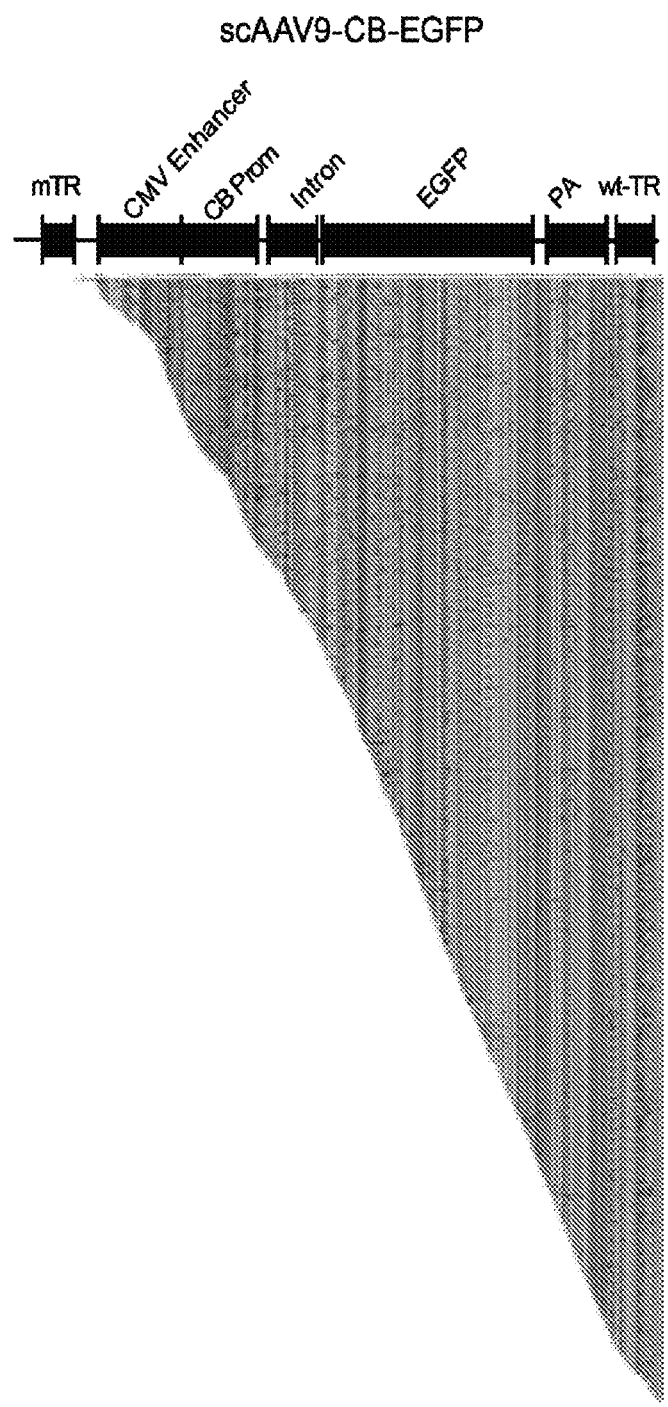
Figure 26A:
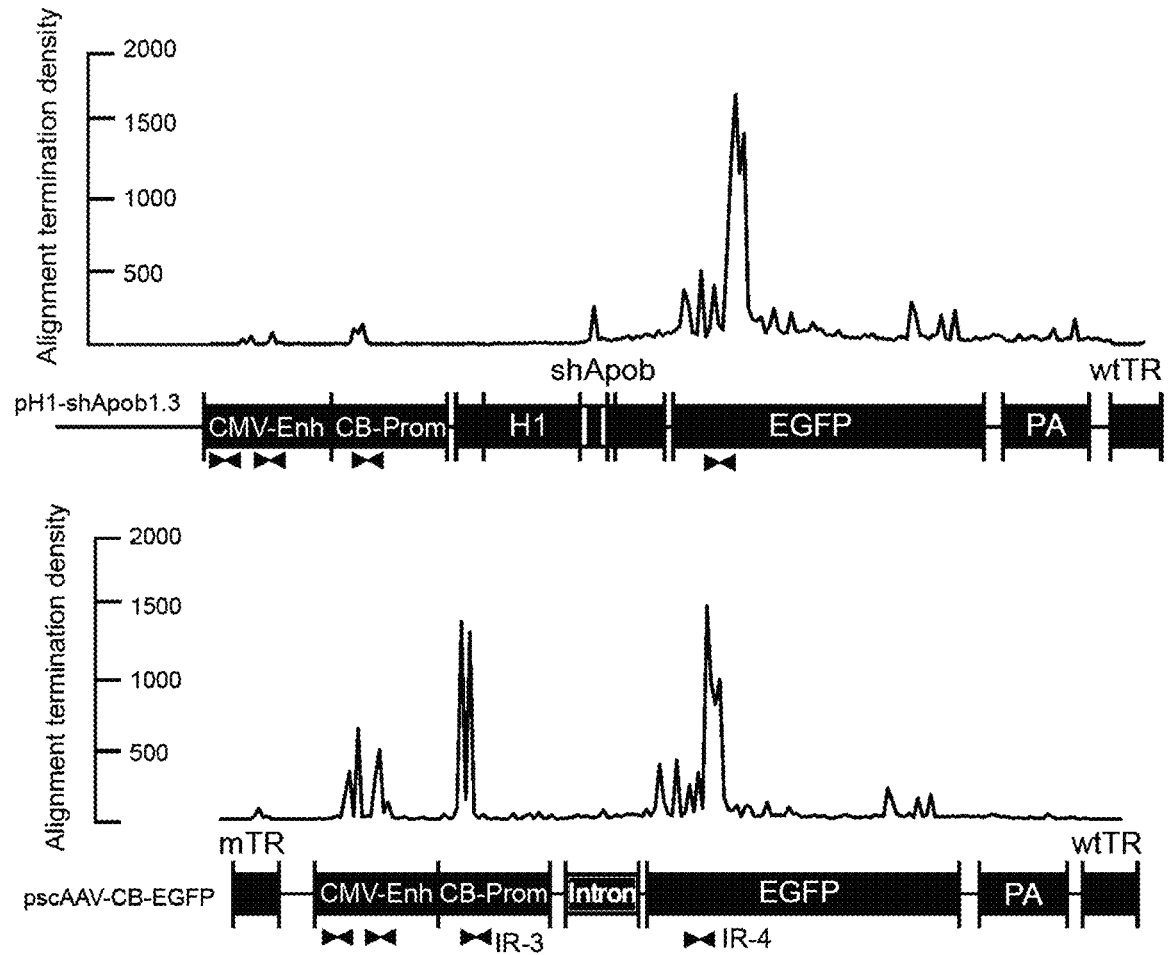
FIGS. 26A-26C show characterization of variable vector genomes generated from shDNA-like sequences.

Other Hairpin-Like Sequences in rAAV Constructs Also can Also Generate Intra-Molecular Double-Stranded Genomes The prevalence of read-through genomes in purified vectors was investigated. Vector genomes were profiled by direct SMRT sequencing of shAAV9-H1-shApob1.3 vectors, followed by alignment to the pH1-shApob1.3 plasmid construct. To determine the abundance of read-through genomes as well as define the exact locations of genome truncation with high confidence, only full and intact alignments that span the wtTR region were considered (FIGS. 25A-25B). It is notable that in addition to the previously identified shAAV genomes, several read-through genomes were identified. A significant portion of these genomes represent vectors that have replicated beyond the shRNA cassette, but terminate at the CMV enhancer or CB promoter regions as intra-molecular double-stranded DNAs, similar to shAAV genomes (FIG. 26A). To tabulate truncation events along the H1-shApob1.3 vector, each alignment was converted to an alignment termination positional tag designated as the most 5' nucleotide of the read-alignment (FIG. 26A, top trace). The most substantial peaks of alignment termination density were within the EGFP transgene, indicating that the majority of vector truncation events are centered at the EGFP transgene. This phenomenon was also observed for the scAAV9-CB-EGFP vector that lacks an shRNA cassette (FIG. 26A, bottom trace).

Figure 26B:
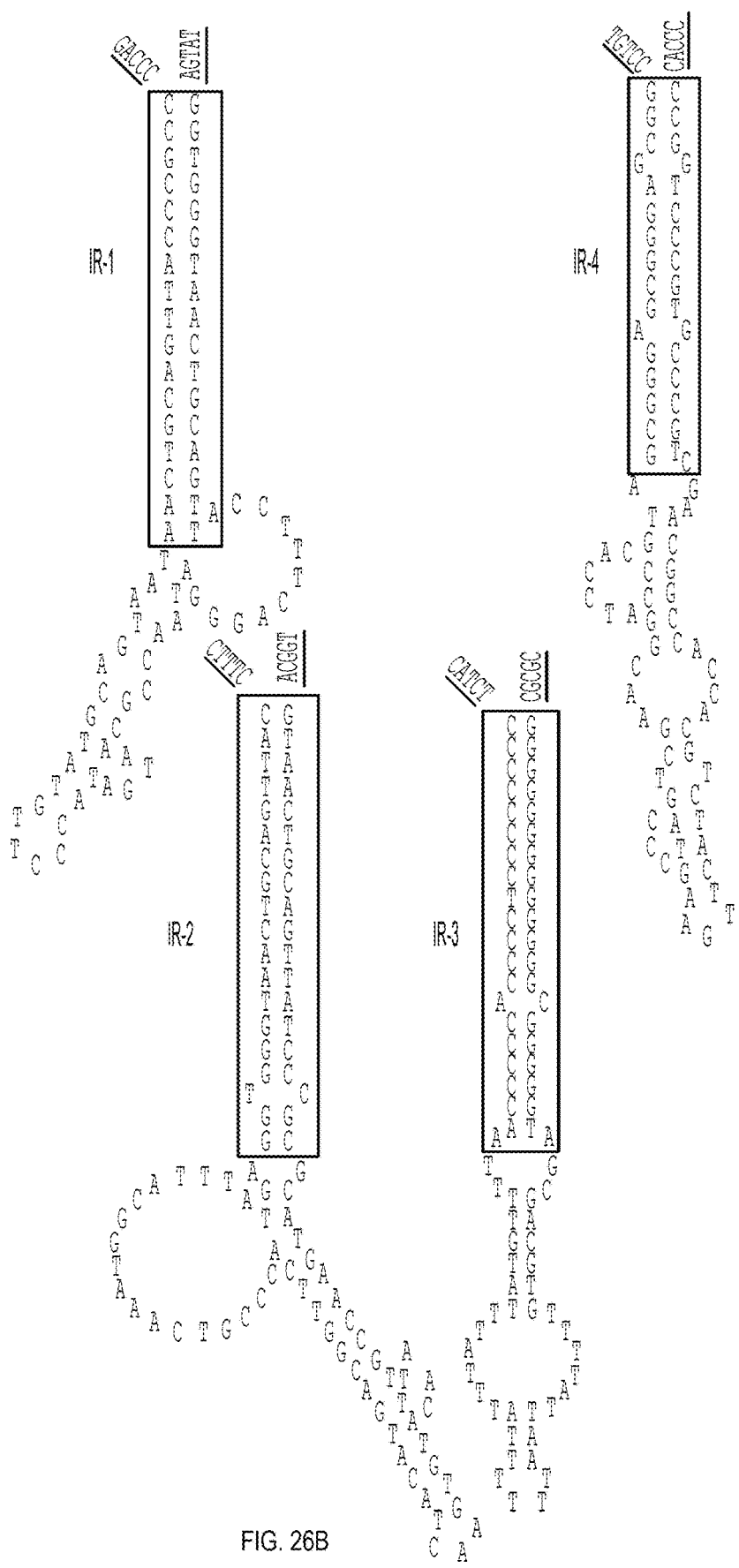
Figure 26C:
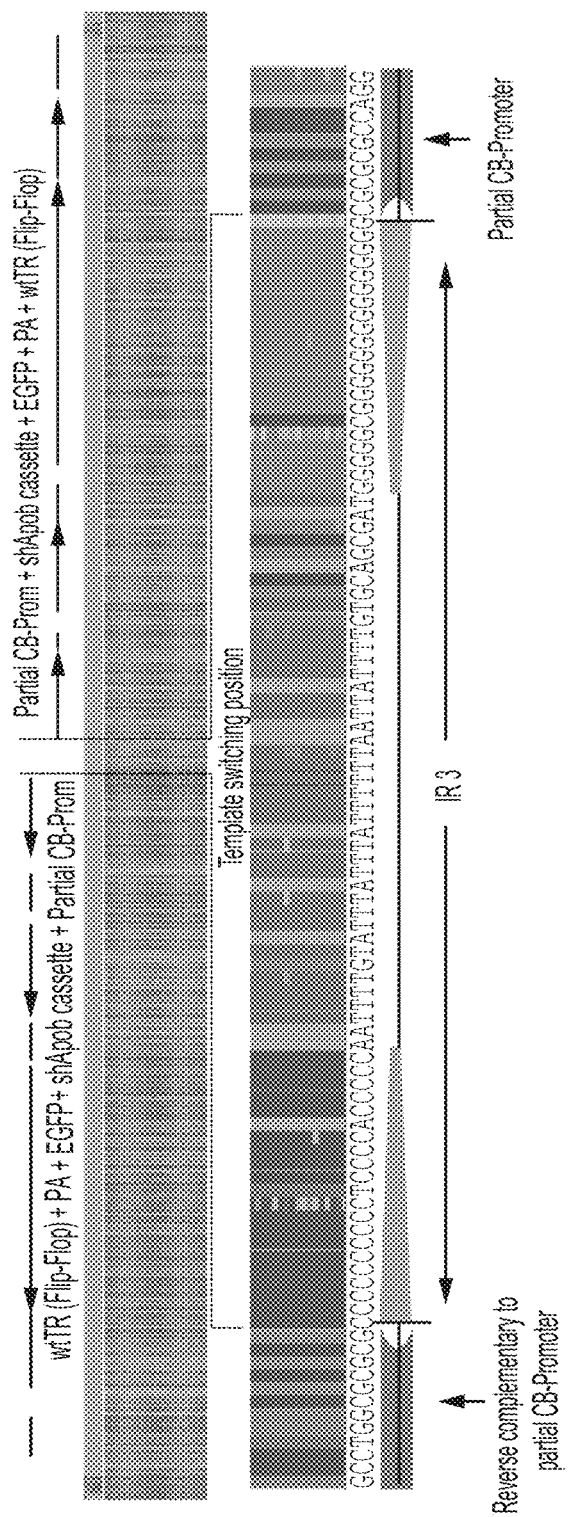
Figure 27:
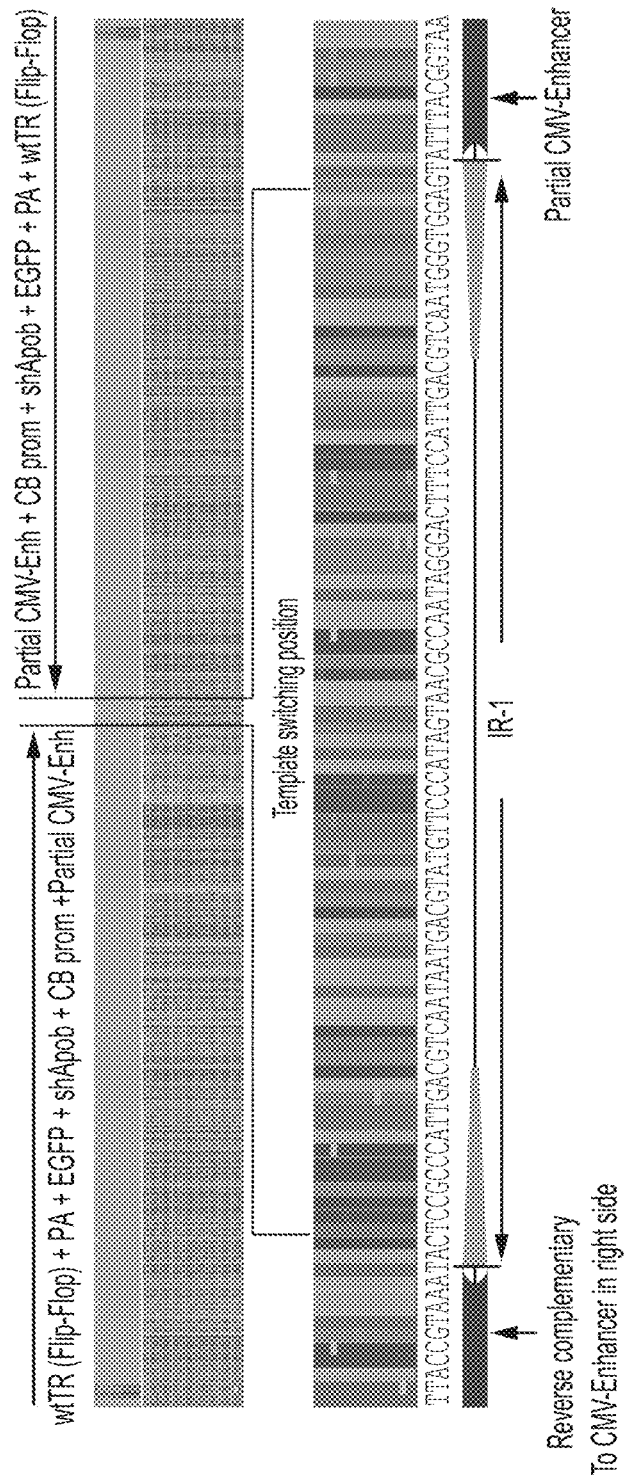
FIG. 27 shows self-complementary genomes with IR 1, IR 2 and IR 4 loops. Alignments were made with reference genomes that contain complementary sequences at two sides and IR 1, IR 2 or IR 4 in the middle to the SMRT reads. The complementary sequences span from the wtTR and the IR 1, IR 2, and IR 4, respectively. The alignment was done in SMRT reads from both shAAV and scAAV vectors. The sequences, from top to bottom, correspond to SEQ ID NOs: 78-80.
Figure 27:
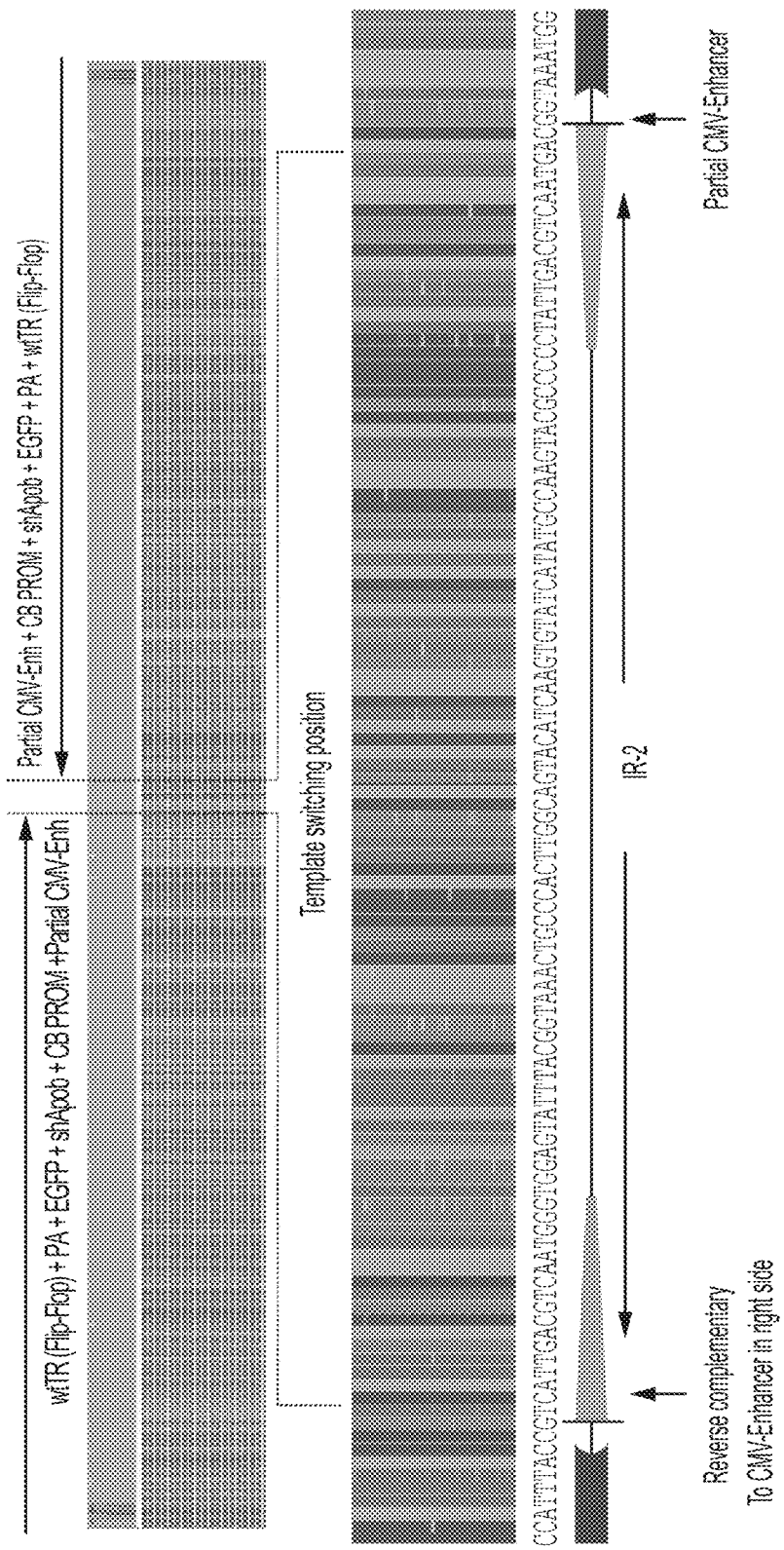
Figure 27:
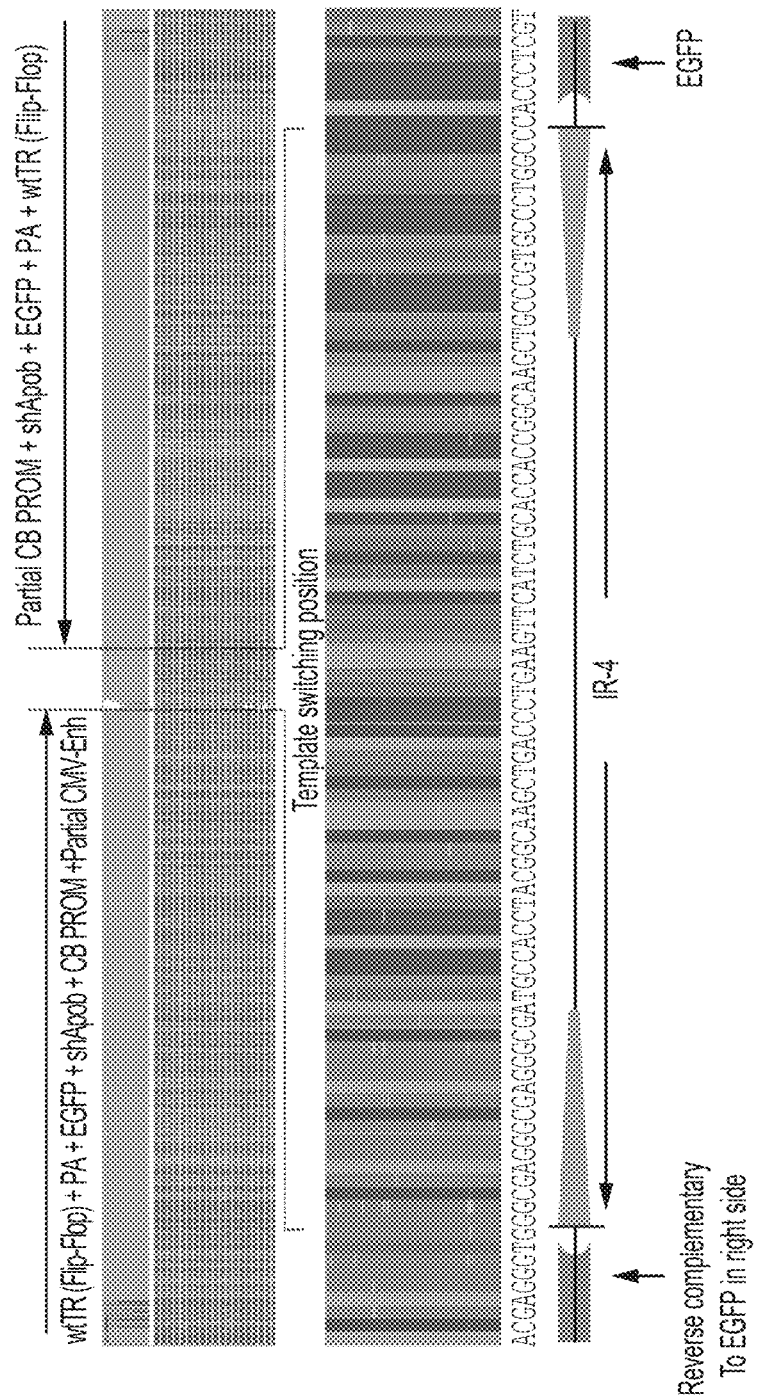

Four regions shared between the shAAV and the scAAV constructs with overlapping termination density peaks were identified and their secondary structures were analyzed: two within the CMV enhancer, one in the CB promoter, and one in the EGFP transgene (FIGS. 26A and 26B). Among these regions, inverted repeat (IR) sequences were identified. Custom references were designed using these inverted repeat sequences as centralized features, flanked by self-complementary strands as illustrated in FIG. 26C. Alignment of SMRT reads to these specific references verified our prediction that intra-molecular double-stranded genomes can also be mediated by sequences that harbor high secondary structure and inverted-repeat sequence (FIG. 26C and FIG. 27). These observations explain how constructs that only carry single wtTR regions and void of mTR or shDNA sequences can be rescued and packaged (FIG. 22B and FIG. 22C). The shDNA-like sequences inherent to the test vectors (e.g., CMV enhancer, CB promoter, and EGFP gene) function as pseudo-mTRs to complete genome replication. However, these shDNA-like sequences can also compromise promoter and transgene functionality in rAAV genomes, leading to low transgene expression in mice (FIG. 20D).

Figure 28:
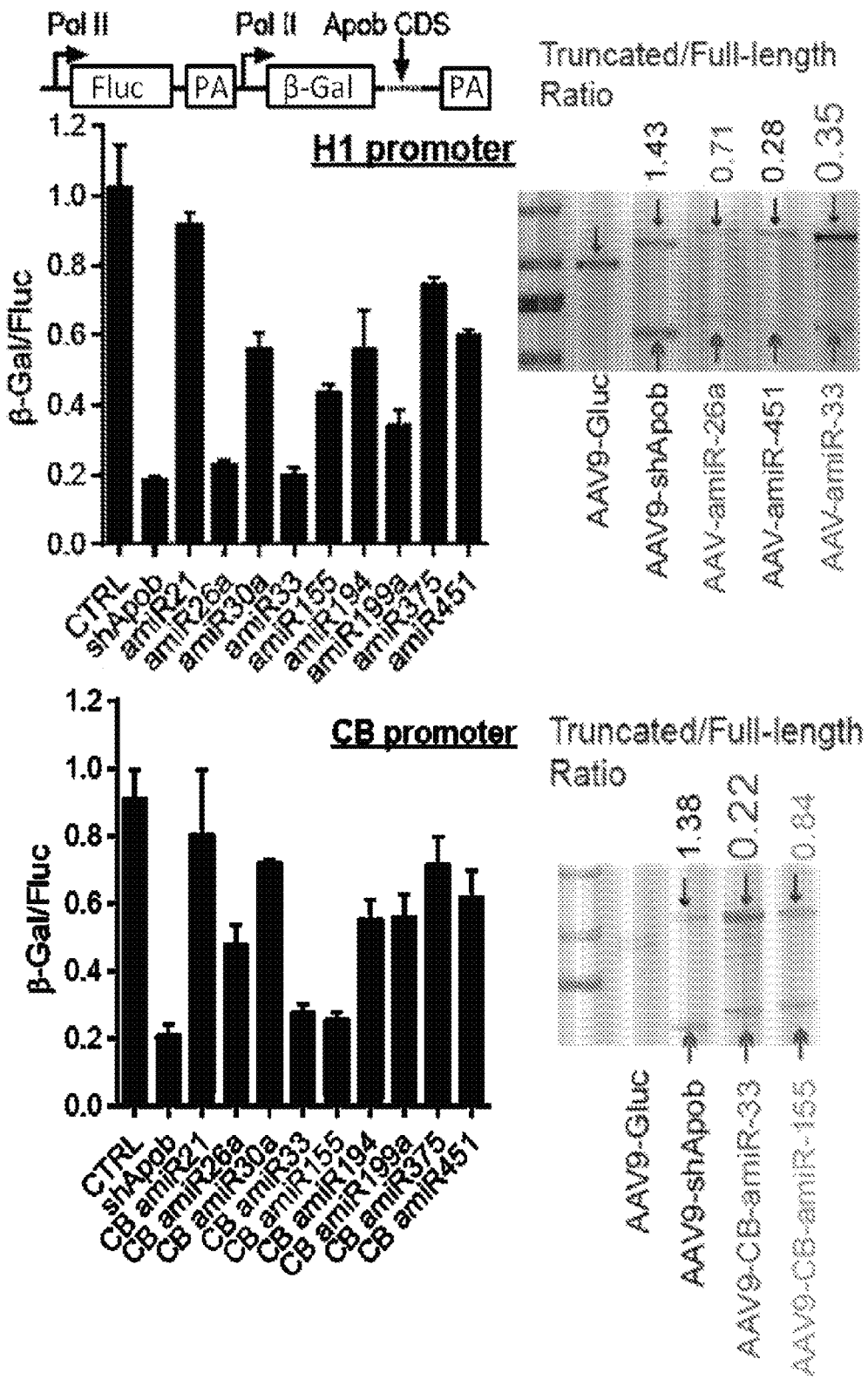
FIG. 28 shows gene silencing by pri-miRNA scaffolds. The gene silencing driven by H1 (top) or CB (bottom) promoters was assessed using omiCHECK-Apob in HEK-293 cells. Fluc and Gal levels were measured and ratio between Gal and Fluc was calculated. Agarose gel electrophoresis of viral genomes was performed (right).

Example 5: rAAV-Based Pri-miRNA Scaffolds Driven by Pol II Promoter to Inhibit Gene Expression Here, rAAV-based pri-miRNA scaffolds driven by Pol II promoter are described. Highly efficient gene silencing was observed from artificial miRNA scaffolds driven by Pol II CMV enhancer/Chicken β-actin promoter (CB), compared to conventional shRNA driven by Pol III H1 promoter (FIG. 28). Improvements to the genomic integrity of rAAV vectors expressing small RNAs by pri-mmu-miR-33 based scaffold (FIG. 28, bottom) have been identified. Switching from the strong constitutive H1 promoter to Pol II promoter enables the approach of AAV delivered small silencing RNA to be regulated and safer in in vivo gene transfer. The Pol II AAV constructs, in some embodiments, achieve greater in vivo gene delivery by minimizing the truncated genomes and transgene expression can be inducible by chemicals or regulated by cell-type specific Pol II promoters.

BRIEF DESCRIPTION OF SEQUENCE LISTING

| Sequence Reference | SEQ ID NO: |
|---|---|
| >pAAVsc\CB6\PI\EGFP\H1\apobsh3\(intron,\5'-3') | 1 |
| >pAAVsc\CB6\PI\EGFP | 2 |
| >pAAVsc\CB\PI\EGFP\ApoBsh3\intron\(3'-5')DmutITR | 3 |
| >pAAVsc\CB\PI\EGFP\ApoBsh3\intron\(5'-3')DmutITR | 4 |
| >pAAVsc\CB6\ApoBsh3\(5')(5'-3')\EGFP\DmutITR | 5 |
| >pAAVsc\CB6\ApoBsh3\(5')(3'-5')\EGFP\DmutITR | 6 |
| >pAAVsc\CB\PI\EGFP\DmutantITR | 7 |
| >pAAVsc\CB\PI\EGFP\ApoBsh3\(3')(5'-3')DwtITR standard; circular DNA | 8 |
| >pAAVsc\CB6\siFluc\(intron)(5'-3')\EGFP\DmutITR standard; circular DNA | 9 |
| >pAAVsc\CB6\siFluc\(intron)(5'-3')\EGFP\DmutITR | 10 |
| >pAAVsc\CB6\ApoBsh3\(5')(5'-3')\EGFP\DmutITR\TshPC1 | 11 |
| >pAAVsc\CB\PI\EGFP\ApoBsh3\intron\(5'-3')DmutITR\WtITRLoop | 12 |
| >pAAVsc\CB\PI\EGFP\ApoBsh3\intron\(5'-3')DmutITR\TshApob | 13 |
| >pAAVsc\CB\PI\EGFP\ApoBsh3\intron\(5'-3')DmutITR\TshPC1 | 14 |
| >pAAVsc\CB6\ApoBsh3\(5')(5'-3')\EGFP\DmutITR\WtITRLoop | 15 |
| >pAAVsc\CB6\ApoBsh3\(5')(5'-3')\EGFP\DmutITR\TshApob | 16 |
| >pAAVsc\CB6\siFluc\(intron)(5'-3')\EGFP\DmutITR\WtITRLoop | 17 |
| >pAAVsc\CB6\siFluc\(intron)(5'-3')\EGFP\DmutITR\T-shApob | 18 |
| >pAAVsc\CB6\siFluc\(intron)(5'-3')\EGFP\DmutITR\T-shPC1 | 19 |
| Apobsensor-F | 20 |
| Apobsensor-R | 21 |
| Apob-F | 22 |
| Apob-R | 23 |
| Actin-F | 24 |
| Actin-R | 25 |
| Intron-R | 26 |
| PA-F | 27 |
| EGFP-F | 28 |
| EGFP-R | 29 |
| EGFP-probe | 30 |
| shApob AS probe | 31 |
| U6 probe | 32 |
| shApob | 33 |
| shFluc | 34 |

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only

What is claimed is:

1. An isolated nucleic acid having one inverted terminal repeat at a first terminus and a promoter operably linked with a sequence encoding a hairpin-forming RNA at a second terminus, wherein the isolated nucleic acid is configured for forming a self-complementary AAV (scAAV) vector.

2. The isolated nucleic acid of claim 1, wherein the sequence encoding a hairpin-forming RNA is substituted at a position of the scAAV vector normally occupied by a mutant ITR, or wherein the sequence encoding a hairpin-forming RNA forms a shRNA, miRNA, or artificial microRNA (AmiRNA).

3. The isolated nucleic acid of claim 2, wherein the wherein the AmiRNA construct comprises:
   (i) a nucleic acid sequence encoding a pri-miRNA scaffold;
   (ii) a nucleic acid sequence encoding a guide strand; and,
   (iii) a nucleic acid sequence encoding a passenger strand, wherein, the pri-miRNA scaffold is derived from a naturally-occurring pri-miRNA and comprises at least one flanking sequence and a loop-forming sequence comprising at least 4 nucleotides.

4. The isolated nucleic acid of claim 3, wherein
   (i) the guide strand and/or the passenger strand share at least 50% complementarity to a target nucleic acid sequence but are not 100% complementary to one another; or
   (ii) the nucleic acid sequence encoding the guide strand and the nucleic acid sequence encoding the passenger strand are inserted into the pri-miRNA scaffold between the flanking sequence and the loop-forming sequence, thereby forming a stem.

5. The isolated nucleic acid of claim 3, wherein the nucleic acid sequence encoding the guide strand and the nucleic acid sequence encoding the passenger strand have at least one base pair mismatch.

6. The isolated nucleic acid of claim 4, wherein the nucleic acid sequence encoding the guide strand and the nucleic acid sequence encoding the passenger strand have mismatches at no more than ten consecutive base pairs.

7. The isolated nucleic acid of claim 3, wherein the pri-miRNA scaffold is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

8. The isolated nucleic acid of claim 3, wherein the guide strand targets a gene associated with a gain of function mutation disease, an oncogene, or a gene associated with a metabolic disorder.

9. The isolated nucleic acid of claim 8, wherein the guide strand targets SOD1, Huntington gene, p53, HER2/neu, LDLR, or beta-glucosidase.

10. A self-complementary adeno-associated virus (scAAV) comprising:
    (i) a viral genome comprising a nucleic acid sequence encoding at least one inverted terminal repeat and a promoter operably linked with a nucleic acid sequence encoding a hairpin-forming RNA; and
    (ii) at least one AAV capsid protein serotype.

11. The scAAV of claim 10, wherein the wherein the sequence encoding a hairpin-forming RNA is substituted at a position of the scAAV normally occupied by a mutant ITR.

12. The scAAV of claim 10, wherein the sequence encoding a hairpin-forming RNA forms a shRNA, miRNA, or AmiRNA, optionally wherein the AmiRNA construct comprises:
    (i) a nucleic acid sequence encoding a pri-miRNA scaffold;
    (ii) a nucleic acid sequence encoding a guide strand; and,
    (iii) a nucleic acid sequence encoding a passenger strand, wherein, the pri-miRNA scaffold is derived from a naturally-occurring pri-miRNA and comprises at least one flanking sequence and a loop-forming sequence comprising at least 4 nucleotides.

13. The scAAV of claim 12, wherein the nucleic acid sequence encoding the guide strand and the nucleic acid sequence encoding the passenger strand are inserted into the pri-miRNA scaffold between the flanking sequence and the loop-forming sequence, thereby forming a stem.

14. The scAAV of any claim 12, wherein the pri-miRNA scaffold is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

15. The scAAV of claim 12, wherein the guide strand targets a gene associated with a gain of function mutation disease, an oncogene, or a gene associated with a metabolic disorder.

16. The isolated nucleic acid of claim 15, wherein the guide strand targets SOD1, Huntington gene, p53, HER2/neu, LDLR, or beta-glucosidase.

17. The scAAV of claim 10, wherein the size of the viral genome is between about 150 bp and 5 kb.

18. The scAAV of claim 10, wherein the at least one capsid protein is an AAV2, AAV3, AAV4, AAV5, AAV6, AAV7, AAV8, AAVrh8, AAV9, AAV10, or AAVrh10 capsid protein.

* * * * *

UNITED STATES PATENT AND TRADEMARK OFFICE
CERTIFICATE OF CORRECTION

| | | |
|---|---|---|
| PATENT NO. | : 12,054,715 B2 | |
| APPLICATION NO. | : 17/316769 | |
| DATED | : August 6, 2024 | |
| INVENTOR(S) | : Guangping Gao et al. | |

It is certified that error appears in the above-identified patent and that said Letters Patent is hereby corrected as shown below:

In the Claims

In Claim 16, Column 154, Line 58, the text "The isolated nucleic acid of claim 15" should read --The scAAV of claim 15--

Signed and Sealed this
Tenth Day of September, 2024

Katherine Kelly Vidal
Director of the United States Patent and Trademark Office